(12) United States Patent
Singh

(10) Patent No.: US 12,227,779 B2
(45) Date of Patent: Feb. 18, 2025

(54) MODIFIED DDAH POLYPEPTIDES AND THEIR USE TO EXTRACORPOREALLY TREAT A PATIENT'S BLOOD TO REDUCE LEVELS OF ADMA

(71) Applicant: THE TRUSTEES OF INDIANA UNIVERSITY, Bloomington, IN (US)

(72) Inventor: Jaipal Singh, Carmel, IN (US)

(73) Assignee: THE TRUSTEES OF INDIANA UNIVERSITY, Bloomington, IN (US)

( * ) Notice: Subject to any disclaimer, the term of this patent is extended or adjusted under 35 U.S.C. 154(b) by 0 days.

(21) Appl. No.: 17/690,657

(22) Filed: Mar. 9, 2022

(65) Prior Publication Data
US 2022/0204961 A1 Jun. 30, 2022

Related U.S. Application Data

(63) Continuation of application No. 16/777,413, filed on Jan. 30, 2020, which is a continuation-in-part of application No. PCT/US2018/044627, filed on Jul. 31, 2018.

(60) Provisional application No. 62/539,261, filed on Jul. 31, 2017.

(51) Int. Cl.
*C12N 9/78* (2006.01)
*A61K 38/50* (2006.01)

(52) U.S. Cl.
CPC .............. *C12N 9/78* (2013.01); *A61K 38/50* (2013.01); *C12Y 305/03018* (2013.01)

(58) Field of Classification Search
CPC ...................................................... C12N 9/78
See application file for complete search history.

(56) References Cited

U.S. PATENT DOCUMENTS

| 2005/0153315 A1 | 7/2005 | Vallance et al. |
| 2005/0176060 A1 | 8/2005 | McDonald et al. |
| 2007/0207952 A1 | 9/2007 | Silva et al. |
| 2008/0108557 A1 | 5/2008 | Behrens et al. |
| 2011/0065633 A1 | 3/2011 | Di Marchi et al. |
| 2012/0220011 A1 | 8/2012 | Schellenberger et al. |
| 2012/0237503 A1 | 9/2012 | Mookerjee et al. |

FOREIGN PATENT DOCUMENTS

| WO | WO 00/44888 | 8/2000 |
| WO | WO 03/089638 | 10/2003 |
| WO | WO 2006/007400 | 1/2006 |
| WO | WO 2021/018758 | * 2/2021 |

OTHER PUBLICATIONS

Murray-Rust et al., "Structural insights into the hydrolysis of cellular nitric oxide synthase inhibitors by dimethylarginine", Nature Structural Biology, 2001, vol. 8, No. 8, pp. 679-683.*
Freitas et al., "Tag-mediated single-step purification and immobilization of recombinant proteins toward protein-engineered advanced materials", Journal of Advanced Research, 2022, vol. 36, pp. 249-264.*
CM5 Sensor Chip Information Data Sheet. Retrieved from < https://www.cytivalifesciences.com/en/us/shop/protein-analysis/spr-label-free-analysis/spr-consumables/spr-sensor-chips/sensor-chip-cm5-p-05858 > May 19, 2023.*
Mariani, S. and Minunni, M., "Surface plasmon resonance applications in clinical analysis", Anal Bioanal Chem (2014) 406:2303-2323. DOI 10.1007/s00216-014-7647-5.*
Stone et al., "Characterization of a Transient Covalent Adduct Formed during Dimethylarginine Dimethylaminohydrolase Catalysis", Biochemistry 2005, 44, 7069-7078.*
Ghebremariam et al., "An Unexpected Effect of Proton Pump Inhibitors: Elevation of the Cardiovascular Risk Factor ADMA", Circulation. Aug. 20, 2013; 128(8):. doi: 10.1161/CIRCULATIONAHA. 113.003602.*
Kimoto et al., "Purification, cDNA cloning and expression of human NG,NG-dimethylarginine", Eur. J. Biochem., vol. 258, pp. 863-868.*
Ghebremariam et al., "Development of a dimethylarginine dimethylaminohydrolase (DDAH) assay for high throughput chemical screening", J. Biomol. Screen., 2012, 17(5): 651-661. doi:10.1177/1087057112441521.*
Veronese FM et al: "PEGylation, successful approach to drug delivery", Drug Discovery Today, Elsevier, Amsterdam, NL, vol. 10, No. 21, Nov. 1, 2005.
Extended European Search Report, EP 18842346.1, Aug. 19, 2021.
Sharma et al. "Tumor-targeted delivery of siRNA using fatty acyl-CGKRK peptide conjugates," Scientific Reports, Jul. 21, 2017 (Jul. 21, 2017), vol. 7, pp. 1-14.
Pang et al. "A modular method for high yield synthesis of site-specific protein-polymer therapeutics," Angewandte Chemie International Edition English, Jul. 21, 2016 (Jul. 21, 2016), vol. 55, No. 35, pp. 10296-10300.
Frey et al. "Structure of the Mammalian NOS Regulator Dimethylarginine Dimethylaminohydrolase: A Basis for the Design of Specific Inhibitors," Structure, May 31, 2006 (May 31, 2006), vol. 14, Iss. 5, pp. 901-911.
Examination Report for copending European patent application No. 18842346.1, mailed Nov. 25, 2024.

* cited by examiner

*Primary Examiner* — Suzanne M Noakes
(74) *Attorney, Agent, or Firm* — Barnes & Thornburg LLP

(57) ABSTRACT

Modified DDAH polypeptides and their uses thereof are provided. Exemplary embodiments provide DDAH polypeptides which include one or more amino acid substitutions, additions, or deletions with natural or non-naturally encoded amino acids, and/or linkage to other biologically active molecules including other DDAH polypeptides, as well as PKEM. Additionally, use of said DDAH polypeptides for treatment of disease, such as heart failure or renal disease, is also provided.

14 Claims, 13 Drawing Sheets
Specification includes a Sequence Listing.

MODIFIED DDAH POLYPEPTIDES AND THEIR USE TO EXTRACORPOREALLY TREAT A PATIENT'S BLOOD TO REDUCE LEVELS OF ADMA

CROSS REFERENCE TO RELATED APPLICATIONS

This application is a continuation of U.S. application Ser. No. 16/777,413, filed on Jan. 30, 2020, which is a continuation in part of International Patent Application No. PCT/US2018/044627, filed on Jul. 31, 2018, which claims priority to U.S. Provisional Patent Application No. 62/539,261 filed Jul. 31, 2017. The disclosure of each application is hereby expressly incorporated by reference in its entirety.

INCORPORATION BY REFERENCE OF MATERIAL SUBMITTED ELECTRONICALLY

Incorporated by reference in its entirety is a computer-readable nucleotide/amino acid sequence listing submitted concurrently herewith and identified as follows: 52 kilobytes ACII (Text) file named "354987_ST25.txt" created on Mar. 9, 2022.

BACKGROUND

Asymmetric dimethylarginine (ADMA), also known as a cardiotoxin, has been recognized as an important mediator of the pathogenesis of cardiovascular and renal disease. ADMA is produced in the body as a result of degradation of argininemethylated proteins and is known to inhibit nitric oxide synthesis (NO). ADMA levels correlate with increased cardiovascular morbidity and mortality and high plasma concentrations of ADMA are found in a number of disease states involving vascular dysfunction including, coronary artery disease, hypertension, heart failure, type 2 diabetes and insulin resistance, peripheral arterial disease, chronic kidney disease and preeclampsia. High plasma concentrations of ADMA can occur in tissues and blood of individuals suffering from disease states where protein degradation rates are high or the mechanisms of ADMA clearance are impaired.

In some conditions such as kidney disease, there may be a 3- to 9-fold increase in plasma levels of ADMA. High levels of ADMA are known to contribute to disease states by acting as a competitive inhibitor for nitric oxide generation by nitric oxide synthase (NOS) as well as cationic amino acid transporter for NOS substrate arginine. ADMA also inhibits phosphorylation of endothelial NOS, thereby, reducing its activity. Deficiency of NO production which may be caused by ADMA is associated with a wide range of vascular diseases including, hypertension, heart failure, pulmonary arterial hypertension, erectile dysfunction, coronary and peripheral arterial disease, renal, disease, insulin resistance, diabetes, atrial fibrillation, sickle cell disease, organ damage, sepsis, preeclampsia, and deficient wound healing, and tissue regeneration.

By reducing NO bioavailability, high levels of ADMA can promote endothelial dysfunction, vasoconstriction, pro-inflammatory and pro-thrombogenic state. In addition, high levels of ADMA can uncouple NOS causing it to produce oxygen free radical which cause organ damage. Since vascular homeostasis plays a fundamental role in normal physiology and survival, a persistent dysfunction of vascular endothelium can lead to a variety of disease states and death. An association of high ADMA levels has been documented with vascular diseases such as retinal venous occlusive disease, early autosomal dominant polycystic kidney disease, proteinuria, erythropoietin resistance, secondary amyloidosis and focal segmental glomerulosclerosis, pre-eclampsia, chronic thromboembolic pulmonary hypertension, diabetes, insulin resistance, obesity, pulmonary hypertension, lung injury, sickle cell disease, depression, congestive heart failure, Alzheimer's disease, cardio-renal syndrome, hyperhomocysteinaemia, hypertension, atherosclerosis and stroke.

A major pathway for ADMA metabolism is by the enzyme dimethylarginine dimemylamino hydrolase (DDAH) which eliminates more than 80% of ADMA. DDAH gene deletion and transgenic animal studies have shown that DDAH levels and activity regulate ADMA levels. Heterologous deletion of gene DDAH−/+ increased ADMA level and impaired vascular responses. Conversely, transgenic expression of DDAH-1 reduced plasma ADMA, increased NO production, and decreased arterial blood pressure and systemic vascular resistance. Thus, ADMA levels in plasma can be modulated by the level of DDAH-1 gene expression.

For example, global deletion of DDAH-1 gene in mice resulted in increased plasma and tissue ADMA, endothelial dysfunction and hypertension. In addition, cardiomyocytes specific DDAH-1 gene deletion exacerbated pressure overload induced left ventricular (LV) hypertrophy and dysfunction. DDAH-1 overexpression studies have shown that ADMA lowering improves angiogenesis in the ischemic hind limb model and protected from myocardial or renal ischemia-reperfusion injury. In a partial nephrectomy rat model of kidney disease, adenoviral-DDAH-1 gene delivery reduced plasma ADMA, deterioration of renal function, tubulointerstitial fibrosis and proteinuria, and improved creatinine clearance. These studies suggested that loss of DDAH contributes to pathological state whereas increase DDAH-1 gene expression is protective.

In disease states where DDAH expression or activity is impaired, ADMA clearance is reduced leading to its accumulation in tissues and blood. For example, in pathological conditions such as diabetes, atherosclerosis, preeclampsia and inflammation, DDAH-1 gene expression is reduced and ADMA is increased. In lung disease such as pulmonary arterial hypertension (PAH), DDAH mRNA and protein expression are reduced and ADMA levels are increased. Therefore, methods that can increase enzyme levels in the body would reduce ADMA and produce therapeutic benefit in prevention or treatment of disease.

Two isoforms of DDAH are encoded by separate genes located on human chromosome 1 (DDAH-1) and 6 (DDAH-2). The two protein shares 63% amino acid homology but exhibit similar catalytic properties. Both enzymes metabolize ADMA into citrulline and dimemylamine. DDAH can hydrolase both the NG-monomemyl-1-arginine (1-NMMA) and ADMA, and therefore it can reduce the inhibitory concentrations of the methylamines and allow more NO generation.

High levels of ADMA are also produced in response to ischemia reperfusion injury. Several human studies have reported a strong association of ADMA levels with cardiovascular events and mortality in patients with known coronary artery disease. ADMA levels were also an independent predictor of cardiovascular (CV) events in patients after coronary angioplasty. ADMA levels are strong predictor of mortality after AMI. ADMA levels are strongly associated with cardiovascular disease and all-cause mortality and to the cardiovascular events in patients undergoing hemodialysis. High levels of ADMA are associated with all-cause mortality, major cardiovascular and cerebrovascular events, and progression of renal disease, chronic heart failure, peripheral arterial disease, and type 2 diabetes. In patients with end-stage renal disease elevated ADMA levels were directly associated with carotid atherosclerosis and cardiovascular mortality.

High levels of ADMA are present in the blood of patients on dialysis and chronic kidney disease. Raising ADMA levels by infusion of ADMA decreases the effective renal plasma flow. High level of ADMA is associated with erythropoietin resistance. Reducing plasma ADMA levels by DDAH therapy is expected to improve endothelial function and renal function in patients on dialysis and impaired kidney function.

Plasma ADMA is also elevated in patients with CAD and CKD and thus may play a role in cardio-renal syndrome. ADMA levels were significantly increased in patients suffering from pulmonary arterial hypertension (PAH) and idiopathic pulmonary arterial hypertension. In animal models of PAH, DDAH expression or activity is reduced. Reducing ADMA levels can improve endothelial function, reduce inflammation, fibrosis and reduce PAH and other inflammatory lung disease. Elevated ADMA levels have also been observed in acute lung injury (ALT). Increased collagen deposition leads to impaired lung function in disease such as asthma and pulmonary fibrosis.

In critically ill patients, endothelial damage and microvascular oxidative stress and deficiency of nitric oxide leads to impaired organ perfusion, inflammation, infection and organ failure. High levels of ADMA have been reported in patients with sepsis, trauma and major surgery. ADMA is also a predictor of mortality in ICU patients. ADMA levels are also elevated in hepatic failure. High ADMA could cause microvascular complications including endothelial dysfunction, microvascular constriction, inflammation, generation of oxygen free radical and thrombosis further contributing to the complications of organ dysfunction.

Deficient NO and endothelial dysfunction are associated with insulin resistance and type 2 diabetes. NO mediates insulin-induced skeletal muscle blood flow which promotes glucose uptake and thereby may regulate insulin sensitivity in the skeletal muscle. Plasma ADMA levels are elevated in patients with type 2 diabetes as well individual with metabolic syndrome. High ADMA levels are associated with glucose intolerance, insulin resistance and diabetes. These studies support that high ADMA may promote insulin resistance and diabetes by reducing NO synthesis.

High level of ADMA and reduced DDAH are found in patients with preeclampsia which may contribute to hypertension, renal injury, reduce fetal growth and premature birth.

It is also well recognized that endothelial nitric oxide is diminished in severe malaria. A recent study of Indonesian adults with malaria suggests that ADMA may contribute to mortality in severe malaria patients. In this prospective longitudinal study, patients with high ADMA levels showed almost 18-fold higher probability of death than those with lower ADMA.

Pharmacological agents that can specifically and effectively lower pathological ADMA levels are not available. Disclosed herein are DDAH analogs that have improved in vivo retention times and the ability to reduce ADMA in animal models.

SUMMARY

As disclosed herein, DDAH peptides are provided that are analogs of native DDAH peptides that have improved stability and activity while retaining the ability to metabolize ADMA. Native DDAH has poor retention times when administered to mammalian species, making the native proteins poor pharmaceutical agents for effectively reducing ADMA in a patient's blood and tissues. Disclosed herein are analogs of native DDAH peptides that have been modified to enhance their ADMA metabolic activity and/or enhance their retention time in the blood and tissues of mammalian species.

DDAH polypeptides and uses thereof are described herein. In exemplary embodiments, the DDAH polypeptides, such as human DDAH-1 and DDAH-2 polypeptides, can include one or more amino acid modifications and/or post-translational modifications that enhance or modulate pharmacokinetic, pharmacodynamic, or time-action properties of the DDAH polypeptide, including linkage to other biologically active molecules such as a half-life extending or pharmacokinetic enhancing moiety. Pharmaceutical compositions and medical use of such DDAH polypeptides are also described.

Described herein are methods and compositions that relate to the use of the DDAH enzyme dimethylarginine diamino hydrolase (DDAH) or a biologically active fragment or modified form of the DDAH enzyme, where the DDAH or fragment or modified form thereof is capable of hydrolyzing asymmetric dimethylarginine (ADMA) to form citrulline and/or other breakdown products of ADMA. A cDNA encoding human DDAH protein has been made and used to express and produce recombinant biologically active human DDAH protein.

The DDAH or biologically active fragment or modified form thereof can be administered to a patient, or contacted with a patient's bodily fluid such as blood, to lower plasma or tissue levels of ADMA. The DDAH or biologically active fragment thereof may be free in solution, or attached to a solid substrate or support, that is contacted with the blood or tissue of a patient. DDAH or biologically active fragment or modified form thereof can be particularly effective to reduce ADMA when utilized in conjunction with or as a part of hemodialysis or plasmapheresis system components in order to extracorporeally treat a patient's blood to reduce levels of ADMA.

There is an urgent need to develop a means to reduce ADMA concentration in the blood of patients with chronic kidney disease, organ failure and those who are receiving hemodialysis treatment for kidney related diseases. The ability to reduce ADMA from the blood of end stage renal disease patients in conjunction with hemodialysis treatment by administering DDAH or a biologically active fragment thereof may reduce ADMA-mediated morbidity and extend life. Described herein are DDAH polypeptides and modified DDAHs, as well as compositions and therapeutic uses thereof. In exemplary embodiments, the modified DDAHs exhibit enhanced or modulated pharmacokinetic, pharmacodynamic, or time-action properties, including an increased or enhanced in vivo half-life relative to wild-type DDAH, such as an in vivo half-life of at least 1, 2, 3, 4, 5, 6, 9, 10, 12, 15, 20, 25 hours, multiple days, or longer.

In one embodiment, the DDAH polypeptide can comprises a wild-type or a modified human DDAH polypeptide or a wild-type or modified non-human DDAH polypeptide. Said DDAH or modified DDAH polypeptide may have at least 80%, 85%, 90%, 95% or 99% sequence identity to the DDAH polypeptide of SEQ ID NO: 1, and/or the DDAH polypeptide of SEQ ID NO: 2 or the corresponding amino acids of SEQ ID NO: 5; SEQ ID NO: 6; SEQ ID NO: 7; SEQ ID NO: 9; SEQ ID NO: 10; SEQ ID NO: 11; SEQ ID NO:

12; SEQ ID NO: 13; SEQ ID NO: 14, SEQ ID NO: 15, SEQ ID NO: 17, SEQ ID NO: 22 or SEQ ID NO: 23.

In accordance with one embodiment the DDAH peptide is an analog of *Pseudomonas aeruginosa* DDAH (SEQ ID NO: 13) that comprises the sequence of SEQ ID NO: 15: MFX$_3$HIIARTPARSLVDGLTSSHLGX$_{25}$PDYAKALEQH NAYIR ALQTX$_{45}$DVDITLLPPDERFPDSVFVEDPVLX$_{70}$ TSRX$_{74}$AIITRPGAEX$_{84}$RRGETE IIEETVQRFYPGX$_{103}$ VERIEAPGTVEAGDIMMVGDHFYIGESARTNAE-GARQ MIAILEKHGLSGSVVRLEX$_{159}$VLHLKTGLAY LEHNNLLAAGEFVSKPEFQDF NIIEIPEEESYAANX$_{205}$ IWVNERVIMPAGYPRTREKIARLGYRVIEVDTSEY RKIDGGVSCMSLRF, wherein $X_3$, $X_{25}$, $X_{103}$, and $X_{159}$ are independently selected from cysteine and lysine, $X_{45}$, $X_7O$ and $X_{205}$ are independently selected from cysteine, alanine and lysine, and $X_{74}$, and $X_{84}$ are independently selected from cysteine, alanine and serine. In one embodiment the DDAH peptide of SEQ ID NO: 15 comprises a C-terminal addition of 1 to 6 histidine residues. In one embodiment the analog of *Pseudomonas aeruginosa* DDAH comprises the sequence of SEQ ID NO: 17. As noted in Table 8 the *Pseudomonas aeruginosa* DDAH polypeptides have been discovered by applicant to have enhanced activity in metabolizing AMAS in rats relative to the human DDAH polypeptides of SEQ ID NO: 1.

In one embodiment a DDAH polypeptide is provided comprising an amino acid sequence having at least 90% or 95% sequence identity to SEQ ID NO: 1; SEQ ID NO: 2; SEQ ID NO: 5; SEQ ID NO: 6; SEQ ID NO: 7; SEQ ID NO: 9; SEQ ID NO: 10; SEQ ID NO: 11; SEQ ID NO: 12; SEQ ID NO: 13; SEQ ID NO: 14, SEQ ID NO: 15, SEQ ID NO: 17 or SEQ ID NO: 22 or fragment thereof and a pharmacokinetic enhancing moiety (PKEM) covalently linked to said DDAH polypeptide, wherein said DDAH polypeptide or fragment thereof has a molecular weight of about 150, 200, or 250 KDa or greater, and exhibits asymmetric dimethylarginine (ADMA) metabolizing activity. In one embodiment the DDAH polypeptide comprises the amino acid sequence of SEQ ID NO: 15 or SEQ ID NO: 17, or an amino acid sequence that differs from SEQ ID NO: 15 or SEQ ID NO: 17 by 1-10 amino acid modifications. In another embodiment the DDAH polypeptide comprises the amino acid sequence of SEQ ID NO: 17 or an amino acid sequence that differs from SEQ ID NO: 17 by 1, 1-2, 1-4, 1-5 or 1-10 amino acid modifications. In one embodiment the amino aci modifications are amino acid substitutions, optionally conservative amino acid substitutions. In another embodiment the DDAH polypeptide comprises an amino acid sequence having at least 95% sequence identity to SEQ ID NO: 1, SEQ ID NO: 13, SEQ ID NO: 15 or SEQ ID NO: 17.

In one embodiment the PKEM is selected from the group consisting of an acyl group, water soluble polymer, lipid, alkyl group, carbohydrate, polypeptide, polynucleotide, polysaccharide, antibody or antibody fragment, serum albumin, XTEN molecule, or adnectin. In one embodiment the DDAH polypeptide comprises two or more of said PKEMs covalently linked to said DDAH polypeptide, wherein the two or more PKEMs are different or the same and independently selected from any of the PKEM moieties disclosed herein including the group consisting of polyethylene glycol (PEG), an acyl group, and an alkyl group. In one embodiment the PKEM is a DDAH polypeptide and the DDAH polymer is a dimer or multimer. In another embodiment the PKEM is an acyl group of the formula: CH3(CH2)12C(=O)—, CH3(CH2)14C(=O)—, CH3(CH2)16C(=O)— or CH3(CH2)18C(=O)—. In a further embodiment the PKEM is polyethylene glycol and the molecular weight of the modified DDAH polypeptide is about 250 kDa or greater.

In one embodiment a method of reducing ADMA levels in a patient is provided, wherein the method comprises the steps of administering a modified DDAH polypeptide to a patient in need of ADMA reduction, wherein the modified DDAH polypeptide comprises an amino acid sequence of SEQ ID NO: 1, SEQ ID NO: 13, SEQ ID NO: 17 or an amino acid sequence having at least 90% or 95% sequence identity with SEQ ID NO: 1, SEQ ID NO: 13 or SEQ ID NO: 17; and a PMET covalently linked to said amino acid sequence, wherein said modified DDAH has a molecular weight of at least about 150, 200 or 250 kDa. In one embodiment the DDAH polypeptide comprises the amino acid sequence of SEQ ID NO: 1, SEQ ID NO: 15 or SEQ ID NO: 17, or an amino acid sequence that differs from SEQ ID NO: 15 or SEQ ID NO: 17 by 1, 1-3 or 1-5 amino acid modifications. In one embodiment the amino acid modifications are amino acid substitutions. In one embodiment the method comprises administering a modified DDAH polypeptide wherein the polypeptide is covalently linked to any of the PKEM moieties as disclosed herein, including a PKEM selected from the group consisting of a DDAH polypeptide, polyethylene glycol (PEG), an acyl group, and an alkyl group, or said DDAH polypeptide comprises a combination said PKEMs linked to the DDAH polypeptide resulting in the modified DDAH polypeptide having a molecular weight of at least about 150, 200 or 250 kDa.

In one embodiment a method of treating patients with elevated ADMA levels is provided, wherein the method comprises the steps of obtaining a biological sample from a patient; measuring ADMA levels in the biological sample to identify patients with elevated levels of ADMA; administering a modified DDAH polypeptide to said patients identified with elevated levels of ADMA in an amount effective to reduce ADMA levels in said patient and thus treat said patient.

In one embodiment, the DDAH or modified DDAH can retain one or more properties of wild-type DDAH that are indicative of clinical efficacy, including hydrolyzing ADMA, in vitro or in vivo activity, and efficacy for treatment of cardiac diseases, heart failure, kidney diseases, lung disease, sepsis or in a model thereof.

In one embodiment, the DDAH or modified DDAH can be linked to at least one pharmacokinetic enhancing moiety (PKEM). Exemplary PKEM include acyl groups, alkyl groups, polyethylene glycol, lipids, serum albumin, XTEN molecules, Fc molecules, adnectins, and albumin binding moieties. For example, the acyl group may comprise a C8-C30 acyl, such as a C12 acyl, C14 acyl, C16 acyl, C18 acyl, or C20 acyl or any alkyl chain of sufficient length to bind serum albumin.

The pharmacokinetic enhancing moiety can be linked to any amino acid residue of the DDAH or modified DDAH amino acid sequence, such as before position 1 (i.e. at the N-terminus), 1, 2, 3, 4, 5, 6, 7, 8, 9, 10, 11, 12, 13, 14, 15, 16, 17, 18, 19, 20, 21, 22, 23, 24, 25, and each amino acid position through the end of the DDAH peptide (i.e. position 285 for SEQ ID NO: 1), and after position 285 (i.e., at the carboxyl terminus of the protein), or the corresponding amino acids in SEQ ID NO: 2, or the corresponding amino acid position in SEQ ID NO: 5; SEQ ID NO: 6; SEQ ID NO: 7; SEQ ID NO: 9; SEQ ID NO: 10; SEQ ID NO: 11; SEQ ID NO: 12; SEQ ID NO: 13; or SEQ ID NO: 14.

In further embodiments, the pharmacokinetic enhancing moiety can be linked to any single position in the DDAH amino acid sequence, or a combination of more than one of these sites, e.g., 2, 3, 4, or more sites, or at least one of these sites in combination with other sites. Positions in said polypeptide chain may be substituted with another amino acid, such as cysteine (Cys, C), e.g., in conjunction with linkage of the pharmacokinetic enhancing moiety to the DDAH polypeptide.

In one embodiment, the DDAH or modified DDAH may include at least one non-naturally encoded amino acid. Said non-naturally encoded amino acid may be linked to the pharmacokinetic enhancing moiety, a linker, a biologically active molecule, or another DDAH polypeptide. For example, the DDAH or modified DDAH may include a pharmacokinetic enhancing moiety linked to a non-naturally encoded amino acid at any position of the DDAH polypeptide.

Also described are DDAH or modified DDAH polypeptides that comprise a substitution of a naturally encoded or non-naturally encoded amino acid substituted in the amino acid sequence, wherein: (a) the DDAH polypeptide comprises a DDAH polypeptide that has a sequence at least 80% identical to SEQ ID NO: 1, or at least 80% identical to SEQ ID NO: 2 or SEQ ID NO: 5; SEQ ID NO: 6; SEQ ID NO: 7; SEQ ID NO: 9; SEQ ID NO: 10; SEQ ID NO: 11; SEQ ID NO: 12; SEQ ID NO: 13; or SEQ ID NO: 14; and (b) the substituted naturally encoded or non-naturally encoded amino acid is linked to a pharmacokinetic enhancing moiety.

In another aspect, the disclosure provides a DDAH or modified DDAH polypeptide comprising up to one, two, three, or four amino acid substitutions or comprising one, two, three or more amino acids added to the carboxy or amino terminus wherein the additional or substitute amino acids are selected from naturally encoded or non-naturally encoded amino acids.

In another aspect, the disclosure provides a DDAH or modified DDAH polypeptide comprising at least one natural amino acid substitution and/or at least one non-naturally encoded amino acid substitution and substituted amino acid is linked to a linker, polymer, or biologically active molecule. In one embodiment a DDAH or modified DDAH polypeptide is provided comprising at least one amino acid added to the carboxy terminus wherein at least one of the added amino acids is linked to a pharmacokinetic enhancing moiety.

Said DDAH polypeptide may include a non-naturally encoded amino acid having the structure:

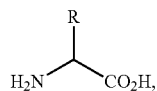

wherein the R group is any substituent other than the side chain found in alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, valine, pyrrolysine, or selenocysteine.

As stated above, in exemplary embodiments the DDAH or modified DDAH is linked to at least one pharmacokinetic enhancing moiety. The pharmacokinetic enhancing moiety can comprise an XTEN molecule. XTEN molecules are also referred to as unstructured recombinant polymers, unstructured recombinant polypeptides, or "URPs", and are generally described in Schellenberger et al., Nat Biotechnol., 2009 December; 27(12):1186-90, U.S. Patent Application Publication No. 2012/0220011, U.S. Pat. No. 7,846,445, and International Publication No. WO/2012/162542, each of which is hereby incorporated by reference in its entirety. As disclosed therein, the half-life of the DDAH or modified DDAH polypeptide may be varied by varying the constitution of the XTEN molecule, e.g., by varying its size. For example, an XTEN molecule may be selected in order to achieve a desired half-life, such as in the range of 1 to 50 hours, such as at least 1, 2, 5, 10, 12, 15, 20, or 25 hours, or longer.

Exemplary XTEN molecules include a URP comprising at least 40 contiguous amino acids, wherein: (a) the URP comprises at least three different types of amino acids selected from the group consisting of glycine (G), aspartate (D), alanine (A), serine (S), threonine (T), glutamate (E) and proline (P) residues, wherein the sum of said group of amino acids contained in the URP constitutes more than about 80% of the total amino acids of the URP, and wherein said URP comprises more than one proline residue, and wherein said URP possesses reduced sensitivity to proteolytic degradation relative to a corresponding URP lacking said more than one proline residue; (b) at least 50% of the amino acids of said URP are devoid of secondary structure as determined by Chou-Fasman algorithm; and (c) the Tepitope score of said URP is less than −5. Additional exemplary XTEN molecules comprise an unstructured recombinant polymer (URP) comprising at least about 40 contiguous amino acids, and wherein (a) the sum of glycine (G), aspartate (D), alanine (A), serine (S), threonine (T), glutamate (E) and proline (P) residues contained in the URP, constitutes at least 80% of the total amino acids of the URP, and the remainder, when present, consists of arginine or lysine, and the remainder does not contain methionine, cysteine, asparagine, and glutamine, wherein said URP comprises at least three different types of amino acids selected from glycine (G), aspartate (D), alanine (A), serine (S), threonine (T), glutamate (E) and proline (P); (b) at least 50% of the at least 40 contiguous amino acids in said URP are devoid of secondary structure as determined by Chou-Fasman algorithm; and (c) wherein the URP has a Tepitope score less than −4.

If desired, multiple DDAH polypeptide molecules can be linked to an XTEN molecule, e.g., up to 1, 2, 3, 4, 5, or more DDAH polypeptide molecules per XTEN molecule. For example, the DDAH polypeptide molecules can be linked to sites on differing portions of the XTEN molecule, e.g., near the N-terminus, near the C-terminus, or near the middle (mid-way between the N- and C-termini) thereof. In this context, the term "near" generally means linked to a site within a region of about 20%, about 15%, about 10%, or about 5% of the residues at the respective terminus or centered at the middle of the XTEN molecule.

Additional exemplary XTEN molecules include a hydrophobic residue (e.g., F, I, L, M, V, W or Y), a side chain amide-containing residue (e.g., N or Q) or a positively charged side chain residue (e.g., H, K or R). In some embodiments, the duration enhancing moiety includes A, E, G, P, S or T. In some embodiments, the XTEN includes glycine at 10-20%, 20-30%, 30-40%, 40-50%, 50-60%, 60-70%, 70-80%, 80-90%, 90-99%, or even glycine at 100%.

In some embodiments the PKEM molecule is linked to the N-terminal or C-terminal of the DDAH or modified DDAH polypeptide, or at another site. The attachment of a PKEM to a DDAH polypeptide described herein is referred to herein as "PKEMylation".

The DDAH or modified DDAH or modified DDAH polypeptide or polypeptides can be linked to the XTEN molecule through a dibenzylcyclooctyne (DBCO).

The XTEN molecule can be further linked to a polyethylene glycol.

In one embodiment, the pharmacokinetic enhancing moiety can comprise an adnectin. Adnectins are disclosed, for example, in U.S. Patent Application Publication No. 2011/0305663, which is hereby incorporated by reference in its entirety. The adnectin can be based on a tenth fibronectin type III domain and can bind to serum albumin. The adnectin can comprise one or more of a BC loop, a DE loop, and an FG loop, or comprises a polypeptide selected from SEQ ID NO: 5, 6, 7, 8, 12, 16, 20, and 24-44 of U.S. Patent Application Publication No. 2011/0305663.

The present disclosure also encompasses conjugates formed with any of the DDAH polypeptides disclosed herein. Exemplary conjugate moieties that can be linked to any of the DDAH polypeptides described herein include but are not limited to a heterologous peptide or polypeptide (including for example, a plasma protein), a targeting agent, an immunoglobulin or portion thereof (e.g. variable region, CDR, or Fc region), a diagnostic label such as a radioisotope, fluorophore or enzymatic label, a polymer including water soluble polymers, or other therapeutic or diagnostic agents. In one embodiment a conjugate is provided comprising a glucagon peptide of the present invention and a plasma protein, wherein the plasma protein is selected from the group consisting of albumin, transferin, fibrinogen and globulins.

In one embodiment, the pharmacokinetic enhancing moiety linked to the DDAH polypeptide can comprise serum albumin, such as human serum albumin. For example, the DDAH or modified DDAH polypeptide can be linked to the Cys 34 residue of human serum albumin.

In one embodiments, the DDAH or modified DDAH polypeptide can be linked to at least one pharmacokinetic enhancing moiety comprising an acyl group. In one embodiment the DDAH polypeptide is covalently linked moiety (e.g., a non-native alkyl or acyl group) that is of sufficient size to irreversibly bind a mammalian plasma protein such as mammalian serum albumin. An example acyl group suitable for use in the present invention can have from 6 to 40 carbon atoms, from 8 to 26 carbon atoms or from 14 to 22 carbon atoms, such as 16, 17, 18, 19, 20 carbon atoms, and may be branched or unbranched. In some embodiments, the acyl group can comprise $CH_3(CH_2)_rCO—$, wherein r is an integer from 4 to 38, such as an integer from 4 to 24, an integer from 6 to 20, or 10 or 12. For example, the acyl group can be $CH_3(CH_2)_6CO—$, $CH_3(CH_2)_8CO—$, $CH_3(CH_2)_{10}CO—$, $CH_3(CH_2)_{12}CO—$, $CH_3(CH_2)_{14}CO—$, $CH_3(CH_2)_{16}CO—$, $CH_3(CH_2)_{18}CO—$, $CH_3(CH_2)_{20}CO—$, or $CH_3(CH_2)_{22}CO—$. In some embodiments, the acyl group can comprise a group negatively charged at pH 7.4. In some embodiments, the acyl group can comprise a terminally attached acidic group. In some embodiments, the acyl group can comprise at least two acidic groups, wherein one of the acidic groups is terminally attached. For example, the acyl group may comprise a linear or branched lipophilic moiety containing 4-40 carbon atoms having a terminal acidic group. Additional exemplary acyl groups are disclosed in U.S. Patent Application Publication No. 2012/0295847, which is hereby incorporated by reference in its entirety.

In one embodiment, the albumin binding moiety can comprise a carboxylic acid group, such as $HOOC(CH_2)_sCO—$, wherein s is an integer from 12 to 22, such as 10, 12, 16 or 18.

In some embodiments, the pharmacokinetic enhancing moiety can be linked to DDAH or modified DDAH polypeptide through a linker (e.g., a bivalent linker). For example, the linker can comprise one or two amino acids which are bound at one end to the pharmacokinetic enhancing moiety (e.g., an albumin binding moiety) and are bound at the other end to any available position on the polypeptide backbone. Other example linkers include hydrophilic linker, such as a chemical moiety which comprises at least 5 non-hydrogen atoms where 30-50% of these are either N or O (e.g., oligo- or polyalkylene oxides, such as oligoethylene glycols and polyethylene glycols). Other linkers which can link the pharmacokinetic enhancing moiety to the DDAH or modified DDAH are disclosed in U.S. Patent Application Publication No. 2012/0295847 and International Publication No. WO/2012/168430, each of which is hereby incorporated by reference in its entirety.

In some embodiments, the modified DDAH polypeptide includes a polyethylene glycol, optionally which may have a molecular weight of from about 2 kDa to 100 kDa (e.g., from 2 kDa to 100 kDa). Said polyethylene glycol may be linked to the DDAH at any suitable position in the amino acid sequence of the polypeptide.

In one embodiment, the DDAH or modified DDAH polypeptide can be a fusion protein comprising DDAH and a proteinaceous pharmacokinetic enhancing moiety (e.g., albumin, an Fc chain, certain XTEN molecules, or a PKE adnectin), which can be fused to any suitable amino acid of the DDAHpolypeptide and may be fused to the N- or C-terminus thereof.

The pharmacokinetic enhancing moiety can be covalently linked to DDAH or modified DDAH polypeptide (e.g., covalently linked to a naturally encoded or a non-naturally encoded amino acid). For example, the DDAH or modified DDAH polypeptide can comprise a pharmacokinetic enhancing moiety linked to a cysteine via a thiol linkage.

Optionally, multiple DDAH or modified DDAH polypeptides may be joined by a linker polypeptide, wherein said linker polypeptide optionally is 1, 1-2, 1-3, 1-4, 1-5, 1-6, 1-7, 1-8, 1-9, 1-10, 1-11, 1-12, and longer in length, wherein optionally the carboxy terminus of one DDAH polypeptide is fused to the amino-terminus of the linker polypeptide and the carboxy terminus of the linker polypeptide is fused to the amino terminus of another DDAH polypeptide. Further exemplary linker polypeptides which may be utilized are disclosed in International Publication No. WO/2013/004607, which is hereby incorporated by reference in its entirety.

In another embodiment, two DDAH polypeptides are linked to form a homodimer of DDAH, or a homodimer of a modified DDAH, or a heterodimer of DDAH and a modified DDAH, or a heterodimer of different modified DDAH polypeptides, or any combination of DDAH polypeptides. The DDAH dimer may be formed by chemical linking of their respective N-termini. It is understood that linking two DDAH polypeptides each having a molecular weight of about 30 kDa, in a head-to-head fashion each at their N-terminus, may result in an enzymatically active molecule that would have an overall molecular weight of about 60 kDa. A polypeptide of this size can have significantly reduced kidney clearance from the bloodstream, which may in turn result in a significantly increased circulating half-life after administration to a patient. Therefore, a dimer of DDAH polypeptides may have the same half-life extending effect compared to monomeric DDAH, as observed using a single DDAH polypeptide chemically linked to a non-DDAH pharmacokinetic enhancing moiety.

In one embodiment, a pharmacokinetic enhancing moiety is linked to a naturally encoded amino acid or a non-naturally encoded amino acid, which can comprise a functional group which reacts and thereby forms a covalent bond with functional group on the pharmacokinetic enhancing moiety.

Also described are polynucleotides encoding the DDAH. The DDAH-coding polynucleotides may be contained in different molecules or in the same molecules, e.g., joined in any order and optionally joined via a nucleotide sequence that encodes a connecting peptide. Said polynucleotide may be isolated. Said polynucleotide may be contained in one or more vectors, plasmids, etc., such as an expression vector. Additional exemplary embodiments provide a composition for translation of said polynucleotides, such as a cell or in vitro translation system comprising said polynucleotides. Further exemplary embodiments provide a host cells, such as a prokaryotic cell (e.g., *E. coli*) or eukaryotic cell (e.g., a yeast or mammalian cell) comprising said polynucleotide and optionally further comprising said orthogonal tRNA. Additional exemplary embodiments provide a method of producing a DDAH or modified DDAH, comprising causing a cell or in vitro translation system to translate said polynucleotide or an mRNA transcribed therefrom.

Optionally, the DDAH or modified DDAH polypeptide can include one or more natural variant sequences of human DDAH1 (SEQ ID NO: 1), such as DDAH2 (SEQ ID NO: 2), or the DDAH1 isoform 2 (SEQ ID NO: 5). Additional natural variant sequences which can be present include sequences in the nucleic acid that encode the secretion signal sequence.

In one embodiment, the DDAH or modified DDAH polypeptide has one or more biological activities of DDAH, such as the hydrolysis of ADMA to citrulline and/or other breakdown products of ADMA.

Also provided are pharmaceutical compositions or medicaments comprising DDAH or the modified DDAH polypeptides described herein. A further embodiment provides the use of said DDAH or a modified DDAH polypeptide described herein for the treatment of a variety of diseases that are associated with high ADMA levels, including but not limited to heart failure, or renal diseases. The compositions described herein may be used for reducing the concentration of ADMA, and/or increasing the levels of citrulline, and/or increasing the levels of NO in patients in need of such treatment. Further provided is the use of the compositions described herein for the prophylaxis and/or treatment of renal disease, sepsis, sickle cell crisis, severe malaria, Mediterranean fever, trauma, ICU patients, acute kidney injury contrast induced kidney injury, decompensated heart failure, diuretic resistant heart failure, cardiac failure and cardiac insufficiency thromboembolic disorders, reperfusion damage following ischemia, micro- and macro-vascular lesions (vasculitis), arterial and venous thromboses, edemas, ischemias such as myocardial infarction, stroke and transient ischemic attacks, for cardio protection in connection with coronary artery bypass operations (coronary artery bypass graft, CABG), primary percutaneous transluminal coronary angioplasties (PTCAs), PTCAs after thrombolysis, rescue PTCA, heart transplants and open-heart operations, and for organ protection in connection with transplants, bypass operations, catheter examinations and other surgical procedures. Also provided are methods of using DDAH or the modified DDAH polypeptide described herein for the prophylaxis and/or treatment of respiratory disorders, such as, for example, chronic obstructive pulmonary disease (chronic bronchitis, COPD), asthma, pulmonary emphysema, bronchiectases, lung injury, cystic fibrosis (mucoviscidosis) and pulmonary hypertension, in particular pulmonary arterial hypertension, preeclampsia and erythropoietin resistance.

Also provided are methods of using DDAH or a modified DDAH polypeptide described herein as a medicament for the prophylaxis and/or treatment of kidney diseases, especially of acute and chronic kidney diseases and acute and chronic renal insufficiencies, as well as acute and chronic renal failure, including acute and chronic stages of renal failure with or without the requirement of dialysis, as well as the underlying or related kidney diseases such as renal hypoperfusion, dialysis induced hypotension, glomerulopathies, glomerular and tubular proteinuria, renal edema, hematuria, primary, secondary, as well as acute and chronic glomerulonephritis, membranous and membranoproliferative glomerulonephritis, Alport-Syndrome, glomerulosclerosis, interstistial tubular diseases, nephropathic diseases, such as primary and inborn kidney diseases, renal inflammation, immunological renal diseases like renal transplant rejection, immune complex induced renal diseases, as well as intoxication induced nephropathic diseases, diabetic and non-diabetic renal diseases, pyelonephritis, cystic kidneys, nephrosclerosis, hypertensive nephrosclerosis, nephrotic syndrome, that are characterized and diagnostically associated with an abnormal reduction in creatinine clearance and/or water excretion, abnormal increased blood concentrations of urea, nitrogen, potassium and/or creatinine, alteration in the activity of renal enzymes, such as glutamylsynthetase, urine osmolarity and urine volume, increased microalbuminuria, macroalbuminuria, glomerular and arteriolar lesions, tubular dilation, hyperphosphatemia and/or the requirement of dialysis.

The DDAH or a modified DDAH polypeptide described herein can be used as a medicament for the prophylaxis and/or treatment of renal carcinomas, after incomplete resection of the kidney, dehydration after overuse of diuretics, uncontrolled blood pressure increase with malignant hypertension, urinary tract obstruction and infection, amyloidosis, as well as systemic diseases associated with glomerular damage, such as Lupus erythematodes, and rheumatic immunological systemic diseases, as well as renal artery stenosis, renal artery thrombosis, renal vein thrombosis, analgetics induced nephropathy and renal tubular acidosis, gastric cancer.

The DDAH or a modified DDAH polypeptide described herein can be used as a medicament for the prophylaxis and/or treatment of contrast medium induced and drug induced acute and chronic interstitial kidney diseases, metabolic syndrome and insulin resistance. The DDAH or a modified DDAH polypeptide described herein can be used as a medicament for the prophylaxis and/or treatment of aftereffects associated with acute and/or chronic kidney diseases, such as diabetic nephropathy, pulmonary edema, heart failure, uremia, anemia, electrolyte disturbances (e.g. hyperkalemia, hyponatremia), as well as bony and carbohydrate metabolism.

Also provided are pharmaceutical compositions comprising DDAH or a modified DDAH polypeptide in a pharmacologically acceptable vehicle. The DDAH or modified DDAH polypeptides can be administrated systemically or locally. Example modes of administration include, but are not limited to, intravenous, intraperitoneal, intraarterial, intranasal, by inhalation, oral, subcutaneous administration, transdermal, by local injection or in a form of a surgical implant. Administration can be accomplished orally or parenterally. Example methods of parenteral delivery include topical, transdermal, intra-arterial, intramuscular, subcutaneous, intramedullary, intrathecal, intraventricular, intravenous, intraperitoneal, or intranasal administration. In certain embodiments, administration may be performed subcutaneously.

Also provided are pharmaceutical compositions comprising a modified DDAH polypeptide, alone or in combination with at least one other agent, such as stabilizing compound, which may be administered in any sterile, biocompatible pharmaceutical carrier, including, but not limited to, saline, buffered saline, dextrose, and water. In one embodiment, the pharmaceutically acceptable carrier may be pharmaceutically inert. Any of these peptides can be administered to a patient alone, or in combination with other agents, drugs or hormones, in pharmaceutical compositions where it is mixed with excipient(s) or pharmaceutically acceptable carriers. In this context, the term combination encompasses any means of concurrent administration, whether or not the DDAH or modified DDAH polypeptide and the other agent are contained in the same composition or administered separately, which administration may be through the same or different modes of administration.

Pharmaceutical compositions for oral administration can be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions and the like, for ingestion by the patient.

Pharmaceutical formulations for parenteral administration include aqueous solutions of active compounds. For injection, the pharmaceutical compositions may be formulated in aqueous solutions, for example in physiologically compatible buffers such as Hank's solution, Ringer's solution, or physiologically buffered saline. Aqueous injection suspensions may contain substances that increase viscosity of the suspension, such as sodium carboxymethyl cellulose, sorbitol, or dextran. Additionally, suspensions of the active compounds may be prepared as appropriate oily injection suspensions. Suitable lipophilic solvents or vehicles may include fatty oils such as sesame oil, or synthetic fatty acid esters, such as ethyl oleate or triglycerides, or liposomes. Suitable liposomes include, but are not limited to, the phospholipid vesicles described in Geho, W., et. al., J Diabetes Sci Technol, Vol 3, Issue 6, November 2009, which is incorporated by reference herein. Optionally, the suspension may also contain suitable stabilizers or agents which increase the solubility of the compounds to allow for the preparation of highly concentrated solutions.

The DDAH or modified DDAH polypeptides described herein can be used alone or in combination with other active compounds. Accordingly, also provided are medicaments comprising at least one DDAH or modified DDAH polypeptide described herein and one or more further active ingredients, in particular for the treatment and/or prevention of the disorders mentioned above. Suitable active ingredients for combination may include, by way of example: active ingredients which modulate lipid metabolism, antidiabetics, hypotensive agents, perfusion-enhancing and/or antithrombotic agents, antioxidants, chemokine receptor antagonists, p38-kinase inhibitors, NPY agonists, orexin agonists, anorectics, PAF-AH inhibitors, antiphlogistics (COX inhibitors, $LTB_4$-receptor antagonists), analgesics for example aspirin, antidepressants and other psychopharmaceuticals.

Also described are combinations of at least one modified DDAH polypeptide with at least one lipid metabolism-altering active ingredient, antidiabetic, blood pressure reducing active ingredient and/or agent having antithrombotic effects. The DDAH or modified DDAH polypeptide can be combined with one or more lipid metabolism-modulating active ingredients, by way of example from the group of the HMG-CoA reductase inhibitors, inhibitors of HMG-CoA reductase expression, squalene synthesis inhibitors, ACAT inhibitors, LDL receptor inductors, cholesterol absorption inhibitors, polymeric bile acid adsorbers, bile acid reabsorption inhibitors, MTP inhibitors, lipase inhibitors, LpL activators, fibrates, niacin, CETP inhibitors, PPAR-α, PPAR-δ and/or PPAR-δ agonists, RXR modulators, FXR modulators, LXR modulators, thyroid hormones and/or thyroid mimetics, ATP citrate lyase inhibitors, Lp(a) antagonists, cannabinoid receptor 1 antagonists, leptin receptor agonists, bombesin receptor agonists, histamine receptor agonists and the antioxidants/radical scavengers, antidiabetics mentioned in the Rote Liste 2004/11, chapter 12, and also, by way of example, those from the group of the sulfonylureas, biguanides, meglitinide derivatives, glucosidase inhibitors, inhibitors of dipeptidyl-peptidase IV (DPP-IV inhibitors), oxadiazolidinones, thiazolidinediones, GLP 1 receptor agonists, glucagon antagonists, insulin sensitizers, CCK 1 receptor agonists, leptin receptor agonists, inhibitors of liver enzymes involved in the stimulation of gluconeogenesis and/or glycogenolysis, modulators of glucose uptake and also potassium channel openers, such as, for example, those disclosed in WO 97/26265 and WO 99/03861; hypotensive active ingredients, by way of example from the group of the calcium antagonists, angiotensin AII antagonists, ACE inhibitors, renin inhibitors, beta-receptor blockers, alpha-receptor blockers, aldosterone antagonists, mineralocorticoid receptor antagonists, ECE inhibitors, ACE/NEP inhibitors and the vasopeptidase inhibitors; and/or antithrombotic agents, by way of example from the group of the platelet aggregation inhibitors or the anticoagulants; diuretics; vasopressin receptor antagonists; organic nitrates and NO donors; compounds with positive inotropic activity; compounds which inhibit the degradation of cyclic guanosine monophosphate (cGMP) and/or cyclic adenosine monophosphate (cAMP), such as, for example, inhibitors of phosphodiesterases (PDE) 1, 2, 3, 4 and/or 5, in particular PDE 5 inhibitors, such as sildenafil, vardenafil and tadalafil, and also PDE 3 inhibitors, such as milrinone; natriuretic peptides, such as, for example, "atrial natriuretic peptide" (ANP, anaritide), "B-type natriuretic peptide" or "brain natriuretic peptide" (BNP, nesiritide), "C-type natriuretic peptide" (CNP) and also urodilatin; agonists of the prostacyclin receptor (IP receptor), such as, by way of example, iloprost, beraprost, cicaprost; inhibitors of the If (funny channel) channel, such as, by way of example, ivabradine; calcium sensitizers, such as, by way of example, levosimendan; potassium supplements; NO-independent, but heme-dependent stimulators of guanylate cyclase, such as, in particular, the compounds described in WO 00/06568, WO 00/06569, WO 02/42301 and WO 03/095451; NO- and heme-independent activators of guanylate cyclase, such as, in particular, the compounds described in WO 01/19355, WO 01/19776, WO 01/19778, WO 01/19780, WO 02/070462 and WO 02/070510; inhibitors of human neutrophil elastase (HNE), such as, for example, sivelestat and DX-890 (Reltran); compounds which inhibit the signal transduction cascade, such as, for example, tyrosine-kinase inhibitors, in particular sorafenib, imatinib, gefitinib and erlotinib; and/or compounds which modulate the energy metabolism of the heart, such as, for example, etomoxir, dichloroacetate, ranolazine and trimetazidine.

In one embodiment, a DDAH or modified DDAH polypeptide can be administered in combination with an HMG-CoA reductase inhibitor from the class of the statins, such as, by way of example, lovastatin, simvastatin, pravastatin, fluvastatin, atorvastatin, rosuvastatin, cerivastatin, or pitavastatin; a thyroid hormone and/or thyroid mimetic, such as, by way of example, D-thyroxine or 3,5,3'-triiodothyronine (T3); an agonist of the niacin receptor, such as, by way of example, niacin, acipimox, acifran or radecol; a PPAR-γ agonist, for example from the class of the thiazolidinediones, such as, by way of example, pioglitazone or rosiglitazone.

In one embodiment, the DDAH or modified DDAH polypeptide can be administered in combination with insulin and modified insulins. In one embodiment, the DDAH or modified DDAH polypeptide can be administered in combination with a sulfonylurea, such as, by way of example, tolbutamide, glibenclamide, glimepiride, glipizide or gliclazide. In one embodiment, the DDAH or modified DDAH polypeptide can be administered in combination with a biguanide, such as, by way of example, metformin. In one embodiment, the DDAH or modified DDAH polypeptide can be administered in combination with a meglitinide derivative, such as, by way of example, repaglinide or nateglinide. In one embodiment, the DDAH or modified DDAH polypeptide can be administered in combination with a glucosidase inhibitor, such as, by way of example, miglitol or acarbose. In one embodiment, the DDAH or modified DDAH polypeptide can be administered in combination with a DPP-W inhibitor, such as, by way of example, sitagliptin and vildagliptin.

In one embodiment, the DDAH or modified DDAH polypeptide can be administered in combination with a calcium antagonist, such as, by way of example, nifedipine, amlodipine, verapamil or diltiazem. In one embodiment, the DDAH or modified DDAH polypeptide can be administered in combination with an ACE inhibitor, such as, by way of example, enalapril, captopril, lisinopril, ramipril, delapril, fosinopril, quinopril, perindopril or trandopril. In one embodiment, the DDAH or modified DDAH polypeptide can be administered in combination with a beta-receptor blocker, such as, by way of example, propranolol, atenolol, timolol, pindolol, alprenolol, oxprenolol, penbutolol, bupranolol, metipranolol, nadolol, mepindolol, carazalol, sotalol, metoprolol, betaxolol, celiprolol, bisoprolol, carteolol, esmolol, labetalol, carvedilol, adaprolol, landiolol, nebivolol, epanolol or bucindolol. In one embodiment, the DDAH or modified DDAH polypeptide can be administered in combination with an alpha-receptor blocker, such as, by way of example, prazosin. In one embodiment, the DDAH or modified DDAH polypeptide can be administered in combination with a diuretic, such as, by way of example, furosemide, bumetanide, torsemide, bendroflumethiazide, chlorothiazide, hydrochlorothiazide, hydroflumethiazide, methyclothiazide, polythiazide, trichloromethiazide, chlorothalidone, indapamide, metolazone, quinethazone, acetazolamide, dichlorophenamide, methazolamide, glycerol, isosorbide, mannitol, amiloride or triamteren.

In one embodiment, the DDAH or modified DDAH polypeptide can be administered in combination with an aldosterone or mineralocorticoid receptor antagonist, such as, by way of example, spironolactone or eplerenone.

In one embodiment, the DDAH or modified DDAH polypeptide can be administered in combination with a vasopressin receptor antagonist, such as by way of example, conivaptan, tolvaptan, lixivaptan or SR-121463.

In one embodiment, the DDAH or modified DDAH polypeptide can be administered in combination with an organic nitrate or NO donor, such as, by way of example, sodium nitroprusside, nitroglycerol, isosorbide mononitrate, isosorbide dinitrate, molsidomin or SIN-1, or in combination with inhalative NO.

In one embodiment, the DDAH or modified DDAH polypeptide can be administered in combination with a positive-inotropic compound, such as, by way of example, cardiac glycosides (digoxin), beta-adrenergic and dopaminergic agonists, such as isoproterenol, adrenaline, noradrenaline, dopamine or dobutamine.

In one embodiment, the DDAH or modified DDAH polypeptide can be administered in combination with antisympathotonics, such as reserpine, clonidine or alpha-methyldopa, or in combination with potassium channel agonists, such as minoxidil, diazoxide, dihydralazine or hydralazine, or with substances which release nitrogen oxide, such as glycerol nitrate or sodium nitroprusside.

In one embodiment, the DDAH or modified DDAH polypeptide can be administered in combination with endothelin receptor antagonists such as ambrisentan, bosentan, mecitentan, etc.

Antithrombotics are to be understood as meaning, for example, compounds from the group of the platelet aggregation inhibitors or the anticoagulants. In an embodiment, the DDAH or modified DDAH polypeptide can be administered in combination with a platelet aggregation inhibitor, such as, by way of example, aspirin, clopidogrel, ticlopidine or dipyridamole. In one embodiment, the DDAH or modified DDAH polypeptide can be administered in combination with a thrombin inhibitor, such as, by way of example, ximelagatran, melagatran, dabigatran, bivalirudin or clexane. In an embodiment, the DDAH or modified DDAH polypeptide can be administered in combination with a GPIIb/IIIa antagonist, such as, by way of example, tirofiban or abciximab. In one embodiment, the DDAH or modified DDAH polypeptide can be administered in combination with a factor Xa inhibitor, such as, by way of example, rivaroxaban (BAY 59-7939), DU-176b, apixaban, otamixaban, fidexaban, razaxaban, fondaparinux, idraparinux, PMD-3112, YM-150, KFA-1982, EMD-503982, MCM-17, MLN-1021, DX 9065a, DPC 906, JTV 803, SSR-126512 or SSR-128428.

A therapeutically effective dose refers to that amount of a DDAH or modified DDAH that ameliorates the symptoms or condition, taking into account the form employed, sensitivity of the patient, and the route of administration. Normal dosage amounts may vary from 0.1 to 1000 milligrams total dose, depending upon the route of administration. Guidance as to particular dosages and methods of delivery is provided in the literature. See U.S. Pat. Nos. 4,657,760; 5,206,344; or 5,225,212. Those skilled in the art will employ different formulations for polynucleotides than for proteins or their inhibitors. Similarly, delivery of polynucleotides or polypeptides will be specific to particular cells, conditions, locations, etc.

In another aspect, the disclosure provides a DDAH or modified DDAH polypeptide comprising and amino acid sequence having at least 80%, 85%, 90%, 95% or 99% identity to SEQ ID NO: 1, 2 or 5, and at least one pharmacokinetic enhancing moiety linked to the DDAH polypeptide, which pharmacokinetic enhancing moiety is optionally linked to at least one amino acid contained in said DDAH or modified DDAH, wherein said DDAH polypeptide is biologically active, and wherein said pharmacokinetic enhancing moiety optionally comprises at least one polyethylene glycol, acyl group, lipid, alkyl group, carbohydrate, polypeptide, polynucleotide, polysaccharide, antibody or antibody fragment, sialic acid(s), a prodrug, serum albumin, XTEN molecule, Fc molecule, adnectin, fibronectin, a biologically active molecule, or a combination thereof.

The DDAH or modified DDAH polypeptide sequence may be at least 90% identical to SEQ ID NO: 1, 2, or 5. Said DDAH or modified DDAH may comprise zero, one, two, three, or four amino acid substitutions, insertions, or deletions, wherein said substitutions are with natural or non-naturally encoded amino acids. Said pharmacokinetic enhancing moiety may be linked to said naturally encoded or non-naturally encoded amino acid that is substituted in the DDAH amino acid sequence.

A naturally encoded or non-naturally encoded amino acid that is incorporated into a modified DDAH polypeptide may comprise a first functional group and the pharmacokinetic enhancing moiety may comprise a second functional group, wherein the first functional group and second functional group are not identical and each comprise a carbonyl group, an aminooxy group, a hydrazide group, a hydrazine group, a semicarbazide group, an azide group, or an alkyne group.

The pharmacokinetic enhancing moiety can comprise at least one polyethylene glycol, acyl group, lipid, alkyl group, serum albumin, XTEN molecule, Fc molecule, adnectin, or a combination thereof.

In some embodiments, the pharmacokinetic enhancing moiety may comprise at least one acyl group. Said acyl group may comprise a branched or unbranched C8-C30 acyl. Said acyl group may comprise a branched or unbranched C14 acyl, C16 acyl, C18 acyl, or C20 acyl. Said acyl group may be of the formula: $CH_3(CH_2)_{12}C(=O)-$ or $CH_3(CH_2)_{14}C(=O)-$. Said acyl group may be of the formula: $CH_3(CH_2)_{16}C(=O)-$ or $CH_3(CH_2)_{18}C(=O)-$.

The pharmacokinetic enhancing moiety can comprise at least one alkyl group. Said alkyl group may be branched or unbranched Said alkyl group may be a C8-C30 alkyl group. Said alkyl group may be a C14, C16, C18, or C20 alkyl group.

The pharmacokinetic enhancing moiety can comprise at least one serum albumin. Said serum albumin may comprise human serum albumin. For example, the DDAH or modified DDAH polypeptide may be linked to the Cys 34 residue of said human serum albumin.

The pharmacokinetic enhancing moiety can comprise at least one XTEN molecule. Said XTEN molecule may be linked to a single modified DDAH polypeptide molecule. The DDAH or modified DDAH polypeptide may be linked to a site at or near the N-terminus of said XTEN molecule. Said XTEN molecule may be linked to multiple modified DDAH polypeptide molecules. Each said XTEN molecule may be linked to one, two, three, four, or five modified DDAH polypeptide molecules. Each said XTEN molecule may be linked to three modified DDAH polypeptide molecules. Said three modified DDAH polypeptide molecules are linked to the XTEN molecule at or near the N-terminus, C-terminus, and middle of the XTEN molecule, respectively. Said XTEN molecule may comprise an unstructured recombinant polymer (URP) comprising at least 40 contiguous amino acids, wherein: (a) the URP comprises at least three different types of amino acids selected from the group consisting of glycine (G), aspartate (D), alanine (A), serine (S), threonine (T), glutamate (E) and proline (P) residues, wherein the sum of said group of amino acids contained in the URP constitutes more than about 80% of the total amino acids of the URP, and wherein said URP comprises more than one proline residue, and wherein said URP possesses reduced sensitivity to proteolytic degradation relative to a corresponding URP lacking said more than one proline residue; (b) at least 50% of the amino acids of said URP are devoid of secondary structure as determined by Chou-Fasman algorithm; and (c) the Tepitope score of said URP is less than −5. Said XTEN molecule may comprise an unstructured recombinant polymer (URP) comprising at least about 40 contiguous amino acids, and wherein (a) the sum of glycine (G), aspartate (D), alanine (A), serine (S), threonine (T), glutamate (E) and proline (P) residues contained in the URP, constitutes at least 80% of the total amino acids of the URP, and the remainder, when present, consists of arginine or lysine, and the remainder does not contain methionine, cysteine, asparagine, and glutamine, wherein said URP comprises at least three different types of amino acids selected from glycine (G), aspartate (D), alanine (A), serine (S), threonine (T), glutamate (E) and proline (P); (b) at least 50% of the at least 40 contiguous amino acids in said URP are devoid of secondary structure as determined by Chou-Fasman algorithm; and (c) wherein the URP has a Tepitope score less than −4. Each modified DDAH polypeptide may be linked to said XTEN molecule through a dibenzylcyclooctyne (DBCO). Said XTEN molecule may be further linked to a polyethylene glycol molecule.

The pharmacokinetic enhancing moiety can comprise at least one adnectin. Said adnectin may comprise one or more of a BC loop, a DE loop, and an FG loop.

The pharmacokinetic enhancing moiety can comprise one or more additional DDAH polypeptides or modified DDAH polypeptides in combination, linked to form a dimer, homodimer, heterodimer, multimer, homomultimer, heteromultimer, or other combinations of DDAH polypeptides and/or modified DDAH polypeptides. Each of these may also be linked to a pharmacokinetic enhancing moiety, such as those disclosed herein, other than a DDAH polypeptide or modified DDAH polypeptide.

The pharmacokinetic enhancing moiety can comprise at least one lipid. Said lipid may comprise a fat-soluble vitamin, fat, wax, sterol, monoglyceride, diglyceride, triglyceride, or phospholipid.

The DDAH or modified DDAH polypeptide can exhibit an in vivo half-life of at least 1, 2, 5, 10, 12, 15, 20, 25 hours, or multiple days. Said in vivo half-life may be determined in human, mouse, rat, dog, cynomolgus monkey, rabbit, horse, cattle, cat, hamster, or rhesus macaque. Said in vivo half-life may be determined following subcutaneous or intravenous administration of said DDAH or modified DDAH polypeptide.

The DDAH or modified DDAH polypeptide can be attached to another biologically active moiety.

Multiple DDAH polypeptides can be joined by a linker polypeptide, wherein said linker polypeptide optionally is 6-14, 7-13, 8-12, 7-11, 9-11, or 9 amino acids in length. Other linkers include but are not limited to small polymers such as PEG, which may be multi-armed allowing for multiple DDAH molecules to be linked together. Multiple DDAH polypeptides and modified DDAH polypeptides may be linked to each other via their N-termini in a head-to-head configuration through the use of such a linker or by direct chemical bonding between the respective N-terminus of each polypeptide. For example, two DDAH polypeptides may be linked to form a dimer by chemical bonding between their N-terminal amino groups or modified N-terminal amino groups. Also, a linking molecule that is designed to comprise multiple chemical functional groups for bonding with the N-terminus of each DDAH polypeptide may be used to join multiple DDAH polypeptides each at their respective N-terminus. In addition, multiple DDAH polypeptides may be linked through bonding between amino acids other than the N-terminal amino acid or C-terminal amino acid. An example of covalent bonds that may be utilized to form the dimmers and multimers of DDAH that are described herein include, but are not limited to disulfide or sulfhydryl or thiol bonds. In addition, certain enzymes, such as sortase, may be used to form covalent bonds between the DDAH polypeptides and the linker, including at the N-termini of the DDAH polypeptides.

In another aspect, the disclosure provides a DDAH or modified DDAH polypeptide or composition containing a DDAH or modified DDAH polypeptide as herein described, wherein said DDAH polypeptide may be conjugated to at least one substance including but not limited to a label, a dye, a polymer, a water-soluble polymer, a derivative of polyethylene glycol, a photocrosslinker, a radionuclide, a cytotoxic compound, a drug, an affinity label, a photoaffinity label, a reactive compound, a resin, another polypeptide or protein, a polypeptide analog, an antibody, an antibody fragment, a metal chelator, a cofactor, a fatty acid, a carbohydrate, a polynucleotide, a DNA, a RNA, an antisense polynucleotide, a saccharide, a water-soluble dendrimer, a cyclodextrin, an inhibitory ribonucleic acid, a biomaterial, a nanoparticle, a spin label, a fluorophore, a metal-containing moiety, a radioactive moiety, a functional group, a group that covalently or noncovalently interacts with other molecules, a photocaged moiety, an actinic radiation excitable moiety, a photoisomerizable moiety, biotin, a derivative of biotin, a biotin analogue, a moiety incorporating a heavy atom, a chemically cleavable group, a photocleavable group, an elongated side chain, a carbon-linked sugar, a redox-active agent, an amino thioacid, a toxic moiety, an isotopically labeled moiety, a biophysical probe, a phosphorescent group, a chemiluminescent group, an electron dense group, a magnetic group, an intercalating group, a chromophore, an energy transfer agent, a biologically active agent, a detectable label, a small molecule, a quantum dot, a nanotransmitter, a radionucleotide, a radiotransmitter, a neutron-capture agent, or any combination of the above.

In another aspect, the disclosure provides an isolated cell, vector, plasmid, prokaryotic cell, eukaryotic cell, virus, prokaryotic cell, eukaryotic cell, mammalian cell, yeast, bacterium, or cell-free translation system comprising one or more polynucleotides that encode the DDAH or modified DDAH to express the DDAH or modified DDAH polypeptide. The method of expression may produce any DDAH or modified DDAH polypeptide as herein described.

In another aspect, the disclosure provides a method of producing any DDAH or modified DDAH polypeptide as herein described, comprising chemically synthesizing said DDAH or modified DDAH polypeptide.

In further embodiments, the DDAH may be administered daily, in an injectable form, an orally-available formulation, as a sustained release formulation, as a prodrug formulation, or as a continuous infusion.

Also provided are methods of increasing renal vasodilation and hyperfiltration, generally comprising administering a formulation comprising an amount of DDAH or modified DDAH polypeptide. These methods are useful in treating a variety of renal pathologies. Accordingly, also provided are methods of treating a renal pathology related to the effects of ADMA.

Also provided are methods of reducing pulmonary hypertension, generally comprising administering a formulation comprising an amount of DDAH or modified DDAH polypeptide.

In some embodiments, the DDAH polypeptide comprises one or more post-translational modifications. In some embodiments, the DDAH polypeptide is linked to a linker, polymer, or biologically active molecule. In some embodiments, the DDAH polypeptide is linked to a bifunctional polymer, bifunctional linker, or at least one additional DDAH polypeptide.

In some embodiments, the DDAH or modified DDAH is linked to a pharmacokinetic enhancing moiety. In some embodiments, the DDAH is linked to the pharmacokinetic enhancing moiety with a linker or is bonded to the pharmacokinetic enhancing moiety. In some embodiments, the pharmacokinetic enhancing moiety is a bifunctional molecule. In some embodiments, the bifunctional molecule is linked to a second polypeptide. In some embodiments, the second polypeptide is a DDAH polypeptide.

In some embodiments, the DDAH polypeptide comprises at least two amino acids linked to a pharmacokinetic enhancing moiety. In some embodiments, at least one amino acid is a non-naturally encoded amino acid.

In some embodiments, one or more naturally encoded or non-naturally encoded amino acids are incorporated in one or more of the following positions in any of the DDAH polypeptide, or proDDAH polypeptides, DDAH analogs, proDDAH, or modified DDAH polypeptide amino acid sequence before position 1 (i.e. at the N-terminus), 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, and at each individual amino acid position up to and including position 285, after position 285 (i.e., at the carboxyl terminus of the protein of SEQ ID NO: 1, the corresponding position in SEQ ID NO: 2, or SEQ ID NO: 5; SEQ ID NO: 6; SEQ ID NO: 7; SEQ ID NO: 9; SEQ ID NO: 10; SEQ ID NO: 11; SEQ ID NO: 12; SEQ ID NO: 13; or SEQ ID NO: 14).

The sites selected for incorporation, deletion, addition, or substitution of a naturally encoded or of a non-naturally encoded amino acid that enhance or modulate pharmacokinetic, pharmacodynamic, or time-action properties of the DDAH polypeptide, and/or for linkage to a pharmacokinetic enhancing moiety or other biologically active molecule may be selected based upon a variety of factors which may be predicted to influence the activity and half-life of the resulting modified DDAH polypeptide. Another factor to consider is the residue's participation in forming multimers including homodimerization, binding of DDAH modulators such as zinc, and substrate binding, or proximity to residues involved in the above activities, wherein modification of that residue can enhance or modulate pharmacokinetic, pharmacodynamic, or time-action properties of the DDAH polypeptide, and/or for linkage to a pharmacokinetic enhancing moiety or other biologically active molecule might interfere with activity. Yet another factor to consider is proximity to residues which may interact with the pharmacokinetic enhancing moiety (PKEM). For example, where the PKEM is a hydrophobic molecule that binds to serum albumin, proximity to surface-exposed hydrophobic residues may cause the PKEM to bind to the DDAH or modified DDAH polypeptide and potentially interfere with the ability of the PKEM to bind to serum albumin effectively increase half-life. Likewise, a hydrophilic PKEM could interact with proximate hydrophilic residues and therefore decrease the ability of the PKEM to improve half-life.

Also provided are formulations. The formulations can comprise a mixture of two or more of a DDAH, a DDAH dimer, a DDAH multimer, a DDAH variant, a DDAH analog, an acylated DDAH, a PKEMylated or acylated or PEGylated DDAH analog. In another embodiment, the formulations containing a mixture of two or more of DDAH, a DDAH analog, an acylated DDAH, or acylated DDAH analog also includes at least one pharmacokinetic enhancing moiety attached to at least one of the DDAH polypeptides.

Also described are heterogeneous mixtures wherein DDAH polypeptides and DDAH analogs are prepared by the methods disclosed herein, and are then mixed so that a formulation may be administered to a patient in need thereof which contains, for example, various percentages of different forms of DDAH polypeptides which have been coupled to a particular pharmacokinetic enhancing moiety, and the remainder consisting of DDAH polypeptide having a different or no PKEM. All different mixtures of different percentage amounts of DDAH polypeptide variants wherein the DDAH polypeptides include a variety (1) with differently sized PKEM, or (2) PKEM are included at different positions in the sequence. In one embodiment, the DDAH polypeptide variants to include in the formulation mixture can be chosen by their varying dissociation times so that the formulation may provide a sustained release of DDAH for a patient in need thereof, or the formulation may provide immediate or fast acting DDAH as well as longer acting DDAH molecules including one or more PKEMs.

Also described are formulation for inhalation. A DDAH analogs with increased pharmacokinetic and pharmacodynamic properties for patient use via administration to the lung, resulting in elevated blood levels of DDAH that are sustained for at least 6 hours, and more typically for at least 8, 10, 12, 14, 18, 24 hours or greater post-administration. Another embodiment allows for mixtures of DDAH analogs for therapeutic formulations designed to be administered to patients as an inhalant.

Also described are embodiments useful for introducing additional, customized sites within the DDAH molecule, for example, for forming a DDAH or modified DDAH having improved resistance to enzymatic degradation. Such an approach provides greater flexibility in the design of an optimized DDAH conjugate having the desired balance of activity, stability, solubility, and pharmacological properties. Mutations can be carried out, i.e., by site specific mutagenesis, at any number of positions within the DDAH molecule. Typically, a pharmacokinetic enhancing moiety is activated with a suitable activating group appropriate for coupling a desired site or sites on the DDAH molecule. An activated pharmacokinetic enhancing moiety may possess a reactive group at a terminus for reaction with DDAH.

Branched PKEMs such as PEGs can include those described in International Patent Publication WO 96/21469. Generally, branched PKEMs can be represented by the formula $R(PKEM-OH)_n$, where R represents the central "core" molecule and n represents the number of arms. Branched PKEMs have a central core from which extend 2 or more "PKEM" arms. In a branched configuration, the branched polymer core possesses a single reactive site for attachment to DDAH. Branched PKEMs can comprise fewer than 4 PKEM arms, and more preferably, will comprise fewer than 3 PKEM arms. Branched PKEMs offer the advantage of having a single reactive site, coupled with a larger, denser polymer cloud than their linear PKEM counterparts. One particular type of branched PKEM can be represented as $(MeO-PKEM-)_p R—X$, where p equals 2 or 3, R is a central core structure such as lysine or glycerol having 2 or 3 PKEM arms attached thereto, and X represents any suitable functional group that is or that can be activated for coupling to DDAH. One particularly preferred branched PEG is mPEG2-NHS (Shearwater Corporation, Alabama) having the structure mPEG2-lysine-succinimide.

In yet another branched architecture, "pendant PKEM" has reactive groups for protein coupling positioned along the PKEM backbone rather than at the end of PKEM chains. The reactive groups extending from the PKEM backbone for coupling to DDAH may be the same or different. Pendant PKEM structures may be useful but are generally less preferred, particularly for compositions for inhalation.

Alternatively, the PKEM may possess a forked structure having a branched moiety at one end of the polymer chain and two free reactive groups (or any multiple of 2) linked to the branched moiety for attachment to DDAH. The forked polyethylene glycol may optionally include an alkyl or "R" group at the opposing end of the polymer chain. More specifically, a forked PKEM-DDAH conjugate in accordance with embodiments described herein has the formula: R-PKEM-L(Y-DDAH)n where R is alkyl, L is a hydrolytically stable branch point and Y is a linking group that provides chemical linkage of the forked polymer to DDAH, and n is a multiple of 2. L may represent a single "core" group, such as "—CH—", or may comprise a longer chain of atoms. Exemplary L groups include lysine, glycerol, pentaerythritol, or sorbitol. Typically, the particular branch atom within the branching moiety is carbon.

In one embodiment, the linkage of the forked PKEM to the DDAH molecule, (Y), is hydrolytically stable. In a preferred embodiment, n is 2. Suitable Y moieties, prior to conjugation with a reactive site on DDAH, include but are not limited to active esters, active carbonates, aldehydes, isocyanates, isothiocyanates, epoxides, alcohols, maleimides, vinylsulfones, hydrazides, dithiopyridines, and iodacetamides. Selection of a suitable activating group will depend upon the intended site of attachment on the DDAH molecule and can be readily determined by one of skill in the art. The corresponding Y group in the resulting PKEM-DDAH conjugate is that which results from reaction of the activated forked polymer with a suitable reactive site on DDAH. For example, if the reactive forked PKEM contains an activated ester, such as a succinimide or maleimide ester, conjugation via an amine site on DDAH will result in formation of the corresponding amide linkage. These particular forked polymers are particularly attractive since they provide conjugates having a molar ratio of DDAH to PKEM of 2:1 or greater. Such conjugates may be less likely to block the DDAH substrate binding or other binding site, while still providing the flexibility in design to protect the DDAH against enzymatic degradation, e.g., by DDAH degrading enzyme.

In one embodiment, the forked PKEM-DDAH conjugate can be represented by the formula: R-[PKEM-L(Y-DDAH) 2]n. In this instance R represents a natural or non-naturally encoded amino acid having attached thereto at least one PKEM-di-DDAH conjugate. Specifically, in some embodiments the forked polymers can be those where n is selected from the group consisting of 1, 2, 3, 4, 5 and 6. In an alternative embodiment, the chemical linkage between the non-natural amino acid within DDAH, DDAH polypeptide, or DDAH analog and the polymer branch point may be degradable (i.e., hydrolytically unstable). Alternatively, one or more degradable linkages may be contained in the polymer backbone to allow generation in vivo of a PKEM-DDAH conjugate having a smaller PKEM chain than in the initially administered conjugate. For example, a large and relatively inert conjugate (i.e., having one or more high molecular weight PKEM chains attached thereto, e.g., one or more PKEM chains having a molecular weight greater than about 10,000, wherein the conjugate possesses essentially no bioactivity) may be administered, which then either in the lung or in the bloodstream, is hydrolyzed to generate a bioactive conjugate possessing a portion of the originally present PKEM chain. Upon in-vivo cleavage of the hydrolytically degradable linkage, either free DDAH (depending upon the position of the degradable linkage) or DDAH having a small polyethylene tag attached thereto, is then released and more readily absorbed through the lung and/or circulated in the blood.

In some embodiments, the poly(ethylene glycol) molecule has a molecular weight of between about 0.1 kDa and about 100 kDa. In some embodiments, the poly(ethylene glycol) molecule has a molecular weight of between 0.1 kDa and 50 kDa.

In some embodiments, the poly(ethylene glycol) molecule is a branched polymer. In some embodiments, each branch of the poly(ethylene glycol) branched polymer has a molecular weight of between 1 kDa and 100 kDa, or between 1 kDa and 50 kDa.

In some cases, a PKEM can terminate on one end with hydroxy or methoxy, i.e., X is H or $CH_3$ ("methoxy PEG"). Alternatively, the PKEM can terminate with a reactive group, thereby forming a bifunctional polymer. Typical reactive groups can include those reactive groups that are commonly used to react with the functional groups found in the 20 common amino acids (including but not limited to, maleimide groups, activated carbonates (including but not limited to, p-nitrophenyl ester), activated esters (including but not limited to, N-hydroxysuccinimide, p-nitrophenyl ester) and aldehydes) as well as functional groups that are inert to the 20 common amino acids but that react specifically with complementary functional groups (including but not limited to, azide groups, alkyne groups). It is noted that the other end of the PKEM, which is shown in the above formula by Y, will attach either directly or indirectly to a DDAH polypeptide via a naturally-occurring or non-naturally encoded amino acid. For instance, Y may be an amide, carbamate or urea linkage to an amine group (including but not limited to, the epsilon amine of lysine or the N-terminus) of the polypeptide. Alternatively, Y may be a maleimide linkage to a thiol group (including but not limited to, the thiol group of cysteine). Alternatively, Y may be a linkage to a residue not commonly accessible via the 20 common amino acids. For example, an azide group on the PKEM can be reacted with an alkyne group on the DDAH polypeptide to form a Huisgen [3+2] cycloaddition product. Alternatively, an alkyne group on the PKEM can be reacted with an azide group present in a DDAH polypeptide to form a similar product. In some embodiments, a strong nucleophile (including but not limited to, hydrazine, hydrazide, hydroxylamine, semicarbazide) can be reacted with an aldehyde or ketone group present in a DDAH polypeptide to form a hydrazone, oxime or semicarbazone, as applicable, which in some cases can be further reduced by treatment with an appropriate reducing agent. Alternatively, the strong nucleophile can be incorporated into the DDAH polypeptide via a non-naturally encoded amino acid and used to react preferentially with a ketone or aldehyde group present in the water-soluble polymer.

Any molecular mass for a PKEM can be used as practically desired, including but not limited to, from about 100 Daltons (Da) to 100,000 Da or more as desired (including but not limited to, sometimes 0.1-50 kDa or 10-40 kDa). The molecular weight of PKEM may be of a wide range, including but not limited to, between about 100 Da and about 100,000 Da or more. PKEM may be between about 100 Da and about 100,000 Da, including but not limited to, 100,000 Da, 95,000 Da, 90,000 Da, 85,000 Da, 80,000 Da, 75,000 Da, 70,000 Da, 65,000 Da, 60,000 Da, 55,000 Da, 50,000 Da, 45,000 Da, 40,000 Da, 35,000 Da, 30,000 Da, 25,000 Da, 20,000 Da, 15,000 Da, 10,000 Da, 9,000 Da, 8,000 Da, 7,000 Da, 6,000 Da, 5,000 Da, 4,000 Da, 3,000 Da, 2,000 Da, 1,000 Da, 900 Da, 800 Da, 700 Da, 600 Da, 500 Da, 400 Da, 300 Da, 200 Da, and 100 Da. In some embodiments, PKEM is between about 100 Da and about 50,000 Da. Branched chain PKEMs, including but not limited to, PKEM molecules with each chain having a MW ranging from 1-100 kDa (including but not limited to, 1-50 kDa or 5-20 kDa) can also be used. The molecular weight of each chain of the branched chain PKEM may be, including but not limited to, between about 1,000 Da and about 100,000 Da or more. The molecular weight of each chain of the branched chain PKEM may be between about 1,000 Da and about 100,000 Da, including but not limited to, 100,000 Da, 95,000 Da, 90,000 Da, 85,000 Da, 80,000 Da, 75,000 Da, 70,000 Da, 65,000 Da, 60,000 Da, 55,000 Da, 50,000 Da, 45,000 Da, 40,000 Da, 35,000 Da, 30,000 Da, 25,000 Da, 20,000 Da, 15,000 Da, 10,000 Da, 9,000 Da, 8,000 Da, 7,000 Da, 6,000 Da, 5,000 Da, 4,000 Da, 3,000 Da, 2,000 Da, and 1,000 Da. In some embodiments, the molecular weight of each chain of the branched chain PKEM is between about 1,000 Da and about 50,000 Da. In some embodiments, the molecular weight of each chain of the branched chain PKEM is between about 1,000 Da and about 40,000 Da. In some embodiments, the molecular weight of each chain of the branched chain PKEM is between about 5,000 Da and about 40,000 Da. In some embodiments, the molecular weight of each chain of the branched chain PKEM is between about 5,000 Da and about 20,000 Da. A wide range of PKEM molecules are described in, including but not limited to, the Shearwater Polymers, Inc. catalog, Nektar Therapeutics catalog, incorporated herein by reference.

Also provided are azide- and acetylene-containing polymer derivatives comprising a water soluble polymer backbone having an average molecular weight from about 800 Da to about 100,000 Da. The polymer backbone of the water-soluble polymer can be poly(ethylene glycol). However, it should be understood that a wide variety of water soluble polymers including but not limited to poly(ethylene) glycol and other related polymers, including poly(dextran) and poly(propylene glycol), are also suitable. The term PEG includes, but is not limited to, poly(ethylene glycol) in any of its forms, including bifunctional PEG, multiarmed PEG, derivatized PEG, forked PEG, branched PEG, pendent PEG (i.e. PEG or related polymers having one or more functional groups pendent to the polymer backbone), or PEG with degradable linkages therein.

In addition to these forms of PKEM, the polymer can also be prepared with weak or degradable linkages in the backbone. For example, PKEM can be prepared with ester linkages in the polymer backbone that are subject to hydrolysis. As shown below, this hydrolysis results in cleavage of the polymer into fragments of lower molecular weight:

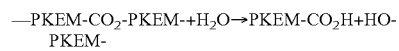

In some embodiments, polymer backbones that are water-soluble, with from 2 to about 300 termini. Examples of suitable polymers include, but are not limited to, other poly(alkylene glycols), such as poly(propylene glycol) ("PPG"), copolymers thereof (including but not limited to copolymers of ethylene glycol and propylene glycol), terpolymers thereof, mixtures thereof, and the like. Although the molecular weight of each chain of the polymer backbone can vary, it is typically in the range of from about 800 Da to about 100,000 Da, often from about 6,000 Da to about 80,000 Da. The molecular weight of each chain of the polymer backbone may be between about 100 Da and about 100,000 Da, including but not limited to, 100,000 Da, 95,000 Da, 90,000 Da, 85,000 Da, 80,000 Da, 75,000 Da, 70,000 Da, 65,000 Da, 60,000 Da, 55,000 Da, 50,000 Da, 45,000 Da, 40,000 Da, 35,000 Da, 30,000 Da, 25,000 Da, 20,000 Da, 15,000 Da, 10,000 Da, 9,000 Da, 8,000 Da, 7,000 Da, 6,000 Da, 5,000 Da, 4,000 Da, 3,000 Da, 2,000 Da, 1,000 Da, 900 Da, 800 Da, 700 Da, 600 Da, 500 Da, 400 Da, 300 Da, 200 Da, and 100 Da. In some embodiments, the molecular weight of each chain of the polymer backbone is between about 100 Da and about 50,000 Da. In some embodiments, the molecular weight of each chain of the polymer backbone is between about 100 Da and about 40,000 Da. In some embodiments, the molecular weight of each chain of the polymer backbone is between about 1,000 Da and about 40,000 Da. In some embodiments, the molecular weight of each chain of the polymer backbone is between about 5,000 Da and about 40,000 Da. In some embodiments, the molecular weight of each chain of the polymer backbone is between about 10,000 Da and about 40,000 Da.

Appropriate physiologically cleavable linkages include but are not limited to ester, carbonate ester, carbamate, sulfate, phosphate, acyloxyalkyl ether, acetal, and ketal. Such conjugates should possess a physiologically cleavable bond that is stable upon storage and upon administration. For instance, a DDAH or modified DDAH linked to a pharmacokinetic enhancing moiety should maintain its integrity upon manufacturing of the final pharmaceutical composition, upon dissolution in an appropriate delivery vehicle, if employed, and upon administration irrespective of route.

In some embodiments, the polypeptide described herein can comprise one or more naturally encoded or non-naturally encoded amino acid substitution, addition, or deletion in the signal sequence. In some embodiments, the polypeptides can comprise one or more naturally encoded or nonnaturally encoded amino acid substitution, addition, or deletion in the signal sequence for DDAH or any of the DDAH analogs or polypeptides disclosed within this specification. In some embodiments, the polypeptides comprise one or more naturally encoded amino acid substitution, addition, or deletion in the signal sequence as well as one or more non-naturally encoded amino acid substitutions, additions, or deletions in the signal sequence for DDAH or any of the DDAH analogs or polypeptides disclosed within this specification. In some embodiments, one or more non-natural amino acids are incorporated in the leader or signal sequence for DDAH or any of the DDAH analogs or polypeptides described herein.

In some embodiments, the DDAH polypeptide comprises a substitution, addition or deletion that modulates affinity of the DDAH polypeptide for ADMA or other binding partner, including but not limited to, a protein, polypeptide, small molecule, or nucleic acid. In some embodiments, the DDAH polypeptide comprises a substitution, addition, or deletion that increases the stability of the DDAH polypeptide when compared with the stability of the corresponding DDAH without the substitution, addition, or deletion. Stability and/or solubility may be measured using a number of different assays known to those of ordinary skill in the art. In some embodiments, the DDAH polypeptide comprises a substitution, addition, or deletion that modulates the immunogenicity of the DDAH polypeptide when compared with the immunogenicity of the corresponding DDAH without the substitution, addition, or deletion. In some embodiments, the DDAH polypeptide comprises a substitution, addition, or deletion that modulates serum half-life or circulation time of the DDAH polypeptide when compared with the serum half-life or circulation time of the corresponding DDAH without the substitution, addition, or deletion. In some embodiments, the DDAH polypeptide comprises a substitution, addition, or deletion that modulates the enzymatic activity of the DDAH polypeptide when compared with the enzymatic activity of the corresponding DDAH without the substitution, addition, or deletion.

In some embodiments, the DDAH polypeptide comprises a substitution, addition, or deletion that increases the aqueous solubility of the DDAH polypeptide when compared to aqueous solubility of the corresponding DDAH without the substitution, addition, or deletion. In some embodiments, the DDAH polypeptide comprises a substitution, addition, or deletion that increases the solubility of the DDAH polypeptide produced in a host cell when compared to the solubility of the corresponding DDAH without the substitution, addition, or deletion. In some embodiments, the DDAH polypeptide comprises a substitution, addition, or deletion that increases the expression of the DDAH polypeptide in a host cell or increases synthesis in vitro when compared to the expression or synthesis of the corresponding DDAH without the substitution, addition, or deletion. The DDAH polypeptide comprising this substitution retains enzymatic activity and retains or improves expression levels in a host cell. In some embodiments, the DDAH polypeptide comprises a substitution, addition, or deletion that increases protease resistance of the DDAH polypeptide during manufacturing processes when compared to the protease resistance of the corresponding DDAH without the substitution, addition, or deletion. In some embodiments, the DDAH polypeptide comprises a substitution, addition, or deletion that modulates DDAH homodimerization, modulator binding such as zinc binding, ADMA hydrolyzing activity, and substrate binding activity of the DDAH polypeptide during manufacturing processes when compared with the activity of the DDAH polypeptide without the substitution, addition, or deletion. In some embodiments, the DDAH polypeptide comprises a substitution, addition, or deletion that modulates its binding to another molecule such as a substrate or modulator or other DDAH polypeptide when compared to the binding of the corresponding DDAH polypeptide without the substitution, addition, or deletion. In some embodiments, the DDAH polypeptide comprises a substitution, addition, or deletion that modulates its enzymatic activity compared to the enzymatic activity of the corresponding DDAH polypeptide without the substitution, addition, or deletion.

In some embodiments, the DDAH polypeptide comprises a substitution, addition, or deletion that modulates the stability of the DDAH polypeptide when compared to stability of the corresponding DDAH without the substitution, addition, or deletion. In some embodiments, the DDAH polypeptide comprises a substitution, addition, or deletion that increases the stability of the DDAH polypeptide produced in a host cell when compared to the stability of the corresponding DDAH without the substitution, addition, or deletion. In some embodiments, the DDAH polypeptide comprises a substitution, addition, or deletion that increases the half-life of enzymatically active circulating DDAH after administration to a patient when compared to the corresponding DDAH without the substitution, addition, or deletion. The DDAH polypeptide comprising this substitution retains enzymatic activity and yet is resistant to deactivation, destabilization, or destruction caused, for example, by proteases or other substances that affect the structural integrity or enzymatic activity of the DDAH polypeptides. In some embodiments, the DDAH polypeptide comprises a substitution, addition, or deletion that increases protease resistance of the DDAH polypeptide when compared to the protease resistance of the corresponding DDAH without the substitution, addition, or deletion. In some embodiments, the DDAH polypeptide comprises a substitution, addition, or deletion that increases DDAH homodimerization, changes modulator binding such as zinc binding, increases ADMA hydrolyzing activity, and increases substrate binding activity of the DDAH polypeptide when compared with the activity of the DDAH polypeptide without the substitution, addition, or deletion. In some embodiments, the DDAH polypeptide comprises a substitution, addition, or deletion that decreases the half-life of enzymatically active circulating DDAH after administration to a patient when compared to the corresponding DDAH without the substitution, addition, or deletion. In some embodiments, the DDAH polypeptide comprises a substitution, addition, or deletion that decreases its binding to another molecule such as a substrate or modulator or other DDAH polypeptide when compared to the binding of the corresponding DDAH polypeptide without the substitution, addition, or deletion. In some embodiments, the DDAH polypeptide comprises a substitution, addition, or deletion that decreases its enzymatic activity compared to the enzymatic activity of the corresponding DDAH polypeptide without the substitution, addition, or deletion.

In some embodiments, one or more amino acid substitutions in the DDAH polypeptide may be with one or more naturally occurring or non-naturally encoded amino acids. In some embodiments the amino acid substitutions in the DDAH polypeptide may be with naturally occurring or non-naturally encoded amino acids, provided that at least one substitution is with a non-naturally encoded amino acid. In some embodiments, one or more amino acid substitutions in the DDAH polypeptide may be with one or more naturally occurring amino acids, and additionally at least one substitution is with a non-naturally encoded amino acid.

In some embodiments, the non-naturally encoded amino acid comprises a carbonyl group, an acetyl group, an aminooxy group, a hydrazine group, a hydrazide group, a semicarbazide group, an azide group, or an alkyne group.

In some embodiments, the non-naturally encoded amino acid comprises a carbonyl group. In some embodiments, the non-naturally encoded amino acid has the structure:

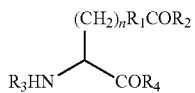

wherein n is 0-10; R1 is an alkyl, aryl, substituted alkyl, or substituted aryl; R2 is H, an alkyl, aryl, substituted alkyl, and substituted aryl; and R3 is H, an amino acid, a polypeptide, or an amino terminus modification group, and R4 is H, an amino acid, a polypeptide, or a carboxy terminus modification group.

Also provided are isolated nucleic acids comprising a polynucleotide that hybridizes under stringent conditions to nucleic acids of SEQ ID NOs: 3, and 4 or to nucleic acids that encode DDAH polypeptides of SEQ ID NOs: 1, and 2. Also provided are isolated nucleic acids comprising a polynucleotide that hybridizes under stringent conditions to nucleic acids that encode DDAH any polypeptide of SEQ ID NOs: 1, 2, 5, 6, 7, 9, 10, 11, 12, 13, and 14. Also provided are isolated nucleic acids comprising a polynucleotide that encodes the polypeptides shown as SEQ ID NOs.: 1, 2, 5, 6, 7, 9, 10, 11, 12, 13, and 14.

Azide- and acetylene-containing amino acids may also be incorporated site-selectively into proteins such as DDAH using the methods known in the art. Thereafter said azide- and acetylene-containing amino acids may be linked to a pharmacokinetic enhancing moiety using methods known in the art.

In a further aspect, also provided are recombinant nucleic acids encoding the DDAH proteins, expression vectors containing the variant nucleic acids, host cells comprising the variant nucleic acids and/or expression vectors, and methods for producing the variant proteins. In an additional aspect, also provided are methods of treating a DDAH responsive disorder by administering to a patient a variant protein, usually with a pharmaceutical carrier, in a therapeutically effective amount. Also provided are methods for modulating immunogenicity (particularly reducing immunogenicity) of DDAH polypeptides by altering MHC Class II epitopes.

In therapeutic applications, compositions containing the modified non-natural amino acid polypeptide can be administered to a patient already suffering from a disease, condition or disorder, in an amount sufficient to cure or at least partially arrest the symptoms of the disease, disorder or condition. Such an amount is defined to be a "therapeutically effective amount," and will depend on the severity and course of the disease, disorder or condition, previous therapy, the patient's health status and response to the drugs, and the judgment of the treating physician In prophylactic applications, compositions containing the DDAH polypeptide are administered to a patient susceptible to or otherwise at risk of a particular disease, disorder or condition. In this use, the precise amounts also depend on the patient's state of health, weight, and the like. It is considered well within the skill of the art to determine such prophylactically effective amounts by routine experimentation (e.g., in clinical trial).

DDAH polypeptides described herein can be used to modulate the concentration of ADMA in a patient. In one embodiment, a patient in need thereof receives a therapeutic amount of a DDAH polypeptide described herein that would decrease the patient's ADMA concentration over the baseline of their seeking treatment by 10%, 15%, 20%, 25%, 30%, 35%, 40%, 45%, 50%, 55%, 60%, 65%, 70%, 75%, 80%, 85%, 90%, 95%, 100%, more than 100%, 150%, more than 150%, 200%, more than 200%. In another embodiment, provided are methods of treatment of a patient in need thereof to increase the patient's NO production by administering a therapeutically effective amount of DDAH polypeptide to increase NO production by 10%, 15%, 20%, 25%, 30%, 35%, 40%, 45%, 50%, 55%, 60%, 65%, 70%, 75%, 80%, 85%, 90%, 95%, 100%, more than 100%, 150%, more than 150%, 200%, more than 200%.

DDAH polypeptides described herein can have up to a 10-fold or more increase in area under the curve (AUC) as compared to a wild type DDAH; 15-fold increase; more than 15-fold increase; 20-fold increase; more than 20-fold increase; 25 fold increase; more than 25-fold increase; 30-fold increase; more than 30-fold increase; 35-fold increase; more than 35-fold increase; 40-fold increase; more than 40-fold increase; 45-fold increase; more than 45-fold increase; 50-fold increase; more than 50-fold increase; 55-fold increase; more than 55-fold increase; 60-fold increase; more than 60-fold increase; 65-fold increase; more than 65-fold increase; 70-fold increase; more than 70-fold increase; 75-fold increase; more than 75-fold increase; 80-fold increase; more than 80-fold increase; 85-fold increase; more than 85-fold increase; 90-fold increase; more than 90-fold increase; 95-fold increase; more than 95-fold increase; 100-fold increase; more than 100-fold increase.

The foregoing summary is not intended to define every aspect of the invention, and additional embodiments are described in other sections, such as the Detailed Description. The entire document is intended to be related as a unified disclosure, and it should be understood that all possible combinations of features described herein may be contemplated, even if the combination of features are not found together in the same sentence, or paragraph, or section of this document.

Moreover, any one or all embodiments disclosed herein that are narrower in scope in any way than the variations defined by specific paragraphs herein are also considered part of the present invention. For example, where certain aspects of this disclosure are described as a genus, it should be understood that every member of a genus is, individually, an embodiment of the invention, and that combinations of two or more members of the genus are embodiments of the invention.

BRIEF DESCRIPTION OF THE DRAWINGS

FIG. 4A shows the activity of rPa-DDAH before (solid line) and after PEGylation (M-DDAH) (dotted line). rPa-DDAH was PEGylated using 10 Kd N-hydroxysuccinaminde. PEGylation was determined using SDS-PAGE as shown in FIG. 4B (Lane 1—molecular weight markers; Lane 2—rPa-DDAH; Lane 3—PEGylated rPa-DDAH (M-DDAH)). FIG. 4C shows the DDAH activity of a control and M-DDAH. As shown in FIG. 4C, the half-life was extended by PEGylation. Briefly, rPa-DDAH (solid line) or M-DDAH 9 (dotted line) was administered to rats (1 mg/kg). Blood samples were collected in heparin tubes at the indicated time points and centrifuged to prepare plasma. DDAH activity in plasma samples was determined as described under DDAH assay.

FIG. 5 shows that M-DDAH significantly attenuated the loss of renal function as indicated by the reduced serum creatinine at 24 hours of injury-reperfusion.

FIG. 7A is a graph showing the activity of rPA-DDAH (-3 mutant; SEQ ID NO: 17) and mutants thereof generated by site directed replacement of lys3, (-6 mutant; SEQ ID NO: 18), lys 25(-9 mutant; SEQ ID NO: 19), lys 103(12 mutant; SEQ ID NO: 20) and lys 159 (-15 mutant; SEQ ID NO: 21) with cysteine. Mutant genes were cloned and expressed in E. coli. Purified proteins were assayed for DDAH activity. FIG. 7B is a graph of the in vitro activity of Mutant 159lys-cys compared to its PEGylated form, wherein the cysteine at position 159 is peglated using $mPEG_{20K}$-maleimide. Activity of the mutant DDAH before (solid circle) and after PEGylation (solid square) are shown. FIG. 7C is a graph of the in vivo activity of PEGylated 75 kDa protein after single administration to rats.

FIG. 9 is a graph showing the response of isolated rat thoracic artery to acetylcholine after treatment with vehicle (designated solid circle), ADMA (solid square) or ADMA and DDAH (solid triangle). FIG. 9 shows that addition of ADMA impaired vasodilation of arteries in response to acetylcholine which was fully restored by treatment with M-DDAH. These data show that ADMA induced vascular dysfunction can be prevented and reversed by treatment with M-DDAH.

FIG. 10 shows that addition of ADMA to endothelial cells significantly inhibited in vitro angiogenesis as measured by the number of nodes, segments and mesh. M-DDAH enhanced the in vitro angiogenic response and reversed the inhibitory effect of ADMA. These data showed that M-DDAH has the potential to improve endothelial function and regenerative response under the conditions such as ischemia and hypoxia where high ADMA levels are produced.

As shown in FIG. 11A, a single intravenous administration to DSS hypertensive rats of M-DDAH (▲) relative to vehicle (●) significantly reduced ADMA. The carotid catheter was connected to a Deltran pressure transducer and mean arterial pressure (MAP) in control a treated was measured up to 4 hours. Measurement of blood pressure using indwelling catheters showed that lowering of ADMA by M-DDAH resulted in a significant and sustained reduction in the blood pressure up to 4.5 hours, the last time point for the study (FIG. 11B). At the end of the study, the kidney was removed and ADMA level were measured (see FIG. 11C). These data showed that reduction in plasma ADMA by M-DDAH clearly produced physiological response in vivo.

FIG. 12 is a graph providing the results of human cardiomyocytes treated with 0.3 uM ADMA in the presence (solid square) or absence (solid circles) of M-DDAH. Cardiomyocyte contractility was measured up to 24 hours.

DETAILED DESCRIPTION

Definitions

Figure 1:
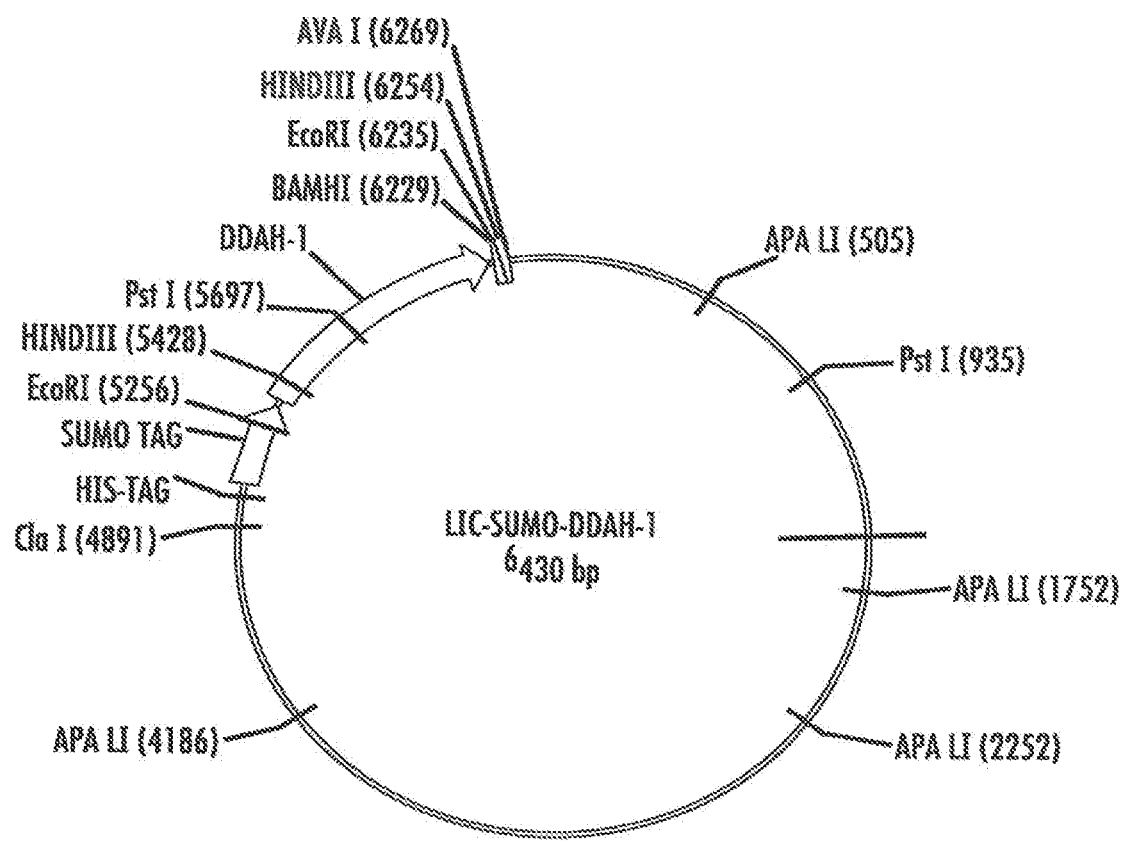
FIG. 1 illustrates the structure of plasmid containing human DDAH or Pa-DDAH.

In describing and claiming the invention, the following terminology will be used in accordance with the definitions set forth below.

The term "about" as used herein means greater or lesser than the value or range of values stated by 10 percent, but is not intended to designate any value or range of values to only this broader definition. Each value or range of values preceded by the term "about" is also intended to encompass the embodiment of the stated absolute value or range of values.

As used herein, the term "pharmaceutically acceptable carrier" includes any of the standard pharmaceutical carriers, such as a phosphate buffered saline solution, water, emulsions such as an oil/water or water/oil emulsion, and various types of wetting agents. The term also encompasses any of the agents approved by a regulatory agency of the US Federal government or listed in the US Pharmacopeia for use in animals, including humans.

As used herein the term "pharmaceutically acceptable salt" refers to salts of compounds that retain the biological activity of the parent compound, and which are not biologically or otherwise undesirable. Many of the compounds disclosed herein are capable of forming acid and/or base salts by virtue of the presence of amino and/or carboxyl groups or groups similar thereto.

The term "asymmetric dimethylarginine (ADMA) metabolizing activity" defines an enzymatic activity that modifies ADMA to form a molecule that has a reduced ability to inhibit NO synthesis. An example of an ADMA metabolizing activity would be hydrolyzing ADMA to form citrulline.

The term "DDAH" or "DDAH polypeptide" or "DDAH enzyme" absent any further modifying language encompasses a polypeptide comprising an amino acid sequence of at least 100 amino acids that has at least 80% sequence identity with an amino acid sequence selected from the group consisting of SEQ ID NOs. 1-14 and retains the ability to metabolize asymmetric dimethylarginine (ADMA), including hydrolyzing ADMA to form citrulline. Accordingly the term encompasses human and non-human DDAH, including but not limited to the amino acid sequences set forth in SEQ ID NO: 1; SEQ ID NO: 2; SEQ ID NO: 5; SEQ ID NO: 6; SEQ ID NO: 7; SEQ ID NO: 9; SEQ ID NO: 10; SEQ ID NO: 11; SEQ ID NO: 12; SEQ ID NO: 13; and SEQ ID NO: 14. Human DDAH is comprised of a 285 amino acid long polypeptide chain that contains no intra-chain disulfide bonds. DDAH is also known to naturally form homodimers (Murray-Rust, J., et. al., Nature Structural Biology, Volume 8, Number 8, August 2001). In addition, DDAH enzymatic activity is known to be modulated by the binding of zinc to a particular site on the DDAH polypeptide such that when zinc is bound to the DDAH polypeptide the enzymatic activity of the DDAH is reduced (Knipp, M., et. al., JBC, Volume 276, Number 44, pp 40449-40456, 2001).

The terms "wild-type DDAH," "WT DDAH," and "wt rhDDAH" refer to a human DDAH polypeptide having the amino acid sequence of SEQ ID NO: 1 or SEQ ID NO: 2, or the corresponding amino acid in SEQ ID NO: 5. The terms "wild-type DDAH," "WT DDAH," and "wt rDDAH" also refer to a non-human DDAH polypeptide having the amino acid sequence SEQ ID NO: 6; SEQ ID NO: 7; SEQ ID NO: 9; SEQ ID NO: 10; SEQ ID NO: 11; SEQ ID NO: 12; SEQ ID NO: 13; or SEQ ID NO: 14. Human WT DDAH-1 and human WT DDAH-2 mature polypeptides in monomeric form each have a predicted molecular weight of about 30 kDa.

As used herein the term "modified DDAH" is a DDAH polypeptide that differs from a DDAH polypeptide of SEQ ID NO: 1-14 by an amino acid modification and/or the linkage of a linked to a pharmacokinetic enhancing moiety, that retains the enzymatic activity of hydrolyzing ADMA to citrulline and/or other ADMA breakdown products.

As used herein, the term "DDAH unit", or DDAH "enzymatic unit", [U], refers to that amount of enzyme (DDAH) which causes the production of 1 mmol of L-citrulline per minute under the conditions described in the reference "Markus Knipp and Milan Vasak, Analytical Biochem., 286, 257 (2000)".

As used herein an "amino acid modification" defines a substitution, addition or deletion of one or more amino acids, and includes substitution with or addition of any of the 20 amino acids commonly found in human proteins, as well as atypical or non-naturally occurring amino acids. Throughout the application, all references to a particular amino acid position by number (e.g. position 28) refer to the amino acid at that position in native human DDAH-1 (SEQ ID NO: 1) or the corresponding amino acid position in any analogs thereof.

The term "DDAH analog" as used herein is a protein exhibiting the enzymatic activity of hydrolyzing ADMA to citrulline and other ADMA breakdown products wherein the amino acid sequence of the DDAH analog differs from the wild-type DDAH by having one or more amino acid deletions, one or more amino acid replacements, and/or one or more amino acid additions that do not destroy the DDAH activity of the DDAH analog. Other examples of DDAH analogs include but are not limited to amino acid differences that enhance or modulate pharmacokinetic, pharmacodynamic, or time-action properties of the DDAH polypeptide, and/or are useful for linkage to a pharmacokinetic enhancing moiety or other biologically active molecule.

The term "pharmacokinetic enhancing moiety" (also referred to herein as "PKEM") refers to a pharmaceutically acceptable moiety, domain, or "vehicle" covalently linked ("conjugated") to the DDAH polypeptide directly or via a linker, that improves at least one pharmacokinetic property of the DDAH polypeptide relative to the non-modified DDAH polypeptide. Examples of such pharmacokinetic properties include preventing or mitigating in vivo proteolytic degradation or other activity-diminishing chemical modification of the DDAH polypeptide, increasing half-life, increasing the rate of absorption, reducing toxicity, improving solubility, increasing biological activity, increasing retention/decreasing excretion, catalytic efficiency and/or target selectivity of the DDAH polypeptide, increasing manufacturability, and/or reducing immunogenicity of the DDAH polypeptide, compared to an unconjugated form of the DDAH polypeptide. The term "pharmacokinetic enhancing moiety" includes non-proteinaceous, PKEM, such as polyethylene glycol (PEG) or hydroxyethyl starch (HES), and proteinaceous PKEM, such as serum albumin, transferrin, adnectins (e.g., PKE adnectins), or Fc domain. Examples of pharmacokinetic enhancing moieties include XTEN polymers, adnectins, polyethylene glycol (PEG), acyl and alkyl polymers, serum albumin (bound directly or indirectly to the moiety), polylactic acid, polyglycolic acid, a polylactic-polyglycolic acid copolymer, polyvinyl alcohol, polyvinylpyrrolidone, polymethoxazoline, polyethyloxazoline, polyhydroxyethyl methacrylate, polyhydroxypropyl methacrylamide, polymethacrylamide, polydimethylacrylamide, and derivatised celluloses such as hydroxymethylcellulose or hydroxyethylcellulose and co-polymers thereof, as well as natural polymers including, for example, albumin, heparin and dextran.

As used herein the term "XTEN" or "URP" is defined as an unstructured recombinant polymers or unstructured recombinant polypeptides, as generally described in Schellenberger et al., Nat Biotechnol., 2009 December; 27(12): 1186-90, U.S. Patent Application Publication No. 2012/0220011, U.S. Pat. No. 7,846,445, and International Publication No. WO/2012/162542, each of which is hereby incorporated by reference in its entirety.

As used herein the term "adnectin" defines any synthetic binding protein constructed using a fibronectin type III domain. Examples of adnectins are provided in U.S. Patent Application Publication No. 2011/0305663, which is hereby incorporated by reference in its entirety.

The term "albumin binding moiety" as used herein refers to any chemical group capable of binding to albumin, i.e. has albumin binding affinity. In one embodiment the albumin binding moiety is an acyl group.

A "non-naturally encoded amino acid" refers to an amino acid that is not one of the 20 common amino acids or pyrrolysine or selenocysteine.

The term "substantially purified" refers to a DDAH polypeptide that may be substantially or essentially free of components that normally accompany or interact with the protein as found in its naturally occurring environment, includes protein having less than about 30%, less than about 25%, less than about 20%, less than about 15%, less than about 10%, less than about 5%, less than about 4%, less than about 3%, less than about 2%, or less than about 1% (by dry weight) of contaminating protein. When the DDAH polypeptide or variant thereof is recombinantly produced by the host cells, the protein may be present at about 30%, about 25%, about 20%, about 15%, about 10%, about 5%, about 4%, about 3%, about 2%, or about 1% or less of the dry weight of the cells. When the DDAH polypeptide or variant thereof is recombinantly produced by the host cells, the protein may be present in the culture medium at about 5 g/L, about 4 g/L, about 3 g/L, about 2 g/L, about 1 g/L, about 750 mg/L, about 500 mg/L, about 250 mg/L, about 100 mg/L, about 50 mg/L, about 10 mg/L, or about 1 mg/L or less of the dry weight of the cells. Thus, "substantially purified" DDAH polypeptide as produced by the methods described herein may have a purity level of at least about 30%, at least about 35%, at least about 40%, at least about 45%, at least about 50%, at least about 55%, at least about 60%, at least about 65%, at least about 70%, specifically, a purity level of at least about 75%, 80%, 85%, and more specifically, a purity level of at least about 90%, a purity level of at least about 95%, a purity level of at least about 99% or greater as determined by appropriate methods such as SDS/PAGE analysis, RP-HPLC, SEC, and capillary electrophoresis.

A "recombinant host cell" or "host cell" refers to a cell that includes an exogenous polynucleotide, regardless of the method used for insertion. The exogenous polynucleotide may be maintained as a nonintegrated vector, for example, a plasmid, or alternatively, may be integrated into the host genome.

As to amino acid sequences, one of ordinary skill in the art will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the deletion of an amino acid, addition of an amino acid, or an amino acid with a chemically similar amino acid. Conservative substitution tables providing functionally similar amino acids are known to those of ordinary skill in the art. The following eight groups each contain amino acids that are conservative substitutions for one another:

| | |
|---|---|
| 1) | Alanine (A), Glycine (G); |
| 2) | Aspartic acid (D), Glutamic acid (E); |
| 3) | Asparagine (N), Glutamine (Q); |
| 4) | Arginine (R), Lysine (K); |
| 5) | Isoleucine (I), Leucine (L), Methionine (M), Valine (V); |
| 6) | Phenylalanine (F), Tyrosine (Y), Tryptophan (W); |
| 7) | Serine (S), Threonine (T); and |
| 8) | Cysteine (C), Methionine (M) |

The term "linkage" or "linker" is used herein to refer to groups or bonds that normally are formed as the result of a chemical reaction and typically are covalent linkages. "Hydrolytically stable linkages" refer to linkages are substantially stable in water and do not react with water at useful pH values, including but not limited to, under physiological conditions for an extended period of time, perhaps even indefinitely. Hydrolytically unstable or degradable linkages mean that the linkages are degradable in water or in aqueous solutions, including for example, blood. Enzymatically unstable or degradable linkages mean that the linkage can be degraded by one or more enzymes. Hydrolytically degradable linkages include, but are not limited to, carbonate linkages; imine linkages resulted from reaction of an amine and an aldehyde; phosphate ester linkages formed by reacting an alcohol with a phosphate group; hydrazone linkages which are reaction product of a hydrazide and an aldehyde; acetal linkages that are the reaction product of an aldehyde and an alcohol; orthoester linkages that are the reaction product of a formate and an alcohol; peptide linkages formed by an amine group, and a carboxyl group of a peptide; and oligonucleotide linkages formed by a phosphoramidite group, including but not limited to, at the end of a polymer, and a 5' hydroxyl group of an oligonucleotide.

Linkers include but are not limited to short linear, branched, multi-armed, or dendrimeric molecules such as polymers.

Table 1 provides various starting electrophiles and nucleophiles which may be combined to create a desired functional group. The information provided is meant to be illustrative and not limiting to the synthetic techniques described herein.

TABLE 1

Examples of Covalent Linkages and Precursors Thereof

| Covalent Linkage Product | Electrophile | Nucleophile |
|---|---|---|
| Carboxamides | Activated esters | amines/anilines |
| Carboxamides | acyl azides | amines/anilines |
| Carboxamides | acyl halides | amines/anilines |
| Esters | acyl halides | alcohols/phenols |
| Esters | acyl nitriles | alcohols/phenols |
| Carboxamides | acyl nitriles | amines/anilines |
| Imines | Aldehydes | amines/anilines |
| Hydrazones | aldehydes or ketones | Hydrazines |
| Oximes | aldehydes or ketones | Hydroxylamines |
| Alkyl amines | alkyl halides | amines/anilines |
| Esters | alkyl halides | carboxylic acids |
| Thioethers | alkyl halides | Thiols |
| Ethers | alkyl halides | alcohols/phenols |
| Thioethers | alkyl sulfonates | Thiols |
| Esters | alkyl sulfonates | carboxylic acids |
| Ethers | alkyl sulfonates | alcohols/phenols |
| Esters | Anhydrides | alcohols/phenols |
| Carboxamides | Anhydrides | amines/anilines |
| Thiophenols | aryl halides | Thiols |
| Aryl amines | aryl halides | Amines |
| Thioethers | Azindines | Thiols |
| Boronate esters | Boronates | Glycols |
| Carboxamides | carboxylic acids | amines/anilines |
| Esters | carboxylic acids | Alcohols |
| hydrazines | Hydrazides | carboxylic acids |
| N-acylureas or Anhydrides | Carbodiimides | carboxylic acids |
| Esters | Diazoalkanes | carboxylic acids |
| Thioethers | Epoxides | Thiols |
| Thioethers | Haloacetamides | Thiols |
| Ammotriazines | Halotriazines | amines/anilines |
| Triazinyl ethers | Halotriazines | alcohols/phenols |
| Amidines | imido esters | amines/anilines |
| Ureas | Isocyanates | amines/anilines |
| Urethanes | Isocyanates | alcohols/phenols |
| Thioureas | Isothiocyanates | amines/anilines |
| Thioethers | Maleimides | Thiols |
| Phosphite esters | Phosphoramidites | Alcohols |
| Silyl ethers | silyl halides | Alcohols |
| Alkyl amines | sulfonate esters | amines/anilines |
| Thioethers | sulfonate esters | Thiols |
| Esters | sulfonate esters | carboxylic acids |
| Ethers | sulfonate esters | Alcohols |
| Sulfonamides | sulfonyl halides | amines/anilines |
| Sulfonate esters | sulfonyl halides | phenols/alcohols |

The terms "chemically coupled" and "chemically couple" and grammatical variations thereof refer to the covalent and noncovalent bonding of molecules and include specifically, but not exclusively, covalent bonding, electrostatic bonding, hydrogen bonding and van der Waals' bonding. The terms encompass both indirect and direct bonding of molecules. Thus, if a first compound is chemically coupled to a second compound, that connection may be through a direct chemical bond, or through an indirect chemical bond via other compounds, linkers or connectors.

The term "substituents" includes but is not limited to "non-interfering substituents". "Non-interfering substituents" are those groups that yield stable compounds. Suitable non-interfering substituents or radicals include, but are not limited to, halo, C1-C10 alkyl, C2-C10 alkenyl, C2-C10 alkynyl, C1-C10 alkoxy, C1-C12 aralkyl, C1-C12 alkaryl, C3-C12 cycloalkyl, C3-C12 cycloalkenyl, phenyl, substituted phenyl, toluoyl, xylenyl, biphenyl, C2-C12 alkoxyalkyl, C2-C12 alkoxyaryl, C7-C12 aryloxyalkyl, C7-C12 oxyaryl, C1-C6 alkylsulfinyl, C1-C10 alkylsulfonyl, —(CH2)m-O—(C1-C10 alkyl) wherein m is from 1 to 8, aryl, substituted aryl, substituted alkoxy, fluoroalkyl, heterocyclic radical, substituted heterocyclic radical, nitroalkyl, —NO2, —CN, —NRC(O)—(C1-C10 alkyl), —C(O)—(C1-C10 alkyl), C2-C10 alkyl thioalkyl, —C(O)O—(C1-C10 alkyl), —OH, —SO$_2$, =S, —COOH, —NR$_2$, carbonyl, —C(O)—(C1-C10 alkyl)-CF$_3$, —C(O)—CF$_3$, —C(O)NR$_2$, —(C1-C10 aryl)-S—(C6-C10 aryl), —C(O)—(C1-C10 aryl), —(CH$_2$)$_m$—O—(—(CH$_2$)m-O—(C1-C10 alkyl) wherein each m is from 1 to 8, —C(O)NR$_2$, —C(S)NR$_2$, —SO$_2$NR$_2$, —NRC(O)NR$_2$, —NRC(S)NR$_2$, salts thereof, and the like. Each R as used herein is H, alkyl or substituted alkyl, aryl or substituted aryl, aralkyl, or alkaryl.

The term "modulated therapeutic half-life" as used herein means the positive or negative change in the half-life of the therapeutically effective amount of DDAH, relative to its non-modified form.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

The term "modified," as used herein refers to any changes made to a given polypeptide, such as changes to the length of the polypeptide, the amino acid sequence, chemical structure, co-translational modification, or post-translational modification of a polypeptide. The form "(modified)" term means that the polypeptides being discussed are optionally modified, that is, the polypeptides under discussion can be modified or unmodified.

The term "post-translationally modified" refers to any modification of a natural or non-natural amino acid that occurs to such an amino acid after it has been incorporated into a polypeptide chain. The term encompasses, by way of example only, co-translational in vivo modifications, co-translational in vitro modifications (such as in a cell-free translation system), post-translational in vivo modifications, and post-translational in vitro modifications.

The term "protected" refers to the presence of a "protecting group" or moiety that prevents reaction of the chemically reactive functional group under certain reaction conditions. protecting groups known in the art may also be used in or with the methods and compositions described herein, including photolabile groups such as Nvoc and MeNvoc. Other protecting groups known in the art may also be used in or with the methods and compositions described herein. By way of example only, blocking/protecting groups may be selected from:

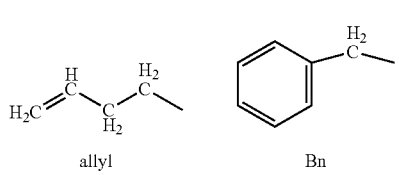

allyl      Bn

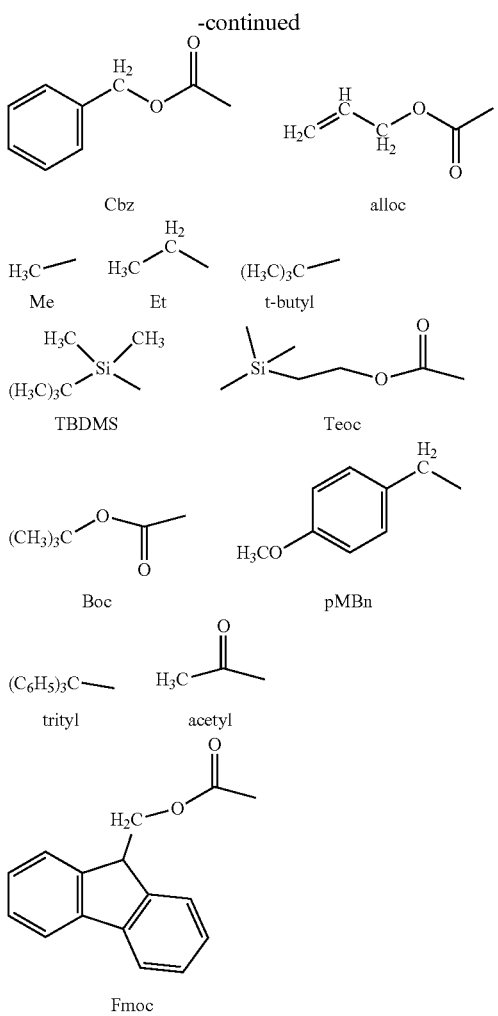

Other protecting groups are described in Greene and Wuts, Protective Groups in Organic Synthesis, 3rd Ed., John Wiley & Sons, New York, NY, 1999.

As used herein, the term "pharmaceutically acceptable carrier" includes any of the standard pharmaceutical carriers, such as a phosphate buffered saline solution, water, emulsions such as an oil/water or water/oil emulsion, and various types of wetting agents. The term also encompasses any of the agents approved by a regulatory agency of the US Federal government or listed in the US Pharmacopeia for use in animals, including humans.

As used herein the term "pharmaceutically acceptable salt" refers to salts of compounds that retain the biological activity of the parent compound, and which are not biologically or otherwise undesirable. Many of the compounds disclosed herein are capable of forming acid and/or base salts by virtue of the presence of amino and/or carboxyl groups or groups similar thereto.

As used herein, the term "treating" includes prophylaxis of the specific disorder or condition, or alleviation of the symptoms associated with a specific disorder or condition and/or preventing or eliminating said symptoms.

As used herein an "effective" amount or a "therapeutically effective amount" of a DDAH polypeptide or modified DDAH polypeptide refers to a nontoxic but sufficient amount of the polypeptide to provide the desired effect. For example one desired effect would be the reduction of ADMA levels to near normal levels in a patient. The amount that is "effective" will vary from subject to subject, depending on the age and general condition of the individual, mode of administration, and the like. Thus, it is not always possible to specify an exact "effective amount." However, an appropriate "effective" amount in any individual case may be determined by one of ordinary skill in the art using routine experimentation.

The term, "parenteral" means not through the alimentary canal but by some other route such as subcutaneous, intramuscular, intraspinal, or intravenous.

The term "isolated" requires that the referenced material be removed from its original environment (e.g., the natural environment if it is naturally occurring). For example, a naturally-occurring polynucleotide present in a living animal is not isolated, but the same polynucleotide, separated from some or all of the coexisting materials in the natural system, is isolated.

As used herein, the term "peptide" encompasses a sequence of 3 or more amino acids and typically less than 50 amino acids, wherein the amino acids are naturally occurring or non-naturally occurring amino acids. Non-naturally occurring amino acids refer to amino acids that do not naturally occur in vivo but which, nevertheless, can be incorporated into the peptide structures described herein.

As used herein, the terms "polypeptide" and "protein" are terms that are used interchangeably to refer to a polymer of amino acids, without regard to the length of the polymer. Typically, polypeptides and proteins have a polymer length that is greater than that of "peptides."

As used herein a general reference to a polypeptide is intended to encompass polypeptides that have modified amino and carboxy termini. For example, an amino acid chain comprising an amide group in place of the terminal carboxylic acid is intended to be encompassed by an amino acid sequence designating the standard amino acids.

As used herein an amino acid "substitution" refers to the replacement of one amino acid residue by a different amino acid residue.

As used herein the general term "polyethylene glycol chain" or "PEG chain", refers to mixtures of condensation polymers of ethylene oxide and water, in a branched or straight chain, represented by the general formula $H(OCH_2CH_2)_nOH$, wherein n is at least 9. Absent any further characterization, the term is intended to include polymers of ethylene glycol with an average total molecular weight selected from the range of 500 to 40,000 Daltons. "polyethylene glycol chain" or "PEG chain" is used in combination with a numeric suffix to indicate the approximate average molecular weight thereof. For example, PEG-5,000 refers to polyethylene glycol chain having a total molecular weight average of about 5,000.

As used herein the term "pegylated" and like terms refers to a compound that has been modified from its native state by linking a polyethylene glycol chain to the compound. A "pegylated DDAH polypeptide" is a DDAH polypeptide that has a PEG chain covalently bound to the DDAH polypeptide.

EMBODIMENTS

As disclosed herein modified DDAH polypeptides are provided for the treatment of patients with elevated ADMA levels. In accordance with one embodiment the modified DDAH polypeptide comprises a DDAH polypeptide having at least 80%, 85%, 90%, 95% or 99% sequence identity to an amino acid sequence selected from the group consisting of SEQ ID NO: 1; SEQ ID NO: 2; SEQ ID NO: 5; SEQ ID NO: 6; SEQ ID NO: 7; SEQ ID NO: 9; SEQ ID NO: 10; SEQ ID NO: 11; SEQ ID NO: 12; SEQ ID NO: 13; and SEQ ID NO: 14, or fragment thereof, wherein the DDAH polypeptide or fragment thereof is biologically active, further wherein the modified DDAH polypeptide is covalently linked to at least one pharmacokinetic enhancing moiety (PKEM). In one embodiment the modified DDAH polypeptide differs from an amino acid sequence selected from the group consisting of SEQ ID NO: 1; SEQ ID NO: 2; SEQ ID NO: 5; SEQ ID NO: 6; SEQ ID NO: 7; SEQ ID NO: 9; SEQ ID NO: 10; SEQ ID NO: 11; SEQ ID NO: 12; SEQ ID NO: 13; and SEQ ID NO: 14 by one, two, three, four or more amino acid substitutions, insertions, or deletions, wherein said substitutions are with natural or non-naturally encoded amino acids. In one embodiment the PKEM is a moiety selected from the group consisting of acyl group, polyethylene glycol, lipid, alkyl group, carbohydrate, polypeptide, polynucleotide, polysaccharide, antibody or antibody fragment, sialic acid(s), a prodrug, serum albumin, XTEN molecule, Fc molecule, adnectin, fibronectin, a biologically active molecule, water soluble polymer, one or more DDAH polypeptides (e.g. hetero- and homo-dimers), and combinations thereof. In one embodiment the PKEM is a moiety selected from the group consisting of acyl group, polyethylene glycol, and alkyl group.

In one embodiment the "DDAH polypeptide" is a compound having a molecular structure similar to that of human DDAH (SEQ ID NO: 1 or 2), and which have DDAH enzymatic activity. As used herein, "DDAH1" or "DDAH2" shall include those polypeptides and proteins that have at least one biological activity of a DDAH enzyme, as well as DDAH analogs, DDAH isoforms, DDAH mimetics, DDAH fragments, hybrid DDAH proteins, fusion proteins oligomers and multimers, homologues, glycosylation pattern variants, and muteins, thereof, regardless of the biological activity of same, and further regardless of the method of synthesis or manufacture thereof including, but not limited to, recombinant (whether produced from cDNA, genomic DNA, synthetic DNA or other form of nucleic acid), synthetic, transgenic, and gene activated methods. The amino acid sequence and polynucleotide sequence for DDAH1 and DDAH2 are shown in Tables 2, 3, 4, 5, 6, and 7 herein. Fusions comprising additional amino acids at the amino terminus, carboxyl terminus, or both, are encompassed by the term "DDAH polypeptide." Exemplary fusions include, but are not limited to, e.g., methionyl DDAH in which a methionine is linked to the N-terminus of DDAH resulting from the recombinant expression of the mature form of DDAH lacking the leader or signal peptide or portion thereof (a methionine is linked to the N-terminus of DDAH resulting from the recombinant expression), fusions for the purpose of purification (including, but not limited to, to poly-histidine or affinity epitopes), fusions with serum albumin binding peptides and fusions with serum proteins such as serum albumin. Chimeric molecules comprising DDAH and one or more other molecules are also included. The chimeric molecule can contain specific regions or fragments of one or both of the DDAH and the other molecule(s). Any such fragments can be prepared from the proteins by standard biochemical methods, or by expressing a polynucleotide encoding the fragment. DDAH, or a fragment thereof, can be produced as a fusion protein comprising human serum albumin (HSA), Fc, or a portion thereof. Such fusion constructs are suitable for enhancing expression of the DDAH, or fragment thereof, in an eukaryotic host cell. Exemplary HSA portions include the N-terminal polypeptide (amino acids 1-369, 1-419, and intermediate lengths starting with amino acid 1), as disclosed in U.S. Pat. No. 5,766,883, and publication WO 97/24445, which are incorporated by reference herein. Other chimeric polypeptides can include a HSA protein with DDAH, or fragments thereof, attached to each of the C-terminal and N-terminal ends of the HSA. Such HSA constructs are disclosed in U.S. Pat. No. 5,876,969, which is incorporated by reference herein. Other fusions may be created by fusion of DDAH with a) the Fc portion of an immunoglobulin; b) an analog of the Fc portion of an immunoglobulin; and c) fragments of the Fc portion of an immunoglobulin.

In accordance with one embodiment a glycosylated DDAH is provided, such as but not limited to, polypeptides glycosylated at any amino acid, N-linked or O-linked glycosylated forms of the polypeptide. Variants containing single nucleotide changes are also considered as biologically active variants of DDAH polypeptide. In addition, splice variants are also included. In one embodiment the DDAH polypeptide is a heterodimer, homodimer, heteromultimer, or homomultimer of any one or more DDAH polypeptides or any other polypeptide, protein, carbohydrate, polymer, small molecule, linker, ligand, or other biologically active molecule of any type, linked by chemical means or expressed as a fusion protein, as well as polypeptide analogues containing, for example, specific deletions or other modifications yet maintain biological activity.

In one embodiment the DDAH polypeptide comprises one or more amino acid substitutions, additions or deletions. DDAH polypeptides modification may be comprised of one or more natural amino acids in conjunction with one or more non-natural amino acid modification. Exemplary substitutions in a wide variety of amino acid positions in naturally-occurring DDAH polypeptides, including but not limited to substitutions that modulate pharmaceutical stability, that modulate one or more of the biological activities of the DDAH polypeptide, such as but not limited to, increase or decrease enzymatic activity, increase or decrease solubility of the DDAH polypeptide, increase or decrease protease susceptibility, increase or decrease homodimerization, increase or decrease zinc binding, increase or decrease stability of the DDAH polypeptide, etc. In some embodiments, the DDAH polypeptide is linked to a pharmacokinetic enhancing moiety or other biologically active molecule, present in a substrate, activity modulator such as zinc, protease cleavage site, or other DDAH polypeptide binding region of the DDAH molecule.

In some embodiments, the DDAH polypeptides further comprise an addition, substitution or deletion that modulates biological activity of the DDAH polypeptide. For example, the additions, substitutions or deletions may modulate one or more properties or activities of DDAH. For example, the additions, substitutions or deletions may modulate affinity for the DDAH substrate, modulate circulating half-life, modulate therapeutic half-life, modulate stability of the polypeptide, modulate cleavage by proteases, modulate dimerization of DDAH, modulate dose, modulate release or bio-availability, facilitate purification, or improve or alter a particular route of administration. Similarly, DDAH polypeptides may comprise protease cleavage sequences, reactive groups, antibody-binding domains (including but not limited to, FLAG or poly-His) or other affinity-based sequences (including but not limited to, FLAG, poly-His, GST, etc.) or linked molecules (including but not limited to, biotin) that improve detection (including but not limited to, GFP), purification or other traits of the polypeptide.

In one embodiment the DDAH polypeptide is a homodimer, heterodimer, homomultimer, or heteromultimer wherein the subunits are linked, including but not limited to, linkage directly via the N-termini, the C-termini, a naturally encoded or non-naturally encoded amino acid side chains, either to the same or different naturally encoded or non-naturally encoded amino acid side chains, to naturally-encoded amino acid side chains, or indirectly via a linker. Exemplary linkers including but are not limited to, small organic compounds, and PKEM.

DDAH polypeptides presented herein may include isotopically-labelled compounds with one or more atoms replaced by an atom having an atomic mass or mass number different from the atomic mass or mass number usually found in nature. Examples of isotopes that can be incorporated into the present compounds include isotopes of hydrogen, carbon, nitrogen, oxygen, fluorine and chlorine, such as 2H, 3H, 13C, 14C, 15N, 18O, 17O, 35S, 18F, 36Cl, respectively. Certain isotopically-labelled compounds described herein, for example those into which radioactive isotopes such as 3H and 14C are incorporated, may be useful in drug and/or substrate tissue distribution assays. Further, substitution with isotopes such as deuterium, i.e., 2H, can afford certain therapeutic advantages resulting from greater metabolic stability, for example increased in vivo half-life or reduced dosage requirements.

In accordance with one embodiment polypeptides comprising at least one amino acid substitution, addition, deletion or insertion are provided. In certain embodiments, the DDAH polypeptide includes at least one post-translational modification. In one embodiment, the at least one post-translational modification comprises attachment of a molecule including but not limited to, a pharmacokinetic enhancing moiety, a label, a dye, a polymer, a water-soluble polymer, a derivative of polyethylene glycol, a photocrosslinker, a radionuclide, a cytotoxic compound, a drug, an affinity label, a photoaffinity label, a reactive compound, a resin, a second protein or polypeptide or polypeptide analog, an antibody or antibody fragment, a metal chelator, a cofactor, a fatty acid, a carbohydrate, a polynucleotide, a DNA, a RNA, an antisense polynucleotide, a saccharide, a water-soluble dendrimer, a cyclodextrin, an inhibitory ribonucleic acid, a biomaterial, a nanoparticle, a spin label, a fluorophore, a metal-containing moiety, a radioactive moiety, a novel functional group, a group that covalently or noncovalently interacts with other molecules, a photocaged moiety, an actinic radiation excitable moiety, a photoisomerizable moiety, biotin, a derivative of biotin, a biotin analogue, a moiety incorporating a heavy atom, a chemically cleavable group, a photocleavable group, an elongated side chain, a carbon-linked sugar, a redox-active agent, an amino thioacid, a toxic moiety, an isotopically labeled moiety, a biophysical probe, a phosphorescent group, a chemiluminescent group, an electron dense group, a magnetic group, an intercalating group, a chromophore, an energy transfer agent, a biologically active agent, a detectable label, a small molecule, a quantum dot, a nanotransmitter, a radionucleotide, a radiotransmitter, a neutron-capture agent, or any combination of the above or any other desirable compound or substance, comprising a second reactive group to at least one amino acid comprising a first reactive group utilizing chemistry methodology that is known to one of ordinary skill in the art to be suitable for the particular reactive groups. In certain embodiments, the post-translational modification is made in vivo in a eukaryotic cell or in a non-eukaryotic cell. A linker, polymer, pharmacokinetic enhancing moiety, or other molecule may attach the molecule to the polypeptide. The molecule may be linked directly to the polypeptide.

In certain embodiments, the protein includes at least one post-translational modification that is made in vivo by one host cell, where the post-translational modification is not normally made by another host cell type. In certain embodiments, the protein includes at least one post-translational modification that is made in vivo by a eukaryotic cell, where the post-translational modification is not normally made by a non-eukaryotic cell. Examples of post-translational modifications include, but are not limited to, glycosylation, acetylation, acylation, lipid-modification, palmitoylation, palmitate addition, phosphorylation, glycolipid-linkage modification, and the like.

In some embodiments, the DDAH polypeptide comprises one or more post-translational modification including but not limited to glycosylation, acetylation, acylation, lipid-modification, palmitoylation, palmitate addition, phosphorylation, or glycolipid-linkage modification of the polypeptide. In one embodiment, the post-translational modification comprises attachment of an oligosaccharide to an asparagine by a GlcNAc-asparagine linkage (including but not limited to, where the oligosaccharide comprises (GlcNAc-Man)2-Man-GlcNAc-GlcNAc, and the like). In another embodiment, the post-translational modification comprises attachment of an oligosaccharide (including but not limited to, Gal-GalNAc, Gal-GlcNAc, etc.) to a serine or threonine by a GalNAc-serine, a GalNAc-threonine, a GlcNAc-serine, or a GlcNAc-threonine linkage. In certain embodiments, a protein or polypeptide described herein can comprise a secretion or localization sequence, an epitope tag, a FLAG tag, a polyhistidine tag, a GST fusion, and/or the like. Examples of secretion signal sequences include, but are not limited to, a prokaryotic secretion signal sequence, a eukaryotic secretion signal sequence, a eukaryotic secretion signal sequence 5'-optimized for bacterial expression, a novel secretion signal sequence, pectate lyase secretion signal sequence, Omp A secretion signal sequence, and a phage secretion signal sequence. Examples of secretion signal sequences, include, but are not limited to, STII (prokaryotic), Fd GIII and M13 (phage), Bgl2 (yeast), and the signal sequence bla derived from a transposon. Any such sequence may be modified to provide a desired result with the polypeptide, including but not limited to, substituting one signal sequence with a different signal sequence, substituting a leader sequence with a different leader sequence, etc.

Provided herein are conjugates of substances having a wide variety of functional groups, substituents or moieties, with other substances including but not limited to a pharmacokinetic enhancing moiety; a label; a dye; a polymer; a water-soluble polymer; a derivative of polyethylene glycol; a photocrosslinker; a radionuclide; a cytotoxic compound; a drug; an affinity label; a photoaffinity label; a reactive compound; a resin; a second protein or polypeptide or polypeptide analog; an antibody or antibody fragment; a metal chelator; a cofactor; a fatty acid; a carbohydrate; a polynucleotide; a DNA; a RNA; an antisense polynucleotide; a saccharide; a water-soluble dendrimer; a cyclodextrin; an inhibitory ribonucleic acid; a biomaterial; a nanoparticle; a spin label; a fluorophore, a metal-containing moiety; a radioactive moiety; a novel functional group; a group that covalently or noncovalently interacts with other molecules; a photocaged moiety; an actinic radiation excitable moiety; a photoisomerizable moiety; biotin; a derivative of biotin; a biotin analogue; a moiety incorporating a heavy atom; a chemically cleavable group; a photocleavable group; an elongated side chain; a carbon-linked sugar; a redox-active agent; an amino thioacid; a toxic moiety; an isotopically labeled moiety; a biophysical probe; a phosphorescent group; a chemiluminescent group; an electron dense group; a magnetic group; an intercalating group; a chromophore; an energy transfer agent; a biologically active agent; a detectable label; a small molecule; a quantum dot; a nanotransmitter; a radionucleotide; a radiotransmitter; a neutron-capture agent; or any combination of the above, or any other desirable compound or substance. Also provided are conjugates of substances having azide or acetylene moieties with pharmacokinetic enhancing moiety derivatives having the corresponding acetylene or azide moieties. For example, a pharmacokinetic enhancing moiety containing an azide moiety can be coupled to a biologically active molecule at a position in the protein that contains a non-genetically encoded amino acid bearing an acetylene functionality.

In some embodiments, provided herein are DDAH polypeptides coupled to another molecule having the formula DDAH-L-M, wherein L is a linking group or a chemical bond, and M is any other molecule. In some embodiments, L is stable in vivo. In some embodiments, L is hydrolyzable in vivo. In some embodiments, L is metastable in vivo.

DDAH and M can be linked together through L using standard linking agents and procedures known to those skilled in the art. In some aspects, DDAH and M are fused directly and L is a bond. In other aspects, DDAH and M are fused through a linking group L. For example, in some embodiments, DDAH and M are linked together via a peptide bond, optionally through a peptide or amino acid spacer. In some embodiments, DDAH and M are linked together through chemical conjugation, optionally through a linking group (L). In some embodiments, L is directly conjugated to each of DDAH and M.

Chemical conjugation can occur by reacting a nucleophilic reactive group of one compound to an electrophilic reactive group of another compound. In some embodiments when L is a bond, DDAH is conjugated to M either by reacting a nucleophilic reactive moiety on DDAH with an electrophilic reactive moiety on Y, or by reacting an electrophilic reactive moiety on DDAH with a nucleophilic reactive moiety on M. In embodiments when L is a group that links DDAH and M together, DDAH and/or M can be conjugated to L either by reacting a nucleophilic reactive moiety on DDAH and/or M with an electrophilic reactive moiety on L, or by reacting an electrophilic reactive moiety on DDAH and/or M with a nucleophilic reactive moiety on L. Nonlimiting examples of nucleophilic reactive groups include amino, thiol, and hydroxyl. Nonlimiting examples of electrophilic reactive groups include carboxyl, acyl chloride, anhydride, ester, succinimide ester, alkyl halide, sulfonate ester, maleimido, haloacetyl, and isocyanate. In embodiments where DDAH and M are conjugated together by reacting a carboxylic acid with an amine, an activating agent can be used to form an activated ester of the carboxylic acid.

The activated ester of the carboxylic acid can be, for example, N-hydroxysuccinimide (NHS), tosylate (Tos), mesylate, triflate, a carbodiimide, or a hexafluorophosphate. In some embodiments, the carbodiimide is 1,3-dicyclohexylcarbodiimide (DCC), 1, 1'-carbonyldiimidazole (CDI), 1-ethyl-3-(3-dimethylaminopropyl)carbodiimide hydrochloride (EDC), or 1,3-diisopropylcarbodiimide (DICD). In some embodiments, the hexafluorophosphate is selected from a group consisting of hexafluorophosphate benzotriazol-1-yl-oxy-tris(dimethylamino)phosphonium hexafluorophosphate (BOP), benzotriazol-1-yl-oxytripyrrolidinophosphonium hexafluorophosphate (PyBOP), 2-(1H-7-azabenzotriazol-1-yl)-1, 1,3,3-tetramethyl uronium hexafluorophosphate (HATU), and o-benzotriazole-N,N,N', N'-tetramethyl-uronium-hexafluoro-phosphate (HBTU).

In some embodiments, DDAH comprises a nucleophilic reactive group (e.g. the amino group, thiol group, or hydroxyl group of the side chain of lysine, cysteine or serine) that is capable of conjugating to an electrophilic reactive group on M or L. In some embodiments, DDAH comprises an electrophilic reactive group (e.g. the carboxylate group of the side chain of Asp or Glu) that is capable of conjugating to a nucleophilic reactive group on M or L. In some embodiments, DDAH is chemically modified to comprise a reactive group that is capable of conjugating directly to M or to L. In some embodiments, DDAH is modified at the C-terminal to comprise a natural or nonnatural amino acid with a nucleophilic side chain. In exemplary embodiments, the C-terminal amino acid of DDAH is selected from the group consisting of lysine, ornithine, serine, cysteine, and homocysteine. For example, the C-terminal amino acid of DDAH can be modified to comprise a lysine residue. In some embodiments, DDAH is modified at the C-terminal amino acid to comprise a natural or nonnatural amino acid with an electrophilic side chain such as, for example, Asp and Glu. In some embodiments, an internal amino acid of DDAH is substituted with a natural or nonnatural amino acid having a nucleophilic side chain, as previously described herein. In exemplary embodiments, the internal amino acid of DDAH that is substituted is selected from the group consisting of lysine, ornithine, serine, cysteine, and homocysteine. For example, an internal amino acid of DDAH can be substituted with a lysine residue. In some embodiments, an internal amino acid of DDAH is substituted with a natural or nonnatural amino acid with an electrophilic side chain, such as, for example, Asp and Glu.

In some embodiments, M comprises a reactive group that is capable of conjugating directly to DDAH or to L. In some embodiments, M comprises a nucleophilic reactive group (e.g. amine, thiol, hydroxyl) that is capable of conjugating to an electrophilic reactive group on DDAH or L. In some embodiments, M comprises electrophilic reactive group (e.g. carboxyl group, activated form of a carboxyl group, compound with a leaving group) that is capable of conjugating to a nucleophilic reactive group on DDAH or L. In some embodiments, M is chemically modified to comprise either a nucleophilic reactive group that is capable of conjugating to an electrophilic reactive group on DDAH or L. In some embodiments, M is chemically modified to comprise an electrophilic reactive group that is capable of conjugating to a nucleophilic reactive group on DDAH or L.

In some embodiments, conjugation can be carried out through organosilanes, e.g., aminosilane treated with glutaraldehyde; carbonyldiimidazole (CDI) activation of silanol groups; or utilization of dendrimers. A variety of dendrimers are known in the art and include poly (amidoamine) (PAMAM) dendrimers, which are synthesized by the divergent method starting from ammonia or ethylenediamine initiator core reagents; a sub-class of PAMAM dendrimers based on a tris-aminoethylene-imine core; radially layered poly(amidoamine-organosilicon) dendrimers (PAMAMOS), which are inverted unimolecular micelles that consist of hydrophilic, nucleophilic polyamidoamine (PAMAM) interiors and hydrophobic organosilicon (OS) exteriors; Poly (Propylene Imine) (PPI) dendrimers, which are generally polyalkyl amines having primary amines as end groups, while the dendrimer interior consists of numerous of tertiary tris-propylene amines; Poly (Propylene Amine) (POPAM)

dendrimers; Diaminobutane (DAB) dendrimers; amphiphilic dendrimers; micellar dendrimers which are unimolecular micelles of water soluble hyper branched polyphenylenes; polylysine dendrimers; and dendrimers based on poly-benzyl ether hyper branched skeleton.

Indirect conjugation via high affinity specific binding partners, e.g. streptavidin/biotin or avidin/biotin or lectin/carbohydrate is also contemplated.

In some embodiments, DDAH and/or M are functionalized to comprise a nucleophilic reactive group or an electrophilic reactive group with an organic derivatizing agent. This derivatizing agent is capable of reacting with selected side chains or the N- or C-terminal residues of targeted amino acids on DDAH and functional groups on M. Reactive groups on DDAH and/or M include, e.g., aldehyde, amino, ester, thiol, a-haloacetyl, maleimido or hydrazino group. Derivatizing agents include, for example, maleimidobenzoyl sulfosuccinimide ester (conjugation through cysteine residues), N-hydroxysuccinimide (through lysine residues), glutaraldehyde, succinic anhydride or other agents known in the art. Alternatively, DDAH and/or M can be linked to each other indirectly through intermediate carriers, such as polysaccharide or polypeptide carriers. Examples of polysaccharide carriers include aminodextran. Examples of suitable polypeptide carriers include polylysine, polyglutamic acid, polyaspartic acid, co-polymers thereof, and mixed polymers of these amino acids and others, e.g., serines, to confer desirable solubility properties on the resultant loaded carrier.

Cysteinyl residues most commonly are reacted with a-haloacetates (and corresponding amines), such as chloroacetic acid or chloroacetamide, to give carboxymethyl or carboxyamidomethyl derivatives. Cysteinyl residues cam are derivatized by reaction with bromotrifluoroacetone, alpha-bromo-β-(5-imidozoyl)propionic acid, chloroacetyl phosphate, N-alkylmaleimides, 3-nitro-2-pyridyl disulfide, methyl 2-pyridyl disulfide, p-chloromercuribenzoate, 2-chloromercuri-4-nitrophenol, or chloro-7-nitrobenzo-2-oxa-1,3-diazole.

Histidyl residues are derivatized by reaction with diethylpyrocarbonate at pH 5.5-7.0 because this agent is relatively specific for the histidyl side chain. Para-bromophenacyl bromide also is useful; the reaction is preferably performed in 0.1 M sodium cacodylate at pH 6.0.

Lysinyl and amino-terminal residues are reacted with succinic or other carboxylic acid anhydrides. Derivatization with these agents has the effect of reversing the charge of the lysinyl residues. Other suitable reagents for derivatizing alpha-amino-containing residues include imidoesters such as methyl picolinimidate, pyridoxal phosphate, pyridoxal, chloroborohydride, trinitrobenzenesulfonic acid, O-methylisourea, 2,4-pentanedione, and transaminase-catalyzed reaction with glyoxylate.

Arginyl residues are modified by reaction with one or several conventional reagents, among them phenylglyoxal, 2,3-butanedione, 1,2-cyclohexanedione, and ninhydrin. Derivatization of arginine residues requires that the reaction be performed in alkaline conditions because of the high pKa of the guanidine functional group. Furthermore, these reagents may react with the groups of lysine as well as the arginine epsilon-amino group.

The modification of tyrosyl residues may be made, with particular interest in introducing spectral labels into tyrosyl residues by reaction with aromatic diazonium compounds or tetranitromethane. Most commonly, N-acetylimidizole and tetranitromethane are used to form O-acetyl tyrosyl species and 3-nitro derivatives, respectively.

Carboxyl side groups (aspartyl or glutamyl) can be selectively modified by reaction with carbodiimides (R—N=C=N—R'), where R and R' are different alkyl groups, such as 1-cyclohexyl-3-(2-morpholinyl-4-ethyl) carbodiimide or 1-ethyl-3-(4-azonia-4,4-dimethylpentyl) carbodiimide. Furthermore, aspartyl and glutamyl residues are converted to asparaginyl and glutaminyl residues by reaction with ammonium ions.

Another type of covalent modification involves chemically or enzymatically coupling glycosides to the peptide at arginine and histidine, (b) free carboxyl groups, (c) free sulfhydryl groups such as those of cysteine, (d) free hydroxyl groups such as those of serine, threonine, or hydroxyproline, (e) aromatic residues such as those of tyrosine, or tryptophan, or (f) the amide group of glutamine, as described in WO87/05330 published 11 Sep. 1987, and in Aplin and Wriston, *CRC Crit. Rev. Biochem.*, pp. 259-306 (1981).

In some embodiments, L is a bond. In these embodiments, DDAH and M are conjugated together by reacting a nucleophilic reactive moiety on DDAH with an electrophilic reactive moiety on M. In alternative embodiments, DDAH and M are conjugated together by reacting an electrophilic reactive moiety on DDAH with a nucleophilic moiety on M. In exemplary embodiments, L is an amide bond that forms upon reaction of an amine on DDAH (e.g. an ε-amine of a lysine residue) with a carboxyl group on M. In alternative embodiments, DDAH and or M are derivatized with a derivatizing agent before conjugation.

In some embodiments, L is linking group, a bifunctional linker and comprises only two reactive groups before conjugation to DDAH and M. In embodiments where both DDAH and M have electrophilic reactive groups, L comprises two of the same or two different nucleophilic groups (e.g. amine, hydroxyl, thiol) before conjugation to DDAH and M. In embodiments where both DDAH and M have nucleophilic reactive groups, L comprises two of the same or two different electrophilic groups (e.g. carboxyl group, activated form of a carboxyl group, compound with a leaving group) before conjugation to DDAH and M. In embodiments where one of DDAH or M has a nucleophilic reactive group and the other of DDAH or M has an electrophilic reactive group, L comprises one nucleophilic reactive group and one electrophilic group before conjugation to DDAH and M.

L can be any molecule with at least two reactive groups (before conjugation to DDAH and M) capable of reacting with each of DDAH and M. In some embodiments L has only two reactive groups and is bifunctional. L (before conjugation to the peptides) can be represented by the formula below:

wherein A and B are independently nucleophilic or electrophillic reactive groups. In some embodiments A and B are either both nucleophilic groups or both electrophilic groups. In some embodiments one of A or B is a nucleophilic group and the other of A or B is an electrophilic group. Nonlimiting combinations of A and B are described below.

In some embodiments, A and B may include alkene and/or alkyne functional groups that are suitable for olefin metathesis reactions. In some embodiments, A and B include moieties that are suitable for click chemistry (e.g. alkene, alkynes, nitriles, azides). Other nonlimiting examples of reactive groups (A and B) include pyridyldithiol, aryl azide, diazirine, carbodiimide, and hydrazide.

In some embodiments, L can be hydrophobic. Hydrophobic linkers are known in the art. See, e.g., Bioconjugate Techniques, G. T. Hermanson (Academic Press, San Diego, CA, 1996), which is incorporated by reference in its entirety. Suitable hydrophobic linking groups known in the art include, for example, 8-hydroxy octanoic acid and 8-mercaptooctanoic acid. Before conjugation to the peptides of the composition, the hydrophobic linking group comprises at least two reactive groups (A and B), as described herein and as shown below:

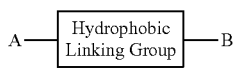

In some embodiments, the hydrophobic linking group comprises either a maleimido or an iodoacetyl group and either a carboxylic acid or an activated carboxylic acid (e.g. NHS ester) as the reactive groups. In these embodiments, the maleimido or iodoacetyl group can be coupled to a thiol moiety on DDAH or M and the carboxylic acid or activated carboxylic acid can be coupled to an amine on DDAH or M with or without the use of a coupling reagent. Any coupling agent known to one skilled in the art can be used to couple the carboxylic acid with the free amine such as, for example, DCC, DIC, HATU, HBTU, TBTU, and other activating agents described herein. In specific embodiments, the hydrophilic linking group comprises an aliphatic chain of 2 to 100 methylene groups wherein A and B are carboxyl groups or derivatives thereof (e.g. succinic acid). In other specific embodiments the L is iodoacetic acid.

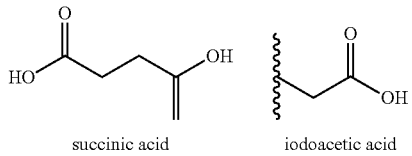

succinic acid    iodoacetic acid

In some embodiments, the linking group is hydrophilic such as, for example, polyalkylene glycol. Before conjugation to the peptides of the composition, the hydrophilic linking group comprises at least two reactive groups (A and B), as described herein and as shown below:

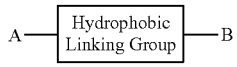

In specific embodiments, the linking group is polyethylene glycol (PEG). The PEG in certain embodiments has a molecular weight (MW) of about 100 Daltons to about 10,000 Daltons, e.g. about 500 Daltons to about 5000 Daltons. The PEG in some embodiments has a MW of about 10,000 Daltons to about 40,000 Daltons.

In some embodiments, the hydrophilic linking group comprises either a maleimido or an iodoacetyl group and either a carboxylic acid or an activated carboxylic acid (e.g. NHS ester) as the reactive groups. In these embodiments, the maleimido or iodoacetyl group can be coupled to a thiol moiety on DDAH or M and the carboxylic acid or activated carboxylic acid can be coupled to an amine on DDAH or M with or without the use of a coupling reagent. Any appropriate coupling agent known to one skilled in the art can be used to couple the carboxylic acid with the amine such as, for example, DCC, DIC, HATU, HBTU, TBTU, and other activating agents described herein. In some embodiments, the linking group is maleimido-PKEM(20 kDa)-COOH, iodoacetyl-PKEM(20 kDa)-COOH, maleimido-PKEM(20 kDa)-NHS, or iodoacetyl-PKEM(20 kDa)-NHS.

In some embodiments, the linking group is comprised of an amino acid, a dipeptide, a tripeptide, or a polypeptide, wherein the amino acid, dipeptide, tripeptide, or polypeptide comprises at least two activating groups, as described herein. In some embodiments, the linking group (L) comprises a moiety selected from the group consisting of: amino, ether, thioether, maleimido, disulfide, amide, ester, thioester, alkene, cycloalkene, alkyne, trizoyl, carbamate, carbonate, cathepsin B-cleavable, and hydrazone.

In some embodiments, L comprises a chain of atoms from 1 to about 60, or 1 to 30 atoms or longer, 2 to 5 atoms, 2 to 10 atoms, 5 to 10 atoms, or 10 to 20 atoms long. In some embodiments, the chain atoms are all carbon atoms. In some embodiments, the chain atoms in the backbone of the linker are selected from the group consisting of C, O, N, and S. Chain atoms and linkers may be selected according to their expected solubility (hydrophilicity) so as to provide a more soluble conjugate. In some embodiments, L provides a functional group that is subject to cleavage by an enzyme or other catalyst or hydrolytic conditions found in the target tissue or organ or cell. In some embodiments, the length of L is long enough to reduce the potential for steric hindrance.

In some embodiments, L is stable in biological fluids such as blood or blood fractions. In some embodiments, L is stable in blood serum for at least 5 minutes, e.g. less than 25%, 20%, 15%, 10% or 5% of the conjugate is cleaved when incubated in serum for a period of 5 minutes. In other embodiments, L is stable in blood serum for at least 10, or 20, or 25, or 30, or 60, or 90, or 120 minutes, or 3, 4, 5, 6, 7, 8, 9, 10, 12, 15, 18 or 24 hours. In these embodiments, L does not comprise a functional group that is capable of undergoing hydrolysis in vivo. In some exemplary embodiments, L is stable in blood serum for at least about 72 hours. Nonlimiting examples of functional groups that are not capable of undergoing significant hydrolysis in vivo include amides, ethers, and thioethers. For example, the following compound does not undergoing significant hydrolysis in vivo:

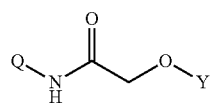

In some embodiments, L is hydrolyzable in vivo. In these embodiments, L comprises a functional group that is capable of undergoing hydrolysis in vivo. Nonlimiting examples of functional groups that are capable of undergoing hydrolysis in vivo include esters, anhydrides, and thioesters. For example the following compound is capable of undergoing hydrolysis in vivo because it comprises an ester group:

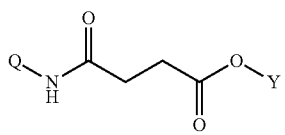

In some embodiments, L is labile and undergoes substantial hydrolysis within 3 hours in blood plasma at 37° C., with complete hydrolysis within 6 hours. In some exemplary embodiments, L is not labile.

In some embodiments, L is metastable in vivo. In these embodiments, L comprises a functional group that is capable of being chemically or enzymatically cleaved in vivo (e.g., an acid-labile, reduction-labile, or enzyme-labile functional group), optionally over a period of time. In these embodiments, L can comprise, for example, a hydrazone moiety, a disulfide moiety, or a cathepsin-cleavable moiety. When L is metastable, and without intending to be bound by any particular theory, the DDAH-L-M conjugate is stable in an extracellular environment, e.g., stable in blood serum for the time periods described above, but labile in the intracellular environment or conditions that mimic the intracellular environment, so that it cleaves upon entry into a cell. In some embodiments when L is metastable, L is stable in blood serum for at least about 24, 25, 26, 27, 28, 29, 30, 31, 32, 33, 34, 35, 36, 42, or 48 hours, for example, at least about 48, 54, 60, 66, or 72 hours, or about 24-48, 48-72, 24-60, 36-48, 36-72, or 48-72 hours.

General Recombinant Nucleic Acid Methods

In some embodiments, nucleic acids encoding a DDAH polypeptide of interest will be isolated, cloned and often altered using recombinant methods. Such embodiments are used, including but not limited to, for protein expression or during the generation of variants, derivatives, expression cassettes, or other sequences derived from a DDAH polypeptide. In some embodiments, the sequences encoding the polypeptides described herein are operably linked to a heterologous promoter.

A nucleotide sequence encoding a DDAH polypeptide include but not limited to, having the amino acid sequence shown in SEQ ID NO: 1; SEQ ID NO: 2; SEQ ID NO: 5; SEQ ID NO: 6; SEQ ID NO: 7; SEQ ID NO: 9; SEQ ID NO: 10; SEQ ID NO: 11; SEQ ID NO: 12; SEQ ID NO: 13; or SEQ ID NO: 14 and then changing the nucleotide sequence so as to effect introduction (i.e., incorporation or substitution) or removal (i.e., deletion or substitution) of the relevant amino acid residue(s). The nucleotide sequence may be conveniently modified by site-directed mutagenesis in accordance with conventional methods.

Various types of mutagenesis are used for a variety of purposes, including but not limited to, to produce novel DDAH polypeptides of interest. They include but are not limited to site-directed, random point mutagenesis, homologous recombination, DNA shuffling or other recursive mutagenesis methods, chimeric construction, mutagenesis using uracil containing templates, oligonucleotide-directed mutagenesis, phosphorothioate-modified DNA mutagenesis, mutagenesis using gapped duplex DNA or the like, PCT-mediated mutagenesis, or any combination thereof. Additional suitable methods include point mismatch repair, mutagenesis using repair-deficient host strains, restriction-selection and restriction-purification, deletion mutagenesis, mutagenesis by total gene synthesis, double-strand break repair, and the like. Mutagenesis, including but not limited to, involving chimeric constructs, are also possible. In one embodiment, mutagenesis can be guided by known information of the naturally occurring molecule or altered or mutated naturally occurring molecule, including but not limited to, sequence, sequence comparisons, physical properties, secondary, tertiary, or quaternary structure, crystal structure or the like.

Also provided are eukaryotic, non-eukaryotic host cells, and organisms for the in vivo incorporation of an unnatural amino acid via orthogonal tRNA/RS pairs. Host cells are genetically engineered (including but not limited to, transformed, transduced or transfected) with the polynucleotides described herein or constructs which include a polynucleotide described herein, including but not limited to, a vector which can be, for example, a cloning vector or an expression vector.

Also described are post-translation modifications includes proteolytic processing of precursors (including but not limited to, proDDAH or a variant or analog thereof), assembly into a multisubunit protein or macromolecular assembly, translation to another site in the cell (including but not limited to, to organelles, such as the endoplasmic reticulum, the Golgi apparatus, the nucleus, lysosomes, peroxisomes, mitochondria, chloroplasts, vacuoles, etc., or through the secretory pathway). In certain embodiments, the protein comprises a secretion or localization sequence, an epitope tag, a FLAG tag, a polyhistidine tag, a GST fusion, or the like.

Location of Modifications in DDAH Polypeptides

The substitution, addition, deletion, or incorporation of one or more naturally encoded or non-naturally-occurring amino acids into DDAH polypeptides are also described. One or more of these modifications may be incorporated at a particular position which does not disrupt activity of the polypeptide. This can be achieved by making "conservative" substitutions, including but not limited to, substituting hydrophobic amino acids with hydrophobic amino acids, bulky amino acids for bulky amino acids, hydrophilic amino acids for hydrophilic amino acids and/or inserting the non-naturally-occurring amino acid in a location that is not required for activity. It is also known that Cys273, His172 and Asp126 of the mammalian DDAH polypeptide are important for enzymatic activity. Therefore, the remaining cysteine residues other than Cys273 may individually, or in combination, or entirely, be substituted with another amino acid, such as but not limited to serine or alanine, in order to remove them from the DDAH polypeptide and test the biological properties of the resulting DDAH polypeptide.

Residues other than those identified as critical to biological activity by alanine or homolog scanning mutagenesis may be good candidates for substitution, deletion, or insertion depending on the desired activity sought for the polypeptide. Alternatively, the sites identified as critical to biological activity may also be good candidates for substitution, insertion or deletion, again depending on the desired activity sought for the polypeptide. Another alternative would be to simply make serial substitutions in each position on the polypeptide chain with a non-naturally encoded amino acid and observe the effect on the activities of the polypeptide. It is readily apparent to those of ordinary skill in the art that any means, technique, or method for selecting a position for substitution with a non-natural amino acid into any polypeptide described herein.

In some embodiments, the DDAH polypeptides described herein can comprise one or more addition or deletion of amino acids, or of substitution of naturally encoded or non-naturally encoded amino acids positioned in a region of the protein that does not disrupt the structure of the polypeptide.

One of ordinary skill in the art recognizes that such analysis of DDAH enables the determination of which amino acid residues are surface exposed compared to amino acid residues that are buried within the tertiary structure of the protein. Therefore, it is an embodiment to substitute, insert or delete one or more amino acid for an amino acid that is a surface exposed residue.

An examination of the crystal structure of DDAH and its interaction with the DDAH substrate, modulator, or another DDAH molecule can indicate which certain amino acid residues have side chains that are fully or partially accessible to solvent. The side chain of an amino acid at these positions may point away from the protein surface and out into the solvent.

In one embodiment, the method further includes incorporating into the protein the unnatural amino acid, where the unnatural amino acid comprises a first reactive group; and contacting the protein with a molecule (including but not limited to, a pharmacokinetic enhancing moiety, a water-soluble polymer, a derivative of polyethylene glycol, a photocrosslinker, a radionuclide, a cytotoxic compound, a drug, an affinity label, a photoaffinity label, a reactive compound, a resin, a second protein or polypeptide or polypeptide analog, an antibody or antibody fragment, a metal chelator, a cofactor, a fatty acid, biotin, a derivative of biotin, a biotin analogue, a moiety incorporating a heavy atom, a chemically cleavable group, a photocleavable group, an elongated side chain, a carbon-linked sugar, a redox-active agent, an amino thioacid, a toxic moiety, an isotopically labeled moiety, a biophysical probe, a phosphorescent group, a chemiluminescent group, or an electron dense group. The first reactive group reacts with the second reactive group to attach the molecule to the unnatural amino acid through a [3+2] cycloaddition. In one embodiment, the first reactive group is an alkynyl or azido moiety and the second reactive group is an azido or alkynyl moiety. For example, the first reactive group is the alkynyl moiety (including but not limited to, in unnatural amino acid p-propargyloxyphenylalanine) and the second reactive group is the azido moiety. In another example, the first reactive group is the azido moiety (including but not limited to, in the unnatural amino acid p-azido-L-phenylalanine) and the second reactive group is the alkynyl moiety.

In some cases, the naturally encoded or non-naturally encoded amino acid substitution(s) will be combined with other additions, substitutions or deletions within the DDAH polypeptide to affect other biological traits of the DDAH polypeptide. In some cases, the other additions, substitutions or deletions may increase the stability (including but not limited to, resistance to proteolytic degradation) of the DDAH polypeptide or increase affinity of the DDAH polypeptide for its substrate, activity modulator, or other DDAH polypeptide. In some cases, the other additions, substitutions or deletions may increase the pharmaceutical stability of the DDAH polypeptide. In some cases, the other additions, substitutions or deletions may enhance the activity/efficacy of the DDAH polypeptide. In some cases, the other additions, substitutions or deletions may increase the solubility (including but not limited to, when expressed in E. coli or other host cells) of the DDAH polypeptide. In some embodiments additions, substitutions or deletions may increase the DDAH polypeptide solubility following expression in E. coli or other recombinant host cells. In some embodiments sites are selected for substitution with a naturally encoded or non-natural amino acid in addition to another site for incorporation of a non-natural amino acid that results in increasing the polypeptide solubility following expression in E. coli or other recombinant host cells. In some embodiments, the DDAH polypeptides comprise another addition, substitution or deletion that modulates affinity for the DDAH polypeptide substrate, modulator such as zinc, binding proteins, or associated ligand, modulates DDAH activity, modulates circulating half-life, modulates release or bio-availability, facilitates purification, or improves or alters a particular route of administration. In some embodiments, the DDAH polypeptides comprise an addition, substitution or deletion that increases the affinity of the DDAH variant for its substrate, modulator, or other DDAH polypeptides. Similarly, DDAH polypeptides can comprise chemical or enzyme cleavage sequences, protease cleavage sequences, reactive groups, antibody-binding domains (including but not limited to, FLAG or poly-His) or other affinity based sequences (including, but not limited to, FLAG, poly-His, GST, etc.) or linked molecules (including, but not limited to, biotin) that improve detection (including, but not limited to, GFP), purification, transport through tissues or cell membranes, prodrug release or activation, DDAH size reduction, or other traits of the polypeptide.

In some embodiments, the substitution of a naturally encoded or non-naturally encoded amino acid generates a DDAH polypeptide that has decreased enzymatic activity but has greater stability when compared to unmodified DDAH. Increasing stability may result in a DDAH polypeptide that has, for example, an increased circulation time after administration to a patient even though the DDAH polypeptide has a decreased enzymatic activity, which may in certain cases be more desirable than the wild type DDAH. In some embodiments, a naturally encoded or non-naturally encoded amino acid is substituted or added in a region involved with substrate, modulator, or DDAH binding. In some embodiments, the modified DDAH polypeptide comprises at least one substitution that causes the DDAH to act as an antagonist of DDAH which may be useful to modulate the activity of a DDAH polypeptide that has been administered to a patient.

In some cases, 1, 2, 3, 4, 5, 6, 7, 8, 9, 10, or more amino acids are substituted with one or more naturally encoded or non-naturally-encoded amino acids. In some cases, the DDAH polypeptide further includes 1, 2, 3, 4, 5, 6, 7, 8, 9, 10, or more substitutions of one or more non-naturally encoded amino acids for naturally-occurring amino acids. For example, in some embodiments, one or more residues in DDAH are substituted with one or more non-naturally encoded amino acids. In some cases, the one or more non-naturally encoded residues are linked to one or more lower molecular weight PKEM, thereby enhancing binding affinity and comparable serum half-life relative to the species attached to a single, higher molecular weight pharmacokinetic enhancing moiety.

Expression in Non-Eukaryotes and Eukaryotes

To obtain high level expression of a cloned DDAH polynucleotide, one typically subclones polynucleotides encoding a DDAH polypeptide described herein into an expression vector that contains a strong promoter to direct transcription, a transcription/translation terminator, and if for a nucleic acid encoding a protein, a ribosome binding site for translational initiation. Eukaryotic expression systems for mammalian cells, yeast, and insect cells are known to those of ordinary skill in the art and are also commercially available. In cases where orthogonal tRNAs and aminoacyl tRNA synthetases (described above) are used to express the DDAH polypeptides described herein, host cells for expression are selected based on their ability to use the orthogonal components. Exemplary host cells include Gram-positive bacteria (including but not limited to *B. brevis, B. subtilis,* or *Streptomyces*) and Gram-negative bacteria (*E. coli, Pseudomonas fluorescens, Pseudomonas aeruginosa,* and *Pseudomonas putida*), as well as yeast and other eukaryotic cells. Cells comprising O-tRNA/O-RS pairs can be used as described herein.

A eukaryotic host cell or non-eukaryotic host cell can provide the ability to biosynthesize proteins that comprise natural or unnatural amino acids in large useful quantities. For example, proteins comprising an unnatural amino acid can be produced at a concentration of, including but not limited to, at least 10 µg/liter, at least 50 µg/liter, at least 75 µg/liter, at least 100 µg/liter, at least 200 µg/liter, at least 250 µg/liter, or at least 500 µg/liter, at least 1 mg/liter, at least 2 mg/liter, at least 3 mg/liter, at least 4 mg/liter, at least 5 mg/liter, at least 6 mg/liter, at least 7 mg/liter, at least 8 mg/liter, at least 9 mg/liter, at least 10 mg/liter, at least 20, 30, 40, 50, 60, 70, 80, 90, 100, 200, 300, 400, 500, 600, 700, 800, 900 mg/liter, 1 g/liter, 5 g/liter, 10 g/liter or more of protein in a cell extract, cell lysate, culture medium, a buffer, and/or the like.

Useful expression vectors for eukaryotic hosts, include but are not limited to, vectors comprising expression control sequences from SV40, bovine papilloma virus, adenovirus and cytomegalovirus. Such vectors include pCDNA3.1(+)\Hyg (Invitrogen, Carlsbad, Calif., USA) and pCI-neo (Stratagene, La Jolla, Calif., USA). Bacterial plasmids, such as plasmids from *E. coli*, including pBR322, pET3a and pET12a, wider host range plasmids, such as RP4, phage DNAs, e.g., the numerous derivatives of phage lambda, e.g., NM989, and other DNA phages, such as M13 and filamentous single stranded DNA phages may be used. The 2µ plasmid and derivatives thereof, the POT1 vector (U.S. Pat. No. 4,931,373 which is incorporated by reference), the pJSO37 vector described in (Okkels, Ann. New York Aced. Sci. 782, 202 207, 1996) and pPICZ A, B or C (Invitrogen) may be used with yeast host cells. For insect cells, the vectors include but are not limited to, pVL941, pBG311 (Cate et al., "Isolation of the Bovine and Human Genes for Mullerian Inhibiting Substance and Expression of the Human Gene In Animal Cells", Cell, 45, pp. 685 98 (1986), pBluebac 4.5 and pMelbac (Invitrogen, Carlsbad, CA).

The nucleotide sequence encoding a DDAH polypeptide may or may not also include sequence that encodes a signal peptide, coding sequence, such as: MPRLFFFHLLGVCLLLNQFSRAVA (SEQ ID NO: 16).

Examples of suitable mammalian host cells may be Chinese hamster ovary (CHO) cells, (e.g. CHO-K1; ATCC CCL-61), Green Monkey cells (COS) (e.g. COS 1 (ATCC CRL-1650), COS 7 (ATCC CRL-1651)); mouse cells (e.g. NS/O), Baby Hamster Kidney (BHK) cell lines (e.g. ATCC CRL-1632 or ATCC CCL-10), and human cells (e.g. HEK 293 (ATCC CRL-1573)), as well as plant cells in tissue culture.

Expression Systems, Culture, and Isolation

DDAH polypeptides may be expressed in any number of suitable expression systems including, for example, yeast, insect cells, mammalian cells, and bacteria.

Yeasts: Various yeasts include, but are not limited to, ascosporogenous yeasts (Endomycetales), basidiosporogenous yeasts and yeasts belonging to the Fungi imperfecti (Blastomycetes) group. The ascosporogenous yeasts are divided into two families, Spermophthoraceae and Saccharomycetaceae. The latter is comprised of four subfamilies, Schizosaccharomycoideae (e.g., genus *Schizosaccharomyces*), Nadsonioideae, Lipomycoideae and Saccharomycoideae (e.g., genera *Pichia, Kluyveromyces* and *Saccharomyces*). The basidiosporogenous yeasts include the genera *Leucosporidium, Rhodosporidium, Sporidiobolus, Filobasidium,* and *Filobasidiella*. Yeasts belonging to the Fungi Imperfecti (Blastomycetes) group are divided into two families, Sporobolomycetaceae (e.g., genera *Sporobolomyces* and *Bullera*) and Cryptococcaceae (e.g., genus *Candida*). In some cases, the yeast can be a species within the genera *Pichia, Kluyveromyces, Saccharomyces, Schizosaccharomyces, Hansenula, Torulopsis,* and *Candida*, including, but not limited to, *P. pastoris, P. guillerimondii, S. cerevisiae, S. carlsbergensis, S. diastaticus, S. douglasii, S. kluyveri, S, norbensis, S. oviformis, K. lactis, K. fragilis, C. albicans, C. maltosa,* or *H. polymorpha*.

Yeast enhancers also may be used with yeast promoters. In addition, synthetic promoters may also function as yeast promoters. For example, the upstream activating sequences (UAS) of a yeast promoter may be joined with the transcription activation region of another yeast promoter, creating a synthetic hybrid promoter. Examples of such hybrid promoters include the ADH regulatory sequence linked to the GAP transcription activation region. See U.S. Pat. Nos. 4,880,734 and 4,876,197, which are incorporated by reference herein. Other examples of hybrid promoters include promoters that consist of the regulatory sequences of the ADH2, GAL4, GAL10, or PHO5 genes, combined with the transcriptional activation region of a glycolytic enzyme gene such as GAP or PyK. See EP 0 164 556. Furthermore, a yeast promoter may include naturally occurring promoters of non-yeast origin that have the ability to bind yeast RNA polymerase and initiate transcription.

Other control elements that may comprise part of the yeast expression vectors include terminators, for example, from GAPDH or the enolase genes (Holland et al., J. BIOL. CHEM. (1981) 256:1385). In addition, the origin of replication from the 2µ plasmid origin is suitable for yeast. Methods of introducing exogenous DNA into yeast include, but are not limited to, either the transformation of spheroplasts or of intact yeast host cells treated with alkali cations.

Baculovirus-Infected Insect Cells: Baculovirus expression of DDAH polypeptides is useful and the use of rDNA technology, polypeptides or precursors thereof because DDAH may be biosynthesized in any number of host cells including bacteria, mammalian cells, insect cells, yeast or fungi. An embodiment includes biosynthesis of DDAH, modified DDAH, DDAH polypeptides, or DDAH analogs in bacteria, yeast or mammalian cells. Another embodiment involves biosynthesis done in *E. coli* or a yeast.

*E. coli, Pseudomonas* species, and other Prokaryotes: In selecting bacterial hosts for expression, suitable hosts may include those shown to have, inter alia, good inclusion body formation capacity, low proteolytic activity, and overall robustness. Industrial/pharmaceutical fermentation generally use bacterial derived from K strains (e.g. W3110) or from bacteria derived from B strains (e.g. BL21). Other examples of suitable *E. coli* hosts include, but are not limited to, strains of BL21, DH10B, or derivatives thereof. In another embodiment of the methods described herein, the *E. coli* host is a protease minus strain including, but not limited to, OMP- and LON-. The host cell strain may be a species of *Pseudomonas*, including but not limited to, *Pseudomonas fluorescens, Pseudomonas aeruginosa,* and *Pseudomonas putida. Pseudomonas fluorescens* biovar 1, designated strain MB101, is known to be useful for recombinant production and is available for therapeutic protein production processes. Examples of a *Pseudomonas* expression system include the system available from The Dow Chemical Company (Midland, MI) as a host strain.

Once a recombinant the expression construct has been introduced into the host cell and host cells with the proper expression construct are isolated, the recombinant host cell strain is cultured under conditions appropriate for production of DDAH polypeptides.

The DDAH polypeptides described herein are normally purified after expression in recombinant systems. In embodiments, amino acid substitutions may readily be made in the DDAH polypeptide that are selected for the purpose of increasing the solubility of the recombinantly produced protein utilizing the methods disclosed herein as well as those known in the art. In the case of insoluble protein, the protein may be collected from host cell lysates by centrifugation and may further be followed by homogenization of the cells. In the case of poorly soluble protein, compounds including, but not limited to, polyethylene imine (PEI) may be added to induce the precipitation of partially soluble protein.

Insoluble or precipitated DDAH polypeptide may then be solubilized using any suitable solubilization agents known to the art such s urea or guanidine hydrochloride.

When a DDAH polypeptide is produced as a fusion protein, the removal of a fusion sequence may be accomplished by enzymatic or chemical cleavage. Enzymatic removal of fusion sequences may be accomplished using methods known to those of ordinary skill in the art. conditions will be specified by the choice of enzyme e.g. TEV or ULP-1 as will be apparent to one of ordinary skill in the art. Methods for purification may include, but are not limited to, size-exclusion chromatography, hydrophobic interaction chromatography, ion-exchange chromatography or dialysis or any combination thereof.

Any of the following exemplary procedures can be employed for purification of DDAH polypeptides: affinity chromatography; anion- or cation-exchange chromatography (using, including but not limited to, DEAE SEPHAROSE); chromatography on silica; high performance liquid chromatography (HPLC); reverse phase HPLC; gel filtration (using, including but not limited to, SEPHADEX G-75); hydrophobic interaction chromatography; size-exclusion chromatography; metal-chelate chromatography; ultrafiltration/diafiltration; ethanol precipitation; ammonium sulfate precipitation; chromatofocusing; displacement chromatography; electrophoretic procedures (including but not limited to preparative isoelectric focusing), differential solubility (including but not limited to ammonium sulfate precipitation), SDS-PAGE, or extraction.

In the case of prokaryotic production of DDAH polypeptide, the DDAH polypeptide thus produced may be misfolded and thus lacks or has reduced biological activity. The bioactivity of the protein may be restored by "refolding by solubilizing (where the DDAH polypeptide is also insoluble), unfolding and reducing the polypeptide chain using, for example, one or more chaotropic agents (e.g. urea and/or guanidine) and a reducing agent capable of reducing disulfide bonds (e.g. dithiothreitol, DTT or 2-mercaptoethanol, 2-ME). At a moderate concentration of chaotrope, an oxidizing agent is then added (e.g., oxygen, cystine or cystamine), which allows the reformation of disulfide bonds. DDAH polypeptide may be refolded using standard methods known in the art, such as those described in U.S. Pat. Nos. 4,511,502, 4,511,503, and 4,512,922, which are incorporated by reference herein. The DDAH polypeptide may also be co-folded with other proteins to form heterodimers or heteromultimers.

The purified DDAH may be at least 90% pure (as measured by reverse phase high performance liquid chromatography, RP-HPLC, or sodium dodecyl sulfate-polyacrylamide gel electrophoresis, SDS-PAGE) or at least 95% pure, or at least 98% pure, or at least 99% or greater pure. Regardless of the exact numerical value of the purity of the DDAH, the DDAH is sufficiently pure for use as a pharmaceutical product or for further processing, such as conjugation with a pharmacokinetic enhancing moiety.

Certain DDAH molecules may be used as therapeutic agents in the absence of other active ingredients or proteins (other than excipients, carriers, and stabilizers, serum albumin and the like), or they may be complexed with another protein or a polymer.

In one embodiment, for example, the DDAH polypeptide may be reduced and denatured by first denaturing the resultant purified DDAH polypeptide in urea, followed by dilution into TRIS buffer containing a reducing agent (such as DTT) at a suitable pH. In another embodiment, the DDAH polypeptide is denatured in urea in a concentration range of between about 2 M to about 9 M, followed by dilution in TRIS buffer at a pH in the range of about 5.0 to about 8.0. The refolding mixture of this embodiment may then be incubated. In one embodiment, the refolding mixture is incubated at room temperature for four to twenty-four hours. The reduced and denatured DDAH polypeptide mixture may then be further isolated or purified.

Ion Exchange Chromatography. In one embodiment, and as an optional, additional step, ion exchange chromatography may be performed on the first DDAH polypeptide mixture. Anion or cation exchange column chromatography may be performed on the DDAH polypeptide at any stage of the purification process to isolate substantially purified DDAH polypeptide.

Reverse-Phase Chromatography. RP-HPLC may be performed to purify proteins following suitable protocols that are known to those of ordinary skill in the art.

Hydrophobic Interaction Chromatography Purification Techniques. Hydrophobic interaction chromatography (HIC) may be performed on the DDAH polypeptide.

Other Purification Techniques. Yet another isolation step using, for example, gel filtration.

In some embodiments, the yield of DDAH after each purification step may be at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, at least about 99.9%, or at least about 99.99%, of the DDAH in the starting material for each purification step.

Purity may be determined using standard techniques, such as SDS-PAGE, or by measuring DDAH polypeptide using Western blot and ELISA assays.

Additional methods that may be employed include, but are not limited to, steps to remove endotoxins.

Previously, it has been shown that unnatural amino acids can be site-specifically incorporated into proteins in vitro by the addition of chemically aminoacylated suppressor tRNAs to protein synthesis reactions programmed with a gene containing a desired amber nonsense mutation. Using these approaches, one can substitute a number of the common twenty amino acids with close structural homologues, e.g., fluorophenylalanine for phenylalanine, using strains auxotropic for a particular amino acid.

A tRNA may be aminoacylated with a desired amino acid by any method or technique, including but not limited to, chemical or enzymatic aminoacylation.

The ability to incorporate unnatural amino acids directly into proteins in vivo offers a wide variety of advantages including but not limited to, high yields of mutant proteins, technical ease, the potential to study the mutant proteins in cells or possibly in living organisms and the use of these mutant proteins in therapeutic treatments and diagnostic uses.

In one attempt to site-specifically incorporate para-F-Phe, a yeast amber suppressor tRNAPheCUA /phenylalanyl-tRNA synthetase pair was used in a p-F-Phe resistant, Phe auxotrophic *Escherichia coli* strain. See, e.g., R. Furter, *Protein Sci.,* 7:419 (1998).

Macromolecular Polymers Coupled to DDAH Polypeptides

Various modifications to the amino acid polypeptides can be effected using the compositions, methods, techniques and strategies including incorporation of further functionality onto the amino acid component of the polypeptide, including but not limited to, a pharmacokinetic enhancing moiety, a label; a dye; a polymer; a water-soluble polymer; a derivative of polyethylene glycol; a photocrosslinker; a radionuclide; a cytotoxic compound; a drug; an affinity label; a photoaffinity label; a reactive compound; a resin; a second protein or polypeptide or polypeptide analog; an antibody or antibody fragment; a metal chelator; a cofactor; a fatty acid; a carbohydrate; a polynucleotide; a DNA; a RNA; an antisense polynucleotide; a saccharide; a water-soluble dendrimer; a cyclodextrin; an inhibitory ribonucleic acid; a biomaterial; a nanoparticle; a spin label; a fluorophore, a metal-containing moiety; a radioactive moiety; a novel functional group; a group that covalently or noncovalently interacts with other molecules; a photocaged moiety; an actinic radiation excitable moiety; a photoisomerizable moiety; biotin; a derivative of biotin; a biotin analogue; a moiety incorporating a heavy atom; a chemically cleavable group; a photocleavable group; an elongated side chain; a carbon-linked sugar; a redox-active agent; an amino thioacid; a toxic moiety; an isotopically labeled moiety; a biophysical probe; a phosphorescent group; a chemiluminescent group; an electron dense group; a magnetic group; an intercalating group; a chromophore; an energy transfer agent; a biologically active agent; a detectable label; a small molecule; a quantum dot; a nanotransmitter; a radionucleotide; a radiotransmitter; a neutron-capture agent; or any combination of the above, or any other desirable compound or substance. As an illustrative, non-limiting example of the compositions, methods, techniques and strategies described herein, the following description will focus on adding macromolecular polymers to the non-natural amino acid polypeptide with the understanding that the compositions, methods, techniques and strategies described thereto are also applicable (with appropriate modifications, if necessary and for which one of skill in the art could make with the disclosures herein) to adding other functionalities, including but not limited to those listed above.

A wide variety of macromolecular polymers and other molecules can be linked to DDAH polypeptides described herein to modulate biological properties of the DDAH polypeptide, and/or provide new biological properties to the DDAH molecule. These macromolecular polymers can be linked to the DDAH polypeptide via a naturally encoded amino acid, via a non-naturally encoded amino acid, or any functional substituent of a natural or non-natural amino acid, or any substituent or functional group added to a natural or non-natural amino acid. The molecular weight of the polymer may be of a wide range, including but not limited to, between about 100 Da and about 100,000 Da or more. The molecular weight of the polymer may be between about 100 Da and about 100,000 Da, including but not limited to, 100,000 Da, 95,000 Da, 90,000 Da, 85,000 Da, 80,000 Da, 75,000 Da, 70,000 Da, 65,000 Da, 60,000 Da, 55,000 Da, 50,000 Da, 45,000 Da, 40,000 Da, 35,000 Da, 30,000 Da, 25,000 Da, 20,000 Da, 15,000 Da, 10,000 Da, 9,000 Da, 8,000 Da, 7,000 Da, 6,000 Da, 5,000 Da, 4,000 Da, 3,000 Da, 2,000 Da, 1,000 Da, 900 Da, 800 Da, 700 Da, 600 Da, 500 Da, 400 Da, 300 Da, 200 Da, and 100 Da. In some embodiments, the molecular weight of the polymer is between about 100 Da and about 50,000 Da. In some embodiments, the molecular weight of the polymer is between about 100 Da and about 40,000 Da. In some embodiments, the molecular weight of the polymer is between about 1,000 Da and about 40,000 Da. In some embodiments, the molecular weight of the polymer is between about 5,000 Da and about 40,000 Da. In some embodiments, the molecular weight of the polymer is between about 10,000 Da and about 40,000 Da.

The polymer selected may be water soluble so that the protein to which it is attached does not precipitate in an aqueous environment, such as a physiological environment. The polymer may be branched or unbranched. For therapeutic use of the end-product preparation, the polymer will be pharmaceutically acceptable.

Examples of polymers include but are not limited to certain half-life extending moieties, polyalkyl ethers and alkoxy-capped analogs thereof (e.g., polyoxyethylene glycol, polyoxyethylene/propylene glycol, and methoxy or ethoxy-capped analogs thereof, especially polyoxyethylene glycol, the latter is also known as polyethyleneglycol or PEG); polyvinylpyrrolidones; polyvinylalkyl ethers; polyoxazolines, polyalkyl oxazolines and polyhydroxyalkyl oxazolines; polyacrylamides, polyalkyl acrylamides, and polyhydroxyalkyl acrylamides (e.g., polyhydroxypropylmethacrylamide and derivatives thereof); polyhydroxyalkyl acrylates; polysialic acids and analogs thereof; hydrophilic peptide sequences; polysaccharides and their derivatives, including dextran and dextran derivatives, e.g., carboxymethyldextran, dextran sulfates, aminodextran; cellulose and its derivatives, e.g., carboxymethyl cellulose, hydroxyalkyl celluloses; chitin and its derivatives, e.g., chitosan, succinyl chitosan, carboxymethylchitin, carboxymethylchitosan; hyaluronic acid and its derivatives; starches; alginates; chondroitin sulfate; albumin; pullulan and carboxymethyl pullulan; polyaminoacids and derivatives thereof, e.g., polyglutamic acids, polylysines, polyaspartic acids, polyaspartamides; maleic anhydride copolymers such as: styrene maleic anhydride copolymer, divinylethyl ether maleic anhydride copolymer; polyvinyl alcohols; copolymers thereof; terpolymers thereof; mixtures thereof; and derivatives of the foregoing.

Those of ordinary skill in the art will recognize that the foregoing list for substantially water-soluble backbones is by no means exhaustive and is merely illustrative, and that all polymeric materials having the qualities described above are contemplated as being suitable.

In some embodiments, the polymer derivatives can be "multi-functional", backbone with at least two termini, and possibly as many as about 300 termini, functionalized or activated with a functional group. Multifunctional polymer derivatives include, but are not limited to, linear polymers having two termini, each terminus being bonded to a functional group which may be the same or different.

In one embodiment, the polymer derivative has the structure:

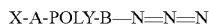

wherein:
N=N=N is an azide moiety;
B is a linking moiety, which may be present or absent;
POLY is a water-soluble non-antigenic polymer;
A is a linking moiety, which may be present or absent and may be the same as B or different; and
X is a second functional group.

Examples of a linking moiety for A and B include, but are not limited to, a multiply-functionalized alkyl group containing up to 18, and may contain between 1-10 carbon atoms. A heteroatom such as nitrogen, oxygen or sulfur may be included with the alkyl chain. The alkyl chain may also be branched at a heteroatom. Other examples of a linking moiety for A and B include, but are not limited to, a multiply functionalized aryl group, containing up to 10 and may contain 5-6 carbon atoms. The aryl group may be substituted with one more carbon atoms, nitrogen, oxygen or sulfur atoms. Other examples of suitable linking groups include those linking groups described in U.S. Pat. Nos. 5,932,462; 5,643,575; and U.S. Pat. Appl. Publication 2003/0143596, each of which is incorporated by reference herein. Those of ordinary skill in the art will recognize that the foregoing list for linking moieties is by no means exhaustive and is merely illustrative, and that all linking moieties having the qualities described above are contemplated to be suitable for use.

Examples of suitable functional groups for use as X include, but are not limited to, hydroxyl, protected hydroxyl, alkoxyl, active ester, such as N-hydroxysuccinimidyl esters and 1-benzotriazolyl esters, active carbonate, such as N-hydroxysuccinimidyl carbonates and 1-benzotriazolyl carbonates, acetal, aldehyde, aldehyde hydrates, alkenyl, acrylate, methacrylate, acrylamide, active sulfone, amine, aminooxy, protected amine, hydrazide, protected hydrazide, protected thiol, carboxylic acid, protected carboxylic acid, isocyanate, isothiocyanate, maleimide, vinylsulfone, dithiopyridine, vinylpyridine, iodoacetamide, epoxide, glyoxals, diones, mesylates, tosylates, tresylate, alkene, ketone, and azide. As is understood by those of ordinary skill in the art, the selected X moiety should be compatible with the azide group so that reaction with the azide group does not occur. The azide-containing polymer derivatives may be homobifunctional, meaning that the second functional group (i.e., X) is also an azide moiety, or heterobifunctional, meaning that the second functional group is a different functional group.

The term "protected" refers to the presence of a protecting group or moiety that prevents reaction of the chemically reactive functional group under certain reaction conditions. The protecting group will vary depending on the type of chemically reactive group being protected. For example, if the chemically reactive group is an amine or a hydrazide, the protecting group can be selected from the group of tert-butyloxycarbonyl (t-Boc) and 9-fluorenylmethoxycarbonyl (Fmoc). If the chemically reactive group is a thiol, the protecting group can be orthopyridyldisulfide. If the chemically reactive group is a carboxylic acid, such as butanoic or propionic acid, or a hydroxyl group, the protecting group can be benzyl or an alkyl group such as methyl, ethyl, or tert-butyl. Other protecting groups known in the art may also be used.

In certain embodiments, the polymer derivatives described herein comprise a polymer backbone having the structure:

wherein:
X is a functional group as described above; and
n is about 20 to about 4000.

In another embodiment, the polymer derivatives described herein comprise a polymer backbone having the structure:

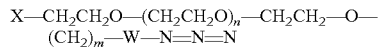

wherein:
W is an aliphatic or aromatic linker moiety comprising between 1-10 carbon atoms;
n is about 20 to about 4000
m is between 1 and 10; and
X is a functional group as described above.

The azide-containing PKEM derivatives described herein can be prepared by a variety of methods known in the art and/or disclosed herein. In one method, shown below, a water-soluble polymer backbone having an average molecular weight from about 800 Da to about 100,000 Da, the polymer backbone having a first terminus bonded to a first functional group and a second terminus bonded to a suitable leaving group, is reacted with an azide anion (which may be paired with any of a number of suitable counter-ions, including sodium, potassium, tert-butylammonium and so forth). The leaving group undergoes a nucleophilic displacement and is replaced by the azide moiety, affording the desired azide-containing PKEM polymer.

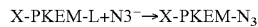

As shown, a suitable polymer backbone can have the formula X-PKEM-L, wherein PKEM is poly(ethylene glycol) and X is a functional group which does not react with azide groups and L is a suitable leaving group. Examples of suitable functional groups include, but are not limited to, hydroxyl, protected hydroxyl, acetal, alkenyl, amine, aminooxy, protected amine, protected hydrazide, protected thiol, carboxylic acid, protected carboxylic acid, maleimide, dithiopyridine, and vinylpyridine, and ketone. Examples of suitable leaving groups include, but are not limited to, chloride, bromide, iodide, mesylate, tresylate, and tosylate.

In another method for preparation of the azide-containing polymer derivatives described herein, a linking agent bearing an azide functionality is contacted with a water soluble polymer backbone having an average molecular weight from about 800 Da to about 100,000 Da, wherein the linking agent bears a chemical functionality that will react selectively with a chemical functionality on the PKEM polymer, to form an azide-containing polymer derivative product wherein the azide is separated from the polymer backbone by a linking group.

An exemplary reaction scheme is shown below:

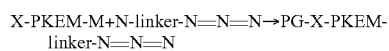

wherein:
PKEM is poly(ethylene glycol) and X is a capping group such as alkoxy or a functional group as described above; and
M is a functional group that is not reactive with the azide functionality but that will react efficiently and selectively with the N functional group.

Examples of suitable functional groups include, but are not limited to, M being a carboxylic acid, carbonate or active ester if N is an amine; M being a ketone if N is a hydrazide or aminooxy moiety; M being a leaving group if N is a nucleophile.

A more specific example is shown below in the case of PKEM diamine, in which one of the amines is protected by a protecting group moiety such as tert-butyl-Boc and the resulting mono-protected PKEM diamine is reacted with a linking moiety that bears the azide functionality:

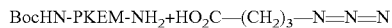

BocHN-PKEM-NH$_2$+HO$_2$C—(CH$_2$)$_3$—N=N=N

In this instance, the amine group can be coupled to the carboxylic acid group using a variety of activating agents such as thionyl chloride or carbodiimide reagents and N-hydroxysuccinimide or N-hydroxybenzotriazole to create an amide bond between the monoamine PKEM derivative and the azide-bearing linker moiety. After successful formation of the amide bond, the resulting N-tert-butyl-Boc-protected azide-containing derivative can be used directly to modify bioactive molecules or it can be further elaborated to install other useful functional groups. For instance, the N-t-Boc group can be hydrolyzed by treatment with strong acid to generate an omega-amino-PKEM-azide. The resulting amine can be used as a synthetic handle to install other useful functionality such as maleimide groups, activated disulfides, activated esters and so forth for the creation of valuable heterobifunctional reagents.

Heterobifunctional derivatives are particularly useful when it is desired to attach different molecules to each terminus of the polymer. For example, the omega-N-amino-N-azido PKEM would allow the attachment of a molecule having an activated electrophilic group, such as an aldehyde, ketone, activated ester, activated carbonate and so forth, to one terminus of the PKEM and a molecule having an acetylene group to the other terminus of the PKEM.

In another embodiment, the polymer derivative has the structure:

X-A-POLY-B—C≡C—R wherein:
R can be either H or an alkyl, alkene, alkyoxy, or aryl or substituted aryl group;
B is a linking moiety, which may be present or absent;
POLY is a water-soluble non-antigenic polymer;
A as linking moiety, may be present or absent and may be the same as B or different; and
X is a second functional group.
Examples of a linking moiety for A and B include, but are not limited to, a multiply-functionalized alkyl group containing up to 18, and may contain between 1-10 carbon atoms. A heteroatom such as nitrogen, oxygen or sulfur may be included with the alkyl chain. The alkyl chain may also be branched at a heteroatom. Other examples of a linking moiety for A and B include, but are not limited to, a multiply functionalized aryl group, containing up to 10 and may contain 5-6 carbon atoms. The aryl group may be substituted with one more carbon atoms, nitrogen, oxygen, or sulfur atoms. Other examples of suitable linking groups include those linking groups described in U.S. Pat. Nos. 5,932,462 and 5,643,575 and U.S. Pat. Appl. Publication 2003/0143596, each of which is incorporated by reference herein. Those of ordinary skill in the art will recognize that the foregoing list for linking moieties is by no means exhaustive and is intended to be merely illustrative, and that a wide variety of linking moieties having the qualities described above are contemplated to be useful.

Examples of suitable functional groups for use as X include hydroxyl, protected hydroxyl, alkoxyl, active ester, such as N-hydroxysuccinimidyl esters and 1-benzotriazolyl esters, active carbonate, such as N-hydroxysuccinimidyl carbonates and 1-benzotriazolyl carbonates, acetal, aldehyde, aldehyde hydrates, alkenyl, acrylate, methacrylate, acrylamide, active sulfone, amine, aminooxy, protected amine, hydrazide, protected hydrazide, protected thiol, carboxylic acid, protected carboxylic acid, isocyanate, isothiocyanate, maleimide, vinylsulfone, dithiopyridine, vinylpyridine, iodoacetamide, epoxide, glyoxals, diones, mesylates, tosylates, and tresylate, alkene, ketone, and acetylene. As would be understood, the selected X moiety should be compatible with the acetylene group so that reaction with the acetylene group does not occur. The acetylene-containing polymer derivatives may be homobifunctional, meaning that the second functional group (i.e., X) is also an acetylene moiety, or heterobifunctional, meaning that the second functional group is a different functional group.

In another embodiment, the polymer derivatives comprise a polymer backbone having the structure:

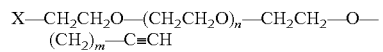

X—CH$_2$CH$_2$O—(CH$_2$CH$_2$O)$_n$—CH$_2$CH$_2$—O—(CH$_2$)$_m$—C≡CH wherein:
X is a functional group as described above;
n is about 20 to about 4000; and
m is between 1 and 10.
Specific examples of each of the heterobifunctional PKEM polymers are shown below.

The acetylene-containing PKEM derivatives described herein be prepared using methods known to those of ordinary skill in the art and/or disclosed herein. In one method, a water-soluble polymer backbone having an average molecular weight from about 800 Da to about 100,000 Da, the polymer backbone having a first terminus bonded to a first functional group and a second terminus bonded to a suitable nucleophilic group, is reacted with a compound that bears both an acetylene functionality and a leaving group that is suitable for reaction with the nucleophilic group on the PKEM. When the PKEM polymer bearing the nucleophilic moiety and the molecule bearing the leaving group are combined, the leaving group undergoes a nucleophilic displacement and is replaced by the nucleophilic moiety, affording the desired acetylene-containing polymer.

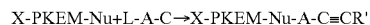

X-PKEM-Nu+L-A-C→X-PKEM-Nu-A-C≡CR'

As shown, a preferred polymer backbone for use in the reaction has the formula X-PKEM-Nu, wherein PKEM is poly(ethylene glycol), Nu is a nucleophilic moiety and X is a functional group that does not react with Nu, L or the acetylene functionality.

Examples of Nu include, but are not limited to, amine, alkoxy, aryloxy, sulfhydryl, imino, carboxylate, hydrazide, aminoxy groups that would react primarily via a SN2-type mechanism. Additional examples of Nu groups include those functional groups that would react primarily via a nucleophilic addition reaction. Examples of L groups include chloride, bromide, iodide, mesylate, tresylate, and tosylate and other groups expected to undergo nucleophilic displacement as well as ketones, aldehydes, thioesters, olefins, alpha-beta unsaturated carbonyl groups, carbonates and other electrophilic groups expected to undergo addition by nucleophiles.

In another embodiment, A is an aliphatic linker of between 1-10 carbon atoms or a substituted aryl ring of between 6-14 carbon atoms. X is a functional group which does not react with azide groups and L is a suitable leaving group.

In another method for preparation of the acetylene-containing polymer derivatives, a PKEM polymer having an average molecular weight from about 800 Da to about 100,000 Da, bearing either a protected functional group or a capping agent at one terminus and a suitable leaving group at the other terminus is contacted by an acetylene anion.

An exemplary reaction scheme is shown below:

wherein:

PKEM is poly(ethylene glycol) and X is a capping group such as alkoxy or a functional group as described above; and R' is either H, an alkyl, alkoxy, aryl or aryloxy group or a substituted alkyl, alkoxyl, aryl or aryloxy group.

In the example above, the leaving group L should be sufficiently reactive to undergo SN2-type displacement when contacted with a sufficient concentration of the acetylene anion. The reaction conditions required to accomplish SN2 displacement of leaving groups by acetylene anions are known to those of ordinary skill in the art.

Purification of the crude product can usually be accomplished by methods known in the art including, but are not limited to, precipitation of the product followed by chromatography, if necessary.

PKEM can be linked to the DDAH polypeptides described herein. The PKEM may be linked via a naturally encoded amino acid, a derivitized naturally encoded amino acid, or a non-naturally encoded amino acid incorporated in the DDAH polypeptide or any functional group or substituent of a non-naturally encoded or naturally encoded amino acid, or any functional group or substituent added to a non-naturally encoded or naturally encoded amino acid. Alternatively, the PKEM are linked to a DDAH polypeptide incorporating a non-naturally encoded amino acid via a naturally-occurring amino acid (including but not limited to, cysteine, lysine or the amine group of the N-terminal residue). In some cases, the DDAH polypeptides comprise 1, 2, 3, 4, 5, 6, 7, 8, 9, 10 non-natural amino acids, wherein one or more non-naturally-encoded amino acid(s) are linked to a pharmacokinetic enhancing moiety or moieties. In some cases, the DDAH polypeptides further comprise 1, 2, 3, 4, 5, 6, 7, 8, 9, 10, or more naturally-encoded amino acid(s) linked to a pharmacokinetic enhancing moiety or moieties. In some cases, the DDAH polypeptides described herein can comprise one or more non-naturally encoded amino acid(s) linked to PKEM and one or more naturally-occurring amino acids linked to PKEM. In some embodiments, the PKEM can enhance the serum half-life of the DDAH polypeptide relative to the unconjugated form.

The number of PKEM linked to a DDAH polypeptide described herein can be adjusted to provide an altered (including but not limited to, increased or decreased) pharmacologic, pharmacokinetic or pharmacodynamic characteristic such as in vivo half-life. In some embodiments, the half-life of DDAH is increased at least about 10, 20, 30, 40, 50, 60, 70, 80, 90 percent, 2-fold, 5-fold, 6-fold, 7-fold, 8-fold, 9-fold, 10-fold, 11-fold, 12-fold, 13-fold, 14-fold, 15-fold, 16-fold, 17-fold, 18-fold, 19-fold, 20-fold, 25-fold, 30-fold, 35-fold, 40-fold, 50-fold, or at least about 100-fold over an unmodified polypeptide.

PKEM Derivatives Containing a Strong Nucleophilic Group (i.e., Hydrazide, Hydrazine, Hydroxylamine or Semicarbazide)

In one embodiment, a DDAH polypeptide comprising a carbonyl-containing non-naturally encoded amino acid is modified with a PKEM derivative that contains a terminal hydrazine, hydroxylamine, hydrazide or semicarbazide moiety that is linked directly to the PKEM backbone.

In some embodiments, the hydroxylamine-terminal PKEM derivative will have the structure:

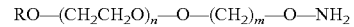

where R is a simple alkyl (methyl, ethyl, propyl, etc.), m is 2-10 and n is 100-1,000 (i.e., average molecular weight is between 5-40 kDa).

In some embodiments, the hydrazine- or hydrazide-containing PKEM derivative will have the structure:

where R is a simple alkyl (methyl, ethyl, propyl, etc.), m is 2-10 and n is 100-1,000 and X is optionally a carbonyl group (C=O) that can be present or absent.

In some embodiments, the semicarbazide-containing PKEM derivative will have the structure:

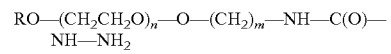

where R is a simple alkyl (methyl, ethyl, propyl, etc.), m is 2-10 and n is 100-1,000.

In another embodiment, a DDAH polypeptide comprising a carbonyl-containing amino acid is modified with a PKEM derivative that contains a terminal hydroxylamine, hydrazide, hydrazine, or semicarbazide moiety that is linked to the PKEM backbone by means of an amide linkage.

In some embodiments, the hydroxylamine-terminal PKEM derivatives have the structure:

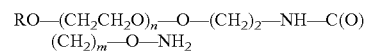

where R is a simple alkyl (methyl, ethyl, propyl, etc.), m is 2-10 and n is 100-1,000 (i.e., average molecular weight is between 5-40 kDa).

In some embodiments, the hydrazine- or hydrazide-containing PKEM derivatives have the structure:

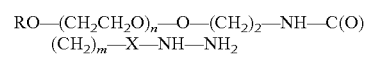

where R is a simple alkyl (methyl, ethyl, propyl, etc.), m is 2-10, n is 100-1,000 and X is optionally a carbonyl group (C=O) that can be present or absent.

In some embodiments, the semicarbazide-containing PKEM derivatives have the structure:

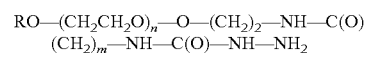

where R is a simple alkyl (methyl, ethyl, propyl, etc.), m is 2-10 and n is 100-1,000.

In another embodiment, a DDAH polypeptide comprising a carbonyl-containing amino acid is modified with a branched PKEM derivative that contains a terminal hydrazine, hydroxylamine, hydrazide or semicarbazide moiety, with each chain of the branched PKEM having a MW ranging from 10-40 kDa and, may be from 5-20 kDa.

In another embodiment, a DDAH polypeptide comprising a non-naturally encoded amino acid is modified with a PKEM derivative having a branched structure. For instance, in some embodiments, the hydrazine- or hydrazide-terminal PKEM derivative will have the following structure:

[RO—(CH$_2$CH$_2$O)$_n$—O—(CH$_2$)$_2$—NH—C(O)]$_2$CH(CH$_2$)$_m$—X—NH—NH$_2$ where R is a simple alkyl (methyl, ethyl, propyl, etc.), m is 2-10 and n is 100-1,000, and X is optionally a carbonyl group (C═O) that can be present or absent.

In some embodiments, the PKEM derivatives containing a semicarbazide group will have the structure:

[RO—(CH$_2$CH$_2$O)$_n$—O—(CH$_2$)$_2$—C(O)—NH—CH$_2$—CH$_2$]$_2$CH—X—(CH$_2$)$_m$—NH—C(O)—NH—NH$_2$ where R is a simple alkyl (methyl, ethyl, propyl, etc.), X is optionally NH, O, S, C(O) or not present, m is 2-10 and n is 100-1,000.

In some embodiments, the PKEM derivatives containing a hydroxylamine group will have the structure:

[RO—(CH$_2$CH$_2$O)$_n$—O—(CH$_2$)$_2$—C(O)—NH—CH$_2$—CH$_2$]$_2$CH—X—(CH$_2$)$_m$—O—NH$_2$ where R is a simple alkyl (methyl, ethyl, propyl, etc.), X is optionally NH, O, S, C(O) or not present, m is 2-10 and n is 100-1,000.

Methods and chemistry for activation of polymers as well as for conjugation of peptides are described in the literature and are known in the art. Commonly used methods for activation of polymers include, but are not limited to, activation of functional groups with cyanogen bromide, periodate, glutaraldehyde, biepoxides, epichlorohydrin, divinylsulfone, carbodiimide, sulfonyl halides, trichlorotriazine, etc. (see, R. F. Taylor, (1991), PROTEIN IMMOBILISATION. FUNDAMENTAL AND APPLICATIONS, Marcel Dekker, N.Y.; S. S. Wong, (1992), CHEMISTRY OF PROTEIN CONJUGATION AND CROSSLINKING, CRC Press, Boca Raton; G. T. Hermanson et al., (1993), IMMOBILIZED AFFINITY LIGAND TECHNIQUES, Academic Press, N.Y.; Dunn, R. L., et al., Eds. POLYMERIC DRUGS AND DRUG DELIVERY SYSTEMS, ACS Symposium Series Vol. 469, American Chemical Society, Washington, D.C. 1991).

Several reviews and monographs on the functionalization and conjugation of PKEM are available. See, for example, Harris, Macromol. Chem. Phys. C25: 325-373 (1985); Scouten, Methods in Enzymology 135: 30-65 (1987); Wong et al., Enzyme Microb. Technol. 14: 866-874 (1992); Delgado et al., Critical Reviews in Therapeutic Drug Carrier Systems 9: 249-304 (1992); Zalipsky, Bioconjugate Chem. 6: 150-165 (1995).

Methods for activation of polymers can also be found in WO 94/17039, U.S. Pat. No. 5,324,844, WO 94/18247, WO 94/04193, U.S. Pat. Nos. 5,219,564, 5,122,614, WO 90/13540, U.S. Pat. No. 5,281,698, and WO 93/15189, and for conjugation between activated polymers and enzymes including but not limited to Coagulation Factor VIII (WO 94/15625), hemoglobin (WO 94/09027), oxygen carrying molecule (U.S. Pat. No. 4,412,989), ribonuclease and superoxide dismutase (Veronese at al., App. Biochem. Biotech. 11: 141-52 (1985)). All references and patents cited are incorporated by reference herein.

PKEMylation (i.e., addition of any water-soluble polymer) of DDAH polypeptides containing a non-naturally encoded amino acid, such as p-azido-L-phenylalanine, is carried out by any convenient method. For example, DDAH polypeptide is PKEMylated with an alkyne-terminated PKEM derivative. Briefly, an excess of solid PKEM(5000)-O—CH$_2$—C≡CH is added, with stirring, to an aqueous solution of p-azido-L-Phe-containing DDAH polypeptide at room temperature. Typically, the aqueous solution is buffered with a buffer having a pKa near the pH at which the reaction is to be carried out (generally about pH 4-10). Examples of suitable buffers for PKEMylation at pH 7.5, for instance, include, but are not limited to, HEPES, phosphate, borate, TRIS-HCl, EPPS, and TES. The pH is continuously monitored and adjusted if necessary. The reaction is typically allowed to continue for between about 1-48 hours.

The reaction products are subsequently subjected to hydrophobic interaction chromatography to separate the PKEMylated DDAH polypeptide variants from free PKEM (5000)-O—CH$_2$—C≡CH and any high-molecular weight complexes of the pegylated DDAH polypeptide which may form when unblocked PKEM is activated at both ends of the molecule, thereby crosslinking DDAH polypeptide variant molecules. The conditions during hydrophobic interaction chromatography are such that free PKEM(5000)-O—CH$_2$—C≡CH flows through the column, while any crosslinked PKEMylated DDAH polypeptide variant complexes elute after the desired forms, which contain one DDAH polypeptide variant molecule conjugated to one or more PKEM groups. Suitable conditions vary depending on the relative sizes of the cross-linked complexes versus the desired conjugates and are readily determined by those of ordinary skill in the art. The eluent containing the desired conjugates is concentrated by ultrafiltration and desalted by diafiltration.

A pharmacokinetic enhancing moiety linked to an amino acid of a DDAH polypeptide can be further derivatized or substituted without limitation.

Azide-Containing PKEM Derivatives

In another embodiment, a DDAH polypeptide is modified with a PKEM derivative that contains an azide moiety that will react with an alkyne moiety present on the side chain of the non-naturally encoded amino acid. In general, the PKEM derivatives will have an average molecular weight ranging from 1-100 kDa and, in some embodiments, from 10-40 kDa.

In some embodiments, the azide-terminal PKEM derivative will have the structure:

RO—(CH$_2$CH$_2$O)$_n$—O—(CH$_2$)$_m$—N$_3$ where R is a simple alkyl (methyl, ethyl, propyl, etc.), m is 2-10 and n is 100-1,000 (i.e., average molecular weight is between 5-40 kDa).

In another embodiment, the azide-terminal PKEM derivative will have the structure:

RO—(CH$_2$CH$_2$O)$_n$—O—(CH$_2$)$_m$—NH—C(O)—(CH$_2$)$_p$—N$_3$ where R is a simple alkyl (methyl, ethyl, propyl, etc.), m is 2-10, p is 2-10 and n is 100-1,000 (i.e., average molecular weight is between 5-40 kDa).

In another embodiment, a DDAH polypeptide comprising a alkyne-containing amino acid is modified with a branched PKEM derivative that contains a terminal azide moiety, with each chain of the branched PKEM having a MW ranging from 10-40 kDa and may be from 5-20 kDa. For instance, in some embodiments, the azide-terminal PKEM derivative will have the following structure:

[RO—(CH$_2$CH$_2$O)$_n$—O—(CH$_2$)$_2$—NH—C(O)]$_2$CH(CH$_2$)$_m$—X—(CH$_2$)$_p$N$_3$ where R is a simple alkyl (methyl, ethyl, propyl, etc.), m is 2-10, p is 2-10, and n is 100-1,000, and X is optionally an O, N, S or carbonyl group (C═O), in each case that can be present or absent.

Alkyne-Containing PKEM Derivatives

In another embodiment, a DDAH polypeptide is modified with a PKEM derivative that contains an alkyne moiety that will react with an azide moiety present on the side chain of the non-naturally encoded amino acid.

In some embodiments, the alkyne-terminal PKEM derivative will have the following structure:

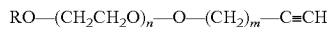

where R is a simple alkyl (methyl, ethyl, propyl, etc.), m is 2-10 and n is 100-1,000 (i.e., average molecular weight is between 5-40 kDa).

In another embodiment, a DDAH polypeptide comprising an alkyne-containing non-naturally encoded amino acid is modified with a PKEM derivative that contains a terminal azide or terminal alkyne moiety that is linked to the PKEM backbone by means of an amide linkage.

In some embodiments, the alkyne-terminal PKEM derivative will have the following structure:

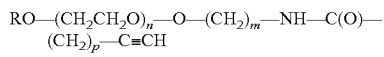

where R is a simple alkyl (methyl, ethyl, propyl, etc.), m is 2-10, p is 2-10 and n is 100-1,000.

In another embodiment, a DDAH polypeptide comprising an azide-containing amino acid is modified with a branched PKEM derivative that contains a terminal alkyne moiety, with each chain of the branched PKEM having a MW ranging from 10-40 kDa and may be from 5-20 kDa. For instance, in some embodiments, the alkyne-terminal PKEM derivative will have the following structure:

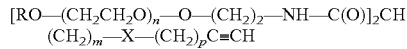

where R is a simple alkyl (methyl, ethyl, propyl, etc.), m is 2-10, p is 2-10, and n is 100-1,000, and X is optionally an O, N, S or carbonyl group (C=O), or not present.

Phosphine-Containing PKEM Derivatives

In another embodiment, a DDAH polypeptide is modified with a PKEM derivative that contains an activated functional group (including but not limited to, ester, carbonate) further comprising an aryl phosphine group that will react with an azide moiety present on the side chain of the non-naturally encoded amino acid. In general, the PKEM derivatives will have an average molecular weight ranging from 1-100 kDa and, in some embodiments, from 10-40 kDa.

In some embodiments, the PKEM derivative will have the structure:

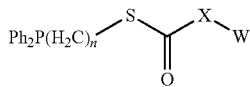

wherein n is 1-10; X can be O, N, S or not present, Ph is phenyl, and W is a pharmacokinetic enhancing moiety.

In some embodiments, the PKEM derivative will have the structure:

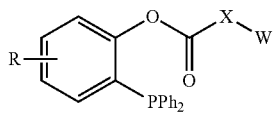

wherein X can be O, N, S or not present, Ph is phenyl, W is a pharmacokinetic enhancing moiety and R can be H, alkyl, aryl, substituted alkyl and substituted aryl groups. Exemplary R groups include but are not limited to —$CH_2$, —$C(CH_3)_3$, —OR', —NR'R", —SR', -halogen, —C(O)R', —CONR'R", —S(O)$_2$R', —S(O)$_2$NR'R", —CN and —NO$_2$. R', R", R''' and R'''' each independently refer to hydrogen, substituted or unsubstituted heteroalkyl, substituted or unsubstituted aryl, including but not limited to, aryl substituted with 1-3 halogens, substituted or unsubstituted alkyl, alkoxy or thioalkoxy groups, or arylalkyl groups. When a compound includes more than one R group, for example, each of the R groups is independently selected as are each R', R", R''' and R'''' groups when more than one of these groups is present. When R' and R" are attached to the same nitrogen atom, they can be combined with the nitrogen atom to form a 5-, 6-, or 7-membered ring. For example, —NR'R" is meant to include, but not be limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (including but not limited to, —$CF_3$ and —$CH_2CF_3$) and acyl (including but not limited to, —C(O)$CH_3$, —C(O)$CF_3$, —C(O)$CH_2OCH_3$, and the like).

Additional polymer and PEG derivatives including but not limited to, hydroxylamine (aminooxy) PEG derivatives, are described in the following patent applications which are all incorporated by reference in their entirety herein: U.S. Patent Publication No. 2006/0194256, U.S. Patent Publication No. 2006/0217532, U.S. Patent Publication No. 2006/0217289, U.S. Provisional Patent No. 60/755,338; U.S. Provisional Patent No. 60/755,711; U.S. Provisional Patent No. 60/755,018; International Patent Application No. PCT/US06/49397; WO 2006/069246; U.S. Provisional Patent No. 60/743,041; U.S. Provisional Patent No. 60/743,040; International Patent Application No. PCT/US06/47822; U.S. Provisional Patent No. 60/882,819; U.S. Provisional Patent No. 60/882,500; and U.S. Provisional Patent No. 60/870,594.

Heterologous Fc Fusion Proteins

The DDAH compounds described above may be fused directly or via a peptide linker to the Fc portion of an immunoglobulin. Immunoglobulins are molecules containing polypeptide chains held together by disulfide bonds, typically having two light chains and two heavy chains. In each chain, one domain (V) has a variable amino acid sequence depending on the antibody specificity of the molecule. The other domains (C) have a rather constant sequence common to molecules of the same class.

Depending on the desired in vivo effect, the heterologous fusion proteins may contain any of the isotypes described above or may contain mutated Fc regions wherein the complement and/or Fc receptor binding functions have been altered. Thus, the heterologous fusion proteins may contain the entire Fc portion of an immunoglobulin, fragments of the Fc portion of an immunoglobulin, or analogs thereof fused to an interferon beta compound.

The fusion proteins described here can include single chain proteins or as multi-chain polypeptides. Two or more Fc fusion proteins can be produced such that they interact through disulfide bonds. These multimers can be homogeneous with respect to the interferon beta compound or they may contain different interferon beta compounds fused at the N-terminus of the Fc portion of the fusion protein.

Regardless of the final structure of the fusion protein, the Fc or Fc-like region may serve to prolong the in vivo plasma half-life of the interferon beta compound fused at the N-terminus.

Heterologous Albumin Fusion Proteins

DDAH described herein may be fused to albumin, such as directly or via a peptide linker, water soluble polymer, or prodrug linker to albumin or an analog, fragment, or derivative thereof. Generally, the albumin proteins that are part of the fusion proteins may be derived from albumin cloned from any species, including human. A variety of polymorphic variants as well as analogs and fragments of albumin have been described. [See Weitkamp, et al., (1973) Ann. Hum. Genet. 37:219]. For example, in EP 322,094, various shorter forms of HSA. Some of these fragments of HSA are disclosed, including HSA(1-373), HSA(1-388), HSA(1-389), HSA(1-369), and HSA(1-419) and fragments between 1-369 and 1-419. EP 399,666 discloses albumin fragments that include HSA(1-177) and HSA(1-200) and fragments between HSA(1-177) and HSA(1-200).

It is understood that the heterologous fusion proteins include DDAH compounds that are coupled to any albumin protein including fragments, analogs, and derivatives wherein such fusion protein is biologically active and has a longer plasma half-life than the DDAH compound alone. Thus, the albumin portion of the fusion protein need not necessarily have a plasma half-life equal to that of native human albumin. Fragments, analogs, and derivatives are known or can be generated that have longer half-lives or have half-lives intermediate to that of native human albumin and the DDAH compound of interest.

The heterologous fusion proteins encompass proteins having conservative amino acid substitutions in the DDAH compound and/or the Fc or albumin portion of the fusion protein. A "conservative substitution" is the replacement of an amino acid with another amino acid that has the same net electronic charge and approximately the same size and shape. Amino acids with aliphatic or substituted aliphatic amino acid side chains have approximately the same size when the total number carbon and heteroatoms in their side chains differs by no more than about four. They have approximately the same shape when the number of branches in their side chains differs by no more than one. Amino acids with phenyl or substituted phenyl groups in their side chains are considered to have about the same size and shape. Except as otherwise specifically provided herein, conservative substitutions are preferably made with naturally occurring amino acids.

Numerous methods exist to characterize the fusion proteins. Some of these methods include, but are not limited to, SDS-PAGE coupled with protein staining methods or immunoblotting using anti-IgG or anti-HSA antibodies. Other methods include matrix assisted laser desorption/ionization-mass spectrometry (MALDI-MS), liquid chromatography/mass spectrometry, isoelectric focusing, analytical anion exchange, chromatofocusing, and circular dichroism.

Enhancing Affinity for Serum Albumin

Various molecules can also be fused to the DDAH polypeptides to modulate the half-life of DDAH polypeptides in serum. In some embodiments, molecules are linked or fused to DDAH polypeptides to enhance affinity for endogenous serum albumin in an animal.

For example, in some cases, a recombinant fusion of a DDAH polypeptide and an albumin binding sequence is made. Exemplary albumin binding sequences include, but are not limited to, the albumin binding domain from streptococcal protein G (see. e.g., Makrides et al., J. Pharmacol. Exp. Ther. 277:534-542 (1996) and Sjolander et al., J, Immunol. Methods 201:115-123 (1997)), or albumin-binding peptides such as those described in, e.g., Dennis, et al., J. Biol. Chem. 277:35035-35043 (2002).

In other embodiments, the DDAH polypeptides can be acylated with fatty acids. In some cases, the fatty acids promote binding to serum albumin.

In other embodiments, the DDAH polypeptides are fused directly with serum albumin (including but not limited to, human serum albumin). Those of skill in the art will recognize that a wide variety of other molecules can also be linked to DDAH polypeptides to modulate binding to serum albumin or other serum components.

Glycosylation of DDAH Polypeptides

Also described are DDAH polypeptides incorporating one or more non-naturally encoded amino acids bearing saccharide residues. The saccharide residues may be either natural (including but not limited to, N-acetylglucosamine) or non-natural (including but not limited to, 3-fluorogalactose). The saccharides may be linked to the non-naturally encoded amino acids either by an N- or O-linked glycosidic linkage (including but not limited to, N-acetylgalactose-L-serine) or a non-natural linkage (including but not limited to, an oxime or the corresponding C- or S-linked glycoside).

The saccharide (including but not limited to, glycosyl) moieties can be added to DDAH polypeptides either in vivo or in vitro. In some embodiments, a DDAH polypeptide comprising a carbonyl-containing non-naturally encoded amino acid is modified with a saccharide derivatized with an aminooxy group to generate the corresponding glycosylated polypeptide linked via an oxime linkage. Once attached to the non-naturally encoded amino acid, the saccharide may be further elaborated by treatment with glycosyltransferases and other enzymes to generate an oligosaccharide bound to the DDAH polypeptide.

In some embodiments, a DDAH polypeptide comprising a carbonyl-containing non-naturally encoded amino acid is modified directly with a glycan with defined structure prepared as an aminooxy derivative. One of ordinary skill in the art will recognize that other functionalities, including azide, alkyne, hydrazide, hydrazine, and semicarbazide, can be used to link the saccharide to the non-naturally encoded amino acid.

In some embodiments, a DDAH polypeptide comprising an azide or alkynyl-containing non-naturally encoded amino acid can then be modified by, including but not limited to, a Huisgen [3+2] cycloaddition reaction with, including but not limited to, alkynyl or azide derivatives, respectively. This method allows for proteins to be modified with extremely high selectivity.

DDAH Dimers and Multimers

Also provided are DDAH and DDAH analog combinations such as dimers, homodimers, heterodimers, multimers, homomultimers, or heteromultimers (i.e., trimers, tetramers, etc.) where a DDAH or DDAH variant polypeptide is bound to another DDAH or DDAH variant thereof or any other polypeptide that is not DDAH or DDAH variant thereof, either directly to the polypeptide N-terminus, C-terminus, or peptide backbone or via a linker or directly through the functional groups or modified functional groups of an amino acid in the DDAH polypeptide. Due to its increased molecular weight compared to monomers, the DDAH dimer or multimer conjugates may exhibit new or desirable properties, including but not limited to different pharmacological, pharmacokinetic, pharmacodynamic, modulated therapeutic half-life, or modulated plasma half-life relative to the monomeric DDAH. In some embodiments, DDAH dimmers or multimers will modulate enzymatic activity of the DDAH.

In some embodiments, one or more of the DDAH molecules present in a DDAH containing dimer or multimer is linked to a pharmacokinetic enhancing moiety.

In some embodiments, the DDAH polypeptides are linked directly, including but not limited to, at their N-termini, via a Gly residue at the N-terminus through the enzyme sortase, via an Asn-Lys amide linkage or Cys-Cys disulfide linkage. In some embodiments, the DDAH polypeptides, and/or the linked non-DDAH molecule, will comprise different amino acids to facilitate dimerization, including but not limited to, an alkyne in one non-naturally encoded amino acid of a first DDAH polypeptide and an azide in a second amino acid of a second molecule will be conjugated via a Huisgen [3+2] cycloaddition. Alternatively, DDAH, and/or the linked non-DDAH molecule comprising a ketone-containing amino acid can be conjugated to a second polypeptide comprising a hydroxylamine-containing amino acid and the polypeptides are reacted via formation of the corresponding oxime.

Alternatively, the two DDAH polypeptides, and/or the linked non-DDAH molecule, are linked via a linker. Any hetero- or homo-bifunctional linker can be used to link the two molecules, and/or the linked non-DDAH molecules, which can have the same or different primary sequence. In some cases, the linker used to tether the DDAH, and/or the linked non-DDAH molecules together can be a bifunctional pharmacokinetic enhancing moiety. The linker may have a wide range of molecular weight or molecular length. Larger or smaller molecular weight linkers may be used to provide a desired spatial relationship or conformation between DDAH and the linked entity or between the linked entity and its binding partner, if any. Linkers having longer or shorter molecular length may also be used to provide a desired space or flexibility between DDAH and the linked entity, or between the linked entity and its binding partner, if any.

Also provided are water-soluble bifunctional linkers that have a dumbbell structure that include: a) an azide, an alkyne, a hydrazine, a hydrazide, a hydroxylamine, or a carbonyl-containing moiety on at least a first end of a polymer backbone; and b) at least a second functional group on a second end of the polymer backbone. The second functional group can be the same or different as the first functional group. The second functional group, in some embodiments, is not reactive with the first functional group. Also provided, in some embodiments, are water-soluble compounds that comprise at least one arm of a branched molecular structure. For example, the branched molecular structure can be dendritic.

In some embodiments, also provided are multimers comprising one or more DDAH polypeptide, formed by reactions with water soluble activated polymers that have the structure:

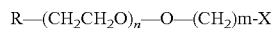

R—(CH$_2$CH$_2$O)$_n$—O—(CH$_2$)m-X wherein n is from about 5 to 3,000, m is 2-10, X can be an azide, an alkyne, a hydrazine, a hydrazide, an aminooxy group, a hydroxylamine, an acetyl, or carbonyl-containing moiety, and R is a capping group, a functional group, or a leaving group that can be the same or different as X. R can be, for example, a functional group selected from the group consisting of hydroxyl, protected hydroxyl, alkoxyl, N-hydroxysuccinimidyl ester, 1-benzotriazolyl ester, N-hydroxysuccinimidyl carbonate, 1-benzotriazolyl carbonate, acetal, aldehyde, aldehyde hydrates, alkenyl, acrylate, methacrylate, acrylamide, active sulfone, amine, aminooxy, protected amine, hydrazide, protected hydrazide, protected thiol, carboxylic acid, protected carboxylic acid, isocyanate, isothiocyanate, maleimide, vinylsulfone, dithiopyridine, vinylpyridine, iodoacetamide, epoxide, glyoxals, diones, mesylates, tosylates, and tresylate, alkene, and ketone.

First, PKEMylation of DDAH is performed to generate a longer half-life DDAH1 adduct. PEGylation of proteins is widely used in order to prolong their in vivo half-life. Several PEGylation sites are identified to be present in DDAH1. PEGylation conditions will be determined to generate an active enzyme with extended half-life, such as a circulating half-life of 6-24 hours. This will enable 1-2 injections daily to reduce ADMA levels for a desired treatment duration depending upon the condition of the patient.

With respect to diseases such as heart failure and fibrotic disease, activity of a DDAH or modified DDAH may also be determined using one or more in vivo assays. Said assays typically involve administration of a DDAH in an animal model of said disease and determining the effect on disease progression, severity, or other indicia of efficacious treatment. Such assays may be used to determine efficacious dosages and treatment regimens in the model system, and based thereon predict a dosing regimen for clinical use, e.g., for human patients. Exemplary HF assays that may be utilized include: 1) the mouse left anterior descending (LAD) coronary ligation model which mimics the cardiac changes of patients suffering a myocardial infarction and progression to HF (Samuel et al., Lab. Investigation 91:675-690, 2011); 2) limited AngII-infusion model in which minimal concentrations AngII are utilized to induce cardiac fibrosis (Xu et al., J. Cardiovasc. Pharmacol. 51:62-70, 2008); 3) Dahl-Salt sensitive rat model which is characterized by hypertension, renal impairment, and blood volume overload (Sakata et al., Circulation 109:2143-2149, 2004); 4) Aged-Spontaneously Hypertensive Rat (SHR) model of cardiac and renal fibrosis which was previously utilized to demonstrate WT-RLX efficacy (Lekgabe et al., Hypertension 46:412-418, 2005); and 5) rat thoracic aortic constriction model of pressure overload (Kuster et al., Circulation 111:420-427, 2005). In addition to these models, activity of modified DDAHs may also be determined in a dog model, such as in normal and tachypacing-induced HF dogs. Additionally, these assays may be performed to determine whether a DDAH or modified DDAH is efficacious when given not only in preventative mode, but also in therapeutic mode. Further, modified DDAHs may be tested in models of fibrosis including renal (Yoshida et al., Nephrol. Dialysis Transplant 27: 2190-2197, 2012), lung (Huang et al., Am. J. Pathol. 179:2751-2765, 2011), and liver fibrosis (Williams et al., Gut 49:577-583, 2001). For example, efficacy of a DDAH or modified DDAH may be compared to efficacy of wild-type DDAH (e.g., wild-type human DDAH).

The exact amount of DDAH, DDAH polypeptides, and/or DDAH analogues described herein is a matter of preference subject to such factors as the exact type and/or severity of the condition being treated, the condition of the patient being treated, as well as the other ingredients in the composition. The compositions and methods described herein also provide for administration of a therapeutically effective amount of another active agent. The amount to be given may be readily determined by one of ordinary skill in the art based upon therapy with DDAH, available DDAH therapies, and/or other DDAH analogues.

In accordance with embodiment 1 a DDAH polypeptide comprising
an amino acid sequence having at least 90% identity to SEQ ID NO: 1; SEQ ID NO: 2; SEQ ID NO: 5; SEQ ID NO: 6; SEQ ID NO: 7; SEQ ID NO: 9; SEQ ID NO:

10; SEQ ID NO: 11; SEQ ID NO: 12; SEQ ID NO: 13; SEQ ID NO: 14, SEQ ID NO: 15, or SEQ ID NO: 22 or fragment thereof; and a pharmacokinetic enhancing moiety (PKEM) covalently linked to said DDAH polypeptide is provided, wherein said DDAH polypeptide or fragment thereof has a molecular weight of at least about 150, 175, 200, 225, 250, 275 or 300 kDa and exhibits asymmetric dimethylarginine (ADMA) metabolizing activity.

In accordance with embodiment 2, the DDAH polypeptide of embodiment 1 is provided wherein said peptide comprises the amino acid sequence of SEQ ID NO: 15 or SEQ ID NO: 17, or an amino acid sequence that differs from SEQ ID NO: 15 or SEQ ID NO: 17 by 1-10 amino acid modifications.

In accordance with embodiment 3 the DDAH polypeptide of embodiment 1 or 2 is provided wherein said peptide comprises the amino acid sequence of SEQ ID NO: 17 or an amino acid sequence that differs from SEQ ID NO: 17 by 1-10 amino acid modifications.

In accordance with embodiment 4 the DDAH polypeptide of any one of embodiments 1-3 is provided wherein said peptide comprises an amino acid sequence having at least 95% sequence identity to SEQ ID NO: 15.

In accordance with embodiment 5 the DDAH polypeptide of any one of embodiments 1-4 is provided wherein said PKEM is selected from the group consisting of an acyl group, water soluble polymer, lipid, alkyl group, carbohydrate, polypeptide, polynucleotide, polysaccharide, antibody or antibody fragment, serum albumin, XTEN molecule, or adnectin, or said DDAH polypeptide comprises a combination said PKEMs linked to the DDAH polypeptide.

In accordance with embodiment 6 the DDAH polypeptide of any one for embodiments 1-5 is provided wherein said PKEM is polyethylene glycol (PEG), an acyl group, alkyl group or said DDAH polypeptide comprises a combination said PKEMs linked to the DDAH polypeptide.

In accordance with embodiment 7 the DDAH polypeptide of any one of embodiments 1-5 is provided wherein said PKEM is a DDAH polypeptide.

In accordance with embodiment 8 the DDAH polypeptide of any one of embodiments 1-5 is provided wherein said PKEM is an acyl group of the formula: $CH_3(CH_2)_{12}C(=O)-$, $CH_3(CH_2)_{14}C(=O)-$, $CH_3(CH_2)_{16}C(=O)-$ or $CH_3(CH_2)_{18}C(=O)-$.

In accordance with embodiment 9 the DDAH polypeptide of any one of embodiments 1-4 is provided wherein said PKEM is polyethylene glycol.

In accordance with embodiment 10 the DDAH polypeptide of any one of embodiments 1-9 is provided wherein said DDAH polypeptide or fragment thereof has a molecular weight of at least about 250 kDa.

In accordance with embodiment 11 the DDAH polypeptide of any one of embodiments 1-10 wherein said PKEM is linked to the side chain of a lysine or cysteine residue of said DDAH polypeptide.

In accordance with embodiment 12, a pharmaceutical composition is provided comprising the DDAH polypeptide of any one of embodiments 1-11 and a pharmaceutically acceptable carrier.

In accordance with embodiment 13, a method of reducing ADMA levels in a patient is provided wherein said method comprises the steps of administering a modified DDAH polypeptide to a patient in need of ADMA reduction, wherein said modified DDAH polypeptide comprises a polypeptide of any one of embodiments 1-11.

In accordance with embodiment 14, the method of embodiment 13 is provided wherein the DDAH polypeptide comprises an amino acid sequence of SEQ ID NO: 1, SEQ ID NO: 13 or an amino acid sequence having at least 95% sequence identity with SEQ ID NO: 1 or SEQ ID NO: 13; and a PMET covalently linked to said amino acid sequence, wherein said modified DDAH has a molecular weight of at least about 150, 175, 200, 225, 250, 275 or 300 kDa.

In accordance with embodiment 15 a DDAH or modified DDAH polypeptide is provided comprising: a DDAH polypeptide having at least 80% identity to SEQ ID NO: 1; SEQ ID NO: 2; SEQ ID NO: 5; SEQ ID NO: 6; SEQ ID NO: 7; SEQ ID NO: 9; SEQ ID NO: 10; SEQ ID NO: 11; SEQ ID NO: 12; SEQ ID NO: 13; or SEQ ID NO: 14, or fragment thereof, wherein said DDAH polypeptide or fragment thereof is biologically active.

In accordance with embodiment 16 the DDAH or modified DDAH polypeptide of embodiment 15 is provided further comprising at least one pharmacokinetic enhancing moiety (PKEM).

In accordance with embodiment 17 the DDAH or modified DDAH polypeptide of embodiment 15, or 16 is provided wherein said DDAH comprises the amino acid sequence of SEQ ID NO: 1; SEQ ID NO: 2; SEQ ID NO: 5; SEQ ID NO: 6; SEQ ID NO: 7; SEQ ID NO: 9; SEQ ID NO: 10; SEQ ID NO: 11; SEQ ID NO: 12; SEQ ID NO: 13; or SEQ ID NO: 14 containing zero, one, two, three, four or more amino acid substitutions, insertions, or deletions, wherein said substitutions are with natural or non-naturally encoded amino acids.

In accordance with embodiment 18 the DDAH or modified DDAH polypeptide of any one of embodiments 15-17 is provided, wherein said PKEM optionally comprises at least one acyl group, polyethylene glycol, lipid, alkyl group, carbohydrate, polypeptide, polynucleotide, polysaccharide, antibody or antibody fragment, sialic acid(s), a prodrug, serum albumin, XTEN molecule, Fc molecule, adnectin, fibronectin, a biologically active molecule, water soluble polymer, one or more DDAH polypeptides, or a combination thereof.

In accordance with embodiment 19 the DDAH polypeptide of any one of embodiments 15-18 is provided, wherein the water-soluble polymer has a molecular weight of between about 0.1 kDa and about 40 kDa or between about 0.1 kDa and about 20 kDa.

In accordance with embodiment 20 the DDAH or modified DDAH polypeptide of any one of embodiments 15-19 is provided wherein said PKEM comprises at least one acyl group optionally selected from a branched or unbranched C8-C30 acyl, a branched or unbranched C14 acyl, C16 acyl, C18 acyl, or C20 acyl, an acyl group of the formula: $CH_3(CH_2)_{12}C(=O)-$, $CH_3(CH_2)_{14}C(=O)-$, $CH_3(CH_2)_{16}C(=O)-$ or $CH_3(CH_2)_{18}C(=O)-$.

In accordance with embodiment 21 the DDAH or modified DDAH polypeptide of any one of embodiments 15-20, wherein said pharmacokinetic enhancing moiety comprises at least one serum albumin molecule or Fc molecule, optionally wherein said serum albumin comprises human serum albumin, optionally wherein said DDAH polypeptide is linked to the Cys 34 residue of said human serum albumin.

In accordance with embodiment 22 the DDAH or modified DDAH polypeptide of any one of embodiments 15-21, wherein said pharmacokinetic enhancing moiety comprises at least one XTEN molecule, optionally wherein said XTEN molecule is linked to a single modified DDAH polypeptide molecule, optionally wherein DDAH or modified DDAH polypeptide is linked to a site at or near the N-terminus of said XTEN molecule, optionally wherein said XTEN molecule is linked to multiple modified DDAH polypeptide molecules, optionally wherein each said XTEN molecule is linked to one, two, three, four, or five modified DDAH polypeptide molecules, optionally wherein each said XTEN molecule is linked to three modified DDAH polypeptide molecules, optionally wherein said three modified DDAH polypeptide molecules are linked to the XTEN molecule at or near the N-terminus, C-terminus, and internal portion of the XTEN molecule, respectively, optionally wherein said XTEN molecule comprises an unstructured recombinant polymer (URP) comprising at least 40 contiguous amino acids, wherein: (a) the URP comprises at least three different types of amino acids selected from the group consisting of glycine (G), aspartate (D), alanine (A), serine (S), threonine (T), glutamate (E) and proline (P) residues, wherein the sum of said group of amino acids contained in the URP constitutes more than about 80% of the total amino acids of the URP, and wherein said URP comprises more than one proline residue, and wherein said URP possesses reduced sensitivity to proteolytic degradation relative to a corresponding URP lacking said more than one proline residue; (b) at least 50% of the amino acids of said URP are devoid of secondary structure as determined by Chou-Fasman algorithm; and (c) the Tepitope score of said URP is less than −5, optionally wherein said XTEN molecule comprises an unstructured recombinant polymer (URP) comprising at least about 40 contiguous amino acids, and wherein (a) the sum of glycine (G), aspartate (D), alanine (A), serine (S), threonine (T), glutamate (E) and proline (P) residues contained in the URP, constitutes at least 80% of the total amino acids of the URP, and the remainder, when present, consists of arginine or lysine, and the remainder does not contain methionine, cysteine, asparagine, and glutamine, wherein said URP comprises at least three different types of amino acids selected from glycine (G), aspartate (D), alanine (A), serine (S), threonine (T), glutamate (E) and proline (P); (b) at least 50% of the at least 40 contiguous amino acids in said URP are devoid of secondary structure as determined by Chou-Fasman algorithm; and (c) wherein the URP has a Tepitope score less than −4.

In accordance with embodiment 23 the DDAH or modified DDAH polypeptide of embodiment 22, wherein each modified DDAH polypeptide is linked to said XTEN molecule through a dibenzylcyclooctyne (DBCO).

In accordance with embodiment 24 the DDAH or modified DDAH polypeptide of any one of embodiments 15-21, wherein said pharmacokinetic enhancing moiety comprises at least one adnectin, optionally wherein said adnectin comprises one or more of a BC loop, a DE loop, and an FG loop.

In accordance with embodiment 25 the DDAH or modified DDAH polypeptide of any one of embodiments 15-21, comprising at least one additional DDAH or modified DDAH polypeptide, optionally wherein said DDAH polypeptides are linked via their N-termini or via their C-termini.

In accordance with embodiment 26 the DDAH or modified DDAH polypeptide of any one of embodiments 1-24, wherein said DDAH or modified DDAH polypeptide, is linked via their N-termini or via their C-termini to said pharmacokinetics enhancing moiety.

In accordance with embodiment 27 the DDAH or modified DDAH polypeptide of any one of embodiments 1-24, wherein said DDAH or modified DDAH polypeptide, is linked to said PKEM via the lysine residues to said DDAH or modified DDAH polypeptide.

In accordance with embodiment 28 the DDAH or modified DDAH polypeptide of any one of embodiments 1-24, wherein said DDAH or modified DDAH polypeptide is linked to said PKEM via the cysteine residues to said DDAH or modified DDAH polypeptide.

In accordance with embodiment 29 the DDAH or modified DDAH polypeptide of any of claims 1-28, which exhibits an in vivo half-life of at least 1, 2, 5, 10, 12, 15, 20, 25 or more hours, optionally wherein said in vivo half-life is determined in human, mouse, rat, dog, cynomolgus monkey, rabbit, horse, cattle, cat, hamster, or rhesus macaque, optionally determined following subcutaneous or intravenous administration of said DDAH or modified DDAH polypeptide.

In accordance with embodiment 30 a composition comprising a DDAH or modified DDAH polypeptide according to any foregoing embodiments 12 and 15-29 and a pharmaceutically acceptable carrier is provided, optionally further comprising one or more other active compounds selected from: antidiabetics, hypotensive agents, perfusion-enhancing agents, lipid metabolism modulators, endothelin antagonist, PDES inhibitors, p38-kinase inhibitors, PAF-AH inhibitors, antiphlogistics, COX inhibitors, LTB4-receptor antagonists, analgesics, prostacyclin analogs, endothelin receptor antagonist, PDES inhibitor, ACE inhibitor, angiotensin receptor antagonist, diuretics and aspirin.

In accordance with embodiment 31 a method of treatment of disease, comprising administering a DDAH or modified DDAH polypeptide or a composition containing a DDAH or modified DDAH polypeptide according to any one of embodiments 1-12 and 15-29 to a subject in need thereof, optionally wherein the disease comprises heart failure or kidney failure, hypertension, resistant hypertension, organ failure or sepsis, pulmonary hypertension, COPD; optionally wherein DDAH or modified DDAH polypeptide or composition containing a DDAH or modified DDAH improves endothelial function; optionally wherein said disease comprises one or more of acute decompensated heart failure, right heart failure, left heart failure, global failure, ischemic cardiomyopathy, dilated cardiomyopathy, heart failure associated with congenital heart defects, heart failure associated with heart valve defects, mitral stenosis, mitral insufficiency, aortic stenosis, aortic insufficiency, tricuspid stenosis, tricuspid insufficiency, pulmonary stenosis, pulmonary valve insufficiency, heart failure associated with combined heart valve defects, myocardial inflammation (myocarditis), chronic myocarditis, acute myocarditis, viral myocarditis, diabetic heart failure, alcoholic cardiomyopathy, heart failure associated with cardiac storage disorders, diastolic heart failure, and systolic heart failure, optionally wherein the disease comprises cardiovascular disease, lung disease, fibrotic disease or kidney disease, optionally wherein the disease comprises pancreatitis, inflammation, cancer, gastric cancer, scleroderma, pulmonary fibrosis, renal fibrosis, hepatic fibrosis, non-alcoholic hepatosteotosis, optionally wherein the disease comprises fibrosis of the lung, heart, kidney, bone marrow, liver, dermatological fibrosis, or a fibrotic eye disorder, optionally wherein the disease comprises of erythropoietin resistance or preeclampsia, optionally wherein the disease comprises one or more of ischemia, Alzheimer's disease, corneal injury, neurodegenerative disease, cardiovascular disease, fibrotic disease, inflammation, cancer, scleroderma, pulmonary fibrosis, renal fibrosis, hepatic fibrosis, thromboembolic disorders, reperfusion damage following ischemia, micro- and macrovascular lesions (vasculitis), arterial and venous thromboses, atrial fibrillation edemas, myocardial infarction, stroke, cardio protection in connection with coronary artery bypass operations, cardio protection in connection with primary percutaneous transluminal coronary angioplasties (PTCAs), PTCAs after thrombolysis, rescue PTCA, heart transplants and open-heart operations, organ protection in connection with transplants, bypass operations, respiratory disorders, chronic obstructive pulmonary disease, chronic bronchitis, asthma, pulmonary emphysema, bronchiectases, and pulmonary hypertension, in particular pulmonary arterial hypertension, kidney disease, acute and chronic kidney diseases and acute and chronic renal insufficiencies, as well as acute and chronic renal failure with or without the requirement of dialysis, underlying or related kidney diseases, renal hypoperfusion, dialysis induced hypotension, glomerulopathies, glomerular and tubular proteinuria, renal edema, hematuria, chronic glomerulonephritis (including primary, secondary, or acute), membranous and membranoproliferative glomerulonephritis, Alport-Syndrome, glomerulosclerosis, interstistial tubular diseases, nephropathic diseases, primary and inborn kidney diseases, renal inflammation, immunological renal diseases, renal transplant rejection, immune complex induced renal diseases, intoxication induced nephropathic diseases, diabetic and non-diabetic renal diseases, pyelonephritis, cystic kidneys, nephrosclerosis, hypertensive nephrosclerosis, nephrotic syndrome, diseases that are characterized and diagnostically associated with an abnormal reduction in creatinine clearance and/or water excretion, abnormal increased blood concentrations of urea, nitrogen, potassium and/or creatinine, alteration in the activity of renal enzymes including without limitation glutamylsynthetase, urine osmolarity and urine volume, increased microalbuminuria, macroalbuminuria, glomerular and arteriolar lesions, tubular dilation, hyperphosphatemia, disease requiring dialysis for treatment, renal carcinomas, after incomplete resection of the kidney, dehydration after overuse of diuretics, uncontrolled blood pressure increase with malignant hypertension, urinary tract obstruction and infection, amyloidosis, systemic diseases associated with glomerular damage, Lupus erythematodes, rheumatic immunological systemic diseases, renal artery stenosis, renal artery thrombosis, renal vein thrombosis, analgetics induced nephropathy, renal tubular acidosis, contrast medium induced and drug induced acute and chronic interstitial kidney diseases, metabolic syndrome, dyslipemia, aftereffects associated with acute and/or chronic kidney diseases, pulmonary edema, heart failure, uremia, anemia, electrolyte disturbances, hyperkalemia, hyponatremia, bony and carbohydrate metabolism, lung diseases, asthmatic disorders, pulmonary arterial hypertension (PAH), pulmonary hypertension (PH), left-heart disease, HIV, sickle cell anemia, thromboembolisms (CTEPH), sarcoidosis, COPD, pulmonary fibrosis-associated pulmonary hypertension, chronic obstructive pulmonary disease (COPD), acute respiratory distress syndrome (ARDS), acute lung injury (ALI), alpha-1-antitrypsin deficiency (AATD), pulmonary fibrosis, pulmonary emphysema (for example pulmonary emphysema induced by cigarette smoke), cystic fibrosis (CF), fibrotic disorders, fibrotic disorders of the internal organs, fibrotic disorders of the lung, fibrotic disorders of the heart, fibrotic disorders of the kidney, fibrotic disorders of the bone marrow fibrotic disorders of the liver, dermatological fibroses, fibrotic eye disorders, osteodegenerative joint dysfunction, angiotensin-II (AngII)-mediated vasoconstriction, endothelin-1 (ET-1)-mediated vasoconstriction, ischemic conditions, ischemia associated with myocardial infarct ischemia associated with wounds, renal pathologies, renal pathologies related to vasoconstriction, or hypertension.

In accordance with embodiment 32 a method according to any one of embodiments 13, 14 or 31 is provided further comprising administration of another therapeutic agent to the subject, optionally wherein the other therapeutic agent includes an antidiabetics, hypotensive agents, perfusion-enhancing agents, lipid metabolism modulators, antithrombotic agents, antioxidants, chemokine receptor antagonists, p38-kinase inhibitors, NPY agonists, orexin agonists, anorectics, PAF-AH inhibitors, antiphlogistics, COX inhibitors, LTB4-receptor antagonists, analgesics, prostacyclin analogs, endothelin receptor antagonist, PDES inhibitor, ACE inhibitor, angiotensin receptor antagonist, diuretics or aspirin.

In accordance with embodiment 33 a composition comprising one or more polynucleotides is provided wherein the polynucleotide encode a DDAH or modified DDAH polypeptide having at least 80%, 85%, 90%, 95% or 99% sequence identity to SEQ ID NO: 1; SEQ ID NO: 2; SEQ ID NO: 5; SEQ ID NO: 6; SEQ ID NO: 7; SEQ ID NO: 9; SEQ ID NO: 10; SEQ ID NO: 11; SEQ ID NO: 12; SEQ ID NO: 13; or SEQ ID NO: 14.

In accordance with embodiment 34 an isolated cell, vector, plasmid, prokaryotic cell, eukaryotic cell, virus, mammalian cell, yeast, bacterium, or cell-free translation system comprising the composition of embodiment 33 is provided.

In accordance with embodiment 35 the DDAH or modified DDAH polypeptide of any one of embodiments 1-12 or 15-29 is provided wherein one, two, three, four or more amino acid substitutions are made relative to the native sequence of SEQ ID NO: 1; SEQ ID NO: 2; SEQ ID NO: 5; SEQ ID NO: 6; SEQ ID NO: 7; SEQ ID NO: 9; SEQ ID NO: 10; SEQ ID NO: 11; SEQ ID NO: 12; SEQ ID NO: 13; or SEQ ID NO: 14, optionally wherein said substitution are a Ser or Ala for 1, 2, 3, 4, or 5 of the Cys residues except for Cys273 of DDAH1 (SEQ ID NO: 1), or 1, 2, 3, or 4 of the Cys residues except for Cys273 of DDAH2 (SEQ ID NO: 2).

In accordance with embodiment 36 the DDAH or modified DDAH polypeptide of any one of embodiments 1-12 or 15-29 is provided wherein said DDAH polypeptide is linked to one, two, three, four or more DDAH polypeptides to form homodimers, homomultimers, heterodimers, or heteromultimers, optionally via their N-termini.

In accordance with embodiment 37 an analog of the DDAH polypeptide of SEQ ID NO: 13 having asymmetric dimethylarginine (ADMA) metabolizing activity is provided wherein said analog having the following characteristics:
   (a) a pharmacokinetic enhancing moiety (PKEM) covalently linked to said DDAH polypeptide;
   (b) a molecular weight of at least about 150 kDa, optional greater than about 250 kDa; and
   (c) 0-10 amino acid modifications relative to SEQ ID NO: 13,
   wherein the analog exhibits at least 1% activity of native GIP at the GIP receptor.

In accordance with embodiment 38 a kit is provided comprising a pharmaceutical composition of any of the embodiments disclosed herein and a device for administering said pharmaceutical composition to a patient.

The invention will now be described in more detail with respect to the following, specific, non-limiting examples.

Example 1

This example details cloning and expression of a DDAH polypeptide in *E. coli*.

Methods for cloning DDAH are known to those of ordinary skill in the art. Polypeptide and polynucleotide sequences for DDAH and cloning of DDAH into host cells are detailed in U.S. Pat. Nos. 4,758,516; 5,166,191; U.S. Pat. Nos. 5,179,195, 5,945,402; and 5,759,807; all of which patents are herein incorporated by reference.

cDNA encoding DDAH 1 and DDAH 2 are shown as SEQ ID NO: 3 and SEQ ID NO: 4 and the DDAH 1 and DDAH 2 polypeptide amino acid sequences are shown as SEQ ID NO: 1 and SEQ ID NO: 2. The polypeptide sequence of bacterial DDAH amino acid sequence *Pseudomonas aeruginosa* is shown in SEQ ID NO: 13.

TABLE 2

Human DDAH Sequences

| SEQ ID NO: | Sequence Name | Sequence |
|---|---|---|
| 1 | Human DDAH1 amino acid sequence | MAGLGHPAAF GRATHAVVRA LPESLGQHAL RSAKGEEVDV ARAERQHQLY VGVLGSKLGL QVVELPADES LPDCVFVEDV AVVCEETALI TRPGAPSRRK EVDMMKEALE KLQLNIVEMK DENATLDGGD VLFTGREFFV GLSKRTNQRG AEILADTFKD YAVSTVPVAD GLHLKSFCSM AGPNLIAIGS SESAQKALKI MQQMSDHRYD KLTVPDDIAA NCIYLNIPNK GHVLLHRTPE EYPESAKVYE KLKDHMLIPV SMSELEKVDGLLTCCSVLIN KKVDS |
| 2 | Human DDAH 2 amino acid sequence | MGTPGEGLGR CSHALIRGVP ESLASGEGAG AGLPALDLAK AQREHGVLGG KLRQRLGLQL LELPPEESLP LGPLLGDTAV IQGDTALITR PWSPARRPEV DGVRKALQDL GLRIVEIGDE NATLDGTDVL FTGREFFVGL SKWTNHRGAE IVADTFRDFA VSTVPVSGPS HLRGLCGMGG PRTVVAGSSD AAQKAVRAMA VLTDHPYASL TLPDDAAADC LFLRPGLPGV PPFLLHRGGG DLPNSQEALQ KLSDVTLVPV SCSELEKAGA GLSSLCLVLS TRPHS |
| 3 | Human DDAH1 mRNA nucleotide sequence | aacttaatgt ttttgcattg gactttgagt taagattatt attaaatcc tgaggactagcattaattga cagctgaccc aggtgctaca cagaagtgga ttcagtgaat ctaggaagacagcagcagac aggattccag gaaccagtgt ttgatgaagc taggactgag gagcaagcgagcaagcagca gttcgtggaa tcctgtctgc tgctgtcttc ctggtttagg agccgacgggcgctcgcagg ctcagcgcgc gctgcccgcg gcaggacccg gccgcctccg ccgccgccgc cgccctaag cctcccgaag ccatggccgg gctcggccac cccgccgcct tcggccgggccacccacgcc gtggtgcggg cgctacccga gtcgctcggc cagcacgcgc tgagaagcgccaagggcgag gaggtggacg tcgcccgcgc ggaacggcag caccagctct acgtgggcgtgctgggcagc aagctgggggc tgcaggtggt ggagctgccg gccgacgaga gccttccggactgcgtcttc gtggaggacg tggccgtggt gtgcgaggag acggccctca tcacccgacc cggggcgccg agccggagga aggaggttga catgatgaaa gaagcattag aaaaacttcagctcaatata gtagagatga aagatgaaaa tgcaacttta gatggcgag atgttttattcacaggcaga gaatttttttg tgggcctttc caaaaggaca aatcaacgag gtgctgaaatcttggctgat acttttaagg actatgcagt ctccacagtg ccagtggcag atgggttgcatttgaagagt ttctgcagca tggctgggcc taacctgatc gcaattgggt ctagtgaatc tgcacagaag gcccttaaga tcatgcaaca gatgagtgac caccgctacg acaaactcactgtgcctgat gacatagcag caaactgtat atatctaaat atccccaaca aagggcacgtcttgctgcac cgaaccccgg aagagtatcc agaaagtgca aaggtttatg agaaactgaaggaccatatg ctgatccccg tgagcatgtc tgaactggaa aaggtggatg ggctgctcacctgctgctca gtttttaatta acaagaaagt agactcctga gctgcagagt ccccccccggt agccggcaag accgcacagg caaggccgat gactctgtgc ccactcctgt tgttttccttgacaatctac tgtgccactg tgctactaac tcttgtttac aaaatttgat tctaagttgaattgcttcat tcaacaccc caccctcct cccrcgagg tggtacctaa gctgtggatttgctaaatga attaagcaac ctagaagata cagagctaat gaattatcaa aatgtgattaatcccagtaa ggaaacactc atttagtgtc tgtattttgt gtgtnaaaat tatttagttg ccagtatatt ctgaagaatg tcttcttgat cagtcagata agcttgcttt ttttttttttttttcatgaa tcatgtttgg ttcctgtgaa agtccctggt ccaggatcc tcctcctactcattactt ctg |
| 4 | Human DDAH2 mRNA nucleotide sequence | ccgcttagac aatgccccgg agccgccaga ccgtcgcgcc cctgccccat cgtagtatatgagctcgcct acacaaggac ccccgctaaa agccagagct cccagtcccc gaggcttgaagacggggact cccttctcca ccaactctgt cctcggggg tggggcccca gccgagatcacagcgcgaca ggagtggggg tggccgctgg agacaggtga agaaacaaga aaactaagaaatccgagcgg ttgaggggg agtctgtgtg gatgggatgg ggacgccggg ggaggggctg ggccgctgct cccatgccct gatccgggga gtcccagaga gcctggcgtc gggggaaggtgcgggggctg gccttcccgc tctggatctg gccaaagctc aaggggagca cggggtgctgggaggtaaac tgaggcaacg actggggcta cagctgctag aactgccacc tgaggagtcattgccgctgg gaccgctgct tggcgacacg gccgtgatcc aagggggacac ggccctaatcacgcggccct ggagcccgc tcgtaggcca gaggtcgatg gagtccgcaa agccctgcaa gacctggggc tccgaattgt ggaaatagga gacgagaacg cgacgctgga tggcactgacgttctcttca ccggccgggga gttttttcgta ggcctctcca aatgaccaa tcaccgaggagctgagatcg tggcggacac gttccgggac ttcgccgtct ccactgtgcc agtctcgggtccctcccacc tgcgcggtct ctgcggcatg gggggacctc gcactgttgt ggcaggcagcagcgacgctg cccaaaaggc tgtccgggca atggcagtgc tgacagatca cccatatgcc tccctgacccc tccagatga cgcagctgct gactgcctct acttcgtcc tgggttgcctggtgtgcccc ctttcctcct gcaccgtgga ggtggggatc tgcccaacag |

TABLE 2-continued

Human DDAH Sequences

| SEQ ID NO: | Sequence Name | Sequence |
|---|---|---|
| | | ccaggaggcactgcagaagc tctctgatgt caccctggta cctgtgtcct gctcagaact ggagaaggctggcgccgggc tcagctccct ctgcttggtg ctcagcacac gcccccacag ctgagggcctggccttgggg tactgctggc caggggtagg atagtatagg aagtagaagg ggaaggaggg ttagatagag aatgctgaat aggcagtagt tgggagagag cctcaatatt gggggagggagagtgtagg gaaaaggatc cactgggtga atcctccctc tcagaaccaa taaaatagaattgaccttt aaaaaaaaaa aaaaaaaaa a |
| 5 | Human DDAH1 isoform 2 amino acid sequence (missing residues 1-103 of DDAH1) | MMKEALEKLQ LNIVEMKDEN ATLDGGDVLF TGREFFVGLS KRTNQRGAEI LADTFKDYAV STVPVADGLH LKSFCSMAGP NLIAIGSSES AQKALKIMQQ MSDHRYDKLT VPDDIAANCI YLNIPNKGHV LLHRTPEEYP ESAKVYEKLK DHMLIPVSMS ELEKVDGLLT CCSVLINKKV DS |

TABLE 3

Bovine DDAH Sequences

| SEQ ID NO: | Sequence Name | Sequence |
|---|---|---|
| 6 | Bovine DDAH1 amino acid sequence | MASLGHPATF GRATHVVVRA LPESLAQQAL RRTKGDEVDF ARAERQHQLY VGVLGSKLGLQVVQLPADES LPDCVFVEDV AVVCEETALI TRPGAPSRRK EADMMKEALE KLQLNIVEMK DENATLDGGD VLFTGREFFV GLSKRTNQRG AEILADTFKD YAVSTVPVVD ALHLKSFCSM AGPNLIAIGS SESAQKALKI MQQMSDHRYD KLTVPDDTAA NCIYLNIPSK GHVLLHRTPE EYPESAKVYE KLKDHMLIPV SNSELEKVDG LLTCSSVLIN KKVDS |
| 7 | Bovine DDAH 2 amino acid sequence | MGTPGEGLGR CSHALIRGVP ESLASGEGAA AGLPALDLAK AQREHGVLGG KLRQRLGLQL VELPPEESLP LGPLLGDTAV IQGDTALITR PWSPARRPEV DGVRKALQDL GLRIVEMGDE NATLDGTDVL FTGREFFVGL SKWTNHRGAE IVADTFRDFA VSTVPVTSTS HLRGLCGMGG PRTVVAGSSE AAQKAVRAMA VLTDHPYASL TLPDDAAADC LFLRPGQPGL PPFLLHRGGG DLPNSQEALQ KLSDVTLVPV SCSELEKAGA GLSSLCLVLS TRPHN |
| 8 | Bovine DDAH1 nucleotide sequence | atggcttctc tcggccaccc agccaccttt ggccgggcca cccatgtcgt ggtacgggcgctgcccgagt ccctcgccca acaggcgctg aggcgcacca agggcgacga ggtggatttcgcccgcgctg agcggcagca ccagctctac gtgggcgtgc tgggcagtaa actggggctgcaggtggtgc agctgcccgc cgacgagagc ctcccagact gcgtgttcgt ggaggacgtggccgtggtgt gcgaggagac ggccctgatc acccgccccg ggcgccgag ccggaggaag gaggctgaca tgatgaaaga agcactagaa aaacttcagc tcaacatagt agagatgaaagatgaaaatg caactttaga tggtggagat gtcttattca caggcagaga atttttgtgggcctttcca aaaggacaaa tcaacgaggt gcggaaatct ggctgataac ttttaaggactatgcggtct ccacggtccc tgtggtggat gctttgcact gaagagttt ctgcagcatggctgggccta acctaatcgc tattggatcc agtgaatctg cacagaaggc cctcaagatc atgcaacaga tgagtgatca tcgctacgac aaactcacag tgcctgatga cacggccgcaaactgcatat acctgaatat ccccagcaaa ggccacgtct gctgcaccg aaccccagaagagtacccag agagtgcaaa ggtttatgaa agctgaagg accatatgct gatcccgtgagcaattctg aactggaaaa ggtgacgggg ctgctcacct gcagctcggt tttaattaacaagaaagtag actcctga |

TABLE 4

Murine DDAH Sequences

| SEQ ID NO: | Sequence Name | Sequence |
|---|---|---|
| 9 | Murine DDAH1 amino acid sequence | MAGLGHPSAF GRATHAVVRA PPESLCRHAL RRSQGEEVDF ARAERQHELY VGVLGSKLGL QVVQLPADES LPDCVFVEDV AVVCEETALI TRPGAPSRRK EVDMMKEALE KLQLNIVEMK DENATLDGGD VLFTGREFFV GLSKRTNQRG AEILADTFKD YAVSTVPVAD SLHLKSFCSM AGPNLIAIGS SESAQKALKI MQQMSDHRYD KLTVPDDMAA NCIYLN1PSK GHVLLHRTPE EYPESAKVYE KLKDHLLIPV SNSEMEKVDG LLTCCSVFIN KKIDS |
| 10 | Murine DDAH 2 amino acid sequence | MGTPGEGLGR CSHALIRGVP ESLASGEGAG AGLPALDLAK AQREHGVLGG KLRQRLGLQL LELPPEESLP LGPLLGDTAV IQGDTALITR PWSPARRPEV DGVRKALQDL GLRIVEMGDE NATLDGTDVL FTGREFFVGL SKWTNHRGAE IVADTFRDFA VSTVPVSGSS HLRGLCGMGG PRTVVAGSSE AAQKAVRAMA ALTDHPYASL TLPDDAASDC LFLRPGLPGA TPFLLHRGGG DLPNSQEALQ KLSDVTLVPV SCSELEKAGA GLSSLCLVLS TRPHC |

TABLE 5

Rat DDAH Sequences

| SEQ ID NO: | Sequence Name | Sequence |
|---|---|---|
| 11 | Rat DDAH1 amino acid sequence | MAGLSHPSVF GRATHAVVRA PPESLCRHAL RRSQGEEVDF ARAERQHQLY VGVLGSKLGLQVVQLPADES LPDCVFVEDV AVVCEETALI TRPGAPSRRK EVDMMKEALE KLQLNIVEMKDENATLDGGD VLFTGREFFV GLSKRTNQRG AEILADTFKD YAVSTVPVAD SLHLKSFCSM AGPNLIAIGS SESAQKALKI MQQMSDHRYD KLTVPDDMAA NCIYLNIPSK GHVLLHRTPE EYPESAKVYE KLKDHLLIPV SNSEMEKVDG LLTCCSVFIN KKTDS |
| 12 | Rat DDAH 2 amino acid sequence | MGTPGEGLGR CSHALIRGVP ESLASGEGAG AGLPALDLAK AQREHGVLGG KLRQRLGLQLLELPPEESLP LGPLLGDTAV IQGDTALITR PWSPARRPEV DGVRKALQDL GLRIVEMGDENATLDGTDVL FTGREFFVGL SKWTNHRGAE IVADTFRDFA VSTVPVSGAS HLRGLCGMGGPRTVVAGSSE AAQKAVRAMA ALTDHPYASL TLPDDAASDC LFLRPGLPGT TPFLLHRGGGDLPNSQEALQ KLSDVTLVPV SCSELEKVGA GLSSLCLVLS TRPHC |

TABLE 6

Bacterial DDAH Sequences

| SEQ ID NO: | Sequence Name | Sequence |
|---|---|---|
| 13 | Bacterial DDAH amino acid sequence *Pseudomonas aeruginosa* | MFKHIIARTP ARS LVDGLTS SHLGKPDYAK ALEQHNAYIR ALQTCDVDIT LLPPDERFPDSVFVEDPVLC TSRCAIITRP GAESRRGETE IIEETVQRFY PGKVERIEAP GTVEAGDIMMVGDHFYIGES ARTNAEGARQ MIAILEKHGL SGSVVRLEKV LHLKTGLAYL EHNNLLAAGEFVSKPEFQDF NIIEIPEEES YAANCIWVNE RVIMPAGYPR TREKIARLGY RVIEVDTSEYRKIDGGVSCM SLRF |

TABLE 7

Non-Human Primate DDAH Sequences

| SEQ ID NO: | Sequence Name | Sequence |
|---|---|---|
| 14 | Rhesus Monkey DDAH1 amino acid sequence | MAGLGHPAAF GRATHAVVRA LPESLGQHAL RS AKGEEVDV ARAERQHQLY VGVLGSKLGLQVVELPADES LPDCVFVEDV AVVCEETALI TRPGAPSRRK EVDMMKEALE KLQLNIVEMK DENATLDGGD VLFTGREFFV GLSKRTNQRG AEILADTFKD YAVSTVPVAD GLHLKSFCSMAGPNLIAIGS SESAQKALKI MQQMSDHRYD KLTVPDDIAA NCIYLNIPNK GHVLLHRTPE EYPESAKVYE KLKDHMLIPV SMSELEKVDG LLTCCSVLIN KKVDS |

The transformation of E. coli with plasmids containing the DDAH or modified DDAH or DDAH analog gene allows for biosynthesis of the DDAH polypeptide.

Wild type mature DDAH is amplified by PCR from a cDNA synthesis reaction using standard protocols and cloned into pET30 (NcoI-BamHI). Alternatively, the DNA sequence was synthesized. Prior to or alternatively following sequence confirmation, DDAH encoding nucleic acid sequences are subcloned into an expression vector under constitutive or inducible control of a synthetic promoter derived from E. coli or other suitable source. Expression of DDAH is under control of the T7 promoter. Any desired mutations are introduced using standard quick change mutation protocols (Stratagene; La Jolla, California). Constructs are sequence verified.

Expression plasmids (e.g. pET and pBAD) are used to transform into the Escherichia coli strain W3110B57 to produce strains of E. coli in which expression of the T7 polymerase is under control of an arabinose-inducible promoter. Overnight bacterial cultures are diluted 1:100 into shake flasks containing 2×YT culture media and grown at 37° C. to an $OD_{600}$ of ~0.8. Protein expression is induced by the addition of arabinose (0.2% final). Cultures are incubated at 37° C. for 5 hours or overnight. Cells are pelleted and resuspended in B-PER lysis buffer (Pierce) 100 ul/OD/ml+10 ug/ml DNase and incubated at 37° C. for 30 min. Cellular material is removed by centrifugation and the supernatant removed. The pellet is re-suspended in an equal amount of SDS-PAGE protein loading buffer. All samples are loaded on a 4-12% PAGE gel with MES and DTT. Methods for purification of DDAH are known to those of ordinary skill in the art and are confirmed by SDS-PAGE, Western Blot analyses, or electrospray-ionization ion trap mass spectrometry and the like.

His-tagged mutant DDAH proteins can be purified using methods known to those of ordinary skill in the art. The ProBond Nickel-Chelating Resin (Life Technologies, Carlsbad, CA) may be used via the standard His-tagged protein purification procedures provided by the manufacturer.

FIG. 1 shows a DDAH plasmid construct used for expression.

This example also details expression of DDAH polypeptides by E. coli. This example describes the scale up of DDAH polypeptide production using a five (5) liter fermentor. These methods and scale up may also be used for 10 L, 30 L, 150 L and 1000 L batches. In some embodiments, at least 2 g (e.g., at least 4 g, at least 6 g, at least 8 g, at least 10 g, at least 15 g, or at least 20 g) of DDAH protein is produced for each liter of cell culture.

DDAH Cloning

Human and PA-DDAH or various mutants were cloned by adding 2 ul of PCR linearized pE-SUMO vector, 2 ul of geneBlock IDT (PA_DDAH _pSUMO or HS_DDAH_p-SUMO), 6 ul of $H_2O$ to In Fusion HD EcoDry Mix. The mixture was incubated at 37° C. for 15 min and then at 50° C. for 15 min. To 100 ul tubes of Stellar competent bacterial cells 2.5 ul of the above reactions mix was added and then incubated on ice for 30 min. The cells were heat shocked at 42° C. for 1 min. Sterile LB (900 ul) was added and placed on shaker at 225 rpm for 1 hr. The cells were centrifuged and 200 ul added to plate on LB agar KAN plates and incubated overnight at 37° C. Colonies were picked and grown in 5 ml of LB+KAN for 12-16 hrs with shaking at 250 rpm at 37° C. DNA was extracted using QIAprep Spin Minikit, purified and plasmid DNA sequence was confirmed.

DDAH Expression

The plasmid was transformed by adding 0.5 ul of DNA to 50 ul of BL21(DE3) cells. Cells were incubated on ice for 30 min and then heat shocked at 42° C. for 1 min. LB, without antibiotics (450 ul) was added to the cells and placed on a shaker at 225 rpm at 37° C. for 60 min. 5-10 ul of the transformed cells were plated on LB-agar KAN plate and grown overnight at 37° C. Colonies were used for inoculation of 5 ml of LB-KAN in culture tubes and placed on shaker at 250 rpm at 37° C. and grown until OD600 reached to ~0.8-0.9. 750 ul was removed for making glycerol stock by adding 50 ul of sterile glycerol. 50 ml of LB-KAN with glycerol stock was inoculated with of BL21(DE) cells and grown overnight. 25 ml was then added to 500 ml of LB-KAN and grown at 37° C. until the OD600 reached to ~0.7. The temperature was then lowered to 25° C. Induction was carried out by adding with 0.2 mM IPTG for ~20 hrs. Cells were then centrifuged for 15 min at 5,000 rpm. Cell extract was prepared by resuspending the pellet in 20 mM Tris, 300 mM NaCl and 1 mM beta mercaptoethanol (BME), pH 8.0 (~20 ml), sonication on ice for 3 min and centrifugation at 30,000 rpm for 30 min at 4° C. Supernatant was used for DDAH purification.

Example 2

DDAH Purification

The supernatant from the cell extract containing DDAH was applied to a 5 ml NiNTA column equilibrated with 20 mM Tris, 300 mM NaCl, 20 mM imidazole, 10% glycerol, 1 mM BME at pH 8.0. The column was washed with 25 ml buffer and then eluted using 20 mM Tris, 300 mM NaCl, 10% glycerol, 500 mM imidazole, 1 mM BME, pH 8.0.

Eluted fractions were assayed for DDAH activity and protein concentration. Active fractions were pooled. Sumo and His-tag from DDAH was cleaved by adding 37.5 ul of ULP-1 to pool DDAH (~4.92 mg/ml). Cleaved preparation was dialyzed against 2 L of 20 mM Tris, 300 mM NaCl, 10% glycerol, 20 mM imidazole, 1 mM BME, pH 8.0. Dialyzed fraction was added to a new 5 ml NiNTA column, equilibrated with 20 mM Tris, 300 mM NaCl, 10% glycerol, 20 mM imidazole, 1 mM BME, pH 8.0. Flow through fractions containing DDAH were collected for activity and SDS-PAGE. Active fractions were pooled. Further purification was achieved by Sepharose Q chromatography.

DDAH enzyme assay: DDAH activity is determined by modification of method published in the art (Markus Knipp and Milan Vašák Analytical Biochemistry 286, 257-264 (2000). The enzyme activity in cell extracts generated by homogenization in 0.1 M sodium phosphate buffer pH 6.9 and purified preparations will be determined by L-citrulline generation from ADMA. A 100 µl of sample will be transferred to a tube and 400 µl of 1 mM ADMA in sodium phosphate buffer will be added and incubated at 37° C. for 45 min. The reaction will be terminated by addition of 500 µl of 4% Sulfosalicyclic acid. The mixture will be centrifuged at 3000 g for 10 minutes. A 60 µl of supernatant will be transferred to NUNC 96 well plate in triplicates. A 200 µl of COLDER (color development regent) will be added. COLDER is prepared by mixing 1 volume of solution A [80 mM DAMO (diacetyl monoxime) and 2.0 mM TSC (thiosemicarbazide)] and 3 volume of solution B [3 M $H_3PO_4$, 6 M $H_2SO_4$, and 2 mM $NH_4Fe(SO_4)_2$]. The plates will be sealed and heated at 95° C. for 20 minutes. After cooling, they will be read at 530 nM. DDAH activity will be expressed as µM citruline produced per gram protein per minute at 37° C.

Determination of dimethylarginines: L-arginine, ADMA and SDMA will be quantified by LC-MS methods descried in the art (Jens Martens-Lobenhoffer J. Mass Spectrom. 2004; 39: 1287-1294) or by high performance liquid chromatography (HPLC) after precolumn derivatization with o-phthaldialdehyde (OPA) [39] L-homoarginine (10 µM) as an internal standard will be added to the tissue homogenate. Samples and standards will be extracted on solid phase extraction cartridges (CBA Bond Elut, Varian, Harbor City, California). The eluents will be dried over nitrogen and resuspended in bi-distilled water. Samples and standards will be incubated for 1 min with OPA reagent (5.4 mg/mL OPA in borate buffer, pH 8.4, containing 0.4% 2-mercaptoethanol) before automatic injection into the HPLC. The OPA derivatives of L-arginine, ADMA and SDMA will be separated on a 250×4.5 mm I.D. 7 µm Nucleosil phenyl column (Supelco, Bellefonte, Pennsylvania) with the fluorescence detector set at $\lambda^{ex}$=340 nm and $\lambda^{em}$=450 nm. Samples will be eluted from the column with 0.96% citric acid/methanol 70:30, pH 6.8, at a flow rate of 1 mL/min. The variability of the method is 7%; the detection limit of the assay is 0.15 µmol/L.

Figure 2:
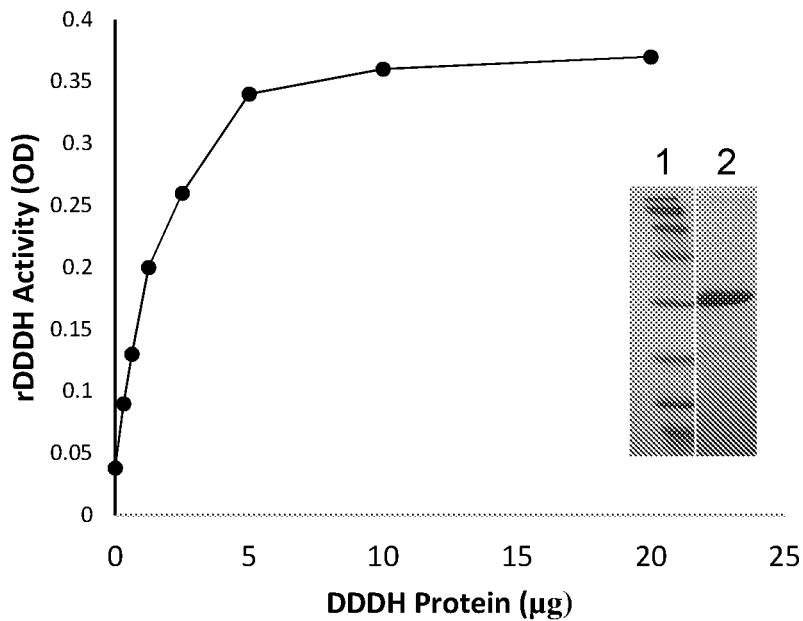
FIG. 2 shows the enzymatic activity and purity of rDDAH. DDAH activity was determined using a colorimetric assay measuring citrulline generation from ADMA. Purity of the rDDAH inset lane 2 was determined by SDS gel electrophoresis, lane 1 is MW markers.

FIG. 2 shows the activity and purity of rDDAH.

Example 3

Representative DDAH Mutants and Activity

Table 8 shows the activity of DDAH mutants. Recombinant human DDAH and *Pseudomonas aeruginosa* are noted as rhDDAH and rPa-DDAH respectively, with the change in amino acid residue is listed in the parenthesis.

TABLE 8

Activity of DDAH mutants.

| DDAH mutants | Activity relative to rHDDAH |
|---|---|
| 1. rhDDAH (SEQ ID NO: 1) | 1.0 |
| 2. N-His-rhDDAH | 1.0 |
| 3. N-His-sumo-rhDDAH | 1.0 |
| 4. rhDDAH (C74A) | 1.2 |
| 5. rhDDAH (C84A) | 2.0 |
| 6. rhDDAH (C178A) | 1.5 |
| 7. rhDDAH(C275A) | 1.0 |
| 8. rhDDAH(C274A) | 0.0 |
| 9. rhDDAH (C74S) | 1.5 |
| 10. rhDDAH (C84S) | 2.2 |
| 11. rhDDAH (C178S) | 1.5 |
| 12. rhDDAH (C275S) | 1.0 |
| 13. rhDDAH ( C274S) | 0.0 |
| 14. rhDDAH (C222S) | 3.0 |
| 15. rhDDAH (C222Q) | 1.0 |
| 16. rhDDAH (C74A + C84A + C275A) | 0.2 |
| 17. rPa-DDAH (SEQ ID NO: 13) | 20.0 |
| 18. N-His-rPa-DDAH | 15.0 |
| 19. C-His-rPa-DDAH (SEQ ID NO: 17) | 50.0 |
| 20. N-His-sumo-rPa-DDAH | 15.0 |
| 21. rPa-DDAH C74A + C84A + C178A | 15.0 |
| 22. rPa-DDAH C74S + C84S + C178S | 0.2 |
| 23. C-Biotinylation site* rPa-DDAH | 20.0 |
| 24. Sephadex conjugated ** rPa-DDAH | 20.0 |

*Biotinylation sequence add at C-terminal
** Conjugated to NHS Sephadex beads
All sequence contain N-terminal methionine extra amino acid.

Example 4 rDDAH lowers ADMA in blood and plasma: 1 ml of heparinized whole blood was incubated with or without rDDAH for 15 minutes at room temperature. The reaction was terminated by addition of 10% trichloric acid. The mixture was centrifuged to remove precipitated proteins. The supernatant was used for determination of ADMA. In another study, human plasma containing 3 uM added ADMA was incubated with different concentration rDDAH for 30 min at room temperature. The reactions were terminated by addition of 10% trichloric acid. The mixture was centrifuged to remove precipitated proteins. The supernatant was used for determination of ADMA.

Figure 3A:
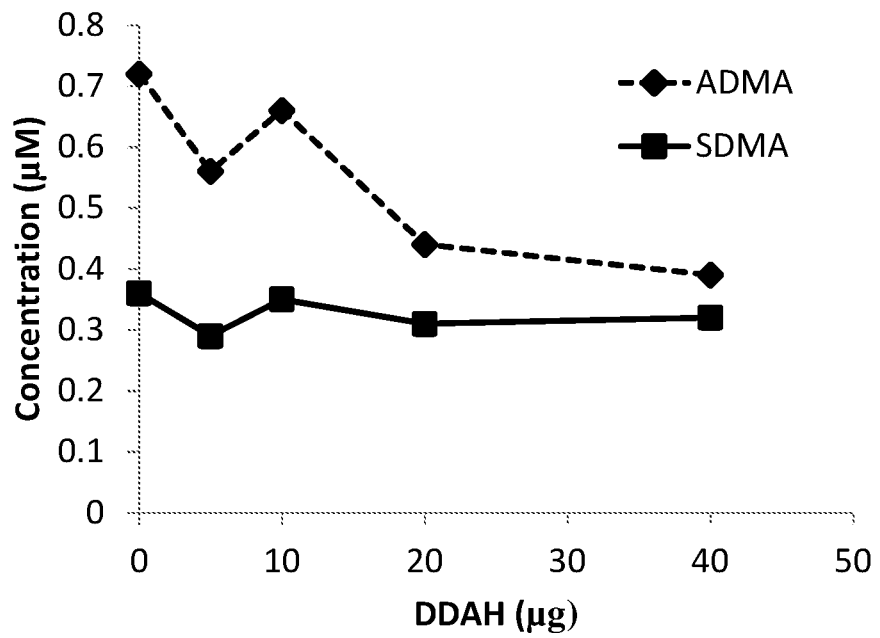
FIGS. 3A and 3B show that rDDAH lowered ADMA in plasma and blood in vitro. Different concentrations of rDDAH was added to whole blood (FIG. 3A) or human plasma with 3 uM exogenous ADMA (FIG. 3B). Samples were incubated at 37° C. for 30 min, ADMA concentration was then determined using LC-MS.
Figure 3B:
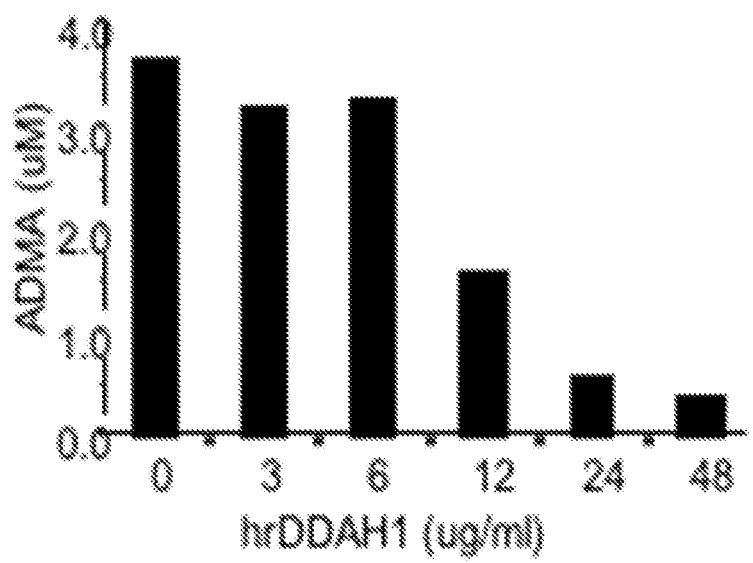

FIGS. 3A & 3B show that rDDAH lowers ADMA in blood and plasma.

Example 5

Recombinant DDAH lowers ADMA in blood of animal model in vivo. rDDAH (10 mg/kg) was administered to mice or rats by single intravenous injection. Blood samples were withdrawn at various times As shown in Table 9, rDDAH lowers ADMA in animal models, but has a relatively short circulating half-life in plasma.

TABLE 9

ADMA levels and DDAH activity over time after intravenous administration of rDDAH to mice.

| Animal Groups | Plasma ADMA (uM) | Plasma DDAH activity |
|---|---|---|
| 1. 0 Min, no rDDAH | 2.7 + 0.4 | 3.4 + 6.3 |
| 2. 15 min after rDDAH | 1.4 + 0.2 | 129.8 + 27.2 |

TABLE 9-continued

ADMA levels and DDAH activity over time after intravenous administration of rDDAH to mice.

| Animal Groups | Plasma ADMA (uM) | Plasma DDAH activity |
|---|---|---|
| 3. 30 min after rDDAH | 2.1 + 0.4 | 38.1 + 28.3 |
| 5. 60 min after rDDAH | 2.5 + 0.2 | 7.3 + 3.1 |

Example 6

PKEMylated recombinant human DDAH, PEGylated recombinant human or Pa-DDAH, or Acylated recombinant human DDAH pharmacokinetics.

Figure 4A:
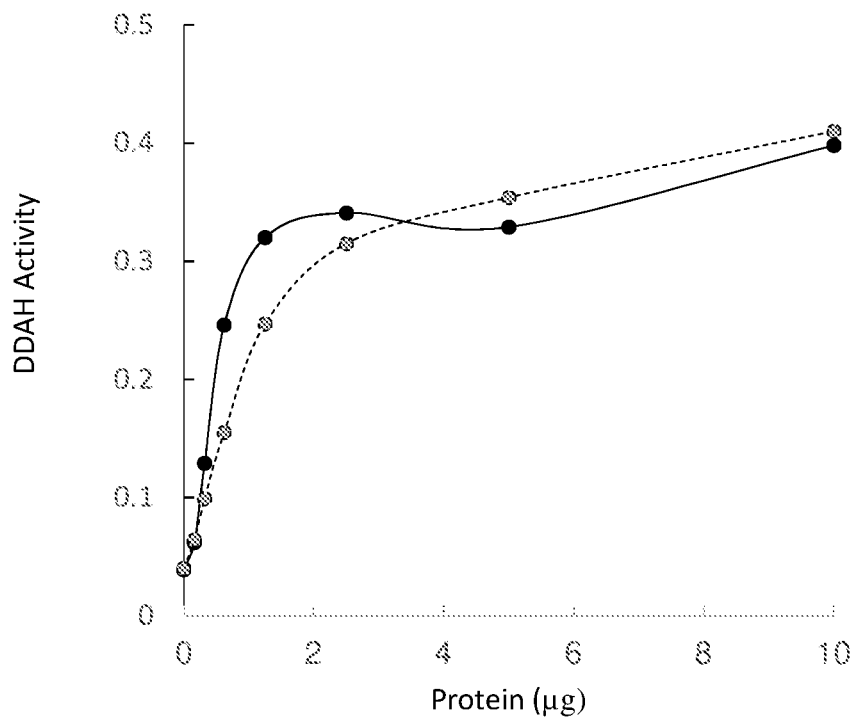
FIGS. 4A-4C show the effect of PEGylation on the activity of a DDAH polypeptide.
Figure 4B:
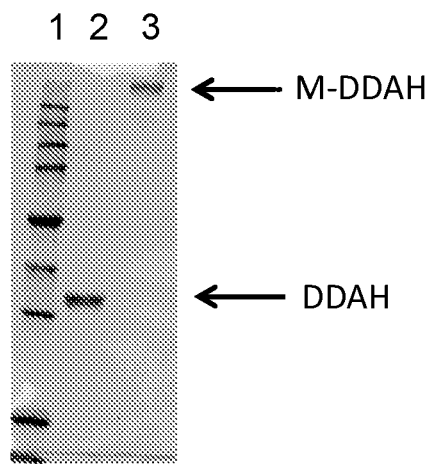
Figure 4C:
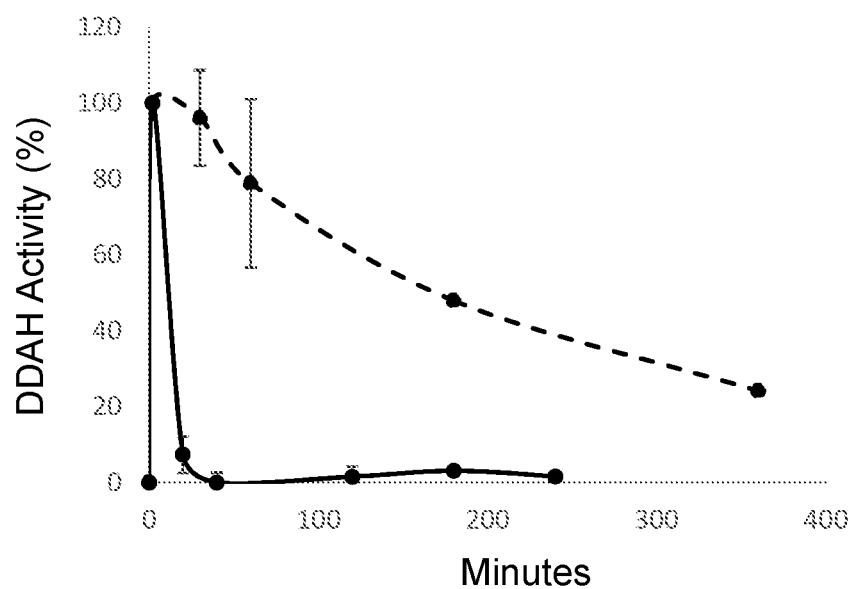

PEGylation of rDDAH was performed by addition of N-hydroxy succinamide PEG (NHS-PEG) (from Nanocs Inc.) with 10 kDa PEG. PEG size from 2 kDa-40 kDa was tested. DDAH (1 mg/ml) was incubated with 10 molar access of NHS-PEG at 4° C. for 24 hours or 37° C. for 3 hours. PEGylation reaction was terminated by adding 1 M Tris. PEGylated DDAH was separated from free PEG by filtering through a membrane of 50 kDa cutoff. PEGylated DDAH was also separated by Sepharose Q column chromatography. PEGylation was also performed using maleimide PEG with or without additional cysteine at the C or N terminal of DDAH. Site specific PEGylation is performed with 20 kDa mPEG-butyraldehyde. Activity of PEGylated DDAH (M-DDAH) is shown in FIGS. 4A-4C.

Example 7

In vivo studies are conducted in mice, rats, dogs and monkeys to characterize the pharmacokinetics (PK) of wild-type and modified DDAH polypeptides after intravenous (i.v.) and subcutaneous (s.c.) dosing. In some embodiments, recombinant human DDAH, PKEMylated recombinant human DDAH, PEGylated recombinant human DDAH, or Acylated recombinant human DDAH polypeptides of the invention are observed to exhibit increased in vivo half-life relative to wild-type. Sprague-Dawley rats are also dosed with wild-type and modified DDAH polypeptides (i.v., 1 mg/kg; s.c., 1 mg/kg) and the PK profile determined. Three rats are bled at each time point and serum samples are analyzed for ADMA method or by DDAH activity method.

Full i.v. pharmacokineticsis also investigated in male Balb/c mice or Sprague Dawley rats for PKEMylated DDAH, C12 or C14-DDAH or PEG-DDAH following a single tail vein bolus injection at a dose of 0.5 mg/kg (N=3 each time point, 5 mL/kg). PKEMylated DDAH, C12 or C14-DDAHor PEG-DDAH is dosed as a solution in 0.2M Tris, 1 M NaCl, 25% propylene glycol, pH 8.5 and the blood samples are collected through retro-orbital bleeding at 0.05, 0.25, 0.5, 1, 3, 5, 7, 9, 24 hours post i.v. dose (0.05, 1, 7 h from one group of 3 mice, 0.25, 3, 9 h from the second group of 3 mice and 0.5, 5, 24 h from the third group of 3 mice).

Subcutaneous (s.c.) pharmacokinetics is investigated in male Balb/c mice or Sprague Dowley rats for PKEMylated DDAH, C12 or C14-DDAHor PEG-DDAH following a single s.c. injection at a dose of 1 mg/kg (N=3 each time point, 7 mL/kg). Each drug is dosed as a solution in 0.2M Tris, 1M NaCl, 25% propylene glycol, pH 8.5 and the blood samples are collected through retro-orbital bleeding at 0.25, 0.5, 1, 3, 7, and 24 hours post dose (0.25, 1, 7 h from one group of 3 mice, and 0.5, 3, 24 h from the other group of 3 mice).

Following collection, blood samples are centrifuged at 10,000 rpm for 10 min at 4° C. to obtain serum and serum samples are stored at −20° C. until analysis. The serum concentration of acylated DDAH is analyzed by enzyme-linked immunosorbent assay (ELISA) or DDAH activity method. Pharmacokinetic parameters are estimated using non-compartmental analysis by Kinetica software (Thermo Fisher Scientific Corporation, version 5.0). The peak concentration ($C_{max}$) and time for $C_{max}$ ($T_{max}$) are recorded directly from experimental observations. The area under the curve from time zero to the last sampling time [$AUC_{last}$] and the area under the curve from time zero to infinity [$AUC_{total}$] are calculated using a combination of linear and log trapezoidal summations. The total plasma clearance, steady-state volume of distribution (Vss), apparent elimination half-life ($t_{half}$), and mean residence time (MRT) are estimated after i.v. administration. Estimations of AUC and $t_{half}$ are made using a minimum of 3 time points with quantifiable concentrations. The absolute s.c. bioavailability (F) is estimated as the ratio of dose-normalized AUC values following s.c. and i.v. doses. The PK parameters are calculated when applicable.

Example 8

Figure 5:
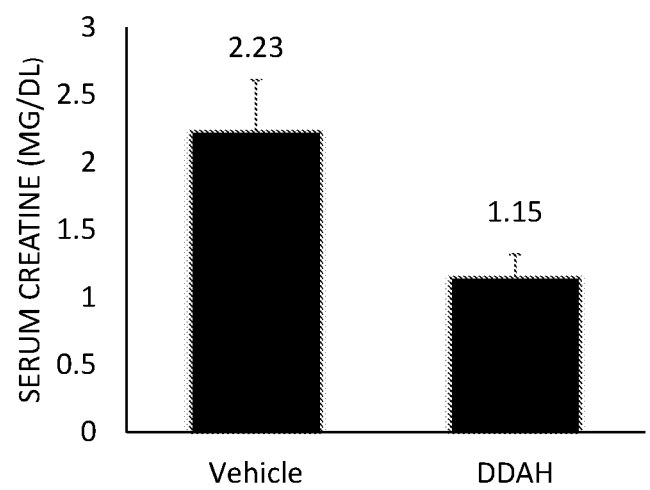
FIG. 5 shows the efficacy of M-DDAH as determined in a rat acute kidney injury model.

In vivo efficacy of M-DDAH. M-DDAH improved renal function in rat model of acute kidney injury. The efficacy of M-DDAH was assessed using a rat model of acute kidney injury (AKI). AKI was produced by 40 min of ligation of renal artery and then allowing reperfusion. In this model, ischemia-reperfusion leads to a major loss in DDAH activity and impairment of kidney function as measured by an increase in creatinine levels in the blood. M-DDAH (0.25 mg/Kg) was administered intravenously 30 min prior to ischemia and a second dose after 3 hours. FIG. 5 shows that M-DDAH significantly attenuated the loss of renal function as indicated by the reduced serum creatinine at 24 hours of reperfusion relative to vehicle injected control rats ($P<0.05$ by Student's t-test: N=7 per group).

As shown in FIG. 5, M-DDAH treatment improved kidney functions in acute kidney injury models as determined by lowering of creatinine levels.

Example 9

Modified human DDAH-2 polypeptides linked to a PKEM including but not limited to C12 or C14 acyl group or a water-soluble polymer such as PEG, are synthesized for pharmacokinetic and pharmacodynamic testing. The DDAH polypeptide has the amino acid sequence of SEQ ID NO: 1 or 2, or comprising one or more naturally encoded or amino acid substituted at a single position. Different modified DDAH polypeptides are produced. The DDAH is then reacted with a linker comprising the PKEM, C12 or C14 acyl group or a water-soluble polymer such as PEG. These modified DDAHs are then tested to determine activity and pharmacokinetic properties as described in the following examples.

Example 10

Pharmacokinetic Studies of C14-acylatedDDAHs

The C14-acylated DDAHs described in Example 5 and tested for activity and specificity in vitro as described in Example 6 are further tested to determine pharmacokinetic (PK) properties in the mouse and rat. As in the preceding examples, the modified DDAH polypeptides each consisted of the DDAH polypeptide of SEQ ID NO: 1 or 2 linked to a linker comprising the PKEM, C12 or C14 acyl group, or a water-soluble polymer such as PEG, as shown in Example 7.

Example 11

In order to evaluate potential sites for chemical conjugation, a new method is developed and carried out in order to assess the potential exposure of fatty acids synthetically attached to the DDAH amino acid located at specified positions on the DDAH molecule. The method is based upon a molecular dynamics protocol which analyzes molecular motions at the atomistic level and is therefore predictive of key biological phenomena. More specifically, a higher relative level of accessibility of the fatty acid is predicted to facilitate its interaction with human serum albumin and therefore should be indicative of increased in vivo half-life.

Accessibility of the fatty acid is assessed by determining the 2-shell water count in an MD simulation of the DDAH or modified DDAH polypeptides. The 2-shell water count is a count of the number of water molecules in direct contact with the pharmacokinetic enhancing moiety (constituting a first shell), as well as a second shell of water molecules in direct contact with the water molecules in the first shell. More specifically, the 2-shell water count includes all waters within 6 Å of the pharmacokinetic enhancing moiety and DDAH.

Accessibility of the fatty acid is also assessed by calculating the SASA (Solvent Accessible Surface Area) for the pharmacokinetic enhancing moiety and the position in the amino acid sequence of DDAH.

The simulation is carried out with a construct composed of a recombinant human DDAH polypeptide linked to a pharmacokinetic enhancing moiety.

Example 12

Specific Lowering of ADMA by Pharmacological DDAH Improves Endothelial Function, Reduces Blood Pressure and Protects Kidney from Ischemia-Reperfusion Induced Injury Methods and Materials Poly(ethylene glycol) was purchased from Nanocs (Massachusetts, USA). Amicon® ultra centrifugal filter units and Chromolith® performance RP-18e column (100×4.6 mm) were purchased from EMD Millipore (Massachusetts, USA). ADMA, phthaldialdehyde reagent (OPA), HiTrap Q FF anion exchange chromatography column were purchased from Sigma-Aldrich (Missouri, USA). Mini-protean® TGX™ precast protein gels were purchased from Bio-Rad (California, USA). Oasis MCX 1 cc Vac Cartridge, 30 mg sorbent, 30 um was purchased from Waters (Massachusetts, USA). Matrigel was purchased from Corning (Corning, NY). Ultrapure water (18 MΩ) was used all through the experiment. All solvents were of analytical grade purchased from commercial sources and used without further purification.

Site Specific DDAH-1 Mutants

Cys DDAH-1 was dialyze against 0.1 M phosphate buffer, pH 6.3 with at least 4 changes to remove any amine and sulfhydryl containing substances for proper reaction between and maleimide and sulfhydryl (—SH) groups. 10× molar excess of mPEG-Mal was added to dialyzed DDAH and incubated for 4 h at room temperature. The reaction mixture was purified using HiTrap Q FF anion exchange chromatography column. The column was equilibrated and loaded with 20 mM Tris pH 8 and serially eluted with 75, 175 and 500 mM NaCl in 20 mM Tris pH 8. The desired molecule was collected in 175 mM fractions. Then purified PEGylated DDAH was verified by SDS-PAGE.

DDAH Activity

DDAH activity was assessed by L-citrulline assay where asymmetric dimethyl arginine (ADMA) was used as the substrate which degrades upon reaction with DDAH-containing samples to produce L-citrulline. The activity was then measured by spectrophotometric analysis at 540 nm.

DDAH-1 PEGylation

PA DDAH-1 was dialyze against 0.1 M phosphate buffer, pH 8 with at least 4 changes to remove any amine containing substances for proper reaction between NHS esters (N-hydroxysuccinimide esters) and primary amines (—NH$_2$). 20× molar excess of mPEG-NHS was added to dialyzed DDAH and incubated for 4 h at room temperature. The reaction mixture was purified using kDa centrifugal filter unit using swing rotor (4500 rpm for 15 min×3 at 4° C.) and fresh 0.1 M phosphate buffer, pH 8. Then purified PEGylated DDAH was verified by SDS-PAGE.

ADMA Measurement

The ADMA analysis was performed after solid-phase extraction (SPE) with a Waters Oasis MCX 1 cc Vac Cartridge, 30 mg sorbent, 30 um particle size. Briefly, the column was conditioned with 1 mL of elution buffer (10/40/50; 28-30% ammonium hydroxide/water/methanol; v/v/v), followed by 1 mL of ultrapure water. Then 40 uL of plasma was mixed with 60 uL of PBS and loaded on the column. The column was lightly centrifuged and rinsed with 1 mL of 0.1 M HCl and 1 mL of MeOH two times. Then analytes were eluted with 450 uL elution buffer and dried under a gentle stream of nitrogen gas. Dried eluates were then reconstituted in 50 uL of ultrapure water and derivatized with ortho-phthaldialdehyde (OPA) reagent (4:1; v/v). After mixing, the analytes were heated at 30° C. for 1 min and 10 uL was injected into the HPLC system, with a fluorescent detector RF-10AXL (ex: 340, em: 455) and Chromolith® performance RP-18e column (100×4.6 mm). Mobile phase A consisted of 25 mM potassium phosphate buffer (pH 6.5) and mobile phase B was methanol/THF (97/3; v/v). Chromatographic separation was performed at room temperature and a flow rate of 2 mL/min using 27 min gradient (10-20% solvent A). Gain switch was adapted into protocol for ADMA detection. After elution, mobile phase was switched to 100% B for cleaning followed by 10% A for equilibration at a flow rate of 3 mL/min for 2 min each.

In Vitro Angiogenesis

Matrigel (200 uL) was pipetted into the 24-well plate placed on ice bucket and then transferred to a 37° C. incubator and incubate for 45 min. After incubation, 60,000 HUVEC in 0.5% FBS medium was transferred into each well carefully without disturbing the Matrigel coating and incubate the plate at 37° C. for 6 h. Then the samples were monitor for tube formation using 4× objective and analyze the parameters using imageJ.

Animals

SD rats were purchased from Harlan Laboratories (Indianapolis, IN). All rats were maintained on normal rodent chow (TD7034, 0.3% NaCl, Harlan Teklad, Madison, WI) and water ad libitum on a 12-h light-dark cycle. Animals were euthanized in accordance to the IACUC approved guidelines established by the American Veterinary Medical Association, to minimize pain or discomfort in the animal, which results in the rapid unconsciousness followed by cardiac or respiratory arrest and ultimate loss of brain function. Dahl salt-sensitive S (DSS) rats. Rats were obtained from the colonies maintained by Dr. Michael Garrett at the University of Mississippi Medical Center.

Blood Pressure Measurements:

Carotid artery and Jugular vein catheters in 7 months age Dahl salt-sensitive S (DSS) rats were inserted the day before M-DDAH infusions/measurements (isoflurane anesthesia, carprofen analgesia). DDAH (1 mg/kg i.v.) and PBS were infused in conscious rats. The carotid catheter was connected to a Deltran pressure transducer (Utah Medical) and mean arterial pressure (MAP) in control a treated was measured up to 4 hours. Data were collected using an amplifier and PowerLab from ADInstruments.

Renal Ischemia-Reperfusion Model

All studies in 1/R model were conducted in male SD rats (~250-300 g) that were purchased from Envigo. Rats were subjected to unilateral (left) 1/R injury by clamping the renal pedicle for a period of 40 minutes. Reestablishment of perfusion was verified by visual examination following removal of the clamps. To facilitate administration of drugs, rats were instrumented with chronic indwelling catheters in the jugular vein. M-DDAH or vehicle was first administered by i.v. injection at 30 min before the ligation and 3 hours after the first administration. Plasma and tissues were collected at 24 hours to evaluate the pharmacodynamics and biological responses to M-DDAH.

Measurements of Renal Function

To measure creatinine, tail blood was collected in heparin-containing tubes and centrifuged to collect plasma. Plasma creatinine was measured using a Pointe Scientific Analyzer and Creatinine Assay reagents using methods outlined by the manufacturer. Urine was collected for 24 hours by placing rats in metabolic cages, and urine volume was determined gravimetrically. Urine creatinine was measured using a colorimetric assay adopted for microplate readers, as previously described (Mason et al Kidney Int. 1984; 26:283-93). Creatinine clearance was measured using Ucr*V/Pcr.

Immune Cells Analysis

Harvested kidneys were minced and digested in liberase (2 µg/ml; Roche) for 15 min at 37° C. with the help of Gentle MACs (Miltenyli). The digested tissue was filtered through a 100-µm filter mesh and washed with tissue culture medium. The lymphocytes were separated by Percoll (Sigma) and counted by hemocytometer. To evaluate T lymphocytes, the cells were stained with antibodies against rat CD4 (PE-Cy7), CD8a (Alexa 647). To evaluate the cytokines secreted by T cells, the cells were stained for CD4 surface marker and then permeabilized using saponin and stained with antibodies against rat IL-17 (FITC). Macrophages were stained using anti-CD11b/c (PE). All antibodies were obtained from BD Bioscences. Cells were scanned using flow cytometry (FACSCalibur, BD Biosciences) and scans were analyzed using Flowjo software (Tree Star, Ashland, OR). The data is expressed a total number of specific cell population per gram of kidney.

Histological Studies

At the time of tissue harvest, kidneys were bisected and one half was fixed by immersion in 10% formalin, embedded in paraffin, and 5-µm sections stained with either hematoxylin and eosin (H&E) or picrosirus red to assess fibrosis. For quantitative analysis, five random images of the airways and the adjacent parenchyma were obtained using Leica DMLB (Scientific Instruments, Columbus, OH) microscope with a ×20 objective. The percent area of picrosirus red stain was calculated relative to total parenchyma area using ImageJ (NIH) similar to methods described previously (Hasegowa et al, The FASEB Journal. 2013; 27:2301-2315). To quantify H&E sections, computer-aided image analysis (Image J, NIH) was used to apply an arbitrary grid (8×10) to define regions within the photomicrograph, and the number of cells and alveoli were manually counted in a subset of 6-8 regions, which were selected a priori based on their location within the photomicrograph. However, in an effort to focus on alveolar structure, regions containing larger airways were excluded. The size of each region counted was ~1.2% of the entire area of the image. Data are presented as the average number cells per region.

Statistical Analysis

Statistical significance was evaluated by one-way analysis of variance (ANOVA), followed by Dunnett's test for multiple comparison between the experimental groups. A P value of <0.05 was considered to be statistically significant. *P<0.05, P<0.01, *P<0.001.

Results

Cloning, Expression and Purification of Recombinant DDAH-1:

The translated sequences of human and *Pseudomonas aeruginosa* (PA) DDAH-1 genes were synthesized and cloned and expressed in *E. coli*. For expression and purification, a His tag was added to the C-terminal of DDAH -1 or to N-terminal of small ubiquitin-related modifier (SUMO) fusion containing DDAH-1. Recombinant protein was successfully expressed and purified using Ni-sepharose column. The two step Ni-sepharose purification produced a single DDAH-1 band when analyzed by SDS gel electrophoresis with greater than 90% purity. The enzymatic activity of recombinant human and PA enzymes was determined by hydrolysis of ADMA to citrulline. Determination of PA-DDAH Km using a sensitive assay showed a of 76 uM, a values close to a previous report using more sensitive assay. We also observed that PA-DDAH (SEQ ID NO: 13) exhibited higher level of expression in *E. coli*, greater in vitro stability during the purification and enzymatic activity as compared to the human DDAH-1 (SEQ ID NO: 1). Since both enzymes selectively degrade ADMA, and exhibit identical catalytic mechanism, biochemical function and substrate or inhibitor profile, we have selected PA-DDAH, designated as rPa-DDAH-1 for further in vivo feasibility studies. rPa-DDAH-1 dose-dependently and relatively rapidly reduced ADMA when added to the plasma in vitro. These data show that rPa-DDAH produced in our studies was effective in lowering ADMA in plasma and was a suitable molecule for investigation of its actions in vivo.

Figure 6A:
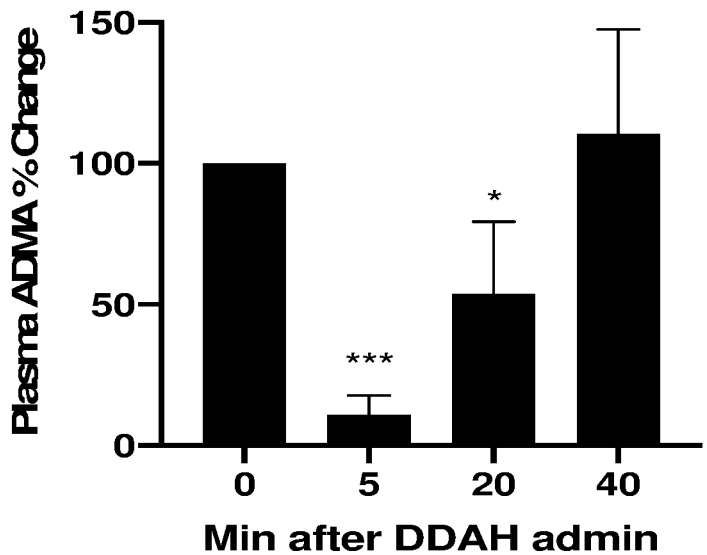
FIGS. 6A-6B In vivo activity of rPA-DDAH in lowering ADMA levels. A single dose of 0.6 mg rPA-DDAH was administered to rats, blood samples were recovered from the test subjects at the indicated time points. Plasma was analyzed to determine the ADMA levels (FIG. 6A) and in vivo activity of rPA-DDAH (FIG. 6B) at the indicated time points after administration of rPA-DDAH.
Figure 6B:
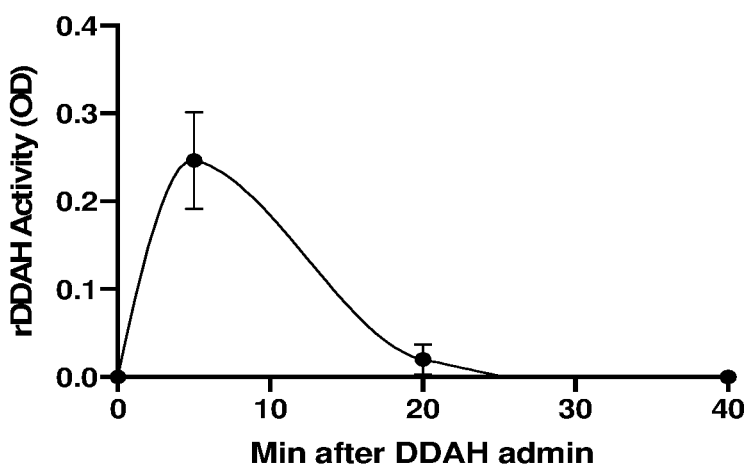

In Vivo ADMA Lowering by rPa-DDAH-1:

In order to determine the effect of rPa-DDAH on ADMA in vivo, we administered a single dose of 2.5 mg rPa-DDAH-1 intravenously to normal rats. Blood was collected at various times after rPa-DDAH-1 administration and plasma was prepared for determination of ADMA and DDAH activity. FIG. 6A shows that ADMA levels in plasma were significantly reduced within 5-7 min of DDAH-1 administration but returned to original levels after 20-40 minutes. Measurement of DDAH activity in plasma from treated animals showed that DDAH activity was rapidly reduced in the circulation FIG. 6B. Western blotting of plasma from the treated animals confirmed that rPa-DDAH protein was similarly reduced in plasma within 30 min. These data showed that the native rPa-DDAH-1 activity was rapidly eliminated from the blood. To test if blood constituent may have inactivated DDAH, we incubated rPa-DDAH with whole blood or plasma. These data showed that the activity was stable in the presence of blood, suggesting that the loss of DDAH activity over time was not simply due to the inactivation of the enzyme in the blood. Rather the enzyme was eliminated from the circulation. These data also showed that continuous presence of DDAH activity may be required to achieve sustained reduction in ADMA.

Figure 7A:
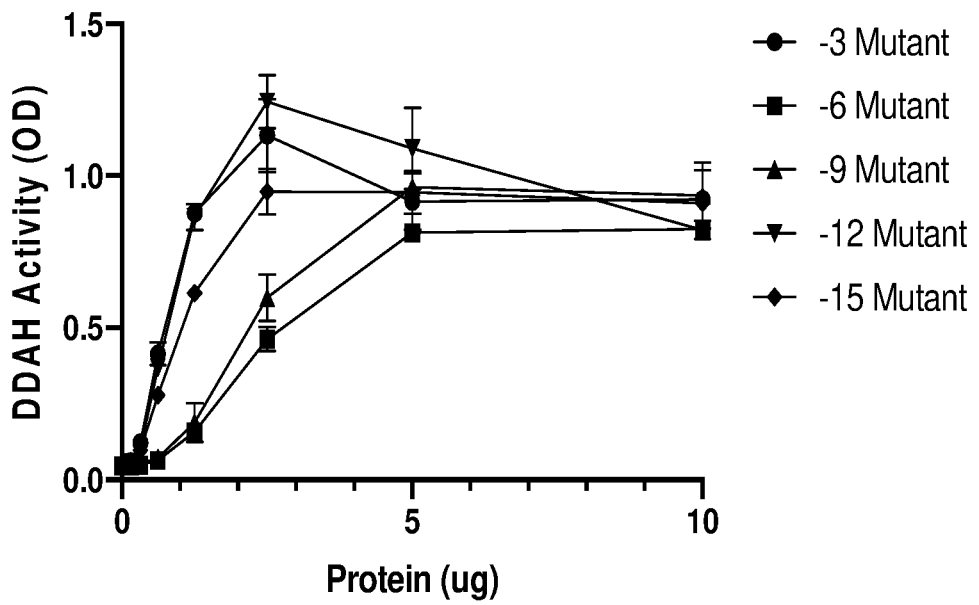
FIGS. 7A-7C Activity of pegylated rPA-DDAH analogs.
Figure 7B:
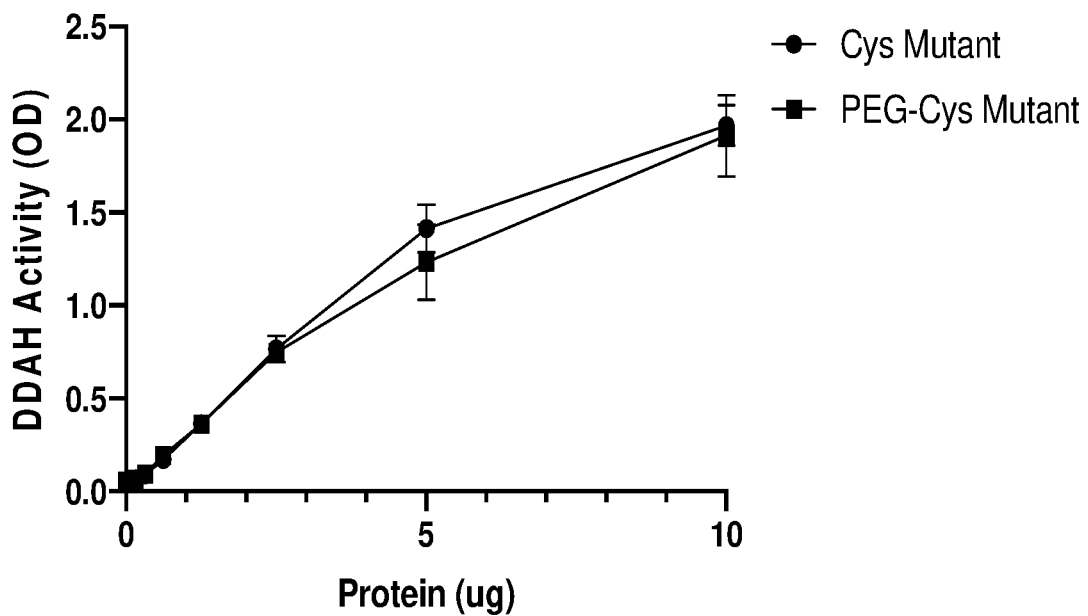
Figure 7C:
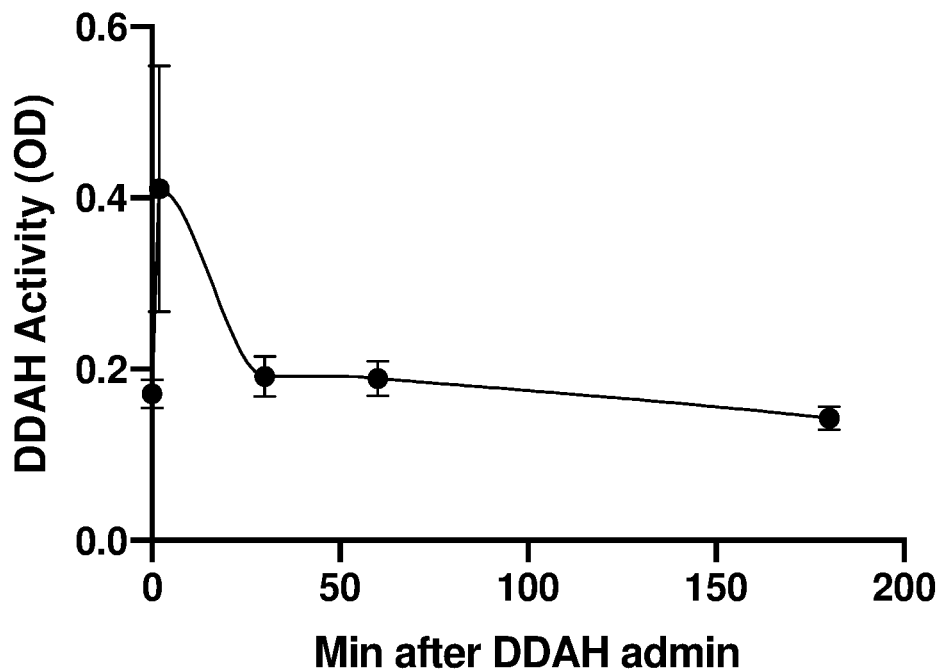

Generation of Long Acting DDAH (M-DDAH):

Several approaches to increase the duration of activity of rPa-DDAH in vivo and to achieve extended reduction of ADMA were investigated. Since the molecular weight of DDAH-1 is on the borderline for elimination by the kidney, we first tested if potential filtration by the kidney can be reduced by increasing the molecular size of the rPa-DDAH protein. For these studies, we prepared a rPa-DDAH-1 that can be used for site specific PEGylation. Our studies showed that PEGylation of native DDAH using mPEG2m-maleimide did not produce significant PEGylation as the cysteine residues were located within the globular structure and not accessible for PEGylation. These data allowed us to devise the scheme to achieve site specific and homogenous PEGylation of rPa-DDAH. Accordingly, we cloned and expressed DDAH mutants in which single lysine residue exposed to the protein surface (residue #3, 25,103 or 159, SEQ ID NOs 17, 18, 19 and 20, respectively) was replaced with cysteine. Each mutant protein was purified using Ni-sepharose column and the tested for enzyme activity. As shown in FIG. 7A, all of the Lys-Cys mutants were active in vitro with some differences in potency. Based on the solubility characteristics, enzyme activity and PEGylation efficiency, we selected 159 lys to cys mutant (SEQ ID NO: 20) for further studies. The 159lys-cys mutant protein was purified and PEGylated using mPEG20K-maleimide. As shown in FIG. 7B, the PEGylated protein with MW of 75 kDa was active in metabolizing ADMA in vitro. In vivo administration of this high MW mutant showed that the PEGylated 159 Lys-Cys activity was also rapidly reduced in circulation (FIG. 7C). These data suggested that the clearance of the site specific PEGylated 159 Lys-Cys may not be due to filtration by the kidney and therefore a different approach to enhance in vivo duration of activity is required.

Figure 8A:
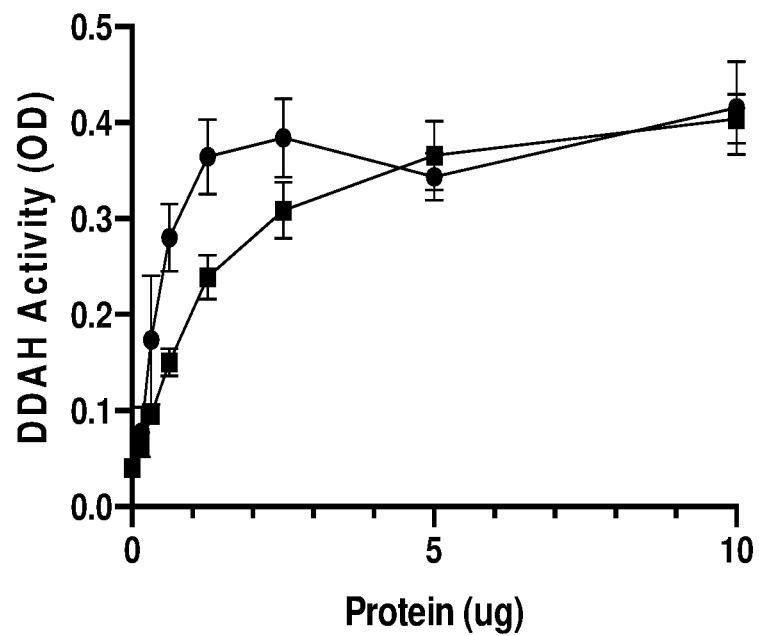
FIGS. 8A-8C Activity of rPA-DDAH pegylated with mPEG20k-NHS (designated M-DDAH). PEGylation conditions were optimized to produce rDDAHrPa-DDAH-1 preparations that showed an average MW of 250 kDa. A graph (FIG. 8A) of PEGylated enzyme (M-DDAH; (solid squares) activity shows the modified peptide maintained 90% enzyme activity in vitro, relative to non-pegylated PA-DDAH (solid circles). Intravenous administration to rats showed that the activity of M-DDAH remained in circulation for a significantly longer duration as compared to non-pegylated rPa-DDAH (FIG. 8B), wherein rPA-DDAH is indicated by solid circles and M-DDAH with solid squares. Consistent with the prolonged activity in vivo, the reduction in plasma ADMA was also prolonged (FIG. 8C). These data showed that as compared to the native rPa-DDAH, M-DDAH exhibited more than 20-fold greater duration of activity in the circulation. The data show the enzyme effectively and rapidly reduced ADMA in vivo.
Figure 8B:
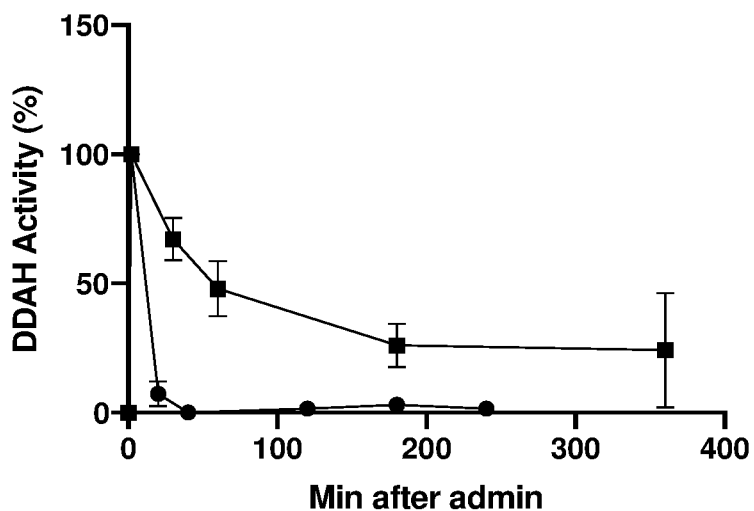
Figure 8C:
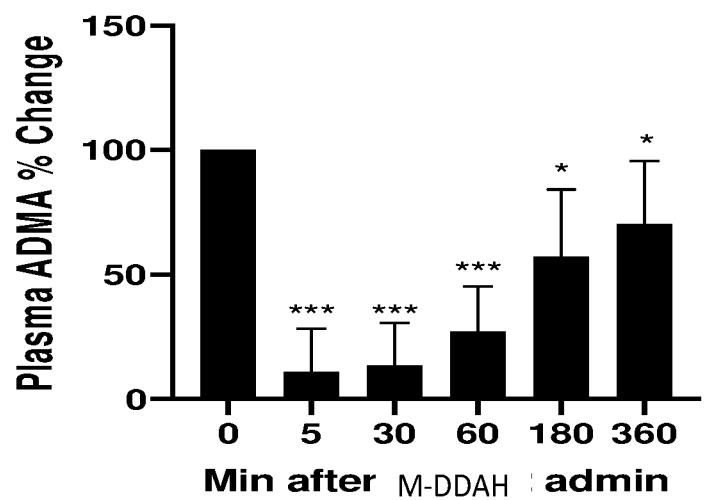

We then PEGylated the rPa-DDAH with mPEG$_{20k}$-NHS which can conjugate with the surface exposed lysine residues. The PEGylation conditions were optimized such that to produce consistent rPa-DDAH-1 preparation that showed an average MW of 250 kDa high. The PEGylated enzyme maintained 90% enzyme activity in vitro (FIG. 8A). The final DDAH preparation was designated as M-DDAH. Intravenous administration to rats showed that the activity of M-DDAH remained in circulation for a significantly longer duration as compared to rPa-DDAH (FIG. 8B). Consistent with the prolonged activity in vivo, the reduction in plasma ADMA was also prolonged (FIG. 8C). These data showed that as compared to the native rPa-DDAH, M-DDAH exhibited more than 20-fold greater duration of activity in the circulation. The data showed that despite the high Km which was 100-200 fold higher than plasma concentration of ADMA, the enzyme effectively and rapidly reduced ADMA in vivo. These data showed that therapeutic levels of DDAH can lower plasma ADMA and suitable for studies in animal models.

Figure 9:
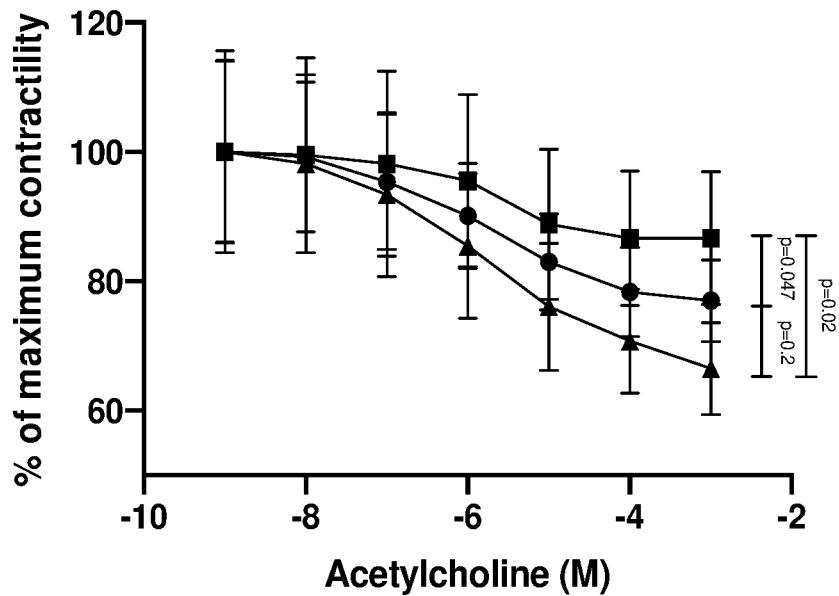
FIG. 9 Effect of M-DDAH on endothelial function. Isolated mouse thoracic arteries were first incubated in the presence of vehicle, 100 uM ADMA or 100 uM ADMA and M-DDAH. Response to acetylcholine was then determined using myography.

Effect of M-DDAH on Vascular Function:

The plasma ADMA levels in human subjects is strongly correlated with the endothelial dysfunction as measured by forearm blood flow and severity of atherosclerotic disease. DDAH-1 gene deletion in mice resulted in high plasma levels, endothelial dysfunction and increased blood pressure. To the test the hypothesis that pharmacological reduction in ADMA will improve endothelial function, and reverse the ADMA induced impairment of vasodilatory response, we have used isolated arteries and examined the effect of M-DDAH on endothelial function. Isolated mouse thoracic arteries were first incubated in the presence of vehicle, 100 uM ADMA or 100 uM ADMA and M-DDAH. Response to acetylcholine was then determined using myography. FIG. 9 shows that addition of ADMA impaired vasodilation of arteries in response to acetylcholine which was fully restored by treatment with M-DDAH. We also found that M-DDAH treatment showed trend of improved acetylcholine response in the absence of exogenous ADMA, suggesting that endogenous ADMA may play an important role in maintaining vascular homeostasis. These data showed that ADMA induced vascular dysfunction can be prevented and reversed by treatment with M-DDAH.

Figure 10:
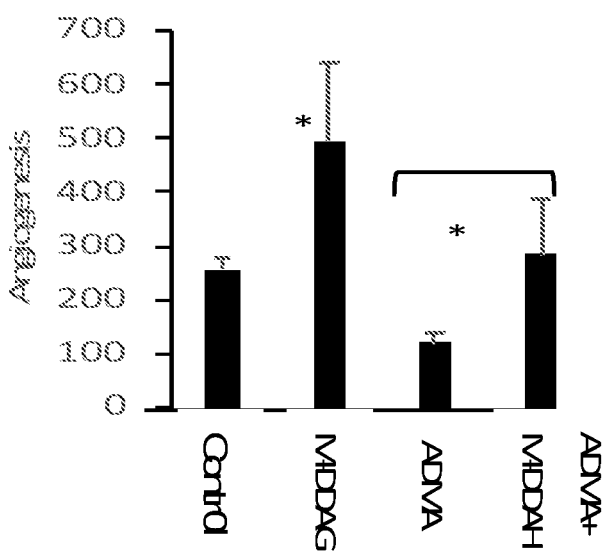
FIG. 10 M-DDAH Promotes in vitro Angiogenesis. The ability of rPA-DDAH pegylated with mPEG20k-NHS (designated M-DDAH) to directly modulate angiogenic activity of endothelium was investigated. In vitro angiogenesis was performed by plating human umbilical vein endothelial cells (HUVEC) in matrigel matrix in the presence or absence of ADMA. The cultures were then treated with M-DDAH.

M-DDAH Promotes In Vitro Angiogenesis:

To further confirm that M-DDAH can enhance other important vascular endothelial functions impacted by ADMA such as angiogenesis and regenerative response, we tested whether reduction in ADMA by M-DDAH can directly modulate angiogenic activity of endothelium. In vitro angiogenesis was performed by plating human umbilical vein endothelial cells (HUVEC) in matrigel matrix in the presence or absence of ADMA. The cultures were then treated with M-DDAH. FIG. 10 shows that addition of ADMA to endothelial cells significantly inhibited in vitro angiogenesis as measured by the number of nodes, segments and mesh. M-DDAH enhanced the in vitro angiogenic response and reversed the inhibitory effect of ADMA. These data showed that M-DDAH has the potential to improve endothelial function and regenerative response under the conditions such as ischemia and hypoxia where high ADMA levels are produced.

Figure 11A:
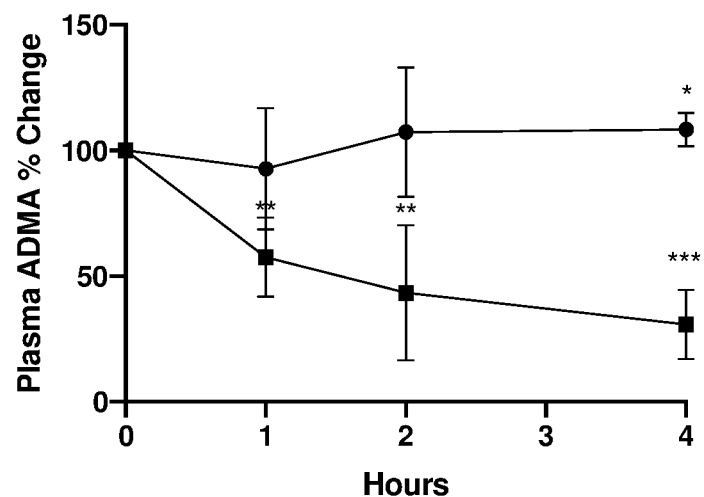
FIGS. 11A-11C Effect of M-DDAH on Blood Pressure in Hypertensive Rats. Dahl salt-sensitive (DSS) hypertensive rat model was used in these studies as the model system has been shown to exhibit increased levels of ADMA. DDAH (1 mg/kg i.v.) (▲) or vehicle (●) was infused in conscious Dahl salt sensitive rats. Blood was collected at the indicated times, and plasma ADMA was determined.
Figure 11B:
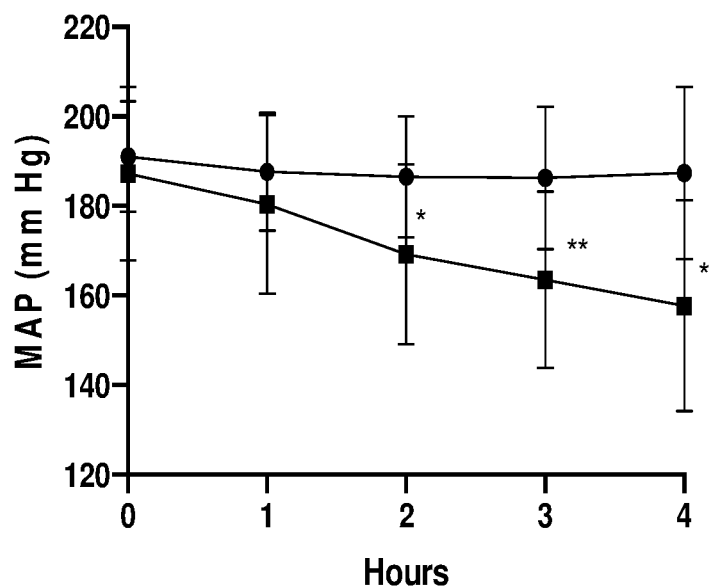
Figure 11C:
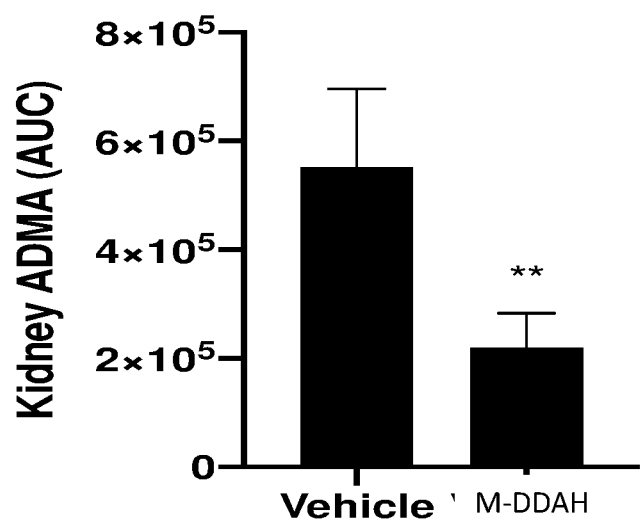

Effect of M-DDAH on Blood Pressure in Hypertensive Rats:

An important pathophysiological consequence of high ADMA is the increase in blood pressure. In clinical studies, ADMA levels correlate with blood pressure in patients. Further, elevation of ADMA levels by administration of ADMA to healthy volunteers resulted in increased blood pressure. Similarly, administration of ADMA to rats increased blood pressure. We investigated whether reduction in ADMA by M-DDAH lowers blood pressure in an animal model of hypertension. For these studies, we used the Dahl salt-sensitive (DSS) hypertensive rat model which has been shown to exhibit increased levels of ADMA. As shown in FIG. 11A, a single intravenous administration of M-DDAH to DSS hypertensive rats significantly reduced ADMA (FIG. 11A). Measurement of blood pressure using indwelling catheters showed that lowering of ADMA by M-DDAH resulted in a significant and sustained reduction in the blood pressure up to 4.5 hours, the last time point for the study (FIG. 11B). Harvested kidneys demonstrate the difference in ADMA levels in M-DDAH treated rats (FIG. 11C). These data showed that reduction in plasma ADMA by M-DDAH clearly produced physiological response in vivo.

M-DDAH Improves Cardiac Function:

Large prospective studies have shown that plasma ADMA was independently associated with all-cause and cardiovascular mortality in patients with stable and unstable ischemic heart disease (Meinitzer A, Seelhorst U, Wellnitz B, Halwachs-Baumann G, Boehm B O, Winkelmann B R and Marz W. *Clin Chem.* 2007; 53:273-83). High levels of ADMA are found in heart failure patients which may be an independent predictor of long-term adverse clinical outcomes. Recently, a large European Prospective Investigation (n=27,548), comprising a random subcohort (n=2224) also reported association between dimethylarginines and heart failure (Wirth et al. Amino Acids 2017; 49 173-182)

We tested the effect of ADMA lowering by M-DDAH on cardiac hemodynamics and cardiac function. At lower doses of M-DDAH which did not significantly reduce blood pressure, M-DDAH treatment of mice produced significant increase in cardiac output (.table - - - ). These effects were unique as no significant effect on heart rate or respiratory rate were observed. These results suggest the potential utility of M-DDAH and DDAH analogs for treatment of acute and chronic heart failure patients.

TABLE 10

M-DDAH Improved Cardia Function in Mice

|  | M-DDAH induced change |
|---|---|
| Cardiac Output | 48.1 + 12.1* |
| Heart Rate | −9.5 + 4.6 |
| Respiration | 18.9 + 14.1 |
| Blood pressure | −2.1 + 1.3 |

The values are changes from the baseline.
*Indicates significant change P > 0.05

TABLE 11

M-DDAH Improved Cardia Function in Mice

|  | Vehicle | M-DDAH |
|---|---|---|
| Cardiac Output | 10.34 | 45.6* |
| Heart Rate | 5.25 | 22.7 |
| Stroke Volume | 1.71 | 9.7 |
| Ejection Fraction | −5.83 | 3.1 |

Cardiac output in vehicle and M-DDAH treated animals was measured 1 hour after M-DDAH administration using echo cardiography. The values are changes from the baseline.
*Indicates significant change P > 0.05

M-DDAH Protects Cardiomyocyte Contractility

Figure 12:
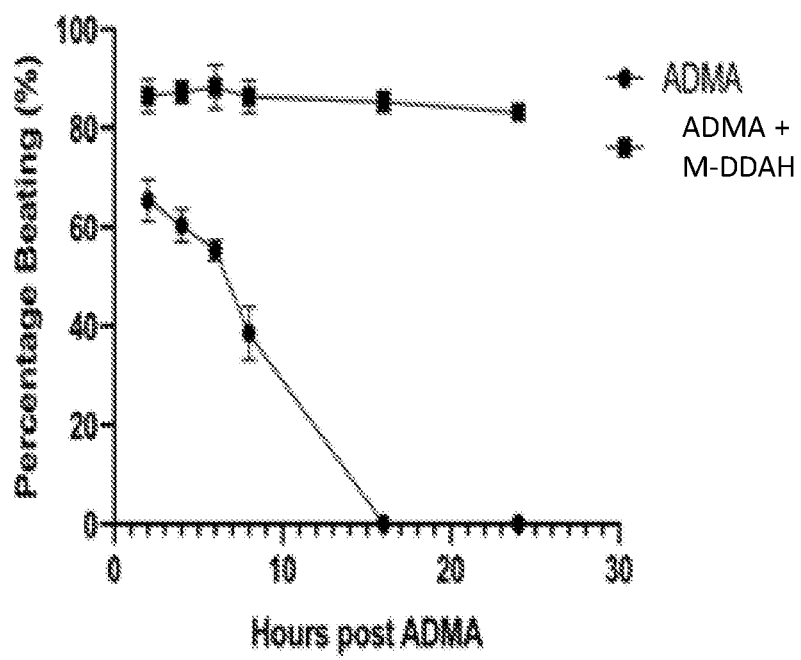
FIG. 12 M-DDAH Protects Cardiomyocytes from ADMA Induced Loss of Contractility.

In order to test if M-DDAH produced direct effect on cardiac cells independent of its vascular actions, we tested effects on M-DDAH in IPS derived human cardiomyocytes in vitro. Treatment of cardiomyocytes with ADMA significantly reduced contractility which was completely reversed by M-DDAH (FIG. 12). These data show that M-DDAH prevents ADMA induced reduction in cardiomyocyte contractility.

M-DDAH Protects Kidney Function in Response to Ischemia-Reperfusion Injury:

ADMA plays an important role in kidney by inducing microcirculation dysfunction which eventually contributes to accelerated renal and cardiovascular disease. Hypoxia or ischemia-reperfusion (I/R) reduces DDAH expression and activity that causes accumulation of ADMA in the target organ. DDAH-1 transgenic animals expressing high levels of DDAH-1 were protected from ischemia-reperfusion injury to the kidney and the heart. In order to assess the effect of M-DDAH on ischemia-reperfusion, we first determined the effect of renal I/R on DDAH and ADMA in the kidney. We used a well characterized model of I/R injury in kidney. Renal ischemia reperfusion in this model produced a time dependent reduction in DDAH-1 mRNA and increase in ADMA in the kidney. Therefore, the rat I/R mode is appropriate to test the effect of M-DDAH. To test the effect of M-DDAH, rats were treated with M-DDAH and then subjected to 30 minutes of ischemia following by reperfusion. The renal function, immune response and injury score were performed after 24 hours of reperfusion. Rats treated with M-DDAH were significantly protected from ischemia-perfusion injury. Renal function was determined by plasma creatinine levels which was significantly lower in M-DDAH treated animals. M-DDAH treated animals also showed significant improvement in serum bicarbonate and acidosis. Measurement of inflammatory response in the kidney showed that M-DDAH treatment significantly reduced the inflammatory cells in the kidney. Histological evaluation of renal injury score showed that M-DDAH treatment significantly reduced injury score. These results showed that reduction of ADMA by M-DDAH produced a significant reduction in inflammatory response in the kidney and injury score, and improvement in renal function in response to ischemia-reperfusion injury.

Measurement of ADMA in the kidney following modified DDAH treatment showed that lowering of ADMA in the blood resulted in lowering of ADMA in the target tissues such as kidney. These data show that the modified DDAH does not need to be present at the target tissue to produce its effects. The lowering of ADMA in kidney may have occurred as a consequence of low blood ADMA and efflux from the cellular compartments by the bidirectional cationic transporter (Cat-1). These experimental data support that lowering of ADMA in blood by a therapeutic drug can reduce ADMA in the target organ affected by disease.

Since high ADMA has been shown to increase blood pressure in human, administration of modified DDAH is likely to reduce blood pressure in patients with hypertension and therefore may provide new therapeutic approach to manage hypertension. The data presented herein also demonstrate that ADMA plays an important role in ischemia-reperfusion injury and that reduction in ADMA by treatment with modified DDAH can reduce the injury response. These studies demonstrate that modified DDAH is a candidate for treatment of acute conditions in the hospital settings such as acute kidney injury (AKI) or acute heart failure. This is particularly relevant to the patients undergoing cardiac surgery where high levels of ADMA are produced and incidence of AKI are high. Cardiac surgery associated-acute kidney injury (CSA-AKI) is the second most common cause of kidney injury in hospitalized patients. Our studies show that modified DDAH may represent an important therapeutic molecule for the preservation of the microcirculatory flow and prevention and treatment of postoperative AKI.

ADMA levels can be readily measured in plasma, urine and saliva the DDAH based therapy representing a precision medical approach where, patients can be identified using ADMA levels and response to treatment can be monitored.

All publications, patents, patent applications, and/or other documents cited in this application are incorporated by reference in their entirety for all purposes to the same extent as if each individual publication, patent, patent application, and/or other document are individually indicated to be incorporated by reference for all purposes.

What is claimed is:

1. A system comprising a DDAH polypeptide for extracorporeally treating a patient's blood and reducing ADMA levels in said blood, said system comprising
a DDAH polypeptide and
a solid support, wherein said DDAH polypeptide is covalently linked to said solid support; and
a device configured to receive a patient's blood and return the blood to the patient's circulation after contact with said solid support, wherein said device comprises said solid support in a configuration that places said solid support in fluid communication with blood that passes through the device, wherein said blood has reduced ADMA levels after contacting the solid support relative to the ADMA levels in the blood prior to contact with the solid support.

2. The system of claim 1, wherein said device comprises a hemodialysis, ultrafiltration or plasmapheresis system.

3. The system of claim 2 wherein said solid support is configured to be releasably attached to said hemodialysis, plasmapheresis or ultrafiltration system, wherein the attachment of said solid support places the DDAH polypeptide in fluid communication with blood as it flows through the hemodialysis, plasmapheresis or ultrafiltration system.

4. The system of claim 1 wherein the DDAH polypeptide comprises an amino acid sequence having at least 95% sequence identity to SEQ ID NO: 1; SEQ ID NO: 2; SEQ ID NO: 5; SEQ ID NO: 6; SEQ ID NO: 7; SEQ ID NO: 9; SEQ ID NO: 10; SEQ ID NO: 11; SEQ ID NO: 12; SEQ ID NO: 13; or SEQ ID NO: 14.

5. The system of claim 1 wherein the DDAH polypeptide comprises an amino acid sequence having at least 95% sequence identity to SEQ ID NO: 13.

6. The system of claim 3 wherein the DDAH polypeptide comprises an amino acid sequence having at least 95% sequence identity to a sequence selected from the group consisting of SEQ ID NO: 1, SEQ ID NO: 2 or SEQ ID NO: 13.

7. The system of claim 3 wherein the DDAH polypeptide comprises SEQ ID NO: 13.

8. A system comprising a DDAH polypeptide for extracorporeally treating a patient's blood and reducing ADMA levels in said blood, said system comprising
a solid support;
two or more different DDAH polypeptides covalently linked to said solid support, wherein the two or more different DDAH polypeptides comprise amino acid sequences independently selected from amino acid sequences having at least 95% sequence identity to SEQ ID NO: 1; SEQ ID NO: 2; SEQ ID NO: 5; SEQ ID NO: 6; SEQ ID NO: 7; SEQ ID NO: 9; SEQ ID NO: 10; SEQ ID NO: 11; SEQ ID NO: 12; or SEQ ID NO: 13; and
a device configured to receive a patient's blood and return the blood to the patient's circulation after contact with said solid support, wherein said device comprises said solid support in a configuration that places said solid support in fluid communication with blood that passes through the device, wherein said blood has reduced ADMA levels after contacting the solid support relative to the ADMA levels in the blood prior to contact with the solid support.

9. The system of claim 8 wherein said solid support comprises two or more different DDAH polypeptides covalently linked to said solid support, wherein a first DDAH polypeptide comprises an amino acid sequence of SEQ ID NO: 13, and a second DDAH polypeptide comprises an amino acid sequence selected from the group consisting of SEQ ID NO: 1; SEQ ID NO: 2; SEQ ID NO: 5; SEQ ID NO: 6; SEQ ID NO: 7; SEQ ID NO: 9; SEQ ID NO: 10; SEQ ID NO: 11; and SEQ ID NO: 12.

10. A system comprising a DDAH polypeptide for extracorporeally treating a patient's blood, said system comprising
a DDAH polypeptide comprising the amino acid sequence of SEQ ID NO: 17;
a solid support, wherein said DDAH polypeptide is covalently linked to said solid support; and
a device configured to receive a patient's blood and return the treated blood to the patient's circulation, wherein said device comprises said solid support in a configuration that places said solid support in fluid communication with blood that passes through the device.

11. The system of claim 10 wherein said solid support comprises two or more different DDAH polypeptides covalently linked to said solid support, wherein a first DDAH polypeptide comprises the amino acid sequence of SEQ ID NO: 17, and a second DDAH polypeptide comprising an amino acid sequence selected from the group consisting of SEQ ID NO: 1; SEQ ID NO: 2; SEQ ID NO: 5; SEQ ID NO: 6; SEQ ID NO: 7; SEQ ID NO: 9; SEQ ID NO: 10; SEQ ID NO: 11; SEQ ID NO: 12; SEQ ID NO: 13; SEQ ID NO: 14; SEQ ID NO: 15, SEQ ID NO: 18, SEQ ID NO: 19, SEQ ID NO: 20, SEQ ID NO: 21, SEQ ID NO: 22, and SEQ ID NO: 23.

12. The system of claim 11 wherein the second DDAH polypeptide comprises an amino acid sequence selected from the group consisting of SEQ ID NO: 18, SEQ ID NO: 19, SEQ ID NO: 20, SEQ ID NO: 21, SEQ ID NO: 22, and SEQ ID NO: 23.

13. A method of reducing levels of ADMA in a patient's blood, said method comprising the steps of
   removing blood from said patient;
   contacting the patient's blood with a DDAH polypeptide; and
   returning the blood to the patient's circulation after the blood has been contacted by said DDAH polypeptide, wherein the returned blood has a lower ADMA concentration than the blood originally taken from the patient.

14. The method of claim 13 wherein the step of contacting the patient's blood with the modified DDAH polypeptide comprises
   passing the patient's blood through a hemodialysis or plasmapheresis system that comprises said DDAH polypeptide, said DDAH polypeptide comprising
   a DDAH amino acid sequence having at least 95% sequence identity to SEQ ID NO: 1; SEQ ID NO: 2; SEQ ID NO: 5; SEQ ID NO: 6; SEQ ID NO: 7; SEQ ID NO: 9; SEQ ID NO: 10; SEQ ID NO: 11; SEQ ID NO: 12; SEQ ID NO: 13; or SEQ ID NO: 14; and
   a solid support, wherein said DDAH polypeptide is covalently linked to said solid support;
   said DDAH polypeptide being in fluid communication with the patient's blood passing through said hemodialysis or plasmapheresis system.

* * * * *

SEQUENCE LISTING

<160> NUMBER OF SEQ ID NOS: 23

<210> SEQ ID NO 1
<211> LENGTH: 285
<212> TYPE: PRT
<213> ORGANISM: Homo sapiens

<400> SEQUENCE: 1

Met Ala Gly Leu Gly His Pro Ala Ala Phe Gly Arg Ala Thr His Ala
1               5                   10                  15

Val Val Arg Ala Leu Pro Glu Ser Leu Gly Gln His Ala Leu Arg Ser
            20                  25                  30

Ala Lys Gly Glu Glu Val Asp Val Ala Arg Ala Glu Arg Gln His Gln
        35                  40                  45

Leu Tyr Val Gly Val Leu Gly Ser Lys Leu Gly Leu Gln Val Val Glu
    50                  55                  60

Leu Pro Ala Asp Glu Ser Leu Pro Asp Cys Val Phe Val Glu Asp Val
65                  70                  75                  80

Ala Val Val Cys Glu Glu Thr Ala Leu Ile Thr Arg Pro Gly Ala Pro
                85                  90                  95

Ser Arg Arg Lys Glu Val Asp Met Met Lys Glu Ala Leu Glu Lys Leu
            100                 105                 110

Gln Leu Asn Ile Val Glu Met Lys Asp Glu Asn Ala Thr Leu Asp Gly
        115                 120                 125

Gly Asp Val Leu Phe Thr Gly Arg Glu Phe Phe Val Gly Leu Ser Lys
    130                 135                 140

Arg Thr Asn Gln Arg Gly Ala Glu Ile Leu Ala Asp Thr Phe Lys Asp
145                 150                 155                 160

Tyr Ala Val Ser Thr Val Pro Val Ala Asp Gly Leu His Leu Lys Ser
                165                 170                 175

Phe Cys Ser Met Ala Gly Pro Asn Leu Ile Ala Ile Gly Ser Ser Glu
            180                 185                 190

Ser Ala Gln Lys Ala Leu Lys Ile Met Gln Gln Met Ser Asp His Arg
        195                 200                 205

Tyr Asp Lys Leu Thr Val Pro Asp Asp Ile Ala Ala Asn Cys Ile Tyr
    210                 215                 220

Leu Asn Ile Pro Asn Lys Gly His Val Leu Leu His Arg Thr Pro Glu
225                 230                 235                 240

Glu Tyr Pro Glu Ser Ala Lys Val Tyr Glu Lys Leu Lys Asp His Met
                245                 250                 255

Leu Ile Pro Val Ser Met Ser Glu Leu Glu Lys Val Asp Gly Leu Leu
            260                 265                 270

Thr Cys Cys Ser Val Leu Ile Asn Lys Lys Val Asp Ser
        275                 280                 285

<210> SEQ ID NO 2
<211> LENGTH: 285
<212> TYPE: PRT
<213> ORGANISM: Homo sapiens

<400> SEQUENCE: 2

Met Gly Thr Pro Gly Glu Gly Leu Gly Arg Cys Ser His Ala Leu Ile
1               5                   10                  15

Arg Gly Val Pro Glu Ser Leu Ala Ser Gly Glu Gly Ala Gly Ala Gly
            20                  25                  30

Leu Pro Ala Leu Asp Leu Ala Lys Ala Gln Arg Glu His Gly Val Leu

```
                35                  40                  45
Gly Gly Lys Leu Arg Gln Arg Leu Gly Leu Gln Leu Leu Glu Leu Pro
 50                  55                  60

Pro Glu Glu Ser Leu Pro Leu Gly Pro Leu Leu Gly Asp Thr Ala Val
 65                  70                  75                  80

Ile Gln Gly Asp Thr Ala Leu Ile Thr Arg Pro Trp Ser Pro Ala Arg
                 85                  90                  95

Arg Pro Glu Val Asp Gly Val Arg Lys Ala Leu Gln Asp Leu Gly Leu
                100                 105                 110

Arg Ile Val Glu Ile Gly Asp Glu Asn Ala Thr Leu Asp Gly Thr Asp
            115                 120                 125

Val Leu Phe Thr Gly Arg Glu Phe Phe Val Gly Leu Ser Lys Trp Thr
130                 135                 140

Asn His Arg Gly Ala Glu Ile Val Ala Asp Thr Phe Arg Asp Phe Ala
145                 150                 155                 160

Val Ser Thr Val Pro Val Ser Gly Pro Ser His Leu Arg Gly Leu Cys
                165                 170                 175

Gly Met Gly Gly Pro Arg Thr Val Val Ala Gly Ser Ser Asp Ala Ala
                180                 185                 190

Gln Lys Ala Val Arg Ala Met Ala Val Leu Thr Asp His Pro Tyr Ala
            195                 200                 205

Ser Leu Thr Leu Pro Asp Asp Ala Ala Ala Asp Cys Leu Phe Leu Arg
210                 215                 220

Pro Gly Leu Pro Gly Val Pro Pro Phe Leu Leu His Arg Gly Gly Gly
225                 230                 235                 240

Asp Leu Pro Asn Ser Gln Glu Ala Leu Gln Lys Leu Ser Asp Val Thr
                245                 250                 255

Leu Val Pro Val Ser Cys Ser Glu Leu Glu Lys Ala Gly Ala Gly Leu
                260                 265                 270

Ser Ser Leu Cys Leu Val Leu Ser Thr Arg Pro His Ser
            275                 280                 285

<210> SEQ ID NO 3
<211> LENGTH: 1633
<212> TYPE: DNA
<213> ORGANISM: Homo sapiens
<220> FEATURE:
<221> NAME/KEY: misc_feature
<222> LOCATION: (1485)..(1485)
<223> OTHER INFORMATION: n is a, c, g, or t

<400> SEQUENCE: 3
aacttaatgt ttttgcattg gactttgagt taagattatt ttttaaatcc tgaggactag      60
cattaattga cagctgaccc aggtgctaca cagaagtgga ttcagtgaat ctaggaagac     120
agcagcagac aggattccag gaaccagtgt ttgatgaagc taggactgag gagcaagcga     180
gcaagcagca gttcgtggaa tcctgtctgc tgctgtcttc ctggtttagg agccgacggg     240
cgctcgcagg ctcagcgcgc gctgcccgcg gcaggacccg gccgcctccg ccgccgccgc     300
cgcccctaag cctcccgaag ccatggccgg gctcggccac cccgccgcct tcggccgggc     360
cacccacgcc gtggtgcggg cgctacccga gtcgctcggc cagcacgcgc tgagaagcgc     420
caagggcgag gaggtggacg tcgcccgcgc ggaacggcag caccagctct acgtgggcgt     480
gctgggcagc aagctgggcc tgcaggtggt ggagctgccg gccgacgaga gccttccgga     540
ctgcgtcttc gtggaggacg tggccgtggt gtgcgaggag acggccctca tcacccgacc     600
```

```
cggggcgccg agccggagga aggaggttga catgatgaaa gaagcattag aaaaacttca      660
gctcaatata gtagagatga aagatgaaaa tgcaacttta gatggcggag atgttttatt      720
cacaggcaga gaattttttg tgggcctttc caaaaggaca aatcaacgag gtgctgaaat      780
cttggctgat acttttaagg actatgcagt ctccacagtg ccagtggcag atgggttgca      840
tttgaagagt ttctgcagca tggctgggcc taacctgatc gcaattgggt ctagtgaatc      900
tgcacagaag gcccttaaga tcatgcaaca gatgagtgac caccgctacg acaaactcac      960
tgtgcctgat gacatagcag caaactgtat atatctaaat atccccaaca aagggcacgt     1020
cttgctgcac cgaaccccgg aagagtatcc agaaagtgca aaggtttatg agaaactgaa     1080
ggaccatatg ctgatccccg tgagcatgtc tgaactggaa aaggtggatg gctgctcac      1140
ctgctgctca gttttaatta acaagaaagt agactcctga gctgcagagt cccccccggt     1200
agccggcaag accgcacagg caaggccgat gactctgtgc ccactcctgt tgttttcctt     1260
gacaatctac tgtgccactg tgctactaac tcttgtttac aaaatttgat tctaagttga     1320
attgcttcat tcaacacccc caccctccct ccccrcgagg tggtacctaa gctgtggatt     1380
tgctaaatga attaagcaac ctagaagata cagagctaat gaattatcaa aatgtgatta     1440
atcccagtaa ggaaacactc atttagtgtc tgtatttttg gtgtnaaaat tatttagttg     1500
ccagtatatt ctgaagaatg tcttcttgat cagtcagata agcttgcttt ttttttttt      1560
ttttcatgaa tcatgtttgg ttcctgtgaa agtccctggt ccagggatcc tcctcctttc     1620
tcttttactt ctg                                                        1633

<210> SEQ ID NO 4
<211> LENGTH: 1351
<212> TYPE: DNA
<213> ORGANISM: Homo sapiens
<400> SEQUENCE: 4
ccgcttagac aatgccccgg agccgccaga ccgtcgcgcc cctgccccat cgtagtatat       60
gagctcgcct acacaaggac ccccgctaaa agccagagct cccagtcccc gaggcttgaa      120
gacggggact cccttctcca ccaactctgt cctcggggg tggggcccca gccgagatca       180
cagcgcgaca ggagtggggg tggccgctgg agacaggtga agaaacaaga aaactaagaa      240
atccgagcgg ttgaggggg agtctgtgtg gatgggatgg ggacgccggg ggaggggctg       300
ggccgctgct cccatgccct gatccgggga gtcccagaga gcctggcgtc gggggaaggt      360
gcggggctg gccttcccgc tctggatctg gccaaagctc aagggagca cggggtgctg        420
ggaggtaaac tgaggcaacg actggggcta cagctgctag aactgccacc tgaggagtca      480
ttgccgctgg gaccgctgct tggcgacacg gccgtgatcc aaggggacac ggccctaatc      540
acgcggccct ggagccccgc tcgtaggcca gaggtcgatg gagtccgcaa agccctgcaa      600
gacctggggc tccgaattgt ggaaatagga gacgagaacg cgacgctgga tggcactgac      660
gttctcttca ccggccggga gttttcgta ggcctctcca aatggaccaa tcaccgagga      720
gctgagatcg tggcggacac gttccgggac ttcgccgtct ccactgtgcc agtctcgggt      780
ccctcccacc tgcgcggtct ctgcggcatg ggggacctc gcactgttgt ggcaggcagc      840
agcgacgctg cccaaaaggc tgtccgggca atggcagtgc tgacagatca cccatatgcc      900
tccctgaccc tcccagatga cgcagctgct gactgcctct tcttcgtcc tgggttgcct      960
ggtgtgcccc ctttcctcct gcaccgtgga ggtgggatc tgcccaacag ccaggaggca     1020
ctgcagaagc tctctgatgt cacccctggta cctgtgtcct gctcagaact ggagaaggct    1080
```

-continued

```
ggcgccgggc tcagctccct ctgcttggtg ctcagcacac gcccccacag ctgagggcct    1140
ggccttgggg tactgctggc cagggctagg atagtatagg aagtagaagg ggaaggaggg    1200
ttagatagag aatgctgaat aggcagtagt tgggagagag cctcaatatt ggggaggggg    1260
agagtgtagg gaaaaggatc cactgggtga atcctccctc tcagaaccaa taaaatagaa    1320
ttgacctttt aaaaaaaaaa aaaaaaaaaa a                                   1351
```

<210> SEQ ID NO 5
<211> LENGTH: 182
<212> TYPE: PRT
<213> ORGANISM: Homo sapiens

<400> SEQUENCE: 5

```
Met Met Lys Glu Ala Leu Glu Lys Leu Gln Leu Asn Ile Val Glu Met
1               5                   10                  15

Lys Asp Glu Asn Ala Thr Leu Asp Gly Gly Asp Val Leu Phe Thr Gly
            20                  25                  30

Arg Glu Phe Phe Val Gly Leu Ser Lys Arg Thr Asn Gln Arg Gly Ala
        35                  40                  45

Glu Ile Leu Ala Asp Thr Phe Lys Asp Tyr Ala Val Ser Thr Val Pro
    50                  55                  60

Val Ala Asp Gly Leu His Leu Lys Ser Phe Cys Ser Met Ala Gly Pro
65                  70                  75                  80

Asn Leu Ile Ala Ile Gly Ser Ser Glu Ser Ala Gln Lys Ala Leu Lys
                85                  90                  95

Ile Met Gln Gln Met Ser Asp His Arg Tyr Asp Lys Leu Thr Val Pro
            100                 105                 110

Asp Asp Ile Ala Ala Asn Cys Ile Tyr Leu Asn Ile Pro Asn Lys Gly
        115                 120                 125

His Val Leu Leu His Arg Thr Pro Glu Glu Tyr Pro Glu Ser Ala Lys
    130                 135                 140

Val Tyr Glu Lys Leu Lys Asp His Met Leu Ile Pro Val Ser Met Ser
145                 150                 155                 160

Glu Leu Glu Lys Val Asp Gly Leu Leu Thr Cys Cys Ser Val Leu Ile
                165                 170                 175

Asn Lys Lys Val Asp Ser
            180
```

<210> SEQ ID NO 6
<211> LENGTH: 285
<212> TYPE: PRT
<213> ORGANISM: Bos taurus

<400> SEQUENCE: 6

```
Met Ala Ser Leu Gly His Pro Ala Thr Phe Gly Arg Ala Thr His Val
1               5                   10                  15

Val Val Arg Ala Leu Pro Glu Ser Leu Ala Gln Gln Ala Leu Arg Arg
            20                  25                  30

Thr Lys Gly Asp Glu Val Asp Phe Ala Arg Ala Glu Arg Gln His Gln
        35                  40                  45

Leu Tyr Val Gly Val Leu Gly Ser Lys Leu Gly Leu Gln Val Val Gln
    50                  55                  60

Leu Pro Ala Asp Glu Ser Leu Pro Asp Cys Val Phe Val Glu Asp Val
65                  70                  75                  80

Ala Val Val Cys Glu Glu Thr Ala Leu Ile Thr Arg Pro Gly Ala Pro
```

```
                    85                  90                  95
Ser Arg Arg Lys Glu Ala Asp Met Met Lys Glu Ala Leu Glu Lys Leu
                100                 105                 110

Gln Leu Asn Ile Val Glu Met Lys Asp Glu Asn Ala Thr Leu Asp Gly
                115                 120                 125

Gly Asp Val Leu Phe Thr Gly Arg Glu Phe Val Gly Leu Ser Lys
130                 135                 140

Arg Thr Asn Gln Arg Gly Ala Glu Ile Leu Ala Asp Thr Phe Lys Asp
145                 150                 155                 160

Tyr Ala Val Ser Thr Val Pro Val Val Asp Ala Leu His Leu Lys Ser
                165                 170                 175

Phe Cys Ser Met Ala Gly Pro Asn Leu Ile Ala Ile Gly Ser Ser Glu
                180                 185                 190

Ser Ala Gln Lys Ala Leu Lys Ile Met Gln Gln Met Ser Asp His Arg
                195                 200                 205

Tyr Asp Lys Leu Thr Val Pro Asp Asp Thr Ala Ala Asn Cys Ile Tyr
            210                 215                 220

Leu Asn Ile Pro Ser Lys Gly His Val Leu Leu His Arg Thr Pro Glu
225                 230                 235                 240

Glu Tyr Pro Glu Ser Ala Lys Val Tyr Glu Lys Leu Lys Asp His Met
                245                 250                 255

Leu Ile Pro Val Ser Asn Ser Glu Leu Glu Lys Val Asp Gly Leu Leu
                260                 265                 270

Thr Cys Ser Ser Val Leu Ile Asn Lys Lys Val Asp Ser
            275                 280                 285

<210> SEQ ID NO 7
<211> LENGTH: 285
<212> TYPE: PRT
<213> ORGANISM: Bos taurus

<400> SEQUENCE: 7

Met Gly Thr Pro Gly Glu Gly Leu Gly Arg Cys Ser His Ala Leu Ile
1               5                   10                  15

Arg Gly Val Pro Glu Ser Leu Ala Ser Gly Glu Gly Ala Ala Ala Gly
                20                  25                  30

Leu Pro Ala Leu Asp Leu Ala Lys Ala Gln Arg Glu His Gly Val Leu
            35                  40                  45

Gly Gly Lys Leu Arg Gln Arg Leu Gly Leu Gln Leu Val Glu Leu Pro
        50                  55                  60

Pro Glu Glu Ser Leu Pro Leu Gly Pro Leu Leu Gly Asp Thr Ala Val
65                  70                  75                  80

Ile Gln Gly Asp Thr Ala Leu Ile Thr Arg Pro Trp Ser Pro Ala Arg
                85                  90                  95

Arg Pro Glu Val Asp Gly Val Arg Lys Ala Leu Gln Asp Leu Gly Leu
                100                 105                 110

Arg Ile Val Glu Met Gly Asp Glu Asn Ala Thr Leu Asp Gly Thr Asp
            115                 120                 125

Val Leu Phe Thr Gly Arg Glu Phe Val Gly Leu Ser Lys Trp Thr
        130                 135                 140

Asn His Arg Gly Ala Glu Ile Val Ala Asp Thr Phe Arg Asp Phe Ala
145                 150                 155                 160

Val Ser Thr Val Pro Val Thr Ser Thr Ser His Leu Arg Gly Leu Cys
                165                 170                 175
```

```
Gly Met Gly Gly Pro Arg Thr Val Val Ala Gly Ser Glu Ala Ala
            180                 185                 190

Gln Lys Ala Val Arg Ala Met Ala Val Leu Thr Asp His Pro Tyr Ala
        195                 200                 205

Ser Leu Thr Leu Pro Asp Asp Ala Ala Ala Asp Cys Leu Phe Leu Arg
    210                 215                 220

Pro Gly Gln Pro Gly Leu Pro Pro Phe Leu Leu His Arg Gly Gly Gly
225                 230                 235                 240

Asp Leu Pro Asn Ser Gln Glu Ala Leu Gln Lys Leu Ser Asp Val Thr
                245                 250                 255

Leu Val Pro Val Ser Cys Ser Glu Leu Glu Lys Ala Gly Ala Gly Leu
            260                 265                 270

Ser Ser Leu Cys Leu Val Leu Ser Thr Arg Pro His Asn
        275                 280                 285

<210> SEQ ID NO 8
<211> LENGTH: 858
<212> TYPE: DNA
<213> ORGANISM: Bos taurus

<400> SEQUENCE: 8
atggcttctc tcggccaccc agccaccttt ggccgggcca cccatgtcgt ggtacgggcg      60
ctgcccgagt ccctcgccca acaggcgctg aggcgcacca agggcgacga ggtggatttc     120
gcccgcgctg agcggcagca ccagctctac gtgggcgtgc tgggcagtaa actggggctg     180
caggtggtgc agctgcccgc cgacgagagc ctcccagact gcgtgttcgt ggaggacgtg     240
gccgtggtgt gcgaggagac ggccctgatc acccgccccg ggcgccgag ccggaggaag      300
gaggctgaca tgatgaaaga agcactagaa aaacttcagc tcaacatagt agagatgaaa     360
gatgaaaatg caactttaga tggtggagat gtcttattca caggcagaga attttttgtg     420
ggccttttcca aaaggacaaa tcaacgaggt gcggaaatct tggctgatac ttttaaggac     480
tatgcggtct ccacggtccc tgtggtggat gctttgcact tgaagagttt ctgcagcatg     540
gctgggccta acctaatcgc tattggatcc agtgaatctg cacagaaggc cctcaagatc     600
atgcaacaga tgagtgatca tcgctacgac aaactcacag tgcctgatga cacggccgca     660
aactgcatat acctgaatat ccccagcaaa ggccacgtct tgctgcaccg aaccccagaa     720
gagtacccag agagtgcaaa ggtttatgaa aagctgaagg accatatgct gatccccgtg     780
agcaattctg aactggaaaa ggtggacggg ctgctcacct gcagctcggt tttaattaac     840
aagaaagtag actcctga                                                   858

<210> SEQ ID NO 9
<211> LENGTH: 285
<212> TYPE: PRT
<213> ORGANISM: Mus musculus

<400> SEQUENCE: 9

Met Ala Gly Leu Gly His Pro Ser Ala Phe Gly Arg Ala Thr His Ala
1               5                   10                  15

Val Val Arg Ala Pro Pro Glu Ser Leu Cys Arg His Ala Leu Arg Arg
            20                  25                  30

Ser Gln Gly Glu Glu Val Asp Phe Ala Arg Ala Glu Arg Gln His Glu
        35                  40                  45

Leu Tyr Val Gly Val Leu Gly Ser Lys Leu Gly Leu Gln Val Val Gln
    50                  55                  60
```

-continued

Leu Pro Ala Asp Glu Ser Leu Pro Asp Cys Val Phe Val Glu Asp Val
65                  70                  75                  80

Ala Val Val Cys Glu Glu Thr Ala Leu Ile Thr Arg Pro Gly Ala Pro
                85                  90                  95

Ser Arg Arg Lys Glu Val Asp Met Met Lys Glu Ala Leu Glu Lys Leu
            100                 105                 110

Gln Leu Asn Ile Val Glu Met Lys Asp Glu Asn Ala Thr Leu Asp Gly
            115                 120                 125

Gly Asp Val Leu Phe Thr Gly Arg Glu Phe Val Gly Leu Ser Lys
        130                 135                 140

Arg Thr Asn Gln Arg Gly Ala Glu Ile Leu Ala Asp Thr Phe Lys Asp
145                 150                 155                 160

Tyr Ala Val Ser Thr Val Pro Val Ala Asp Ser Leu His Leu Lys Ser
                165                 170                 175

Phe Cys Ser Met Ala Gly Pro Asn Leu Ile Ala Ile Gly Ser Ser Glu
            180                 185                 190

Ser Ala Gln Lys Ala Leu Lys Ile Met Gln Gln Met Ser Asp His Arg
            195                 200                 205

Tyr Asp Lys Leu Thr Val Pro Asp Asp Met Ala Asn Cys Ile Tyr
210                 215                 220

Leu Asn Ile Pro Ser Lys Gly His Val Leu His Arg Thr Pro Glu
225                 230                 235                 240

Glu Tyr Pro Glu Ser Ala Lys Val Tyr Glu Lys Leu Lys Asp His Leu
                245                 250                 255

Leu Ile Pro Val Ser Asn Ser Glu Met Glu Lys Val Asp Gly Leu Leu
            260                 265                 270

Thr Cys Cys Ser Val Phe Ile Asn Lys Lys Ile Asp Ser
            275                 280                 285

<210> SEQ ID NO 10
<211> LENGTH: 285
<212> TYPE: PRT
<213> ORGANISM: Mus musculus

<400> SEQUENCE: 10

Met Gly Thr Pro Gly Glu Gly Leu Gly Arg Cys Ser His Ala Leu Ile
1               5                   10                  15

Arg Gly Val Pro Glu Ser Leu Ala Ser Gly Glu Gly Ala Gly Ala Gly
            20                  25                  30

Leu Pro Ala Leu Asp Leu Ala Lys Ala Gln Arg Glu His Gly Val Leu
        35                  40                  45

Gly Gly Lys Leu Arg Gln Arg Leu Gly Leu Gln Leu Leu Glu Leu Pro
    50                  55                  60

Pro Glu Glu Ser Leu Pro Leu Gly Pro Leu Leu Gly Asp Thr Ala Val
65                  70                  75                  80

Ile Gln Gly Asp Thr Ala Leu Ile Thr Arg Pro Trp Ser Pro Ala Arg
                85                  90                  95

Arg Pro Glu Val Asp Gly Val Arg Lys Ala Leu Gln Asp Leu Gly Leu
            100                 105                 110

Arg Ile Val Glu Met Gly Asp Glu Asn Ala Thr Leu Asp Gly Thr Asp
            115                 120                 125

Val Leu Phe Thr Gly Arg Glu Phe Val Gly Leu Ser Lys Trp Thr
        130                 135                 140

Asn His Arg Gly Ala Glu Ile Val Ala Asp Thr Phe Arg Asp Phe Ala
145                 150                 155                 160

```
Val Ser Thr Val Pro Val Ser Gly Ser Ser His Leu Arg Gly Leu Cys
                165                 170                 175

Gly Met Gly Gly Pro Arg Thr Val Val Ala Gly Ser Ser Glu Ala Ala
            180                 185                 190

Gln Lys Ala Val Arg Ala Met Ala Ala Leu Thr Asp His Pro Tyr Ala
        195                 200                 205

Ser Leu Thr Leu Pro Asp Asp Ala Ala Ser Asp Cys Leu Phe Leu Arg
    210                 215                 220

Pro Gly Leu Pro Gly Ala Thr Pro Phe Leu Leu His Arg Gly Gly Gly
225                 230                 235                 240

Asp Leu Pro Asn Ser Gln Glu Ala Leu Gln Lys Leu Ser Asp Val Thr
                245                 250                 255

Leu Val Pro Val Ser Cys Ser Glu Leu Glu Lys Ala Gly Ala Gly Leu
            260                 265                 270

Ser Ser Leu Cys Leu Val Leu Ser Thr Arg Pro His Cys
        275                 280                 285

<210> SEQ ID NO 11
<211> LENGTH: 285
<212> TYPE: PRT
<213> ORGANISM: Rattus rattus

<400> SEQUENCE: 11

Met Ala Gly Leu Ser His Pro Ser Val Phe Gly Arg Ala Thr His Ala
1               5                   10                  15

Val Val Arg Ala Pro Pro Glu Ser Leu Cys Arg His Ala Leu Arg Arg
            20                  25                  30

Ser Gln Gly Glu Glu Val Asp Phe Ala Arg Ala Glu Arg Gln His Gln
        35                  40                  45

Leu Tyr Val Gly Val Leu Gly Ser Lys Leu Gly Leu Gln Val Val Gln
    50                  55                  60

Leu Pro Ala Asp Glu Ser Leu Pro Asp Cys Val Phe Val Glu Asp Val
65                  70                  75                  80

Ala Val Val Cys Glu Glu Thr Ala Leu Ile Thr Arg Pro Gly Ala Pro
                85                  90                  95

Ser Arg Arg Lys Glu Val Asp Met Met Lys Glu Ala Leu Glu Lys Leu
            100                 105                 110

Gln Leu Asn Ile Val Glu Met Lys Asp Glu Asn Ala Thr Leu Asp Gly
        115                 120                 125

Gly Asp Val Leu Phe Thr Gly Arg Glu Phe Phe Val Gly Leu Ser Lys
    130                 135                 140

Arg Thr Asn Gln Arg Gly Ala Glu Ile Leu Ala Asp Thr Phe Lys Asp
145                 150                 155                 160

Tyr Ala Val Ser Thr Val Pro Val Ala Asp Ser Leu His Leu Lys Ser
                165                 170                 175

Phe Cys Ser Met Ala Gly Pro Asn Leu Ile Ala Ile Gly Ser Ser Glu
            180                 185                 190

Ser Ala Gln Lys Ala Leu Lys Ile Met Gln Gln Met Ser Asp His Arg
        195                 200                 205

Tyr Asp Lys Leu Thr Val Pro Asp Asp Met Ala Ala Asn Cys Ile Tyr
    210                 215                 220

Leu Asn Ile Pro Ser Lys Gly His Val Leu Leu His Arg Thr Pro Glu
225                 230                 235                 240

Glu Tyr Pro Glu Ser Ala Lys Val Tyr Glu Lys Leu Lys Asp His Leu
```

```
                245                 250                 255
Leu Ile Pro Val Ser Asn Ser Glu Met Glu Lys Val Asp Gly Leu Leu
            260                 265                 270

Thr Cys Cys Ser Val Phe Ile Asn Lys Lys Thr Asp Ser
        275                 280                 285

<210> SEQ ID NO 12
<211> LENGTH: 285
<212> TYPE: PRT
<213> ORGANISM: Rattus rattus

<400> SEQUENCE: 12

Met Gly Thr Pro Gly Glu Gly Leu Gly Arg Cys Ser His Ala Leu Ile
1               5                   10                  15

Arg Gly Val Pro Glu Ser Leu Ala Ser Gly Glu Gly Ala Gly Ala Gly
            20                  25                  30

Leu Pro Ala Leu Asp Leu Ala Lys Ala Gln Arg Glu His Gly Val Leu
        35                  40                  45

Gly Gly Lys Leu Arg Gln Arg Leu Gly Leu Gln Leu Leu Glu Leu Pro
    50                  55                  60

Pro Glu Ser Leu Pro Leu Gly Pro Leu Leu Gly Asp Thr Ala Val
65                  70                  75                  80

Ile Gln Gly Asp Thr Ala Leu Ile Thr Arg Pro Trp Ser Pro Ala Arg
                85                  90                  95

Arg Pro Glu Val Asp Gly Val Arg Lys Ala Leu Gln Asp Leu Gly Leu
            100                 105                 110

Arg Ile Val Glu Met Gly Asp Glu Asn Ala Thr Leu Asp Gly Thr Asp
        115                 120                 125

Val Leu Phe Thr Gly Arg Glu Phe Phe Val Gly Leu Ser Lys Trp Thr
    130                 135                 140

Asn His Arg Gly Ala Glu Ile Val Ala Asp Thr Phe Arg Asp Phe Ala
145                 150                 155                 160

Val Ser Thr Val Pro Val Ser Gly Ala Ser His Leu Arg Gly Leu Cys
                165                 170                 175

Gly Met Gly Gly Pro Arg Thr Val Val Ala Gly Ser Ser Glu Ala Ala
            180                 185                 190

Gln Lys Ala Val Arg Ala Met Ala Ala Leu Thr Asp His Pro Tyr Ala
        195                 200                 205

Ser Leu Thr Leu Pro Asp Asp Ala Ala Ser Asp Cys Leu Phe Leu Arg
    210                 215                 220

Pro Gly Leu Pro Gly Thr Thr Pro Phe Leu Leu His Arg Gly Gly Gly
225                 230                 235                 240

Asp Leu Pro Asn Ser Gln Glu Ala Leu Gln Lys Leu Ser Asp Val Thr
                245                 250                 255

Leu Val Pro Val Ser Cys Ser Glu Leu Glu Lys Val Gly Ala Gly Leu
            260                 265                 270

Ser Ser Leu Cys Leu Val Leu Ser Thr Arg Pro His Cys
        275                 280                 285

<210> SEQ ID NO 13
<211> LENGTH: 254
<212> TYPE: PRT
<213> ORGANISM: Pseudomonas aeruginosa

<400> SEQUENCE: 13

Met Phe Lys His Ile Ile Ala Arg Thr Pro Ala Arg Ser Leu Val Asp
```

Gly Leu Thr Ser Ser His Leu Gly Lys Pro Asp Tyr Ala Lys Ala Leu
            20                  25                  30

Glu Gln His Asn Ala Tyr Ile Arg Ala Leu Gln Thr Cys Asp Val Asp
            35                  40                  45

Ile Thr Leu Leu Pro Pro Asp Glu Arg Phe Pro Asp Ser Val Phe Val
 50                      55                  60

Glu Asp Pro Val Leu Cys Thr Ser Arg Cys Ala Ile Ile Thr Arg Pro
 65                  70                  75                  80

Gly Ala Glu Ser Arg Arg Gly Glu Thr Glu Ile Ile Glu Glu Thr Val
                     85                  90                  95

Gln Arg Phe Tyr Pro Gly Lys Val Glu Arg Ile Glu Ala Pro Gly Thr
                 100                 105                 110

Val Glu Ala Gly Asp Ile Met Met Val Gly Asp His Phe Tyr Ile Gly
                115                 120                 125

Glu Ser Ala Arg Thr Asn Ala Glu Gly Ala Arg Gln Met Ile Ala Ile
            130                 135                 140

Leu Glu Lys His Gly Leu Ser Gly Ser Val Val Arg Leu Glu Lys Val
145                 150                 155                 160

Leu His Leu Lys Thr Gly Leu Ala Tyr Leu Glu His Asn Asn Leu Leu
                165                 170                 175

Ala Ala Gly Glu Phe Val Ser Lys Pro Glu Phe Gln Asp Phe Asn Ile
                180                 185                 190

Ile Glu Ile Pro Glu Glu Glu Ser Tyr Ala Ala Asn Cys Ile Trp Val
            195                 200                 205

Asn Glu Arg Val Ile Met Pro Ala Gly Tyr Pro Arg Thr Arg Glu Lys
        210                 215                 220

Ile Ala Arg Leu Gly Tyr Arg Val Ile Glu Val Asp Thr Ser Glu Tyr
225                 230                 235                 240

Arg Lys Ile Asp Gly Gly Val Ser Cys Met Ser Leu Arg Phe
                    245                 250

<210> SEQ ID NO 14
<211> LENGTH: 285
<212> TYPE: PRT
<213> ORGANISM: Macaca fascicularis

<400> SEQUENCE: 14

Met Ala Gly Leu Gly His Pro Ala Ala Phe Gly Arg Ala Thr His Ala
 1               5                  10                  15

Val Val Arg Ala Leu Pro Glu Ser Leu Gly Gln His Ala Leu Arg Ser
            20                  25                  30

Ala Lys Gly Glu Glu Val Asp Val Ala Arg Ala Glu Arg Gln His Gln
        35                  40                  45

Leu Tyr Val Gly Val Leu Gly Ser Lys Leu Gly Leu Gln Val Val Glu
 50                  55                  60

Leu Pro Ala Asp Glu Ser Leu Pro Asp Cys Val Phe Val Glu Asp Val
 65                  70                  75                  80

Ala Val Val Cys Glu Glu Thr Ala Leu Ile Thr Arg Pro Gly Ala Pro
                 85                  90                  95

Ser Arg Arg Lys Glu Val Asp Met Met Lys Glu Ala Leu Glu Lys Leu
                100                 105                 110

Gln Leu Asn Ile Val Glu Met Lys Asp Glu Asn Ala Thr Leu Asp Gly
            115                 120                 125

```
Gly Asp Val Leu Phe Thr Gly Arg Glu Phe Val Gly Leu Ser Lys
            130                 135                 140

Arg Thr Asn Gln Arg Gly Ala Glu Ile Leu Ala Asp Thr Phe Lys Asp
145                 150                 155                 160

Tyr Ala Val Ser Thr Val Pro Val Ala Asp Gly Leu His Leu Lys Ser
                165                 170                 175

Phe Cys Ser Met Ala Gly Pro Asn Leu Ile Ala Ile Gly Ser Ser Glu
                180                 185                 190

Ser Ala Gln Lys Ala Leu Lys Ile Met Gln Gln Met Ser Asp His Arg
                195                 200                 205

Tyr Asp Lys Leu Thr Val Pro Asp Asp Ile Ala Ala Asn Cys Ile Tyr
210                 215                 220

Leu Asn Ile Pro Asn Lys Gly His Val Leu Leu His Arg Thr Pro Glu
225                 230                 235                 240

Glu Tyr Pro Glu Ser Ala Lys Val Tyr Glu Lys Leu Lys Asp His Met
                245                 250                 255

Leu Ile Pro Val Ser Met Ser Glu Leu Glu Lys Val Asp Gly Leu Leu
                260                 265                 270

Thr Cys Cys Ser Val Leu Ile Asn Lys Lys Val Asp Ser
                275                 280                 285

<210> SEQ ID NO 15
<211> LENGTH: 254
<212> TYPE: PRT
<213> ORGANISM: Pseudomonas aeruginosa
<220> FEATURE:
<221> NAME/KEY: MISC_FEATURE
<222> LOCATION: (3)..(3)
<223> OTHER INFORMATION: Xaa at position 3 is cysteine or lysine
<220> FEATURE:
<221> NAME/KEY: MISC_FEATURE
<222> LOCATION: (25)..(25)
<223> OTHER INFORMATION: Xaa at position 25 is cysteine or lysine
<220> FEATURE:
<221> NAME/KEY: MISC_FEATURE
<222> LOCATION: (45)..(45)
<223> OTHER INFORMATION: Xaa at position 45 is alanine, cysteine or
     lysine
<220> FEATURE:
<221> NAME/KEY: MISC_FEATURE
<222> LOCATION: (70)..(70)
<223> OTHER INFORMATION: Xaa at position 70 is alanine, cysteine or
     lysine
<220> FEATURE:
<221> NAME/KEY: MISC_FEATURE
<222> LOCATION: (74)..(74)
<223> OTHER INFORMATION: Xaa at position 74 is cysteine, alanine or
     serine
<220> FEATURE:
<221> NAME/KEY: MISC_FEATURE
<222> LOCATION: (84)..(84)
<223> OTHER INFORMATION: Xaa at position 84 is cysteine, alanine or
     serine
<220> FEATURE:
<221> NAME/KEY: MISC_FEATURE
<222> LOCATION: (103)..(103)
<223> OTHER INFORMATION: Xaa at position 103 is cysteine or lysine
<220> FEATURE:
<221> NAME/KEY: MISC_FEATURE
<222> LOCATION: (159)..(159)
<223> OTHER INFORMATION: Xaa at position 159 is cysteine or lysine
<220> FEATURE:
<221> NAME/KEY: MISC_FEATURE
<222> LOCATION: (205)..(205)
<223> OTHER INFORMATION: Xaa at position 205 is alanine, cysteine or
     lysine

<400> SEQUENCE: 15
```

Met Phe Xaa His Ile Ile Ala Arg Thr Pro Ala Arg Ser Leu Val Asp
1               5                   10                  15

Gly Leu Thr Ser Ser His Leu Gly Xaa Pro Asp Tyr Ala Lys Ala Leu
            20                  25                  30

Glu Gln His Asn Ala Tyr Ile Arg Ala Leu Gln Thr Xaa Asp Val Asp
        35                  40                  45

Ile Thr Leu Leu Pro Pro Asp Glu Arg Phe Pro Asp Ser Val Phe Val
50                  55                  60

Glu Asp Pro Val Leu Xaa Thr Ser Arg Xaa Ala Ile Ile Thr Arg Pro
65                  70                  75                  80

Gly Ala Glu Xaa Arg Arg Gly Glu Thr Glu Ile Ile Glu Glu Thr Val
                85                  90                  95

Gln Arg Phe Tyr Pro Gly Xaa Val Glu Arg Ile Glu Ala Pro Gly Thr
                100                 105                 110

Val Glu Ala Gly Asp Ile Met Met Val Gly Asp His Phe Tyr Ile Gly
            115                 120                 125

Glu Ser Ala Arg Thr Asn Ala Glu Gly Ala Arg Gln Met Ile Ala Ile
        130                 135                 140

Leu Glu Lys His Gly Leu Ser Gly Ser Val Val Arg Leu Glu Xaa Val
145                 150                 155                 160

Leu His Leu Lys Thr Gly Leu Ala Tyr Leu Glu His Asn Asn Leu Leu
                165                 170                 175

Ala Ala Gly Glu Phe Val Ser Lys Pro Glu Phe Gln Asp Phe Asn Ile
            180                 185                 190

Ile Glu Ile Pro Glu Glu Glu Ser Tyr Ala Ala Asn Xaa Ile Trp Val
        195                 200                 205

Asn Glu Arg Val Ile Met Pro Ala Gly Tyr Pro Arg Thr Arg Glu Lys
210                 215                 220

Ile Ala Arg Leu Gly Tyr Arg Val Ile Glu Val Asp Thr Ser Glu Tyr
225                 230                 235                 240

Arg Lys Ile Asp Gly Gly Val Ser Cys Met Ser Leu Arg Phe
                245                 250

<210> SEQ ID NO 16
<211> LENGTH: 23
<212> TYPE: PRT
<213> ORGANISM: Artificial Sequence
<220> FEATURE:
<223> OTHER INFORMATION: Signal peptide

<400> SEQUENCE: 16

Met Pro Arg Leu Phe Phe His Leu Leu Gly Val Cys Leu Leu Leu Asn
1               5                   10                  15

Gln Phe Ser Arg Ala Val Ala
            20

<210> SEQ ID NO 17
<211> LENGTH: 260
<212> TYPE: PRT
<213> ORGANISM: Pseudomonas aeruginosa

<400> SEQUENCE: 17

Met Phe Lys His Ile Ile Ala Arg Thr Pro Ala Arg Ser Leu Val Asp
1               5                   10                  15

Gly Leu Thr Ser Ser His Leu Gly Lys Pro Asp Tyr Ala Lys Ala Leu
            20                  25                  30

Glu Gln His Asn Ala Tyr Ile Arg Ala Leu Gln Thr Cys Asp Val Asp

```
            35                  40                  45
Ile Thr Leu Leu Pro Pro Asp Glu Arg Phe Pro Asp Ser Val Phe Val
 50                  55                  60

Glu Asp Pro Val Leu Cys Thr Ser Arg Cys Ala Ile Ile Thr Arg Pro
 65                  70                  75                  80

Gly Ala Glu Ser Arg Arg Gly Glu Thr Glu Ile Ile Glu Glu Thr Val
                 85                  90                  95

Gln Arg Phe Tyr Pro Gly Lys Val Glu Arg Ile Glu Ala Pro Gly Thr
                100                 105                 110

Val Glu Ala Gly Asp Ile Met Met Val Gly Asp His Phe Tyr Ile Gly
                115                 120                 125

Glu Ser Ala Arg Thr Asn Ala Glu Gly Ala Arg Gln Met Ile Ala Ile
            130                 135                 140

Leu Glu Lys His Gly Leu Ser Gly Ser Val Val Arg Leu Glu Lys Val
145                 150                 155                 160

Leu His Leu Lys Thr Gly Leu Ala Tyr Leu Glu His Asn Asn Leu Leu
                165                 170                 175

Ala Ala Gly Glu Phe Val Ser Lys Pro Glu Phe Gln Asp Phe Asn Ile
                180                 185                 190

Ile Glu Ile Pro Glu Glu Glu Ser Tyr Ala Ala Asn Cys Ile Trp Val
                195                 200                 205

Asn Glu Arg Val Ile Met Pro Ala Gly Tyr Pro Arg Thr Arg Glu Lys
210                 215                 220

Ile Ala Arg Leu Gly Tyr Arg Val Ile Glu Val Asp Thr Ser Glu Tyr
225                 230                 235                 240

Arg Lys Ile Asp Gly Gly Val Ser Cys Met Ser Leu Arg Phe His His
                245                 250                 255

His His His His
            260

<210> SEQ ID NO 18
<211> LENGTH: 260
<212> TYPE: PRT
<213> ORGANISM: Pseudomonas aeruginosa

<400> SEQUENCE: 18

Met Phe Cys His Ile Ile Ala Arg Thr Pro Ala Arg Ser Leu Val Asp
  1               5                  10                  15

Gly Leu Thr Ser Ser His Leu Gly Lys Pro Asp Tyr Ala Lys Ala Leu
                 20                  25                  30

Glu Gln His Asn Ala Tyr Ile Arg Ala Leu Gln Thr Cys Asp Val Asp
             35                  40                  45

Ile Thr Leu Leu Pro Pro Asp Glu Arg Phe Pro Asp Ser Val Phe Val
 50                  55                  60

Glu Asp Pro Val Leu Cys Thr Ser Arg Cys Ala Ile Ile Thr Arg Pro
 65                  70                  75                  80

Gly Ala Glu Ser Arg Arg Gly Glu Thr Glu Ile Ile Glu Glu Thr Val
                 85                  90                  95

Gln Arg Phe Tyr Pro Gly Lys Val Glu Arg Ile Glu Ala Pro Gly Thr
                100                 105                 110

Val Glu Ala Gly Asp Ile Met Met Val Gly Asp His Phe Tyr Ile Gly
                115                 120                 125

Glu Ser Ala Arg Thr Asn Ala Glu Gly Ala Arg Gln Met Ile Ala Ile
            130                 135                 140
```

```
Leu Glu Lys His Gly Leu Ser Gly Ser Val Val Arg Leu Glu Lys Val
145                 150                 155                 160

Leu His Leu Lys Thr Gly Leu Ala Tyr Leu Glu His Asn Asn Leu Leu
                165                 170                 175

Ala Ala Gly Glu Phe Val Ser Lys Pro Glu Phe Gln Asp Phe Asn Ile
            180                 185                 190

Ile Glu Ile Pro Glu Glu Ser Tyr Ala Ala Asn Cys Ile Trp Val
        195                 200                 205

Asn Glu Arg Val Ile Met Pro Ala Gly Tyr Pro Arg Thr Arg Glu Lys
    210                 215                 220

Ile Ala Arg Leu Gly Tyr Arg Val Ile Glu Val Asp Thr Ser Glu Tyr
225                 230                 235                 240

Arg Lys Ile Asp Gly Gly Val Ser Cys Met Ser Leu Arg Phe His His
                245                 250                 255

His His His His
        260

<210> SEQ ID NO 19
<211> LENGTH: 260
<212> TYPE: PRT
<213> ORGANISM: Pseudomonas aeruginosa

<400> SEQUENCE: 19

Met Phe Lys His Ile Ile Ala Arg Thr Pro Ala Arg Ser Leu Val Asp
1               5                   10                  15

Gly Leu Thr Ser Ser His Leu Gly Cys Pro Asp Tyr Ala Lys Ala Leu
            20                  25                  30

Glu Gln His Asn Ala Tyr Ile Arg Ala Leu Gln Thr Cys Asp Val Asp
        35                  40                  45

Ile Thr Leu Leu Pro Pro Asp Glu Arg Phe Pro Asp Ser Val Phe Val
    50                  55                  60

Glu Asp Pro Val Leu Cys Thr Ser Arg Cys Ala Ile Ile Thr Arg Pro
65                  70                  75                  80

Gly Ala Glu Ser Arg Arg Gly Glu Thr Glu Ile Ile Glu Thr Val
                85                  90                  95

Gln Arg Phe Tyr Pro Gly Lys Val Glu Arg Ile Glu Ala Pro Gly Thr
                100                 105                 110

Val Glu Ala Gly Asp Ile Met Met Val Gly Asp His Phe Tyr Ile Gly
            115                 120                 125

Glu Ser Ala Arg Thr Asn Ala Glu Gly Ala Arg Gln Met Ile Ala Ile
        130                 135                 140

Leu Glu Lys His Gly Leu Ser Gly Ser Val Val Arg Leu Glu Lys Val
145                 150                 155                 160

Leu His Leu Lys Thr Gly Leu Ala Tyr Leu Glu His Asn Asn Leu Leu
                165                 170                 175

Ala Ala Gly Glu Phe Val Ser Lys Pro Glu Phe Gln Asp Phe Asn Ile
            180                 185                 190

Ile Glu Ile Pro Glu Glu Ser Tyr Ala Ala Asn Cys Ile Trp Val
        195                 200                 205

Asn Glu Arg Val Ile Met Pro Ala Gly Tyr Pro Arg Thr Arg Glu Lys
    210                 215                 220

Ile Ala Arg Leu Gly Tyr Arg Val Ile Glu Val Asp Thr Ser Glu Tyr
225                 230                 235                 240

Arg Lys Ile Asp Gly Gly Val Ser Cys Met Ser Leu Arg Phe His His
                245                 250                 255
```

His His His His
        260

<210> SEQ ID NO 20
<211> LENGTH: 260
<212> TYPE: PRT
<213> ORGANISM: Pseudomonas aeruginosa

<400> SEQUENCE: 20

Met Phe Lys His Ile Ile Ala Arg Thr Pro Ala Arg Ser Leu Val Asp
1               5                   10                  15

Gly Leu Thr Ser Ser His Leu Gly Lys Pro Asp Tyr Ala Lys Ala Leu
            20                  25                  30

Glu Gln His Asn Ala Tyr Ile Arg Ala Leu Gln Thr Cys Asp Val Asp
        35                  40                  45

Ile Thr Leu Leu Pro Pro Asp Glu Arg Phe Pro Asp Ser Val Phe Val
    50                  55                  60

Glu Asp Pro Val Leu Cys Thr Ser Arg Cys Ala Ile Ile Thr Arg Pro
65                  70                  75                  80

Gly Ala Glu Ser Arg Arg Gly Glu Thr Glu Ile Ile Glu Thr Val
            85                  90                  95

Gln Arg Phe Tyr Pro Gly Cys Val Glu Arg Ile Glu Ala Pro Gly Thr
            100                 105                 110

Val Glu Ala Gly Asp Ile Met Met Val Gly Asp His Phe Tyr Ile Gly
            115                 120                 125

Glu Ser Ala Arg Thr Asn Ala Glu Gly Ala Arg Gln Met Ile Ala Ile
        130                 135                 140

Leu Glu Lys His Gly Leu Ser Gly Ser Val Val Arg Leu Glu Lys Val
145                 150                 155                 160

Leu His Leu Lys Thr Gly Leu Ala Tyr Leu Glu His Asn Asn Leu Leu
                165                 170                 175

Ala Ala Gly Glu Phe Val Ser Lys Pro Glu Phe Gln Asp Phe Asn Ile
            180                 185                 190

Ile Glu Ile Pro Glu Glu Glu Ser Tyr Ala Ala Asn Cys Ile Trp Val
            195                 200                 205

Asn Glu Arg Val Ile Met Pro Ala Gly Tyr Pro Arg Thr Arg Glu Lys
        210                 215                 220

Ile Ala Arg Leu Gly Tyr Arg Val Ile Glu Val Asp Thr Ser Glu Tyr
225                 230                 235                 240

Arg Lys Ile Asp Gly Gly Val Ser Cys Met Ser Leu Arg Phe His His
                245                 250                 255

His His His His
        260

<210> SEQ ID NO 21
<211> LENGTH: 260
<212> TYPE: PRT
<213> ORGANISM: Pseudomonas aeruginosa

<400> SEQUENCE: 21

Met Phe Lys His Ile Ile Ala Arg Thr Pro Ala Arg Ser Leu Val Asp
1               5                   10                  15

Gly Leu Thr Ser Ser His Leu Gly Lys Pro Asp Tyr Ala Lys Ala Leu
            20                  25                  30

Glu Gln His Asn Ala Tyr Ile Arg Ala Leu Gln Thr Cys Asp Val Asp
        35                  40                  45

Ile Thr Leu Leu Pro Pro Asp Glu Arg Phe Pro Asp Ser Val Phe Val
        50                      55                      60

Glu Asp Pro Val Leu Cys Thr Ser Arg Cys Ala Ile Ile Thr Arg Pro
 65                  70                      75                      80

Gly Ala Glu Ser Arg Arg Gly Glu Thr Glu Ile Ile Glu Glu Thr Val
                        85                      90                      95

Gln Arg Phe Tyr Pro Gly Lys Val Glu Arg Ile Glu Ala Pro Gly Thr
                100                     105                     110

Val Glu Ala Gly Asp Ile Met Met Val Gly Asp His Phe Tyr Ile Gly
                115                     120                     125

Glu Ser Ala Arg Thr Asn Ala Glu Gly Ala Arg Gln Met Ile Ala Ile
                130                     135                     140

Leu Glu Lys His Gly Leu Ser Gly Ser Val Val Arg Leu Glu Cys Val
145                     150                     155                     160

Leu His Leu Lys Thr Gly Leu Ala Tyr Leu Glu His Asn Asn Leu Leu
                165                     170                     175

Ala Ala Gly Glu Phe Val Ser Lys Pro Glu Phe Gln Asp Phe Asn Ile
                180                     185                     190

Ile Glu Ile Pro Glu Glu Glu Ser Tyr Ala Ala Asn Cys Ile Trp Val
                195                     200                     205

Asn Glu Arg Val Ile Met Pro Ala Gly Tyr Pro Arg Thr Arg Glu Lys
                210                     215                     220

Ile Ala Arg Leu Gly Tyr Arg Val Ile Glu Val Asp Thr Ser Glu Tyr
225                     230                     235                     240

Arg Lys Ile Asp Gly Gly Val Ser Cys Met Ser Leu Arg Phe His His
                245                     250                     255

His His His His
        260

<210> SEQ ID NO 22
<211> LENGTH: 260
<212> TYPE: PRT
<213> ORGANISM: Bacterial DDAH

<400> SEQUENCE: 22

Met Phe Cys His Ile Ile Ala Arg Thr Pro Ala Arg Ser Leu Val Asp
 1               5                      10                      15

Gly Leu Thr Ser Ser His Leu Gly Cys Pro Asp Tyr Ala Lys Ala Leu
                20                      25                      30

Glu Gln His Asn Ala Tyr Ile Arg Ala Leu Gln Thr Cys Asp Val Asp
            35                      40                      45

Ile Thr Leu Leu Pro Pro Asp Glu Arg Phe Pro Asp Ser Val Phe Val
        50                      55                      60

Glu Asp Pro Val Leu Cys Thr Ser Arg Cys Ala Ile Ile Thr Arg Pro
 65                  70                      75                      80

Gly Ala Glu Ser Arg Arg Gly Glu Thr Glu Ile Ile Glu Glu Thr Val
                        85                      90                      95

Gln Arg Phe Tyr Pro Gly Cys Val Glu Arg Ile Glu Ala Pro Gly Thr
                100                     105                     110

Val Glu Ala Gly Asp Ile Met Met Val Gly Asp His Phe Tyr Ile Gly
                115                     120                     125

Glu Ser Ala Arg Thr Asn Ala Glu Gly Ala Arg Gln Met Ile Ala Ile
                130                     135                     140

Leu Glu Lys His Gly Leu Ser Gly Ser Val Val Arg Leu Glu Cys Val

```
                145                 150                 155                 160
Leu His Leu Lys Thr Gly Leu Ala Tyr Leu Glu His Asn Asn Leu Leu
                165                 170                 175

Ala Ala Gly Glu Phe Val Ser Lys Pro Glu Phe Gln Asp Phe Asn Ile
                180                 185                 190

Ile Glu Ile Pro Glu Glu Ser Tyr Ala Ala Asn Cys Ile Trp Val
                195                 200                 205

Asn Glu Arg Val Ile Met Pro Ala Gly Tyr Pro Arg Thr Arg Glu Lys
                210                 215                 220

Ile Ala Arg Leu Gly Tyr Arg Val Ile Glu Val Asp Thr Ser Glu Tyr
225                 230                 235                 240

Arg Lys Ile Asp Gly Gly Val Ser Cys Met Ser Leu Arg Phe His His
                245                 250                 255

His His His His
                260

<210> SEQ ID NO 23
<211> LENGTH: 254
<212> TYPE: PRT
<213> ORGANISM: Pseudomonas aeruginosa
<220> FEATURE:
<221> NAME/KEY: MISC_FEATURE
<222> LOCATION: (45)..(45)
<223> OTHER INFORMATION: Xaa at position 45 is alanine or cysteine
<220> FEATURE:
<221> NAME/KEY: MISC_FEATURE
<222> LOCATION: (70)..(70)
<223> OTHER INFORMATION: Xaa at position 70 is alanine or lysine
<220> FEATURE:
<221> NAME/KEY: MISC_FEATURE
<222> LOCATION: (74)..(74)
<223> OTHER INFORMATION: Xaa at position 74 is cysteine or alanine
<220> FEATURE:
<221> NAME/KEY: MISC_FEATURE
<222> LOCATION: (205)..(205)
<223> OTHER INFORMATION: Xaa at position 205 is alanine, cysteine or
      lysine

<400> SEQUENCE: 23

Met Phe Cys His Ile Ile Ala Arg Thr Pro Ala Arg Ser Leu Val Asp
1               5                   10                  15

Gly Leu Thr Ser Ser His Leu Gly Cys Pro Asp Tyr Ala Lys Ala Leu
                20                  25                  30

Glu Gln His Asn Ala Tyr Ile Arg Ala Leu Gln Thr Xaa Asp Val Asp
                35                  40                  45

Ile Thr Leu Leu Pro Pro Asp Glu Arg Phe Pro Asp Ser Val Phe Val
                50                  55                  60

Glu Asp Pro Val Leu Xaa Thr Ser Arg Xaa Ala Ile Ile Thr Arg Pro
65                  70                  75                  80

Gly Ala Glu Ser Arg Arg Gly Glu Thr Glu Ile Ile Glu Glu Thr Val
                85                  90                  95

Gln Arg Phe Tyr Pro Gly Lys Val Glu Arg Ile Glu Ala Pro Gly Thr
                100                 105                 110

Val Glu Ala Gly Asp Ile Met Met Val Gly Asp His Phe Tyr Ile Gly
                115                 120                 125

Glu Ser Ala Arg Thr Asn Ala Glu Gly Ala Arg Gln Met Ile Ala Ile
                130                 135                 140

Leu Glu Lys His Gly Leu Ser Gly Ser Val Val Arg Leu Glu Lys Val
145                 150                 155                 160

Leu His Leu Lys Thr Gly Leu Ala Tyr Leu Glu His Asn Asn Leu Leu
```

-continued

```
                165                 170                 175
Ala Ala Gly Glu Phe Val Ser Lys Pro Glu Phe Gln Asp Phe Asn Ile
            180                 185                 190

Ile Glu Ile Pro Glu Glu Glu Ser Tyr Ala Ala Asn Xaa Ile Trp Val
        195                 200                 205

Asn Glu Arg Val Ile Met Pro Ala Gly Tyr Pro Arg Thr Arg Glu Lys
    210                 215                 220

Ile Ala Arg Leu Gly Tyr Arg Val Ile Glu Val Asp Thr Ser Glu Tyr
225                 230                 235                 240

Arg Lys Ile Asp Gly Gly Val Ser Cys Met Ser Leu Arg Phe
                245                 250
```